United States Patent
Lin et al.

(10) Patent No.: US 9,624,175 B2
(45) Date of Patent: Apr. 18, 2017

(54) FUSED-BICYCLIC ARYL QUINOLINONE DERIVATIVES AS MUTANT-ISOCITRATE DEHYDROGENASE INHIBITORS

(71) Applicant: Forma Therapeutics, Inc., Watertown, MA (US)

(72) Inventors: Jian Lin, Acton, MA (US); Anna Ericsson, Acton, MA (US); Ann-Marie Campbell, Monroe, CT (US); Gary Gustafson, Ridgefield, CT (US); Zhongguo Wang, Lexington, MA (US); R. Bruce Diebold, Waltham, MA (US); Susan Ashwell, Carlisle, MA (US); David R. Lancia, Jr., Boston, MA (US); Justin Andrew Caravella, Cambridge, MA (US); Wei Lu, Newton, MA (US)

(73) Assignee: FORMA THERAPEUTICS, INC., Watertown, MA (US)

( * ) Notice: Subject to any disclaimer, the term of this patent is extended or adjusted under 35 U.S.C. 154(b) by 0 days.

(21) Appl. No.: 14/858,159

(22) Filed: Sep. 18, 2015

(65) Prior Publication Data

US 2016/0311774 A1   Oct. 27, 2016

Related U.S. Application Data

(60) Provisional application No. 62/150,815, filed on Apr. 21, 2015.

(51) Int. Cl.
| | | |
|---|---|---|
| *C07D 215/227* | (2006.01) | |
| *C07D 403/12* | (2006.01) | |
| *C07D 401/12* | (2006.01) | |
| *C07D 405/12* | (2006.01) | |
| *C07D 413/12* | (2006.01) | |
| *C07D 417/12* | (2006.01) | |
| *C07D 487/04* | (2006.01) | |
| *C07D 471/04* | (2006.01) | |
| *C07D 498/04* | (2006.01) | |

(52) U.S. Cl.
CPC ....... *C07D 215/227* (2013.01); *C07D 401/12* (2013.01); *C07D 403/12* (2013.01); *C07D 405/12* (2013.01); *C07D 413/12* (2013.01); *C07D 417/12* (2013.01); *C07D 471/04* (2013.01); *C07D 487/04* (2013.01); *C07D 498/04* (2013.01)

(58) Field of Classification Search
CPC  C07D 215/227; C07D 403/12; C07D 405/12; C07D 401/12; C07D 498/04; C07D 417/12; C07D 413/12; C07D 487/04
See application file for complete search history.

(56) References Cited

U.S. PATENT DOCUMENTS 5,262,564 A    11/1993  Kun et al.
9,073,941 B2 *  7/2015  Wong

FOREIGN PATENT DOCUMENTS

WO    2006054912    *  3/2006

OTHER PUBLICATIONS

Tintori, Chem Med Chem, vol. 8, 1353-1360, 2013.*
Badr, Bull Chem Soc Jpn, vol. 56, 326-330, 1983.*
DiNardo, Blood, 121(24), 4917-4924, 2013.*
Dang, L et al., Nature, 2009, 462:739-44.

* cited by examiner

*Primary Examiner* — D M Seaman
(74) *Attorney, Agent, or Firm* — Cooley LLP

(57) ABSTRACT

The invention relates to inhibitors of mutant isocitrate dehydrogenase (mt-IDH) proteins with neomorphic activity useful in the treatment of cell-proliferation disorders and cancers, having the Formula:

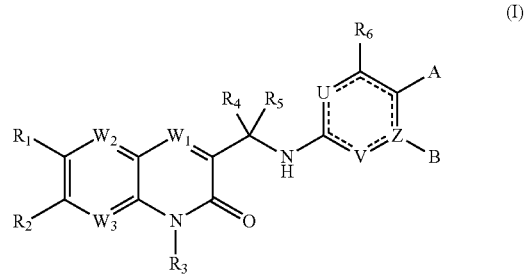

(I)

where A, B, U, V, Z, $W_1$, $W_2$, $W_3$, and $R_1$-$R_6$ are described herein.

39 Claims, 1 Drawing Sheet

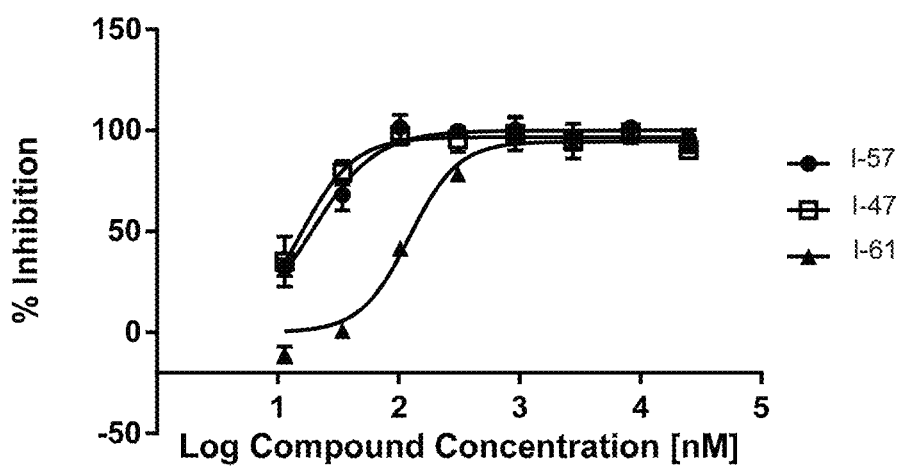

FUSED-BICYCLIC ARYL QUINOLINONE DERIVATIVES AS MUTANT-ISOCITRATE DEHYDROGENASE INHIBITORS

CROSS-REFERENCE TO RELATED APPLICATIONS

This application claims the benefit of priority of U.S. Provisional Application No. 62/150,815, filed Apr. 21, 2015, all of which is incorporated herein by reference in its entirety.

FIELD OF INVENTION

The present invention is directed to inhibitors of mutant isocitrate dehydrogenase (mt-IDH) proteins with neomorphic activity useful in the treatment of diseases or disorders associated with such mutant IDH proteins including cell-proliferation disorders and cancers. Specifically, the invention is concerned with compounds and compositions inhibiting mt-IDH, methods of treating diseases or disorders associated with mt-IDH, and methods of synthesis of these compounds.

BACKGROUND OF THE INVENTION

Isocitrate dehydrogenases (IDHs) are enzymes that participate in the citric acid cycle (cellular metabolism). They catalyze the oxidative decarboxylation of isocitrate to 2-oxoglutarate (i.e., α-ketoglutarate, α-KG). There are three isoforms within the IDH family. IDH-1, expressed in the cytoplasm and peroxisome, IDH-2, localized in the mitochondria, both utilize NADP$^+$ as the cofactor and exist as homodimers. IDH-3 is localized in mitochondrial matrix and utilizes NAD$^+$ as a cofactor and exists as tetramer. Mutations in IDH-1 (cytosolic) and IDH-2 (mitochondrial) have been identified in various diseases or disorders including glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, and melanoma (L. Deng et al., *Trends Mol. Med.*, 2010, 16, 387; T. Shibata et al., *Am. J. Pathol.*, 201 1, 178 (3), 1395; Gaal et al., *J. Clin. Endocrinol. Metab.* 2010; Hayden et al., *Cell Cycle*, 2009; Balss et al., *Acta Neuropathol.*, 2008). The mutations have been found at or near key residues in the active site: G97D, R100, R132, H133Q, and A134D for IDH1, and R140 and R172 for IDH2. (See L. Deng et al., *Nature*, 2009, 462, 739; L. Sellner et al., *Eur. J. Haematol.*, 2011, 85, 457).

Mutant forms of IDH-1 and IDH-2 have been shown to lose wild type activity, and instead exhibit a neomorphic activity (also known as a gain of function activity), of reducing alpha-ketoglutarate to 2-hydroxyglutarate (2-HG). (See P. S. Ward et al., *Cancer Cell*, 2010, 17, 225; Zhao et. al., *Science* 324, 261 (2009); Dang et. al *Nature* 462, 739 (2009)). In general, production of 2-HG is enantiospecific, resulting in generation of the D-enantiomer (also known as the R enantiomer or R-2-HG). Normal cells have low basal levels of 2-HG, whereas cells harboring mutations in IDH1 or IDH2 show significantly elevated levels of 2-HG. High levels of 2-HG have also been detected in tumors harboring the mutations. For example, high levels of 2-HG have been detected in the plasma of patients with mutant IDH containing AML. (See S. Gross et al., *J. Exp. Med.*, 2010, 207 (2), 339). High levels of 2-HG have been shown to block α-KG dependent DNA and histone demethylases, and ultimately to result in improper dedifferentiation of hematopoietic progenitor cells in AML patients (Wang et. al., Science 340, 622 (2013); Losman et al., Science 339, 1621 (2013)).

Furthermore, patients with Oilier Disease and Mafucci Syndrome (two rare disorders that predispose to cartilaginous tumors) have been shown to be somatically mosaic for IDH1 and 2 mutations and exhibit high levels of D-2-HG. (See Amary et al., *Nature Genetics*, 2011 and Pansuriya et al., *Nature Genetics*, 2011).

The inhibition of mt-IDHs and their neomorphic activity with small molecule inhibitors therefore has the potential to be a treatment for cancers and other disorders of cellular proliferation.

SUMMARY OF THE INVENTION

A first aspect of the invention relates to compounds of Formula (I):

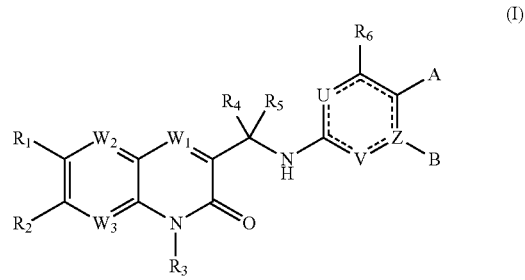

and pharmaceutically acceptable salts, enantiomers, hydrates, solvates, prodrugs, isomers, and tautomers thereof, wherein:

each $W_1$ and $W_2$ is independently CH, CF, or N;
$W_3$ is CF, $CR_2$, or N;
U is N or $CR_6$;
V is N or $CR_9$;
Z is N or C;
═══ indicates a single or double bond but never two double bonds adjacent to one another in the ring in which the ═══ occurs;
A and B, A and $R_6$, or B and $R_9$ are taken together with the atoms to which they are attached to form an aryl or a 5 to 7-membered heterocyclyl or heteroaryl ring system which can be further substituted with one or more $R_{10}$ substituents;
A and B, when not part of the fused aryl, heteroaryl, or 5 to 7-membered heterocyclyl, are each independently H, $R_6$, CN, $C_1$-$C_6$ alkyl, or $C_1$-$C_6$ alkoxy;
$R_1$ is independently H, OH, CN, halogen, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, 3 to 8-membered heterocyclyl, aryl, or heteroaryl, wherein each $C_1$-$C_6$ alkyl, $C_2$-$C_6$ alkenyl, $C_2$-$C_6$ alkynyl, $C_3$-$C_8$ cycloalkyl, $C_3$-$C_8$ heterocyclyl, aryl, or heteroaryl is optionally substituted one or more times with substituents selected from the group consisting of halogen, OH, $NH_2$, CN, $C_1$-$C_6$ alkyl, and $C_1$-$C_6$ alkoxy;
$R_2$ is independently H, OH, CN, halogen, $CF_3$, $CHF_2$, $C_1$-$C_6$ alkyl, $C_1$-$C_6$ alkoxy, $NH_2$, —O($CH_2$)$_n$$R_7$, —O($CH_2$)$_n$C(O)$NHR_7$, —O($CH_2$)$_n$C(O)$R_7$, $NHR_7$, —N($R_7$)($R_8$), NHC(O)$R_7$, NHS(O)$R_7$, NHS(O)$_2$$R_7$, NHC(O)$OR_7$, NHC(O)$NHR_7$, —S(O)$_2$$NHR_7$, NHC(O)N($R_8$)($R_7$), OCH($R_7$)($R_8$), or —CH($R_7$)($R_8$), wherein $C_1$-$C_6$ alkyl, $C_1$-$C_6$ alkoxy is optionally substituted with one or more substituents selected from the group consisting of $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, or 3 to 8-membered hetecyclyl substituted with one or more halogen, 3 to 8-membered heterocyclyl, aryl, -heteroaryl-C(O)NH$_2$, and heteroaryl;

$R_3$ is H or $C_1$-$C_6$ alkyl;

$R_4$ and $R_5$ are independently H, halogen, CH$_2$OH, $C_1$-$C_3$ alkyl, or $C_1$-$C_3$ haloalkyl, or $R_4$ and $R_5$ when combined can form a $C_3$-$C_6$ cycloalkyl or 3 to 8-membered heterocyclyl;

$R_6$ is H, halogen, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, $C_2$-$C_6$ alkynyl, $C_3$-$C_8$ cycloalkyl, 3 to 8-membered heterocyclyl, aryl, or heteroaryl;

$R_7$ and $R_8$ are independently H, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, 3 to 8-membered heterocyclyl, aryl, and heteroaryl; or when combined $R_7$ and $R_8$ can form a 3 to 8-membered heterocyclyl or heteroaryl ring; and $R_9$ is independently selected from the group consisting of H, =O, halogen, OH, CN, —CH$_2$CN, $C_1$-$C_6$ alkyl, $R_7$S(O)$_2$—, $C_1$-$C_6$ alkoxy, $C_2$-$C_6$ alkenyl, $C_2$-$C_6$ alkenyl, $C_3$-$C_8$ cycloalkyl, $C_3$-$C_8$ cycloalkylalkyl, 3 to 8-membered heterocyclyl, aryl, and heteroaryl, wherein alkyl, alkoxy, alkenyl, cycloalkyl, cycloalkylalkyl, 3 to 8-membered heterocyclyl, aryl, and heteroaryl are optionally further substituted with one or more substituents selected from the group consisting of OH, halogen, $C_1$-$C_6$ alkoxy, NH$_2$, $R_7$S(O)$_2$—, CN, $C_3$-$C_8$ cycloalkyl, 3 to 8-membered heterocyclyl, aryl, heteroaryl, and $R_7$S(O)—;

each $R_{10}$ is independently H, OH, CN, =O, —COOR$_{11}$, —C(O)R$_{11}$, —CH$_2$CN, $C_1$-$C_6$ alkyl, $C_1$-$C_6$ haloalkyl $R_{11}$S(O)$_2$—, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, $C_3$-$C_8$ heterocyclyl, aryl, or heteroaryl; and each $R_{11}$ is independently H, $C_1$-$C_6$ alkyl, $C_1$-$C_6$ haloalkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, $C_3$-$C_8$ heterocyclyl, aryl, or heteroary; provided that:

(1) when A and B or A and $R_6$ form a 1,4-dioxane ring, $R_1$ and $R_2$ are not both methyl;

(2) when A and B or A and $R_6$ form a 1,3-dioxolane ring, $R_1$ is not H or methyl;

(3) when A and B or A and $R_6$ form a pyridine ring, $R_1$ is not H or $R_2$ is not methyl;

(4) when A and B or A and $R_6$ form a pyrazole ring, $R_1$ is not H, ethyl, or ethoxy;

(5) when A and B or A and $R_6$ form a pyrazole ring and $R_1$ is methyl, $R_2$ is not H; or (6) when A and B or A and $R_6$ form a phenyl ring, $R_1$ is not H.

Another aspect of the invention relates to a method of treating a disease or disorder associated with mutant isocitrate dehydrogenase. The method comprises administering to a patient in need of a treatment for diseases or disorders associated with mutant isocitrate dehydrogenase an effective amount of a compound of Formula (I).

Another aspect of the invention is directed to a method inhibiting mutant isocitrate dehydrogenase. The method involves administering to a patient in need thereof an effective amount of a compound of Formula (I).

Another aspect of the invention relates to method of reducing 2-hydroxyglutarate.

The method comprises administering to a patient in need thereof an effective amount of a compound of Formula (I).

Another aspect of the invention is directed to pharmaceutical compositions comprising a compound of Formula (I) and a pharmaceutically acceptable carrier. The pharmaceutically acceptable carrier may further include an excipient, diluent, or surfactant.

The present invention further provides methods of treating cell proliferative diseases and cancers including, without limitation, glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), myeloproliferative disease (MPD), and other solid tumors, comprising administering to a patient suffering from at least one of said diseases or cancers a compound of Formula (I). The inhibitors of the present invention may target mutated IDH1 at residue 97, 100 or 132, for example G97D, R100Q, R132H, R132C, R132S, R132G, R132L, and R132V. The inhibitors of the present invention may target mutated IDH2 at residue 140 or 172, for example R140Q, R172K, R172M, R172S, R172G, and R172W.

Another aspect of the invention provides for a compound of Formula (I), or a pharmaceutically acceptable salt thereof, in combination with another therapeutic agent.

BRIEF DESCRIPTION OF THE DRAWINGS OF THE INVENTION

FIG. 1 illustrates a graph showing the potency of IDH1 inhibitors in an IDH1-132H enzyme assay.

DETAILED DESCRIPTION OF THE INVENTION

IDH1 or IDH2 mutations are genetically validated targets in many solid and hematologic cancers, but there are currently no targeted therapies available for patients in need of treatment for specific conditions associated with mt-IDH activity. Non-mutant IDH (e.g., wild-type) catalyze the oxidative decarboxylation of isocitrate to α-ketoglutarate thereby reducing NAD$^+$ (NADP$^+$) to NADH (NADPH) (WO 2013/102431 to Cianchetta et al., hereby incorporated by reference in its entirety). Mutations of IDH present in certain cancer cells result in a new ability of the enzyme to catalyze the NADPH-dependent reduction of α-ketoglutarate R(−)-2-hydroxyglutarate (2HG). 2HG is not formed by wild-type IDH. The production of 2HG contributes to the formation and progression of cancer (Dang, L et al., Nature, 2009, 462:739-44, hereby incorporated by reference in its entirety). The present invention provides inhibitors of mt-IDH, and prophylactic measures to reduce the formation and progression of 2HG in cells.

In a first aspect of the invention, are described the compounds of Formula (I):

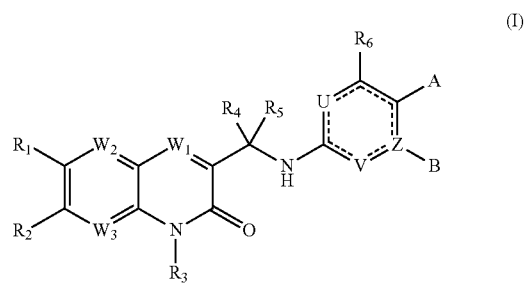

and pharmaceutically acceptable salts, enantiomers, hydrates, solvates, prodrugs, isomers, and tautomers thereof, where A, B, U, V, Z, $W_1$, $W_2$, $W_3$, and $R_1$-$R_6$ are described as above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DEFINITIONS

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, =O, CN, —COOH, —CH$_2$CN, —O—C$_1$-C$_6$alkyl, C$_1$-C$_6$alkyl, —OC$_1$-C$_6$alkenyl, —OC$_1$-C$_6$alkynyl, —C$_1$-C$_6$alkenyl, —C$_1$-C$_6$alkynyl, —OH, —OP(O)(OH)$_2$, —OC(O)C$_1$-C$_6$alkyl, —C(O)C$_1$-C$_6$alkyl, —OC(O)OC$_1$-C$_6$alkyl, NH$_2$, NH(C$_1$-C$_6$alkyl), N(C$_1$-C$_6$alkyl)$_2$, —NHC(O)C$_1$-C$_6$alkyl, —C(O)NHC$_1$-C$_6$alkyl, —S(O)$_2$—C$_1$-C$_6$alkyl, —S(O)NHC$_1$-C$_6$alkyl, and S(O)N(C$_1$-C$_6$alkyl)$_2$ Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—C$_1$-C$_6$alkyl, C$_1$-C$_6$alkyl, —OC$_1$-C$_6$alkenyl, —OC$_1$-C$_6$alkynyl, —C$_1$-C$_6$alkenyl, —C$_1$-C$_6$alkynyl, —OH, —OP(O)(OH)$_2$, —OC(O)C$_1$-C$_6$alkyl, —C(O)C$_1$-C$_6$alkyl, —OC(O)OC$_1$-C$_6$alkyl, NH$_2$, NH(C$_1$-C$_6$alkyl), N(C$_1$-C$_6$alkyl)$_2$, —S(O)$_2$—C$_1$-C$_6$alkyl, —S(O)NHC$_1$-C$_6$alkyl, and S(O)N(C$_1$-C$_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical of 5 to 10 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a C$_1$-C$_6$ alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain. Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. Examples of alkenyl groups include ethenyl, propenyl, n-butenyl, iso-butenyl, pentenyl, or hexenyl.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl.

"Cycloalkyl" means monocyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl.

"Cycloalkylalkyl" means monocyclic saturated carbon rings containing 3-18 carbon atoms further substituted with C$_1$-C$_6$ alkyl groups. In general cycloalkylalkyl groups herein described display the following formula

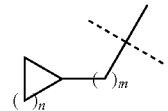

where m is an integer from 1 to 6 and n is an integer from 1 to 16.

"Heterocyclyl" or "heterocycloalkyl" monocyclic rings containing carbon and heteroatoms taken from oxygen, nitrogen, or sulfur and wherein there is not delocalized π electrons (aromaticity) shared among the ring carbon or heteroatoms; heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. In accordance with the present invention, 3- to 8-membered heterocyclyl refers to saturated or partially saturated non aromatic rings structures containing between 3 and 8 atoms in which there is at least one heteroatoms selected from the group N, O, or S.

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

In one embodiment, the compounds of Formula I have the Formula Ia:

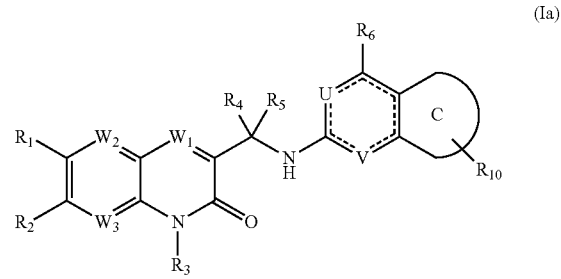

(Ia)

where the C ring is pyrrolidinyl, piperidinyl, phenyl, thienyl, oxazolyl, dioxanyl, dioxolanyl, thiazolyl, isoxazolyl, isothiazolyl, pyrrolyl, pyrazolyl, oxadiazolyl, thiadiazolyl, furyl, imidazolyl, pyridyl, pyrimidinyl, pyrrolyl, furyl, oxazolyl, thiazolyl, isoxazolyl, isothiazolyl, dazolyl, pyrazolyl, oxadiazolyl, thiadiazolyl, triazolyl, tetrazolyl, pyrazinyl, pyridazinyl, triazinyl, pyridinyl, pyrimidinyl, morpholinyl, thiomorpholinyl, oxazolonyl, oxazinonyl, dihydrooxazinonyl, imidazolonyl, pyrrolonyl, thiazolonyl, dihydropyridinonyl, dihydrothiazinedioxide, dihydrodioxinyl, dihydropyranonyl, dihydrothiophenedioxide, piperidinonyl, or dihydrooxazinonyl;

$R_{10}$ is independently H, OH, CN, =O, —COOR$_{11}$, —C(O)R$_{11}$, —CH$_2$CN, $C_1$-$C_6$ alkyl, $C_1$-$C_6$ haloalkyl R$_{11}$S (O)$_2$—, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, $C_3$-$C_8$ heterocyclyl, aryl, or heteroaryl; and each $R_{11}$ is independently H, $C_1$-$C_6$ alkyl, $C_1$-$C_6$ haloalkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, $C_3$-$C_8$ heterocyclyl, aryl, or heteroary.

In some embodiments of the compounds of Formula Ia, $R_{10}$ is methyl, ethyl, isopropyl, or isobutyl.

In another embodiment, the compounds of Formula I have the Formula Ib:

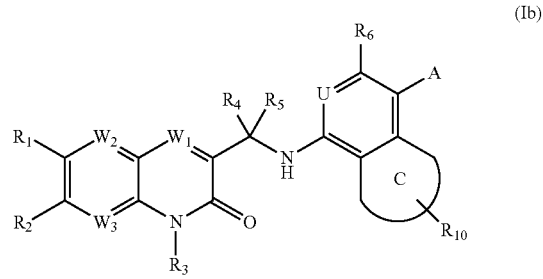

(Ib)

where the C ring is pyrrolidinyl, piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl, pyrrolyl, furyl, oxazolyl, thiazolyl, isoxazolyl, isothiazolyl, dazolyl, pyrazolyl, oxadiazolyl, thiadiazolyl, triazolyl, tetrazolyl, pyrazinyl, pyridazinyl, triazinyl, pyridinyl, pyrimidinyl, morpholinyl, thiomorpholinyl, oxazolonyl, oxazinonyl, dihydrooxazinonyl, imidazolonyl, pyrrolonyl, thiazolonyl, dihydropyridinonyl, dihydrothiazinedioxide, dihydrodioxinyl, dihydropyranonyl, dihydrothiophenedioxide, piperidinonyl, or dihydrooxazinonyl;

$R_{10}$ is independently H, OH, CN, =O, —COOR$_{11}$, —C(O)R$_{11}$, —CH$_2$CN, $C_1$-$C_6$ alkyl, $C_1$-$C_6$ haloalkyl R$_{11}$S(O)$_2$—, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, $C_3$-$C_8$ heterocyclyl, aryl, or heteroaryl; and each $R_{11}$ is independently H, $C_1$-$C_6$ alkyl, $C_1$-$C_6$ haloalkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, $C_3$-$C_8$ heterocyclyl, aryl, or heteroary.

In some embodiments of any of the foregoing Formula Ib, $R_{10}$ is methyl, ethyl, isopropyl, or isobutyl.

In some embodiments of any of the foregoing Formula, $R_4$ and $R_5$ are H.

In some embodiments of any of the foregoing Formula, $R_4$ is H and $R_5$ is methyl.

In some embodiments of any of the foregoing Formula, $R_4$ is H and $R_5$ is (S)-methyl.

In some embodiments of any of the foregoing Formula, $R_4$ and $R_5$ are halogen.

In some embodiments of any of the foregoing Formula, $R_4$ is F and $R_5$ is methyl.

In some embodiments of any of the foregoing Formula $R_4$ and $R_5$ can combine to form a $C_3$-$C_6$ cycloalkyl.

In some embodiments of any of the foregoing Formula, $W_1$, $W_2$, and $W_3$ are independently CH or CF.

In some embodiments of any of the foregoing Formula, $W_1$, $W_2$, or $W_3$ is N.

In some embodiments of any of the foregoing Formula, $R_1$ can be halogen.

In some embodiments of any of the foregoing Formula, $R_1$ is chloro.

In some embodiments of any of the foregoing Formula, $R_2$ can be H or $C_1$-$C_6$ alkoxy.

In some embodiments of any of the foregoing Formula, $R_2$ is $C_1$-$C_6$ alkoxy substituted with heteroaryl or $C_3$-$C_8$ heterocyclyl.

In some embodiments of any of the foregoing Formula, illustrative compounds of the invention include:

3-{[(1,3-benzoxazol-4-yl)amino]methyl}-6-chloro-1,2-dihydroquinolin-2-one;
6-chloro-3-{[(3-methyl-2-oxo-2,3-dihydro-1,3-benzoxazol-5-yl)amino]methyl}-1,2-dihydroquinolin-2-one;
6-chloro-3-{[(2-oxo-2,3-dihydro-1,3-benzoxazol-5-yl)amino]methyl}-1,2-dihydroquinolin-2-one;
6-chloro-3-{[(2-oxo-2H-chromen-6-yl)amino]methyl}-1,2-dihydroquinolin-2-one;
6-chloro-3-{[(1-methyl-2-oxo-1,2,3,4-tetrahydroquinolin-6-yl)amino]methyl}-1,2-dihydroquinolin-2-one;
6-chloro-3-{[(isoquinolin-3-yl)amino]methyl}-1,2-dihydroquinolin-2-one;
4-{[(6-chloro-2-oxo-1,2-dihydroquinolin-3-yl)methyl]amino}naphthalene-1-carbonitrile;
6-chloro-3-{[(quinolin-8-yl)amino]methyl}-1,2-dihydroquinolin-2-one;
6-chloro-3-{[(2,3-dihydro-1-benzofuran-7-yl)amino]methyl}-1,2-dihydroquinolin-2-one;
7-{[(6-chloro-2-oxo-1,2-dihydroquinolin-3-yl)methyl]amino}-4-methyl-3,4-dihydro-2H-1,4-benzoxazin-3-one;
7-{[(6-chloro-2-oxo-1,2-dihydroquinolin-3-yl)methyl]amino}-3,4-dihydro-2H-1,4-benzoxazin-3-one;
3-({[2-(1H-1,3-benzodiazol-5-yl)-1H-1,3-benzodiazol-5-yl]amino}methyl)-6,7-dimethoxy-1,2-dihydroquinolin-2-one;
6-chloro-3-{[(2-oxo-2,3-dihydro-1H-indol-6-yl)amino]methyl}-1,2-dihydroquinolin-2-one;
6-chloro-3-{[(3-methyl-2-oxo-2,3-dihydro-1,3-benzoxazol-6-yl)amino]methyl}-1,2-dihydroquinolin-2-one;
6-chloro-3-{[(isoquinolin-8-yl)amino]methyl}-1,2-dihydroquinolin-2-one;
6-chloro-3-{[(3,4-dihydro-2H-1-benzopyran-8-yl)amino]methyl}-1,2-dihydroquinolin-2-one;
6-chloro-3-{[(6-methoxy-2-oxo-1,2,3,4-tetrahydroquinolin-7-yl)amino]methyl}-1,2-dihydroquinolin-2-one;
6-chloro-3-{[(2-oxo-1,2,3,4-tetrahydroquinolin-7-yl)amino]methyl}-1,2-dihydroquinolin-2-one;
6-chloro-3-{[(3-methyl-1H-indazol-6-yl)amino]methyl}-1,2-dihydroquinolin-2-one;
6-chloro-3-{[(2-oxo-1,2,3,4-tetrahydroquinolin-6-yl)amino]methyl}-1,2-dihydroquinolin-2-one;
6-methoxy-3-{[(2-methyl-1,3-benzothiazol-5-yl)amino]methyl}-1,2-dihydroquinolin-2-one;
6-chloro-3-{[(5-oxo-5,6,7,8-tetrahydronaphthalen-1-yl)amino]methyl}-1,2-dihydroquinolin-2-one;
6-chloro-3-[({[1,2,4]triazolo[4,3-b]pyridazin-6-yl}amino)methyl]-1,2-dihydroquinolin-2-one;
3-{[(1H-1,3-benzodiazol-5-yl)amino]methyl}-6-chloro-1,2-dihydroquinolin-2-one;
6-chloro-3-{[(1H-indazol-6-yl)amino]methyl}-1,2-dihydroquinolin-2-one;
3-{[(1,3-benzothiazol-6-yl)amino]methyl}-6-chloro-1,2-dihydroquinolin-2-one;
6-chloro-3-{[(quinolin-6-yl)amino]methyl}-1,2-dihydroquinolin-2-one;
6-chloro-3-({[2-(trifluoromethyl)-1H-1,3-benzodiazol-5-yl]amino}methyl)-1,2-dihydroquinolin-2-one;
3-{[(1,3-benzothiazol-5-yl)amino]methyl}-6-chloro-1,2-dihydroquinolin-2-one;
3-{[(2,3-dihydro-1,4-benzodioxin-6-yl)amino]methyl}-6-methoxy-1,2-dihydroquinolin-2-one;
3-{[(1H-indazol-6-yl)amino]methyl}-6,7-dimethyl-1,2-dihydroquinolin-2-one;
6-chloro-3-{[(2-methylquinolin-6-yl)amino]methyl}-1,2-dihydroquinolin-2-one;
6-chloro-3-{[(2,3-dihydro-1,4-benzodioxin-6-yl)amino]methyl}-1,2-dihydroquinolin-2-one;
3-{[(1H-indazol-6-yl)amino]methyl}-6-methoxy-1,2-dihydroquinolin-2-one;
6-methoxy-3-{[(2-methylquinolin-6-yl)amino]methyl}-1,2-dihydroquinolin-2-one;
3-{[(1,3-benzothiazol-6-yl)amino]methyl}-6-methoxy-1,2-dihydroquinolin-2-one;
6,7-dimethyl-3-{[(2-methylquinolin-6-yl)amino]methyl}-1,2-dihydroquinolin-2-one;
6-chloro-3-{[(1H-indazol-5-yl)amino]methyl}-1,2-dihydroquinolin-2-one;
6-methoxy-3-{[(quinolin-6-yl)amino]methyl}-1,2-dihydroquinolin-2-one;
3-{[(1,3-benzothiazol-6-yl)amino]methyl}-6,7-dimethyl-1,2-dihydroquinolin-2-one;
6-tert-butyl-3-{[(1H-indazol-5-yl)amino]methyl}-1,2-dihydroquinolin-2-one;
3-[(1S)-1-({1-acetyl-1H,2H,3H-pyrrolo[3,2-c]pyridin-4-yl}amino)ethyl]-6-chloro-1,2-dihydroquinolin-2-one;

6-chloro-3-[(1S)-1-({1-methanesulfonyl-1H,2H,3H-pyrrolo[3,2-c]pyridin-4-yl}amino)ethyl]-1,2-dihydroquinolin-2-one;

3-[(1S)-1-({1-acetyl-1H,2H,3H-pyrido[3,4-b][1,4]oxazin-5-yl}amino)ethyl]-6-chloro-1,2-dihydroquinolin-2-one;

6-chloro-3-[(1S)-1-({1H-pyrazolo[3,4-d]pyrimidin-6-yl}amino)ethyl]-1,2-dihydroquinolin-2-one;

6-chloro-3-[(1S)-1-{[1-(2-methylpropyl)-2-oxo-1H,2H,4H-pyrimido[4,5-d][1,3]oxazin-7-yl]amino}ethyl]-1,2-dihydroquinolin-2-one;

6-chloro-3-[(1S)-1-({1-methyl-2-oxo-1H,2H,4H-pyrimido[4,5-d][1,3]oxazin-7-yl}amino)ethyl]-1,2-dihydroquinolin-2-one;

6-chloro-3-[(1S)-1-({1-methyl-2-oxo-1H,2H,4H-pyrimido[4,5-d][1,3]oxazin-7-yl}amino)ethyl]-7-(pyridin-2-ylmethoxy)-1,2-dihydroquinolin-2-one;

6-chloro-3-[(1S)-1-({2-oxo-1H,2H,4H-pyrimido[4,5-d][1,3]oxazin-7-yl}amino)ethyl]-1,2-dihydroquinolin-2-one;

6-chloro-7-methoxy-3-[1-({1-methyl-2-oxo-1H,2H,4H-pyrimido[4,5-d][1,3]oxazin-7-yl}amino)ethyl]-1,2-dihydroquinolin-2-one;

6-chloro-7-methoxy-3-[(1S)-1-({1-methyl-2-oxo-1H,2H,4H-pyrimido[4,5-d][1,3]oxazin-7-yl}amino)ethyl]-1,2-dihydroquinolin-2-one;

6-chloro-7-methoxy-3-[(1R)-1-({1-methyl-2-oxo-1H,2H,4H-pyrimido[4,5-d][1,3]oxazin-7-yl}amino)ethyl]-1,2-dihydroquinolin-2-one;

6-chloro-7-fluoro-3-[(1R)-1-({1-methyl-2-oxo-1H,2H,4H-pyrimido[4,5-d][1,3]oxazin-7-yl}amino)ethyl]-1,2-dihydroquinolin-2-one;

6-chloro-3-[(1S)-1-({1-methyl-2-oxo-1H,2H,4H-pyrimido[4,5-d][1,3]oxazin-7-yl}amino)ethyl]-1,2-dihydro-1,8-naphthyridin-2-one;

6-chloro-3-[(1S)-1-{[3-(2-methylpropyl)-2-oxo-2H,3H-[1,3]oxazolo[4,5-d]pyrimidin-5-yl]amino}ethyl]-1,2-dihydroquinolin-2-one;

6-chloro-3-[(1S)-1-({2-oxo-2H,3H-[1,3]oxazolo[4,5-d]pyrimidin-5-yl}amino)ethyl]-1,2-dihydroquinolin-2-one;

6-chloro-3-[(1S)-1-({3-methyl-2-oxo-2H,3H-[1,3]oxazolo[4,5-d]pyrimidin-5-yl}amino)ethyl]-1,2-dihydroquinolin-2-one;

6-chloro-3-[(1S)-1-[(9-methyl-8-oxo-8,9-dihydro-7H-purin-2-yl)amino]ethyl]-1,2-dihydroquinolin-2-one;

6-chloro-3-[(1S)-1-[(8-oxo-8,9-dihydro-7H-purin-2-yl)amino]ethyl]-1,2-dihydroquinolin-2-one;

6-chloro-3-[(1S)-1-({6-oxo-5H,6H,7H-pyrrolo[2,3-d]pyrimidin-2-yl}amino)ethyl]-1,2-dihydroquinolin-2-one;

6-chloro-3-[(1S)-1-({7-methyl-6-oxo-5H,6H,7H-pyrrolo[2,3-d]pyrimidin-2-yl}amino)ethyl]-1,2-dihydroquinolin-2-one; and 6-chloro-3-[(1S)-1-({7-oxo-5H,6H,7H,8H-pyrido[2,3-d]pyrimidin-2-yl}amino)ethyl]-1,2-dihydroquinolin-2-one.

In another embodiment, illustrative compounds of the invention include:

6-chloro-3-[(1S)-1-({1-cyclopropyl-2-oxo-1H,2H,4H-pyrimido[4,5-d][1,3]oxazin-7-yl}amino)ethyl]-1,2-dihydroquinolin-2-one;

6-chloro-3-[(1S)-1-{[2-oxo-1-(propan-2-yl)-1H,2H,4H-pyrimido[4,5-d][1,3]oxazin-7-yl]amino}ethyl]-1,2-dihydroquinolin-2-one;

6-chloro-3-[(1S)-1-({1-methyl-2-oxo-1H,2H,4H-pyrido[4,3-d][1,3]oxazin-7-yl}amino)ethyl]-1,2-dihydroquinolin-2-one;

6-{[(1S)-1-(6-chloro-2-oxo-1,2-dihydroquinolin-3-yl)ethyl]amino}-1-methyl-1H,3H-2λ⁶,1,5,7-[1λ⁶,2]thiazolo[3,4-d]pyrimidine-2,2-dione;

6-{[(1S)-1-(6-chloro-2-oxo-1,2-dihydroquinolin-3-yl)ethyl]amino}-1-methyl-1H,3H-2λ⁶,1,5-[1λ⁶,2]thiazolo[4,3-c]pyridine-2,2-dione;

6-chloro-3-[(1S)-1-({3-methyl-2-oxo-2H,3H-[1,3]thiazolo[4,5-d]pyrimidin-5-yl}amino)ethyl]-1,2-dihydroquinolin-2-one;

6-chloro-3-[(1S)-1-({1-methyl-2-oxo-1H,2H-[1,3]thiazolo[5,4-c]pyridin-6-yl}amino)ethyl]-1,2-dihydroquinolin-2-one;

6-chloro-3-[(1S)-1-({1-oxo-1H,2H,3H-pyrrolo[3,4-c]pyridin-4-yl}amino)ethyl]-1,2-dihydroquinolin-2-one;

4-{[(1S)-1-(6-chloro-2-oxo-1,2-dihydroquinolin-3-yl)ethyl]amino}-2H,3H-1λ⁶,2,5-[1λ⁶,2]thiazolo[4,5-c]pyridine-1,1-dione;

5-{[(1S)-1-(6-chloro-2-oxo-1,2-dihydroquinolin-3-yl)ethyl]amino}-1,2,3,4-tetrahydro-2,6-naphthyridin-1-one;

6-chloro-3-[(1S)-1-({3-oxo-1H,2H,3H,4H-pyrimido[4,5-c]pyridazin-7-yl}amino)ethyl]-1,2-dihydroquinolin-2-one;

6-chloro-3-[(1S)-1-({6-oxo-6H-pyrano[3,2-d]pyrimidin-2-yl}amino)ethyl]-1,2-dihydroquinolin-2-one;

6-chloro-3-[(1S)-1-({1-methyl-2-oxo-1H,2H-pyrido[3,4-b]pyrazin-7-yl}amino)ethyl]-1,2-dihydroquinolin-2-one;

6-chloro-3-[(1S)-1-({3-oxo-1H,2H,3H,4H-pyrido[4,3-c]pyridazin-7-yl}amino)ethyl]-1,2-dihydroquinolin-2-one 2-{[(1S)-1-(6-chloro-2-oxo-1,2-dihydroquinolin-3-yl)ethyl]amino}-8-methyl-7,8-dihydropteridin-7-one;

6-chloro-3-[(1S)-1-({2-methyl-1-oxo-1H,2H,3H-pyrrolo[3,4-c]pyridin-4-yl}amino)ethyl]-1,2-dihydroquinolin-2-one;

6-chloro-3-[(1S)-1-{[6-(2-oxo-1,3-oxazolidin-3-yl)-[1,3]oxazolo[4,5-c]pyridin-4-yl]amino}ethyl]-1,2-dihydroquinolin-2-one;

4-{[(1S)-1-(6-chloro-2-oxo-1,2-dihydroquinolin-3-yl)ethyl]amino}-[1,3]oxazolo[4,5-c]pyridine-7-carbonitrile;

N-(4-{[(1S)-1-(6-chloro-2-oxo-1,2-dihydroquinolin-3-yl)ethyl]amino}-[1,3]oxazolo[4,5-c]pyridin-6-yl)acetamide;

3-[(1S)-1-[(1H-1,3-benzodiazol-4-yl)amino]ethyl]-6-chloro-1,2-dihydroquinolin-2-one;

6-chloro-3-[(1S)-1-({1H-imidazo[4,5-c]pyridin-4-yl}amino)ethyl]-1,2-dihydroquinolin-2-one;

4-{[(1S)-1-(6-chloro-2-oxo-1,2-dihydroquinolin-3-yl)ethyl]amino}-1H-imidazo[4,5-c]pyridine-7-carbonitrile;

6-chloro-3-[(1S)-1-({1-ethyl-1H-imidazo[4,5-c]pyridin-4-yl}amino)ethyl]-1,2-dihydroquinolin-2-one;

6-chloro-3-{[(2-oxo-1,2,3,4-tetrahydroquinolin-7-yl)amino]methyl}-1,2-dihydroquinolin-2-one;

6-chloro-3-[({[1,2,4]triazolo[4,3-b]pyridazin-6-yl}amino)methyl]-1,2-dihydroquinolin-2-one;

6-chloro-3-{[(3-methyl-1H-indazol-6-yl)amino]methyl}-1,2-dihydroquinolin-2-one;

6-chloro-3-{[(3-methyl-2-oxo-2,3-dihydro-1,3-benzoxazol-6-yl)amino]methyl}-1,2-dihydroquinolin-2-one;

6-chloro-3-{[(6-methoxy-2-oxo-1,2,3,4-tetrahydroquinolin-7-yl)amino]methyl}-1,2-dihydroquinolin-2-one;

6-chloro-3-{[(2-oxo-1,2,3,4-tetrahydroquinolin-6-yl)amino]methyl}-1,2-dihydroquinolin-2-one;

6-chloro-3-{[(1-methyl-2-oxo-1,2,3,4-tetrahydroquinolin-6-yl)amino]methyl}-1,2-dihydroquinolin-2-one;

6-chloro-3-{[(3-methyl-2-oxo-2,3-dihydro-1,3-benzoxazol-5-yl)amino]methyl}-1,2-dihydroquinolin-2-one;

6-chloro-3-{[(2-oxo-2H-chromen-6-yl)amino]methyl}-1,2-dihydroquinolin-2-one;

6-chloro-3-{[(2-oxo-2,3-dihydro-1,3-benzoxazol-5-yl)amino]methyl}-1,2-dihydroquinolin-2-one;

6-chloro-3-{[(2-oxo-2,3-dihydro-1H-indol-6-yl)amino]methyl}-1,2-dihydroquinolin-2-one;

7-{[(6-chloro-2-oxo-1,2-dihydroquinolin-3-yl)methyl]
amino}-3,4-dihydro-2H-1,4-benzoxazin-3-one;
7-{[(6-chloro-2-oxo-1,2-dihydroquinolin-3-yl)methyl]
amino}-4-methyl-3,4-dihydro-2H-1,4-benzoxazin-3-one;
6-chloro-3-[(1S)-1-{[1-(2-methylpropyl)-2-oxo-1H,2H,4H-pyrimido[4,5-d][1,3]oxazin-7-yl]amino}ethyl]-1,2-dihydroquinolin-2-one;
6-chloro-3-[(1S)-1-({3-methyl-2-oxo-2H,3H-[1,3]oxazolo[4,5-d]pyrimidin-5-yl}amino)ethyl]-1,2-dihydroquinolin-2-one;
6-chloro-3-[(1S)-1-{[7-oxo-8-(propan-2-yl)-5H,6H,7H,8H-[1,3]diazino[4,5-d]pyrimidin-2-yl]amino}ethyl]-1,2-dihydroquinolin-2-one;
6-chloro-3-[(1S)-1-({8-ethyl-7-oxo-5H,6H,7H,8H-[1,3]diazino[4,5-d]pyrimidin-2-yl}amino)ethyl]-1,2-dihydroquinolin-2-one;
6-chloro-3-[(1S)-1-{[2-oxo-1-(propan-2-yl)-1H,2H,4H-pyrido[4,3-d][1,3]oxazin-7-yl]amino}ethyl]-1,2-dihydroquinolin-2-one;
7-{[(1S)-1-(6-chloro-2-oxo-1,2-dihydroquinolin-3-yl)ethyl]
amino}-1-methyl-2,4-dihydro-1H-3,1-benzoxazin-2-one;
6-chloro-3-[(1S)-1-({1-ethyl-2-oxo-1H,2H,4H-pyrido[4,3-d][1,3]oxazin-7-yl}amino)ethyl]-1,2-dihydroquinolin-2-one;
7-{[(1S)-1-(6-chloro-2-oxo-1,2-dihydroquinolin-3-yl)ethyl]
amino}-2,4-dihydro-1H-3,1-benzoxazin-2-one;
3-[(1S)-1-({1-acetyl-1H,2H,3H-pyrrolo[3,2-b]pyridin-5-yl}amino)ethyl]-6-chloro-1,2-dihydroquinolin-2-one;
6-chloro-3-[(1S)-1-{[1-(2-methylpropyl)-2-oxo-1,2,3,4-tetrahydroquinolin-6-yl]amino}ethyl]-1,2-dihydroquinolin-2-one;
6-chloro-3-[(1S)-1-{[8-(2-methylpropyl)-7-oxo-5H,6H,7H,8H-[1,3]diazino[4,5-d]pyrimidin-2-yl]amino}ethyl]-1,2-dihydroquinolin-2-one;
7-{[(1S)-1-(6-chloro-2-oxo-1,2-dihydroquinolin-3-yl)ethyl]
amino}-1-(2-methylpropyl)-2,4-dihydro-1H-3,1-benzoxazin-2-one;
6-chloro-3-[(1S)-1-{[1-(2-methylpropyl)-2-oxo-1H,2H,4H-pyrido[4,3-d][1,3]oxazin-7-yl]amino}ethyl]-1,2-dihydroquinolin-2-one;
6-{[(1S)-1-(6-chloro-2-oxo-1,2-dihydroquinolin-3-yl)ethyl]
amino}-1-methyl-4-(2-methylpropyl)-1,2,3,4-tetrahydroquinoxalin-2-one;
6-chloro-3-[(1S)-1-{[4-methyl-1-(2-methylpropyl)-3-oxo-1H,2H,3H,4H-pyrido[3,4-b]pyrazin-7-yl]amino}ethyl]-1,2-dihydroquinolin-2-one;
6-chloro-3-[(1S)-1-{[(4R)-1-methyl-4-(2-methylpropyl)-2-oxo-1,2,3,4-tetrahydroquinolin-6-yl]amino}ethyl]-1,2-dihydroquinolin-2-one;
6-chloro-3-[(1S)-1-{[9-(2-methylpropyl)-9H-purin-2-yl]
amino}ethyl]-1,2-dihydroquinolin-2-one;
6-chloro-3-[(1S)-1-{[3-(2-methylpropyl)-2-oxo-2,3-dihydro-1,3-benzoxazol-6-yl]amino}ethyl]-1,2-dihydroquinolin-2-one;
6-chloro-3-[(1S)-1-{[3-(2-methylpropyl)-2-oxo-2,3-dihydro-1,3-benzoxazol-5-yl]amino}ethyl]-1,2-dihydroquinolin-2-one;
6-chloro-3-[(1S)-1-{[1-(2-methylpropyl)-2-oxo-1H,2H-[1,3]oxazolo[5,4-c]pyridin-6-yl]amino}ethyl]-1,2-dihydroquinolin-2-one;
6-chloro-3-[(1S)-1-{[2-oxo-3-(propan-2-yl)-2H,3H-[1,3]oxazolo[4,5-d]pyrimidin-5-yl]amino}ethyl]-1,2-dihydroquinolin-2-one;
6-chloro-3-[(1S)-1-{[9-(propan-2-yl)-9H-purin-2-yl]
amino}ethyl]-1,2-dihydroquinolin-2-one;
6-chloro-3-[(1S)-1-{[1-(propan-2-yl)-1H-pyrazolo[3,4-d]pyrimidin-6-yl]amino}ethyl]-1,2-dihydroquinolin-2-one;
6-chloro-3-[(1S)-1-{[2-oxo-1-(propan-2-yl)-1H,2H-[1,3]oxazolo[5,4-c]pyridin-6-yl]amino}ethyl]-1,2-dihydroquinolin-2-one;
6-chloro-3-[(1S)-1-{[6-methyl-7-oxo-8-(propan-2-yl)-5H,6H,7H,8H-[1,3]diazino[4,5-d]pyrimidin-2-yl]
amino}ethyl]-1,2-dihydroquinolin-2-one;
6-{[(1S)-1-(6-chloro-2-oxo-1,2-dihydroquinolin-3-yl)ethyl]
amino}-4-methyl-1-(2-methylpropyl)-1,2,3,4-tetrahydroquinoxalin-2-one;
6-chloro-3-[(1S)-1-[(2-oxo-2,3-dihydro-1,3-benzoxazol-6-yl)amino]ethyl]-1,2-dihydroquinolin-2-one;
6-chloro-3-[(1S)-1-({2-oxo-2H,3H-[1,3]oxazolo[4,5-c]pyridin-6-yl}amino)ethyl]-1,2-dihydroquinolin-2-one;
6-chloro-3-[(1S)-1-[(2-oxo-2,3-dihydro-1,3-benzoxazol-5-yl)amino]ethyl]-1,2-dihydroquinolin-2-one;
6-chloro-3-[(1S)-1-({2-oxo-1H,2H-[1,3]oxazolo[5,4-c]pyridin-6-yl}amino)ethyl]-1,2-dihydroquinolin-2-one;
6-chloro-3-[(1S)-1-({2-oxo-1H,2H-[1,3]oxazolo[5,4-d]pyrimidin-5-yl}amino)ethyl]-1,2-dihydroquinolin-2-one;
6-chloro-3-[(1S)-1-[(1-methyl-2-oxo-1,2,3,4-tetrahydroquinolin-6-yl)amino]ethyl]-1,2-dihydroquinolin-2-one;
6-{[(1S)-1-(6-chloro-2-oxo-1,2-dihydroquinolin-3-yl)ethyl]
amino}-1,4-dimethyl-1,2,3,4-tetrahydroquinoxalin-2-one
6-{[(1S)-1-(6-chloro-2-oxo-1,2-dihydroquinolin-3-yl)ethyl]
amino}-1,2,3,4-tetrahydroquinoxalin-2-one;
6-chloro-3-[(1S)-1-[(3-methyl-2-oxo-2,3-dihydro-1,3-benzoxazol-5-yl)amino]ethyl]-1,2-dihydroquinolin-2-one;
6-{[(1S)-1-(6-chloro-2-oxo-1,2-dihydroquinolin-3-yl)ethyl]
amino}-1-methyl-1,2,3,4-tetrahydro-1,7-naphthyridin-2-one;
6-chloro-3-[(1S)-1-({1-methyl-2-oxo-1H,2H-[1,3]oxazolo[5,4-c]pyridin-6-yl}amino)ethyl]-1,2-dihydroquinolin-2-one;
6-chloro-3-[(1S)-1-({1-cyclopropyl-2-oxo-1H,2H-[1,3]oxazolo[5,4-c]pyridin-6-yl}amino)ethyl]-1,2-dihydroquinolin-2-one;
6-chloro-3-[(1S)-1-({1-cyclobutyl-2-oxo-1H,2H-[1,3]oxazolo[5,4-c]pyridin-6-yl}amino)ethyl]-1,2-dihydroquinolin-2-one;
6-chloro-3-[(1S)-1-({1-ethyl-2-oxo-1H,2H-[1,3]oxazolo[5,4-c]pyridin-6-yl}amino)ethyl]-1,2-dihydroquinolin-2-one;
6-chloro-3-[(1S)-1-({1-cyclobutyl-2-oxo-1H,2H,4H-pyrido[4,3-d][1,3]oxazin-7-yl}amino)ethyl]-1,2-dihydroquinolin-2-one;
6-chloro-3-[(1S)-1-({1-cyclopropyl-2-oxo-1H,2H,4H-pyrido[4,3-d][1,3]oxazin-7-yl}amino)ethyl]-1,2-dihydroquinolin-2-one;
6-chloro-3-[(1S)-1-({5-methyl-6-oxo-5H,6H,7H,8H-pyrido[3,2-d]pyrimidin-2-yl}amino)ethyl]-1,2-dihydroquinolin-2-one;
6-{[(6-chloro-2-oxo-1,2-dihydroquinolin-3-yl)methyl]
amino}-2-(prop-2-yn-1-yl)-1H-1,3-benzodiazol-3-ium;
6-chloro-3-{[(2-ethynyl-1,3-benzoxazol-6-yl)amino]
methyl}-1,2-dihydroquinolin-2-one;
6-chloro-3-{[(2-ethynyl-1,3-benzoxazol-5-yl)amino]
methyl}-1,2-dihydroquinolin-2-one;
6-chloro-3-{[(1-methyl-2-oxo-2,3-dihydro-1H-indol-6-yl)
amino]methyl}-1,2-dihydroquinolin-2-one;
6-chloro-3-[({1-methyl-2-oxo-1H,2H,3H-pyrrolo[3,2-c]
pyridin-6-yl}amino)methyl]-1,2-dihydroquinolin-2-one;
6-chloro-3-{[(5-fluoro-2-oxo-2,3-dihydro-1H-indol-6-yl)
amino]methyl}-1,2-dihydroquinolin-2-one;
6-chloro-3-{[(4-methyl-2-oxo-2,3-dihydro-1H-indol-6-yl)
amino]methyl}-1,2-dihydroquinolin-2-one;
6-chloro-3-[({2-oxo-1H,2H,3H-pyrrolo[3,2-c]pyridin-6-yl}amino)methyl]-1,2-dihydroquinolin-2-one;

6-chloro-3-({[(1R)-1-oxo-2,3-dihydro-1λ⁴-benzothiophen-6-yl]amino}methyl)-1,2-dihydroquinolin-2-one;
6-chloro-3-[({5H,7H,8H-pyrano[4,3-d]pyrimidin-2-yl}amino)methyl]-1,2-dihydroquinolin-2-one;
6-chloro-3-{[(1-methyl-1,3-dihydro-2,1-benzoxazol-6-yl)amino]methyl}-1,2-dihydroquinolin-2-one;
3-[({3-tert-butyl-[1,2,4]triazolo[4,3-a]pyridin-6-yl}amino)methyl]-6-chloro-1,2-dihydroquinolin-2-one;
6-chloro-3-[(1R)-1-{[1-(2-methylpropyl)-2-oxo-1H,2H,4H-pyrimido[4,5-d][1,3]oxazin-7-yl]amino}ethyl]-1,2-dihydroquinolin-2-one;
(4R)-6-{[(1S)-1-(6-chloro-2-oxo-1,2-dihydroquinolin-3-yl)ethyl]amino}-1-methyl-4-(2-methylpropyl)-1,2,3,4-tetrahydro-1,5-naphthyridin-2-one
6-{[(6-chloro-2-oxo-1,2-dihydroquinolin-3-yl)methyl]amino}-2-(propan-2-yl)imidazo[1,2-a]pyridin-1-ium;
6-chloro-3-({[3-(propan-2-yl)-[1,2,4]triazolo[4,3-a]pyridin-6-yl]amino}methyl)-1,2-dihydroquinolin-2-one;
6-chloro-3-({[3-(propan-2-yl)-2H-indazol-5-yl]amino}methyl)-1,2-dihydroquinolin-2-one;
6-chloro-3-({[3-(propan-2-yl)-1,2-benzoxazol-6-yl]amino}methyl)-1,2-dihydroquinolin-2-one
6-chloro-3-[({3-propyl-[1,2,4]triazolo[4,3-a]pyridin-6-yl}amino)methyl]-1,2-dihydroquinolin-2-one;
6-chloro-3-{[(1-ethyl-2-oxo-2,3-dihydro-1H-indol-6-yl)amino]methyl}-1,2-dihydroquinolin-2-one;
6-chloro-3-({[(3 S)-3-ethyl-2-oxo-2,3-dihydro-1H-indol-6-yl]amino}methyl)-1,2-dihydroquinolin-2-one;
6-chloro-3-({[(3 S)-3-ethyl-2-oxo-2,3-dihydro-1H-indol-5-yl]amino}methyl)-1,2-dihydroquinolin-2-one;
6-chloro-3-[({3-ethyl-7-methyl-[1,2,4]triazolo[4,3-a]pyridin-6-yl}amino)methyl]-1,2-dihydroquinolin-2-one;
6-chloro-3-[({3-ethyl-[1,2,4]triazolo[4,3-a]pyridin-6-yl}amino)methyl]-1,2-dihydroquinolin-2-one;
6-chloro-3-[({3-ethyl-8-methyl-[1,2,4]triazolo[4,3-a]pyridin-6-yl}amino)methyl]-1,2-dihydroquinolin-2-one;
6-chloro-3-{[(3-ethyl-6-methyl-2H-indazol-5-yl)amino]methyl}-1,2-dihydroquinolin-2-one;
6-chloro-3-{[(3-ethyl-7-methyl-1,2-benzoxazol-5-yl)amino]methyl}-1,2-dihydroquinolin-2-one;
6-chloro-3-{[(2-methyl-2,3-dihydro-1,2-benzoxazol-6-yl)amino]methyl}-1,2-dihydroquinolin-2-one;
6-{[(6-chloro-2-oxo-1,2-dihydroquinolin-3-yl)methyl]amino}-1-methyl-2-oxo-1,2,3,4-tetrahydroquinoline-8-carboxamide;
6-{[(6-chloro-2-oxo-1,2-dihydroquinolin-3-yl)methyl]amino}-4-fluoro-2-methyl-1H-1,3-benzodiazol-3-ium;
6-{[(6-chloro-2-oxo-1,2-dihydroquinolin-3-yl)methyl]amino}-2,3-dimethylimidazo[1,2-a]pyridin-1-ium;
6-{[(6-chloro-2-oxo-1,2-dihydroquinolin-3-yl)methyl]amino}-2,5-dimethylimidazo[1,2-a]pyridin-1-ium;
6-chloro-3-({[6-(dimethylamino)-8,9-dimethyl-9H-purin-2-yl]amino}methyl)-1,2-dihydroquinolin-2-one;
6-chloro-3-{[(5-fluoro-2-methyl-1,3-benzoxazol-6-yl)amino]methyl}-1,2-dihydroquinolin-2-one;
6-chloro-3-{[(2,7-dimethyl-1,3-benzoxazol-5-yl)amino]methyl}-1,2-dihydroquinolin-2-one;
6-chloro-3-{[(7-fluoro-2-methyl-1,3-benzoxazol-5-yl)amino]methyl}-1,2-dihydroquinolin-2-one;
6-{[(6-chloro-2-oxo-1,2-dihydroquinolin-3-yl)methyl]amino}-3-methyl-1-benzofuran-5-carbonitrile;
6-chloro-3-({[2-oxo-4-(trifluoromethyl)-2H-chromen-7-yl]amino}methyl)-1,2-dihydroquinolin-2-one;
5-{[(6-chloro-2-oxo-1,2-dihydroquinolin-3-yl)methyl]amino}-2-cyano-1H-1,3-benzodiazol-1-ide;
6-{[(6-chloro-2-oxo-1,2-dihydroquinolin-3-yl)methyl]amino}-1H-indole-2-carbonitrile;
6-{[(6-chloro-2-oxo-1,2-dihydroquinolin-3-yl)methyl]amino}imidazo[1,2-a]pyridine-2-carbonitrile;
6-{[(6-chloro-2-oxo-1,2-dihydroquinolin-3-yl)methyl]amino}-1,3-benzothiazole-2-carbonitrile;
6-{[(6-chloro-2-oxo-1,2-dihydroquinolin-3-yl)methyl]amino}-2H-indazole-3-carbonitrile;
5-{[(6-chloro-2-oxo-1,2-dihydroquinolin-3-yl)methyl]amino}-2H-indazole-3-carbonitrile;
6-{[(6-chloro-2-oxo-1,2-dihydroquinolin-3-yl)methyl]amino}-2-methyl-1H-indole-3-carbonitrile;
6-{[(6-chloro-2-oxo-1,2-dihydroquinolin-3-yl)methyl]amino}-7-methyl-1H-indole-3-carbonitrile;
5-{[(6-chloro-2-oxo-1,2-dihydroquinolin-3-yl)methyl]amino}-7-methyl-1H-indole-3-carbonitrile;
6-{[(6-chloro-2-oxo-1,2-dihydroquinolin-3-yl)methyl]amino}-5-methyl-1H-indole-3-carbonitrile;
3-{[(6-chloro-2-oxo-1,2-dihydroquinolin-3-yl)methyl]amino}isoquinoline-8-carbonitrile;
6-chloro-3-{[(2-methyl-1-oxo-2,3-dihydro-1H-isoindol-5-yl)amino]methyl}-1,2-dihydroquinolin-2-one;
5-{[(6-chloro-2-oxo-1,2-dihydroquinolin-3-yl)methyl]amino}-2-oxo-2,3-dihydro-1,3-benzoxazole-7-carboxamide;
6-chloro-3-{[(7-methyl-2-oxo-2,3-dihydro-1,3-benzoxazol-5-yl)amino]methyl}-1,2-dihydroquinolin-2-one;
6-chloro-3-{[(7-fluoro-2-oxo-2,3-dihydro-1,3-benzoxazol-5-yl)amino]methyl}-1,2-dihydroquinolin-2-one;
6-chloro-3-{[(7-methoxy-2-oxo-2,3-dihydro-1,3-benzoxazol-5-yl)amino]methyl}-1,2-dihydroquinolin-2-one;
6-chloro-3-[({4-methyl-2-oxo-1H,2H-[1,3]oxazolo[5,4-c]pyridin-6-yl}amino)methyl]-1,2-dihydroquinolin-2-one;
6-chloro-3-{[(7-methyl-2-oxo-2,3-dihydro-1,3-benzoxazol-6-yl)amino]methyl}-1,2-dihydroquinolin-2-one;
6-chloro-3-[({2-oxo-2H,3H-[1,3]oxazolo[4,5-b]pyridin-5-yl}amino)methyl]-1,2-dihydroquinolin-2-one;
6-{[(6-chloro-2-oxo-1,2-dihydroquinolin-3-yl)methyl]amino}-2-oxo-2H-chromene-8-carboxamide;
6-chloro-3-{[(8-methyl-2-oxo-2H-chromen-6-yl)amino]methyl}-1,2-dihydroquinolin-2-one;
6-chloro-3-{[(8-methoxy-2-oxo-2H-chromen-6-yl)amino]methyl}-1,2-dihydroquinolin-2-one
6-chloro-3-[({8-methyl-2-oxo-2H-pyrano[2,3-c]pyridin-6-yl}amino)methyl]-1,2-dihydroquinolin-2-one
5-{[(6-chloro-2-oxo-1,2-dihydroquinolin-3-yl)methyl]amino}-3-methyl-2-oxo-2,3-dihydro-1,3-benzoxazole-7-carboxamide;
6-chloro-3-{[(7-methoxy-3-methyl-2-oxo-2,3-dihydro-1,3-benzoxazol-5-yl)amino]methyl}-1,2-dihydroquinolin-2-one;
6-chloro-3-[({1,4-dimethyl-2-oxo-1H,2H-[1,3]oxazolo[5,4-c]pyridin-6-yl}amino)methyl]-1,2-dihydroquinolin-2-one;
6-chloro-3-[({3-methyl-2-oxo-2H,3H-[1,3]oxazolo[4,5-b]pyridin-5-yl}amino)methyl]-1,2-dihydroquinolin-2-one;
6-chloro-3-({[2-(hydroxymethyl)-1,3-benzoxazol-6-yl]amino}methyl)-1,2-dihydroquinolin-2-one;
6-chloro-3-({[2-(hydroxymethyl)-1,3-benzoxazol-5-yl]amino}methyl)-1,2-dihydroquinolin-2-one;
6-chloro-3-({[3-(hydroxymethyl)-1,2-benzoxazol-5-yl]amino}methyl)-1,2-dihydroquinolin-2-one;
6-chloro-3-{[(3-hydroxy-1-benzothiophen-6-yl)amino]methyl}-1,2-dihydroquinolin-2-one;
3-{[(6-chloro-2-oxo-1,2-dihydroquinolin-3-yl)methyl]amino}isoquinoline-5-carboxylate;
4-chloro-5-{[(6-chloro-2-oxo-1,2-dihydroquinolin-3-yl)methyl]amino}-1H-1,3-benzodiazol-3-ium;

3-chloro-6-{[(6-chloro-2-oxo-1,2-dihydroquinolin-3-yl)
methyl]amino}imidazo[1,2-a]pyridin-1-ium;
6-{[(6-chloro-2-oxo-1,2-dihydroquinolin-3-yl)methyl]
amino}-7-formylimidazo[1,2-a]pyridin-1-ium;
6-chloro-3-[({2-oxo-1H,2H,3H-imidazo[4,5-b]pyridin-5-
yl}amino)methyl]-1,2-dihydroquinolin-2-one;
6-chloro-3-{[(6-methyl-2-oxo-2,3-dihydro-1,3-benzoxazol-
5-yl)amino]methyl}-1,2-dihydroquinolin-2-one;
6-chloro-3-{[(5-methyl-2-oxo-2,3-dihydro-1,3-benzoxazol-
6-yl)amino]methyl}-1,2-dihydroquinolin-2-one;
6-chloro-3-{[(5-fluoro-2-oxo-2,3-dihydro-1,3-benzoxazol-
6-yl)amino]methyl}-1,2-dihydroquinolin-2-one;
6-chloro-3-{[(2-oxo-2,3-dihydro-1,3-benzoxazol-6-yl)
amino]methyl}-1,2-dihydroquinolin-2-one;
6-chloro-3-{[(4-methyl-2-oxo-2,3-dihydro-1,3-benzoxazol-
6-yl)amino]methyl}-1,2-dihydroquinolin-2-one;
6-chloro-3-[({2-oxo-1H,2H-[1,3]oxazolo[5,4-c]pyridin-6-
yl}amino)methyl]-1,2-dihydroquinolin-2-one;
6-chloro-3-{[(2-oxo-2,3-dihydro-1,3-benzothiazol-6-yl)
amino]methyl}-1,2-dihydroquinolin-2-one;
6-chloro-3-{[(2-oxo-2,3-dihydro-1,3-benzothiazol-5-yl)
amino]methyl}-1,2-dihydroquinolin-2-one;
5-{[(6-chloro-2-oxo-1,2-dihydroquinolin-3-yl)methyl]
amino}-6-cyano-1H-1,3-benzodiazol-3-ium;
6-chloro-5-{[(6-chloro-2-oxo-1,2-dihydroquinolin-3-yl)
methyl]amino}-1H-1,3-benzodiazol-3-ium;
7-chloro-5-{[(6-chloro-2-oxo-1,2-dihydroquinolin-3-yl)
methyl]amino}-1H-1,3-benzodiazol-3-ium;
6-chloro-3-{[(7-methyl-1H-1,2,3-benzotriazol-5-yl)amino]
methyl}-1,2-dihydroquinolin-2-one;
6-chloro-3-{[(7-methoxy-1H-1,2,3-benzotriazol-5-yl)
amino]methyl}-1,2-dihydroquinolin-2-one;
6-chloro-3-{[(7-ethyl-2H-indazol-6-yl)amino]methyl}-1,2-
dihydroquinolin-2-one;
6-chloro-3-{[(7-ethyl-2H-indazol-5-yl)amino]methyl}-1,2-
dihydroquinolin-2-one;
6-chloro-3-{[(6-methyl-1H-indol-5-yl)amino]methyl}-1,2-
dihydroquinolin-2-one;
6-chloro-3-{[(6-methyl-1H-indazol-5-yl)amino]methyl}-1,
2-dihydroquinolin-2-one;
6-chloro-3-{[(6-methyl-1-benzofuran-5-yl)amino]methyl}-
1,2-dihydroquinolin-2-one;
6-chloro-3-{[(6-fluoro-2-methyl-1,3-benzoxazol-5-yl)
amino]methyl}-1,2-dihydroquinolin-2-one;
6-chloro-3-({[6-(dimethylamino)-1H-indol-5-yl]
amino}methyl)-1,2-dihydroquinolin-2-one;
6-chloro-3-{[(6-hydroxy-3-methyl-1,2-benzoxazol-5-yl)
amino]methyl}-1,2-dihydroquinolin-2-one;
6-chloro-3-{[(7-methyl-3-oxo-2,3-dihydro-1H-isoindol-5-
yl)amino]methyl}-1,2-dihydroquinolin-2-one;
6-chloro-3-{[(7-methyl-1H-indol-5-yl)amino]methyl}-1,2-
dihydroquinolin-2-one;
6-chloro-3-{[(7-methyl-1H-indazol-5-yl)amino]methyl}-1,
2-dihydroquinolin-2-one;
6-chloro-3-{[(7-methyl-1,2-benzoxazol-5-yl)amino]
methyl}-1,2-dihydroquinolin-2-one;
6-chloro-3-{[(3,7-dimethyl-1,2-benzoxazol-5-yl)amino]
methyl}-1,2-dihydroquinolin-2-one;
6-chloro-3-{[(7-cyclopropyl-1,2-benzoxazol-5-yl)amino]
methyl}-1,2-dihydroquinolin-2-one;
6-chloro-3-{[(7-fluoro-2-oxo-2,3-dihydro-1H-indol-5-yl)
amino]methyl}-1,2-dihydroquinolin-2-one;
6-chloro-3-{[(7-methoxy-3-methyl-1H-indol-5-yl)amino]
methyl}-1,2-dihydroquinolin-2-one;
6-chloro-3-{[(7-methoxy-1,2-benzoxazol-5-yl)amino]
methyl}-1,2-dihydroquinolin-2-one;
6-chloro-3-{[(2-methyl-3-oxo-2,3-dihydro-1H-isoindol-5-
yl)amino]methyl}-1,2-dihydroquinolin-2-one;
6-chloro-3-{[(3-oxo-1,3-dihydro-2-benzofuran-5-yl)amino]
methyl}-1,2-dihydroquinolin-2-one;
6-chloro-3-{[(1-methyl-2-oxo-2,3-dihydro-1H-indol-5-yl)
amino]methyl}-1,2-dihydroquinolin-2-one;
6-chloro-3-{[(2-oxo-2,3-dihydro-1H-indol-5-yl)amino]
methyl}-1,2-dihydroquinolin-2-one;
6-chloro-3-({[(3R)-3-methyl-2-oxo-2,3-dihydro-1H-indol-
5-yl]amino}methyl)-1,2-dihydroquinolin-2-one;
6-chloro-3-{[(2-oxo-2,3-dihydro-1-benzofuran-5-yl)amino]
methyl}-1,2-dihydroquinolin-2-one;
6-{[(6-chloro-2-oxo-1,2-dihydroquinolin-3-yl)methyl]
amino}-3,4-dihydro-2H-1,4-benzoxazin-3-one;
6-chloro-3-({[(1R)-1-methyl-3-oxo-2,3-dihydro-1H-isoin-
dol-5-yl]amino}methyl)-1,2-dihydroquinolin-2-one;
6-chloro-3-({[(1R)-1-methyl-3-oxo-1,3-dihydro-2-benzo-
furan-5-yl]amino}methyl)-1,2-dihydroquinolin-2-one;
6-chloro-3-({[(1S)-1-methyl-3-oxo-2,3-dihydro-1H-isoin-
dol-5-yl]amino}methyl)-1,2-dihydroquinolin-2-one;
6-chloro-3-{[(3-methyl-2-oxo-2,3-dihydro-1H-1,3-benzodi-
azol-5-yl)amino]methyl}-1,2-dihydroquinolin-2-one;
6-chloro-3-[({2,4,5,7-tetraazatricyclo[6.4.0.0$^{2,6}$]dodeca-1
(12),3,5,8,10-pentaen-11-yl}amino)methyl]-1,2-dihydro-
quinolin-2-one;
6-chloro-3-{[(3-methyl-1H-indol-5-yl)amino]methyl}-1,2-
dihydroquinolin-2-one;
6-chloro-3-{[(3-cyclopropyl-1H-indol-5-yl)amino]methyl}-
1,2-dihydroquinolin-2-one;
6-chloro-3-{[(3-methyl-1H-indazol-5-yl)amino]methyl}-1,
2-dihydroquinolin-2-one;
6-chloro-3-{[(3-cyclopropyl-1H-indazol-5-yl)amino]
methyl}-1,2-dihydroquinolin-2-one;
6-chloro-3-{[(1-methyl-1H-1,2,3-benzotriazol-6-yl)amino]
methyl}-1,2-dihydroquinolin-2-one;
6-chloro-3-{[(1-hydroxy-1H-1,2,3-benzotriazol-6-yl)
amino]methyl}-1,2-dihydroquinolin-2-one;
6-chloro-3-{[(3-oxo-2,3-dihydro-1,2-benzoxazol-5-yl)
amino]methyl}-1,2-dihydroquinolin-2-one;
6-chloro-3-{[(3-methyl-1-benzofuran-5-yl)amino]methyl}-
1,2-dihydroquinolin-2-one;
3-{[(1,2-benzoxazol-5-yl)amino]methyl}-6-chloro-1,2-di-
hydroquinolin-2-one;
6-chloro-3-{[(3-methoxy-1,2-benzoxazol-5-yl)amino]
methyl}-1,2-dihydroquinolin-2-one;
6-chloro-3-{[(3-hydroxy-1-benzothiophen-5-yl)amino]
methyl}-1,2-dihydroquinolin-2-one;
6-chloro-3-{[(3-methyl-1,2-benzothiazol-5-yl)amino]
methyl}-1,2-dihydroquinolin-2-one;
6-chloro-3-[({3-oxo-2H,3H,4H-pyrido[3,2-b][1,4]oxazin-7-
yl}amino)methyl]-1,2-dihydroquinolin-2-one;
6-{[(6-chloro-2-oxo-1,2-dihydroquinolin-3-yl)methyl]
amino}-1H,2H,3H,4H-pyrido[2,3-d]pyrimidine-2,4-di-
one;
6-chloro-3-[({1-methyl-1H-pyrazolo[3,4-b]pyridin-5-
yl}amino)methyl]-1,2-dihydroquinolin-2-one;
6-chloro-3-({[5-(pyrrolidin-1-yl)-[1,2,4]triazolo[1,5-c]py-
rimidin-7-yl]amino}methyl)-1,2-dihydroquinolin-2-one;
6-chloro-3-[({1-methyl-2-oxo-1H,2H,3H-pyrrolo[2,3-c]
pyridin-5-yl}amino)methyl]-1,2-dihydroquinolin-2-one;
6-chloro-3-[({2-oxo-1H,2H,3H-pyrrolo[2,3-c]pyridin-5-
yl}amino)methyl]-1,2-dihydroquinolin-2-one;
6-chloro-3-[({2-oxo-2H-pyrano[2,3-c]pyridin-6-yl}amino)
methyl]-1,2-dihydroquinolin-2-one;
6-chloro-3-[({1-methyl-2-oxo-1H,2H-[1,3]oxazolo[5,4-c]
pyridin-6-yl}amino)methyl]-1,2-dihydroquinolin-2-one;

6-chloro-3-{[(1,5-dimethyl-2-oxo-1,2,3,4-tetrahydroquinolin-6-yl)amino]methyl}-1,2-dihydroquinolin-2-one;
6-chloro-3-{[(4-methyl-2-oxo-2,3-dihydro-1H-indol-5-yl)amino]methyl}-1,2-dihydroquinolin-2-one;
6-chloro-3-{[(4-methyl-1H-indol-5-yl)amino]methyl}-1,2-dihydroquinolin-2-one;
6-chloro-3-{[(4-methyl-1H-indazol-5-yl)amino]methyl}-1,2-dihydroquinolin-2-one;
6-chloro-3-{[(5-methyl-2-oxo-2H-chromen-6-yl)amino]methyl}-1,2-dihydroquinolin-2-one;
6-chloro-3-{[(4-methyl-1-benzofuran-5-yl)amino]methyl}-1,2-dihydroquinolin-2-one;
6-chloro-3-[({4-chloro-1-methyl-1H-pyrazolo[3,4-b]pyridin-5-yl}amino)methyl]-1,2-dihydroquinolin-2-one;
6-chloro-3-{[(4-fluoro-3-oxo-2,3-dihydro-1H-isoindol-5-yl)amino]methyl}-1,2-dihydroquinolin-2-one;
6-chloro-3-{[(4-methoxy-7-methyl-1H-indol-5-yl)amino]methyl}-1,2-dihydroquinolin-2-one;
6-chloro-3-{[(4-methoxy-1-benzofuran-5-yl)amino]methyl}-1,2-dihydroquinolin-2-one;
6-chloro-3-{[(2-methyl-1-oxo-1,2,3,4-tetrahydroisoquinolin-6-yl)amino]methyl}-1,2-dihydroquinolin-2-one;
6-chloro-3-{[(1-oxo-1,2,3,4-tetrahydroisoquinolin-6-yl)amino]methyl}-1,2-dihydroquinolin-2-one;
6-chloro-3-({[(3R)-3-methyl-2-oxo-2,3-dihydro-1H-indol-6-yl]amino}methyl)-1,2-dihydroquinolin-2-one;
6-chloro-3-{[(3-methyl-1H-indol-6-yl)amino]methyl}-1,2-dihydroquinolin-2-one;
6-chloro-3-{[(3-cyclopropyl-1H-indol-6-yl)amino]methyl}-1,2-dihydroquinolin-2-one;
6-chloro-3-{[(3-methoxy-1H-indazol-6-yl)amino]methyl}-1,2-dihydroquinolin-2-one;
6-chloro-3-{[(3-methyl-2H-indazol-6-yl)amino]methyl}-1,2-dihydroquinolin-2-one;
6-chloro-3-[({3-cyclobutyl-[1,2,4]triazolo[4,3-a]pyridin-6-yl}amino)methyl]-1,2-dihydroquinolin-2-one;
7-{[(6-chloro-2-oxo-1,2-dihydroquinolin-3-yl)methyl]amino}-4-methyl-1,2-dihydro-1,8-naphthyridin-2-one;
6-chloro-3-{[(1,8-dimethyl-2-oxo-1,2,3,4-tetrahydroquinolin-6-yl)amino]methyl}-1,2-dihydroquinolin-2-one;
6-chloro-3-{[(3,4-dimethyl-1,2-benzoxazol-6-yl)amino]methyl}-1,2-dihydroquinolin-2-one;
6-chloro-3-{[(8-methoxy-1-methyl-2-oxo-1,2,3,4-tetrahydroquinolin-6-yl)amino]methyl}-1,2-dihydroquinolin-2-one;
6-chloro-3-{[(1,5-naphthyridin-2-yl)amino]methyl}-1,2-dihydroquinolin-2-one;
6-chloro-3-{[(quinoxalin-2-yl)amino]methyl}-1,2-dihydroquinolin-2-one;
6-chloro-3-({[6-(thiophen-2-yl)-9H-purin-2-yl]amino}methyl)-1,2-dihydroquinolin-2-one;
6-chloro-3-({[6-(furan-3-yl)-9H-purin-2-yl]amino}methyl)-1,2-dihydroquinolin-2-one;
6-chloro-3-({[6-(morpholin-4-yl)-9H-purin-2-yl]amino}methyl)-1,2-dihydroquinolin-2-one;
6-chloro-3-[({4,7-dimethyl-5-oxo-5H,6H-pyrimido[4,5-d][1,3]diazin-2-yl}amino)methyl]-1,2-dihydroquinolin-2-one;
6-chloro-3-{[(7-hydroxy-1,2,4-benzotriazin-3-yl)amino]methyl}-1,2-dihydroquinolin-2-one;
6-chloro-3-{[(7-methyl-1H-indol-6-yl)amino]methyl}-1,2-dihydroquinolin-2-one;
6-chloro-3-{[(5-methyl-1H-indol-6-yl)amino]methyl}-1,2-dihydroquinolin-2-one;
6-chloro-3-{[(5-ethyl-1H-indol-6-yl)amino]methyl}-1,2-dihydroquinolin-2-one;
6-chloro-3-{[(4-methyl-1H-indol-6-yl)amino]methyl}-1,2-dihydroquinolin-2-one;
6-chloro-3-{[(4-ethyl-1H-indol-5-yl)amino]methyl}-1,2-dihydroquinolin-2-one;
6-chloro-3-[({5-fluoro-1H-pyrrolo[2,3-b]pyridin-6-yl}amino)methyl]-1,2-dihydroquinolin-2-one;
3-[({4-bromo-1H-pyrrolo[2,3-b]pyridin-6-yl}amino)methyl]-6-chloro-1,2-dihydroquinolin-2-one;
6-chloro-3-[({4-chloro-7H-pyrrolo[2,3-d]pyrimidin-2-yl}amino)methyl]-1,2-dihydroquinolin-2-one;
3-{[(6-chloro-2-oxo-1,2-dihydroquinolin-3-yl)methyl]amino}quinoxaline-2-carbonitrile;
6-chloro-3-{[(5-methyl-1-benzofuran-6-yl)amino]methyl}-1,2-dihydroquinolin-2-one;
6-chloro-3-{[(4-methoxy-1-benzofuran-6-yl)amino]methyl}-1,2-dihydroquinolin-2-one;
6-chloro-3-{[(1,6-naphthyridin-2-yl)amino]methyl}-1,2-dihydroquinolin-2-one;
6-chloro-3-{[(1-methyl-1H-indazol-6-yl)amino]methyl}-1,2-dihydroquinolin-2-one;
6-chloro-3-[({1-methyl-1H-pyrazolo[3,4-d]pyrimidin-6-yl}amino)methyl]-1,2-dihydroquinolin-2-one;
6-chloro-3-[({4-chloro-1-methyl-1H-pyrazolo[3,4-d]pyrimidin-6-yl}amino)methyl]-1,2-dihydroquinolin-2-one;
5-{[(6-chloro-2-oxo-1,2-dihydroquinolin-3-yl)methyl]amino}-1,2-benzoxazole-7-carbonitrile;
6-chloro-3-{[(7-methyl-1,2-benzoxazol-6-yl)amino]methyl}-1,2-dihydroquinolin-2-one;
3-{[(1,2-benzoxazol-6-yl)amino]methyl}-6-chloro-1,2-dihydroquinolin-2-one;
6-chloro-3-{[(4-methyl-1,2-benzoxazol-6-yl)amino]methyl}-1,2-dihydroquinolin-2-one;
6-chloro-3-[({3H-imidazo[4,5-b]pyridin-5-yl}amino)methyl]-1,2-dihydroquinolin-2-one;
6-chloro-3-{[(6-chloro-9H-purin-2-yl)amino]methyl}-1,2-dihydroquinolin-2-one;
6-chloro-3-({[6-(dimethylamino)-9H-purin-2-yl]amino}methyl)-1,2-dihydroquinolin-2-one;
6-chloro-3-[({imidazo[1,2-a]pyrazin-6-yl}amino)methyl]-1,2-dihydroquinolin-2-one;
6-chloro-3-[({imidazo[1,2-b]pyridazin-6-yl}amino)methyl]-1,2-dihydroquinolin-2-one;
6-chloro-3-[({3-methyl-3H-imidazo[4,5-b]pyridin-6-yl}amino)methyl]-1,2-dihydroquinolin-2-one;
6-chloro-3-({[5-(methylsulfanyl)-[1,2,4]triazolo[1,5-c]pyrimidin-7-yl]amino}methyl)-1,2-dihydroquinolin-2-one;
3-{[(6-chloro-2-oxo-1,2-dihydroquinolin-3-yl)methyl]amino}-[1,2,4]triazolo[3,2-c][1,2,4]triazin-4-olate;
6-chloro-3-[({[1,2,4]triazolo[1,5-a]pyridin-6-yl}amino)methyl]-1,2-dihydroquinolin-2-one;
6-chloro-3-{[(4,7-dimethyl-1,3-benzoxazol-5-yl)amino]methyl}-1,2-dihydroquinolin-2-one;
6-chloro-3-{[(5-hydroxy-1,3-benzoxazol-6-yl)amino]methyl}-1,2-dihydroquinolin-2-one;
3-{[(1,3-benzoxazol-6-yl)amino]methyl}-6-chloro-1,2-dihydroquinolin-2-one;
3-{[(1,3-benzoxazol-5-yl)amino]methyl}-6-chloro-1,2-dihydroquinolin-2-one;
6-chloro-3-{[(4-methyl-1,3-benzoxazol-5-yl)amino]methyl}-1,2-dihydroquinolin-2-one;
6-chloro-3-{[(6-methyl-1,3-benzothiazol-5-yl)amino]methyl}-1,2-dihydroquinolin-2-one;
6-chloro-3-{[(4-hydroxy-1,3-benzothiazol-6-yl)amino]methyl}-1,2-dihydroquinolin-2-one;
6-chloro-3-{[(4-methyl-1,3-benzothiazol-5-yl)amino]methyl}-1,2-dihydroquinolin-2-one;

6-chloro-3-({[3-(trifluoromethyl)-[1,2,4]triazolo[4,3-b]pyridazin-6-yl]amino}methyl)-1,2-dihydroquinolin-2-one;
6-chloro-3-[({3,5-dimethyl-[1,2,4]triazolo[4,3-a]pyridin-6-yl}amino)methyl]-1,2-dihydroquinolin-2-one;
6-chloro-3-[({3-methyl-[1,2,4]triazolo[4,3-a]pyridin-6-yl}amino)methyl]-1,2-dihydroquinolin-2-one;
3-[({8-bromo-3-methyl-[1,2,4]triazolo[4,3-a]pyridin-6-yl}amino)methyl]-6-chloro-1,2-dihydroquinolin-2-one;
6-chloro-3-[({3-methyl-[1,2,4]triazolo[4,3-a]pyridin-7-yl}amino)methyl]-1,2-dihydroquinolin-2-one;
6-chloro-3-({[3-(hydroxymethyl)-[1,2,4]triazolo[4,3-a]pyridin-6-yl]amino}methyl)-1,2-dihydroquinolin-2-one;
6-chloro-3-[({5-methyl-[1,2,4]triazolo[4,3-a]pyridin-6-yl}amino)methyl]-1,2-dihydroquinolin-2-one;
6-chloro-3-[({7-methyl-[1,2,4]triazolo[4,3-a]pyridin-6-yl}amino)methyl]-1,2-dihydroquinolin-2-one;
6-chloro-3-[({8-methyl-[1,2,4]triazolo[4,3-a]pyridin-6-yl}amino)methyl]-1,2-dihydroquinolin-2-one;
6-chloro-3-[({7-methyl-[1,2,3,4]tetrazolo[1,5-a]pyridin-6-yl}amino)methyl]-1,2-dihydroquinolin-2-one;
6-chloro-3-[({[1,2,3,4]tetrazolo[1,5-a]pyridin-6-yl}amino)methyl]-1,2-dihydroquinolin-2-one;
3-{[(1,2,3-benzoxadiazol-6-yl)amino]methyl}-6-chloro-1,2-dihydroquinolin-2-one;
6-chloro-3-{[(5-fluoro-1,2,3-benzothiadiazol-6-yl)amino]methyl}-1,2-dihydroquinolin-2-one;
3-{[(2,1,3-benzoxadiazol-5-yl)amino]methyl}-6-chloro-1,2-dihydroquinolin-2-one;
6-chloro-3-{[(6-methyl-2,1,3-benzothiadiazol-5-yl)amino]methyl}-1,2-dihydroquinolin-2-one;
6-chloro-3-{[(7-methyl-2,1,3-benzothiadiazol-5-yl)amino]methyl}-1,2-dihydroquinolin-2-one;
6-chloro-3-{[(4-methyl-2,1,3-benzothiadiazol-5-yl)amino]methyl}-1,2-dihydroquinolin-2-one;
6-chloro-3-{[(4-hydroxy-2,1,3-benzothiadiazol-5-yl)amino]methyl}-1,2-dihydroquinolin-2-one;
6-chloro-3-({[7-(propan-2-yl)-1,3-benzoxazol-5-yl]amino}methyl)-1,2-dihydroquinolin-2-one;
6-chloro-3-{[(7-methyl-1,3-benzothiazol-5-yl)amino]methyl}-1,2-dihydroquinolin-2-one;
6-chloro-3-{[(7-methyl-1,3-benzothiazol-6-yl)amino]methyl}-1,2-dihydroquinolin-2-one;
6-chloro-3-[(1S)-1-({2-oxo-1H,2H,3H-pyrrolo[3,2-c]pyridin-6-yl}amino)ethyl]-1,2-dihydroquinolin-2-one;
6-chloro-3-[(1S)-1-({2-oxo-1H,2H,3H-pyrrolo[2,3-c]pyridin-5-yl}amino)ethyl]-1,2-dihydroquinolin-2-one;
6-chloro-3-[(1S)-1-({2-oxo-1H,2H,3H-pyrrolo[2,3-b]pyridin-6-yl}amino)ethyl]-1,2-dihydroquinolin-2-one;
6-chloro-3-[(1S)-1-({2-oxo-1H,2H,3H-pyrrolo[3,2-b]pyridin-5-yl}amino)ethyl]-1,2-dihydroquinolin-2-one;
6-chloro-3-[(1S)-1-({2-oxo-2H,3H-[1,3]oxazolo[4,5-b]pyridin-5-yl}amino)ethyl]-1,2-dihydroquinolin-2-one;
6-chloro-3-[(1S)-1-({2-oxo-1H,2H-[1,3]oxazolo[5,4-b]pyridin-5-yl}amino)ethyl]-1,2-dihydroquinolin-2-one;
2-{[(1S)-1-(6-chloro-2-oxo-1,2-dihydroquinolin-3-yl)ethyl]amino}-5H,7H-6$\lambda^6$,1,3-[1$\lambda^6$]thieno[3,4-d]pyrimidine-6,6-dione;
6-{[(1S)-1-(6-chloro-2-oxo-1,2-dihydroquinolin-3-yl)ethyl]amino}-1H,3H-2$\lambda^6$,1,5,7-[1$\lambda^6$,2]thiazolo[3,4-d]pyrimidine-2,2-dione;
2-{[(1S)-1-(6-chloro-2-oxo-1,2-dihydroquinolin-3-yl)ethyl]amino}-5H,6H,8H-7$\lambda^6$,1,3-[1$\lambda^6$]thiopyrano[3,4-d]pyrimidine-7,7-dione;
2-{[(1S)-1-(6-chloro-2-oxo-1,2-dihydroquinolin-3-yl)ethyl]amino}-5H,7H,8H-6$\lambda^6$,1,3-[1$\lambda^6$]thiopyrano[4,3-d]pyrimidine-6,6-dione;
6-chloro-3-[(1S)-1-({6-methyl-7-oxo-5H,6H,7H,8H,9H-pyrimido[4,5-e][1,4]diazepin-2-yl}amino)ethyl]-1,2-dihydroquinolin-2-one;
6-chloro-3-[(1S)-1-({5H,6H,7H,8H,9H-pyrimido[4,5-b]azepin-2-yl}amino)ethyl]-1,2-dihydroquinolin-2-one;
6-chloro-3-[(1S)-1-({2-oxo-1H,2H,4H-pyrimido[4,5-d][1,3]oxazin-7-yl}amino)ethyl]-1,2-dihydroquinolin-2-one;
6-chloro-3-[(1S)-1-({1-methyl-2-oxo-1H,2H,4H-pyrimido[4,5-d][1,3]oxazin-7-yl}amino)ethyl]-1,2-dihydroquinolin-2-one;
6-chloro-3-[({3-methyl-2-oxo-2H,3H-[1,3]oxazolo[4,5-d]pyrimidin-5-yl}amino)methyl]-1,2-dihydroquinolin-2-one;
6-chloro-3-[({1-methyl-2-oxo-1H,2H,4H-pyrimido[4,5-d][1,3]oxazin-7-yl}amino)methyl]-1,2-dihydroquinolin-2-one;
(S)-7-((1-(6-chloro-2-oxo-1,2-dihydroquinolin-3-yl)ethyl)amino)-6H-pyrido[1,2-a]pyrazin-6-one;
(S)-6-((1-(6-chloro-2-oxo-1,2-dihydroquinolin-3-yl)ethyl)amino)-5H-[1,2,4]oxadiazolo[4,5-a]pyridin-5-one;
(S)-6-((1-(6-chloro-2-oxo-1,2-dihydroquinolin-3-yl)ethyl)amino)-2,3-dihydro-5H-oxazolo[3,2-a]pyridin-5-one;
(S)-6-chloro-3-(1-((5-oxo-1,5-dihydro-[1,2,4]triazolo[4,3-a]pyridin-6-yl)amino)ethyl)quinolin-2(1H)-one; and
(S)-6-chloro-3-(1-((5-oxo-1,5-dihydro-[1,2,4]triazolo[1,5-a]pyridin-6-yl)amino)ethyl)quinolin-2(1H)-one.

In another embodiment of the invention, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

In another embodiment of the invention, the compounds of Formula I contain isotopes of atoms forming the structure of Formula I. Isotopes herein means, each of two or more forms of the same element (e.g., H and D; $^{12}$C and $^{13}$C) that contain equal numbers of protons but different numbers of neutrons in their nuclei, and hence differ in relative atomic mass.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention formula (I) can be synthesized by following the steps outlined in Schemes 1-2, which comprise different sequences of assembling intermediates II, III, IV, V, and VI. Starting materials are either commercially available or made by known procedures in the reported literature or as illustrated.

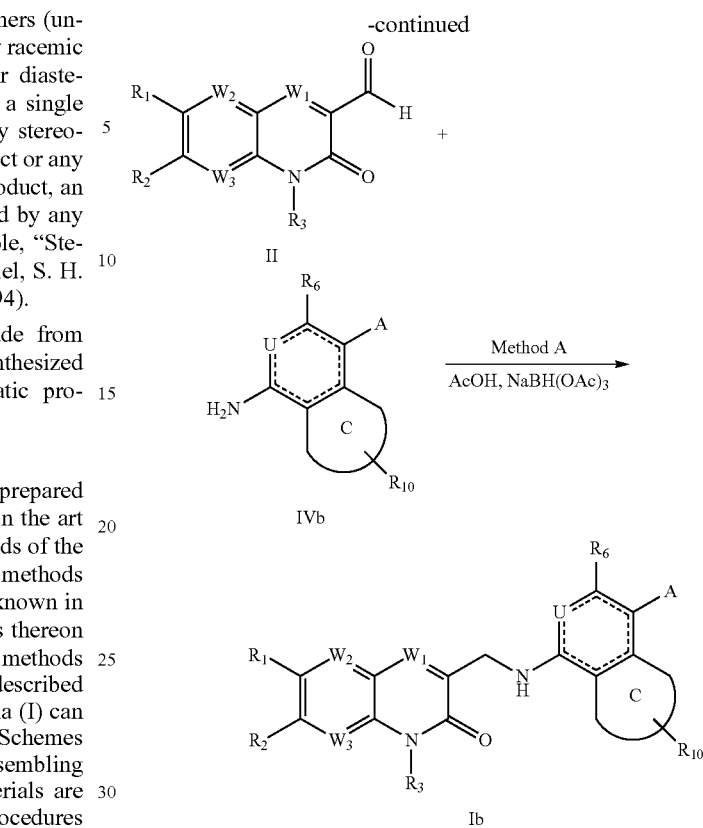

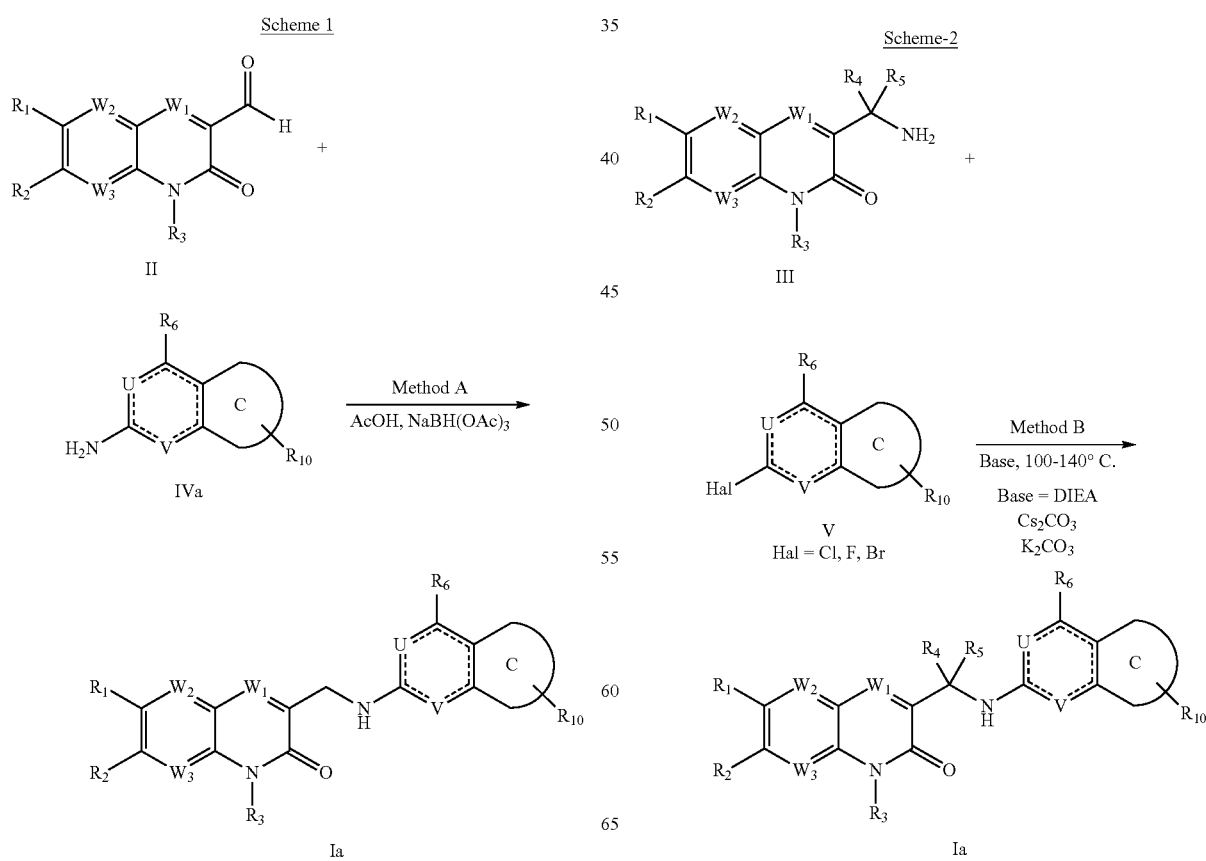

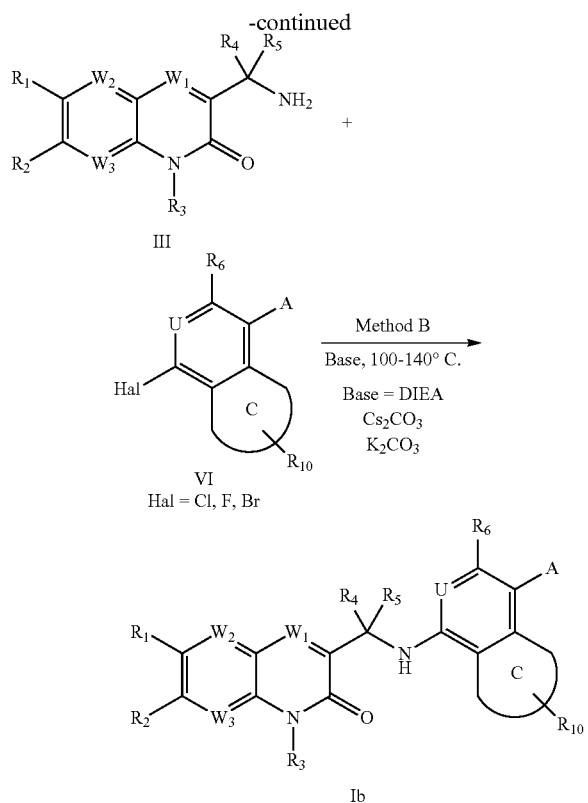

wherein A, B, U, V, $R_1$-$R_{10}$, $W_1$, $W_2$, and $W_3$ are defined in Formula (I)

The general ways of preparing target molecules Ia and Ib by using intermediates II, III, IV, V, and VI are outlined in Scheme 1-2. Reductive amination of aldehyde (II) with amine (IVa & IVb) is performed under standard procedure (AcOH and NaBH(OAc)$_3$) to prepare the compound of formula I (Ia & Ib). Displacement of aryl halides (V & VI) with intermediates amine (III) under standard nucleophilic substitution conditions using base such as N,N-diisopropylethylamine, and/or potassium carbonate, cesium carbonate in solvent DMSO or DMF gives the compounds of Formula I (Ia & Ib). A mixture of enantiomers, diastereomers, cis/trans isomers resulted from the process can be separated into their single components by chiral salt technique, chromatography using normal phase, reverse phase or chiral column, depending on the nature of the separation.

It should be understood that in the description and formulae shown above, the various groups A, B, $W_1$, $W_2$, $W_3$, U, V, Z, and $R_1$-$R_{10}$ and other variables are as defined above, except where otherwise indicated. Furthermore, for synthetic purposes, the compounds of schemes 1 and 2 are mere representative with elected radicals to illustrate the general synthetic methodology of the compound of formula I as defined herein.

Methods of Using the Disclosed Compounds

Another aspect of the invention relates to a method of treating a disease or disorder associated with mutant isocitrate dehydrogenase. The method involves administering to a patient in need of a treatment for diseases or disorders associated with mutant isocitrate dehydrogenase an effective amount of the compositions and compounds of Formula (I).

Another aspect of the invention is directed to a method of inhibiting mutant isocitrate dehydrogenase. The method involves administering to a patient in need thereof an effective amount of a compound of Formula (I).

Examples of a mutant IDH protein having a neomorphic activity are mutant IDH1 and mutant IDH2. A neomorphic activity associated with mutant IDH1 and mutant IDH2 is the ability to produce 2-hydroxyglutarate (2-HG neomorphic activity), specifically R-2-HG (R-2-HG neomorphic activity). Mutations in IDH 1 associated with 2-HG neomorphic activity, specifically R-2-HG neomorphic activity, include mutations at residues 97, 100, and 132, e.g. G97D, R100Q, R132H, R132C, R132S, R132G, R132L, and R132V. Mutations in IDH2 associated with 2-HG neoactivity, specifically R-2-HG neomorphic activity, include mutations at residues 140 and 172, e.g. R140Q, R140G, R172K, R172M, R172S, R172G, and R172W.

Another aspect of the invention relates to method of reducing 2-hydroxyglutarate. The method comprises administering to a patient in need thereof an effective amount of a compound of Formula (I).

One therapeutic use of the compounds or compositions of the present invention which inhibit mt-IDH is to provide treatment to patients or subjects suffering from cell proliferative diseases and cancers including, without limitation, glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), myeloproliferative disease (MPD), and other solid tumors.

Targeted treatments for these cancers and cell proliferative diseases are not currently available to patients suffering from these conditions. Therefore, there is a need for new therapeutic agents selective to these conditions.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Table 6 provides activity of illustrative compounds of Formula I in IDH1-R132H, IDH1-R132C, IDH1-MS-HTC116-R132H, and IDH1-MS-HTC116-R132C assays.
Analytical Methods, Materials, and Instrumentation Unless otherwise noted, reagents and solvents were used as received from commercial suppliers. Proton nuclear magnetic resonance (NMR) spectra were obtained on either Bruker or Varian spectrometers at 300 MHz. Spectra are given in ppm (δ) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)). High performance liquid chromatograph (HPLC) analyses were obtained using a XBridge Phenyl or C18 column (5 μm, 50×4.6 mm, 150×4.6 mm or 250×4.6 mm) with UV detection (Waters 996 PDA) at 254 nm or 223 nm using a standard solvent gradient program (Method 1-4).
LCMS Method 1 (ESI, 4 Min Method):
Instruments:

| | |
|---|---|
| HPLC: Waters HT2790 Alliance | MS: Waters ZQ Single Quad Mass Spectrometer |
| UV: Waters 996 PDA | 95% water/5% methanol with 0.1% Formic Acid |

Conditions:

| | |
|---|---|
| Mobile phase A | |
| Mobile phase B (B) | 95% methanol/5% water with 0.1% Formic Acid |

-continued

| Column | XBridge Phenyl or C18, 5 μm 4.6 × 50 mm |
|---|---|
| Column temperature | Ambient |
| LC gradient | Linear 5-95% B in 2.5 min, hold 95% B to 3.5 min |
| LC Flow rate | 3 mL/min |
| UV wavelength | 220 nm and 254 nm |
| Ionization Mode | Electrospray Ionization; positive/negative |

LCMS Method 2 (ESI, 10 Min Method):

Instruments:

| HPLC: Waters HT2790 Alliance | MS: Waters ZQ Single Quad Mass Spectrometer |
|---|---|
| UV: Waters 996 PDA | |

Conditions:

| Mobile phase A (A) | 95% water/5% methanol with 0.1% Formic Acid |
|---|---|
| Mobile phase B (B) | 95% methanol/5% water with 0.1% Formic Acid |
| Column | XBridge C18, 5 μm 4.6 × 150 mm |
| Column temperature | Ambient |
| LC gradient | Linear 5-95% B in 5.5 min, hold 95% B to 7.5 min |
| LC Flow rate | 1.2 mL/min |
| UV wavelength | 220 nm and 254 nm |
| Ionization Mode | Electrospray Ionization; positive/negative |

LCMS Method 3: (APCI, 20 Min)

Instruments and Conditions:

HPLC-Agilent 1100 series.

Column: Agela Technologies Durashell C18, 3 μm, 4.6×50 mm,).

Mobile Phase A: ACN+0.1% TFA.

Mobile Phase B: Water+0.1% TFA.

| Gradient: | Time (min) | % B |
|---|---|---|
| | 00 | 95 |
| | 15 | 05 |
| | 18 | 05 |
| | 20 | 95 |

Flow Rate: 1 mL/min.

ColumnTemperature: Ambient.

Detector: 254 nm.

LCMS Method 4 (ESI, 2.5 Min Method):

Instruments and Conditions:

| HPLC: Waters Acquity Binary Solvent Manager | MS: Waters ZQ Mass Detector |
|---|---|
| UV: Waters Acquity PDA | |
| Mobile phase A (A) | 95% water/5% acetonitrile with 0.1% formic acid in 10 mM ammonium formate |
| Mobile phase B (B) | 95% acetonitrile/5% water with 0.09% formic acid |
| Column | Waters Acquity UPLC BEH C18, 1.7 μm, 2.1 × 50 mm |
| Column temperature | 35° C. |
| LC gradient | 5-100% B in 2.0 min, hold 100% B to 2.2 min |
| LC Flow rate | 0.6 mL/min |
| UV wavelength | 220 nm and 254 nm |
| Ionization Mode | Electrospray Ionization; positive/negative |

ABBREVIATIONS USED IN THE FOLLOWING EXAMPLES AND ELSEWHERE HEREIN ARE $Ac_2O$ acetic anhydride ACN Acetonitrile BOP ammonium 4-(3-(pyridin-3-ylmethyl)ureido)benzenesulfinate $CDCl_3$ deuterated chloroform CDI 1,1'-Carbonyldiimidazole $Cs_2CO_3$ cesium carbonate $CuSO_4$ copper sulfate δ chemical shift DCM dichloromethane or methylene chloride DCE 1,2-dichloroethane DEAD diethyl azodicarboxylate DIAD diisopropyl azodicarboxylate DIEA N,N-diisopropylethylamine DMA N,N-dimethylacetamide DME dimethoxyethane DMF N,N-dimethylformamide DMP Dess-Martin Periodinane DMSO dimethylsulfoxide DMSO-$d_6$ deuterated dimethylsulfoxide dppf 1,1'-Bis(diphenylphosphino)ferrocene EDCI N-(3-dimethylaminopropyl)-N'-ethylcarbodiimide hydrochloride EDTA ethylenediaminetetraacetic acid ee enantiomeric excess EtOAc ethyl acetate EtOH ethanol $^1$H NMR proton nuclear magnetic resonance HOAc acetic acid HATU 2-(3H-[1,2,3]triazolo[4,5-b]pyridin-3-yl)-1,1,3,3-tetramethylisouronium hexafluorophosphate HCl hydrochloric acid HOBT 1H-benzo[d][1,2,3]triazol-1-ol hydrate HPLC high pressure liquid chromatography Hz hertz IPA isopropyl alcohol KOAc potassium acetate $K_2CO_3$ potassium carbonate LAH lithium aluminum hydride LCMS liquid chromatography/mass spectrometry (M+1) mass+1 m-CPBA m-chloroperbenzoic acid

MeOH methanol

MeMgBr methyl magnesium bromide

MS mass spectrometry $NaBH_4$ sodium borohydride $Na_2SO_4$ sodium sulfate

Pd(dppf)$Cl_2$ [1,1'-Bis(diphenylphosphino)ferrocene]dichloropalladium(II)

Palladium tetrakis Tetrakis(triphenylphosphine)palladium (0)

Rt retention time

TBDMS-Cl Tert-butyl dimethylsilyl chloride

TEA triethylamine

THF tetrahydrofuran

TLC thin layer chromatography

Xantphos 4,5-Bis(diphenylphosphino)-9,9-dimethylxanthene

Example 1

Intermediate III-1: (S)-3-(1-aminoethyl)-6-chloroquinolin-2(1H)-one hydrochloride

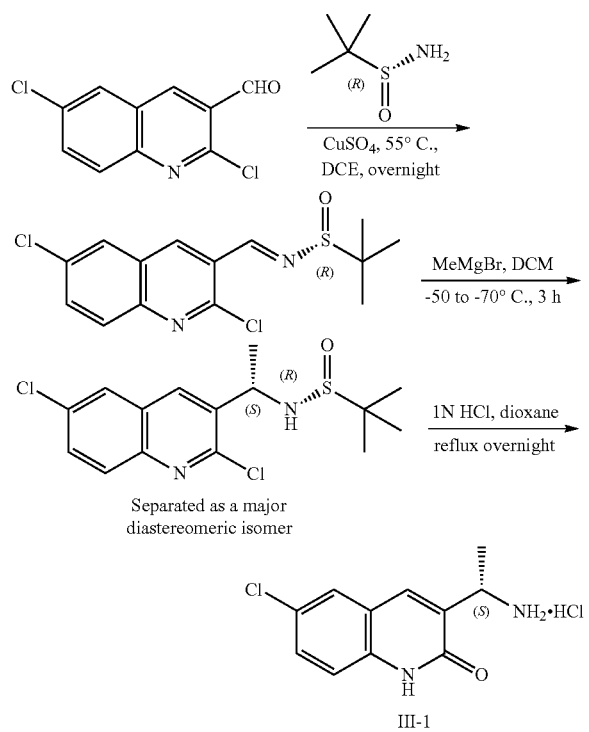

Step-1: (R,E)-N-((2,6-dichloroquinolin-3-yl)methylene)-2-methylpropane-2-sulfinamide

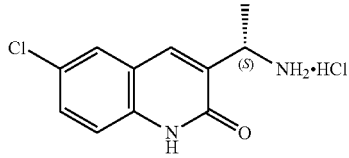

To a mixture of 2,6-dichloroquinoline-3-carbaldehyde (15.0 g, 66.37 mmol) and (R)-2-methylpropane-2-sulfinamide (8.85 g, 73.14 mmol) in 1,2-dichloroethane (150 mL) was added $CuSO_4$ (16.0 g, 100.25 mmol). The resulting mixture was heated to 55° C. and stirred at 55° C. overnight. After TLC and MS showed complete disappearance of starting materials, the mixture was cooled to room temperature and filtered through a pad of Celite®. The pad of celite was then rinsed with $CH_2Cl_2$. The filtrate was evaporated to dryness in vacuo and purified by $SiO_2$ column chromatography (0 to 25% hexanes/EtOAc) to afford the title compound, (R,E)-N-((2,6-dichloroquinolin-3-yl)methylene)-2-methylpropane-2-sulfinamide, as a yellow solid (17.7 g, 81% yield).

Step-2: (R)—N—((S)-1-(2,6-dichloroquinolin-3-yl)ethyl)-2-methylpropane-2-sulfinamide

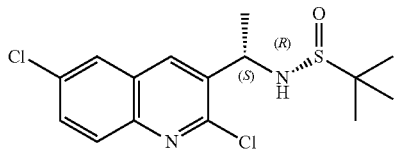

To a solution of (R,E)-N-((2,6-dichloroquinolin-3-yl)methylene)-2-methylpropane-2-sulfinamide (8.85 g, 26.88 mmol) in anhydrous $CH_2Cl_2$ (200 mL) at −60 OC was added drop wise MeMgBr (3M solution in diethyl ether, 13.5 mL, 40.54 mmol). The resulting reaction mixture was stirred at about −60 to −50° C. for 3 hours and then stirred at −20° C. overnight under an atmosphere of $N_2$. After TLC and MS showed complete disappearance of starting materials, saturated $NH_4Cl$ (163 mL) was added at −20° C. and the resulting mixture was stirred for 10 minutes. The aqueous phase was extracted with $CH_2Cl_2$ (100 mL×3), dried over anhydrous $Na_2SO_4$, filtered, and evaporated. The residue was purified by column chromatography on an ISCO® chromatography system ($SiO_2$: Gold column; gradient; hexanes to 100% EtOAc) to provide the title compound, (R)—N—((S)-1-(2,6-dichloroquinolin-3-yl)ethyl)-2-methylpropane-2-sulfinamide, as a yellow solid (5.8 g, 63% yield).

Step-3: (S)-3-(1-aminoethyl)-6-chloroquinolin-2(1H)-one hydrochloride (III-1)

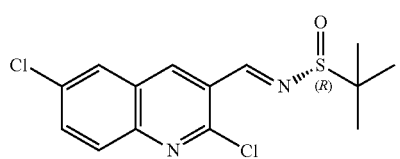

A mixture of (R)—N—((S)-1-(2,6-dichloroquinolin-3-yl)ethyl)-2-methylpropane-2-sulfinamide (6.6 g, 19.13 mmol) in 1,4-dioxane (41 mL) and 1N HCl (41 mL) was heated at reflux overnight. The solvents were evaporated in vacuo and the resulting residue was dissolved in hot water and lyophilized. The crude product was triturated with diethyl ether to afford the title compound III-1 as a yellow solid (quant. yield, ee: 98.4%). $^1$H NMR (300 MHz, DMSO-$d_6$): δ ppm 12.4 (br s, 1H), 8.32 (br s, 2H), 8.07 (s, 1H), 7.85 (d, J=2.2 Hz, 1H), 7.63 (dd, $J_1$=8.8 Hz, $J_2$=2.5 Hz, 1H), 7.40 (d, J=8.8 Hz, 1H), 4.40-4.45 (m, 1H), 1.53 (d, J=8.5 Hz, 3H). LCMS (Method 3): Rt 3.42 min, m/z 223.1 [M+H]$^+$.

Example 2

Intermediate III-2: (R)-3-(1-aminoethy)-6-chloroquinolin-2(1H)-one hydrochloride

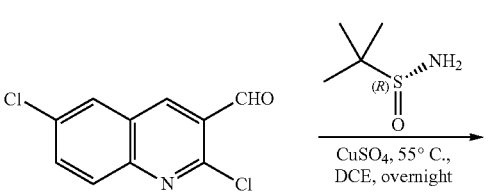

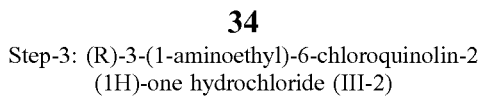

Step-3: (R)-3-(1-aminoethyl)-6-chloroquinolin-2(1H)-one hydrochloride (III-2)

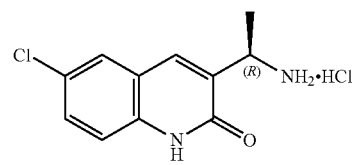

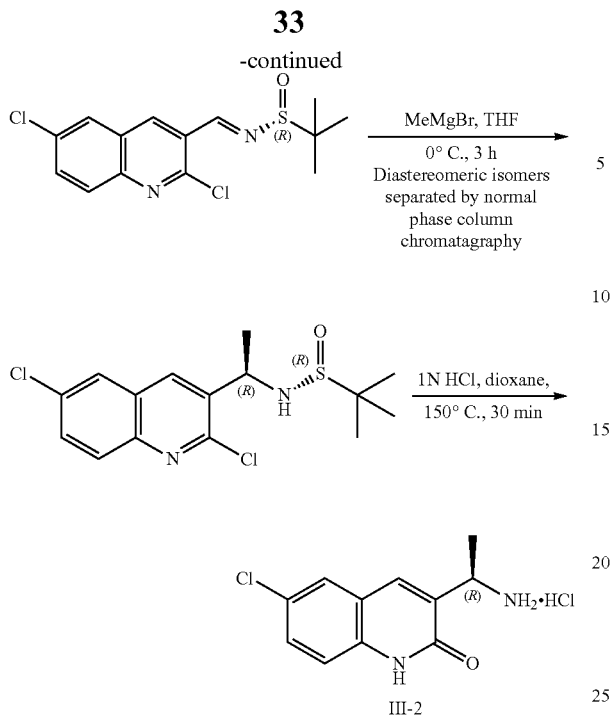

Step-1: (R)—N—((2,6-dichloroquinolin-3-yl)methylene)-2-methylpropane-2-sulfinamide To a mixture of 2,6-dichloroquinoline-3-carbaldehyde (500 mg, 2.21 mmol) and (R)-2-methylpropane-2-sulfinamide (295 g, 2.43 mmol) in 1,2-dichloroethane (15 mL) was added CuSO₄ (530 mg, 3.31 mmol). The resulting mixture was heated to 55° C. and stirred at 55° C. for 18 hours. Once TLC and MS showed complete disappearance of starting materials, the reaction mixture was cooled to room temperature and filtered through a pad of Celite®. The pad of celite was then rinsed with CH₂Cl₂. The filtrate was evaporated to dryness in vacuo and purified by column chromatography on an ISCO® chromatography system (SiO₂; hexanes to 60% EtOAc/hexanes) to afford the title compound, (R)—N-((2,6-dichloroquinolin-3-yl)methylene)-2-methylpropane-2-sulfinamide, as a yellow solid (510 mg, 70% yield).

Step-2: (R)—N—((R)-1-(2,6-dichloroquinolin-3-yl)ethyl)-2-methylpropane-2-sulfinamide To a solution of (R)—N-((2,6-dichloroquinolin-3-yl)methylene)-2-methylpropane-2-sulfinamide (505 mg, 1.534 mmol) in anhydrous THF (8 mL) at 0° C. was added drop wise MeMgBr (3M solution in diethyl ether, 0.56 mL, 1.687 mmol). The mixture was stirred at 0° C. for 3 hours under an atmosphere of N₂. After TLC and MS showed complete disappearance of starting materials, saturated NH₄Cl (5 mL) was added at 0° C. and the resulting mixture was stirred for 10 minutes. The aqueous phase was extracted with EtOAc (10 mL×3), dried over anhydrous Na₂SO₄, filtered, and evaporated. The residue was purified by column chromatography on an ISCO® chromatography system (SiO₂: hexanes to 80% EtOAc/hexanes) to afford the title compound as the R,R isomer as a pale yellow solid (200 mg, 38%) and the R,S isomer as a pale yellow solid (93 mg, 18% yield).

A mixture of (R)—N—((R)-1-(2,6-dichloroquinolin-3-yl)ethyl)-2-methylpropane-2-sulfinamide (190 mg, 0.55 mmol) in 1,4-dioxane (2 mL) and 1N HCl (1.1 mL, 1.1 mmol) was heated to 150° C. for 30 minutes in a microwave reactor. The solvents were evaporated and the residue was dissolved in hot water and lyophilized to afford the title compound III-2 as a yellow solid (148 mg, quantitative yield). ¹H NMR (300 MHz, DMSO-d₆): δ ppm 12.35 (br s, 1H), 8.28 (br s, 2H), 8.05 (s, 1H), 7.86 (d, J=2.2 Hz, 1H), 7.63 (dd, J₁=8.8 Hz, J₂=2.5 Hz, 1H), 7.40 (d, J=8.8 Hz, 1H), 4.40-4.45 (m, 1H), 1.53 (d, J=8.5 Hz, 3H). LCMS (Method 3): Rt 3.40 min, m/z 223.1 [M+H]⁺.

Example 3

An Alternative Approach to Intermediate III-1

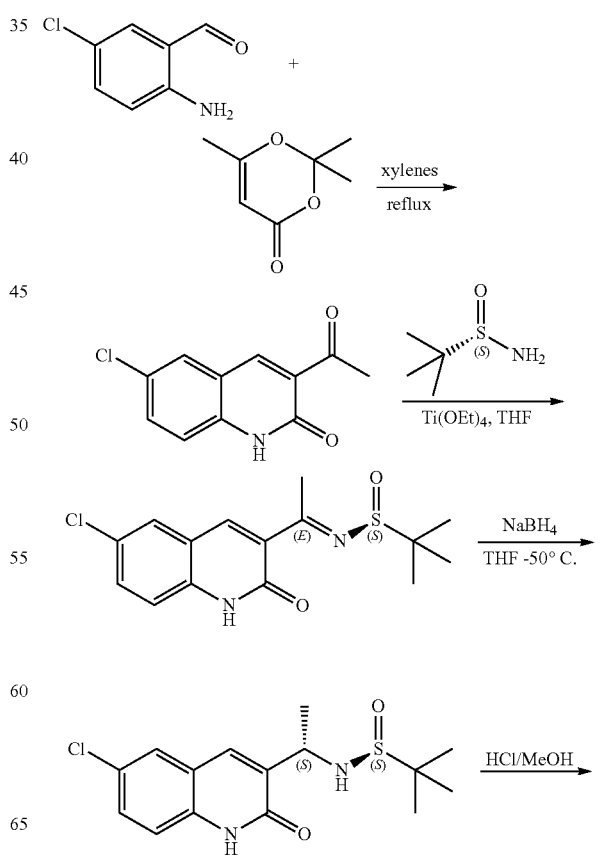

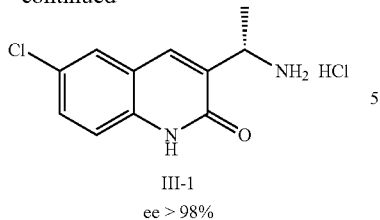

III-1
ee > 98%

Step-1: 3-acetyl-6-chloroquinolin-2(1H)-one

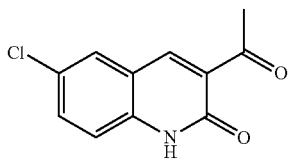

A mixture of 2-amino-5-chlorobenzaldehyde (0.5 g, 3.21 mmol) and 2,2,6-trimethyl-4H-1,3-dioxin-4-one (0.594 g, 4.18 mmol) in xylenes (10 mL) under an atmosphere of nitrogen was heated to reflux for 3 hours and then cooled to room temperature. The reaction mixture was filtered and washed with xylenes twice to afford the title compound, 3-acetyl-6-chloroquinolin-2(1H)-one (330 mg, 46.3%). $^1$H NMR (300 MHz, DMSO-d$_6$): δ ppm 12.22 (br, 1H), 8.41 (s, 2 H), 8.00 (s, 1H), 7.63 (d, J=8.8 Hz, 1H), 7.32 (dd, J$_1$=8.8 Hz, J$_2$=2.5 Hz, 1H), 2.58 (s, 3H). LCMS (Method 1): m/z 222.94 [M+H]$^+$.

Step-2: ((S)—N—((S)-1-(6-chloro-2-oxo-1,2-dihydroquinolin-3-yl)ethyl)-2-methyl propane-2-sulfinamide

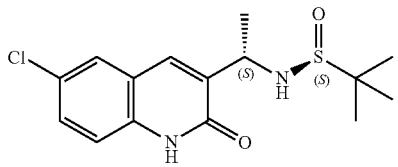

A mixture of tetraethoxytitanium (144 mg, 0.632 mmol), (S)-2-methylpropane-2-sulfinamide (38.3 mg, 0.316 mmol), and 3-acetyl-6-chloroquinolin-2(1H)-one (70 mg, 0.316 mmol) in THF (20 mL) was heated to 80° C. overnight and then cooled to room temperature. To this mixture was added NaBH$_4$ (59.7 mg, 1.579 mmol) at −50° C. The mixture was then slowly warmed up to room temperature overnight. MeOH (2 mL) was added to quench excess NaBH$_4$ and was followed by the addition of water. The resulting mixture was filtered to remove solids and the aqueous phase was extracted with EtOAc twice, dried over Na$_2$SO$_4$ and concentrated. The residue was purified on a Biotage® chromatography system using a 25 g SiO$_2$ column with gradient elution (20% to 100% EtOAc/Hexanes, then 0-5% MeOH/DCM) to afford (S)—N—((S)-1-(2,6-dichloroquinolin-3-yl)ethyl)-2-methylpropane-2-sulfinamide (39 mg, 38% yield). $^1$H NMR (300 MHz, DMSO-d$_6$): δ ppm 12.05 (br, 1H), 7.95 (s, 1H), 7.84 (s, 1H), 7.38 (d, J=8.8 Hz, 1H), 5.76 (d, J=8.06 Hz, 1H), 5.37 (m, 1H), 4.55 (m, 1H), 1.44 (d, J=6.82 Hz, 3H), 1.18 (s, 9H). LCMS (Method 1): Rt 2.22 min; m/z 327.96 [M+H]$^+$.

Step-3: (S)-3-(1-aminoethyl)-6-chloroquinolin-2(1H)-one hydrochloride (III-1)

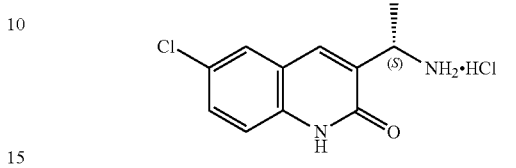

To a solution of ((S)—N—((S)-1-(6-chloro-2-oxo-1,2-dihydroquinolin-3-yl)ethyl)-2-methyl propane-2-sulfinamide (150 mg, 0.459 mmol) in MeOH (5 mL) was added HCl (2 mL, 8.0 mmol, 4M in 1,4-dioxane). The mixture was stirred at room temperature overnight. To this mixture was added 6 mL of ethyl ether and the resulting precipitate was collected by filtration, washed with ethyl ether (2 x), and then dried to afford (S)-3-(1-aminoethyl)-6-chloroquinolin-2(1H)-one hydrochloride (50 mg, 42% yield). $^1$H NMR (300 MHz, DMSO-d$_6$): δ ppm 12.4 (br s, 1H), 8.32 (br s, 2H), 8.07 (s, 1H), 7.85 (d, J=2.2 Hz, 1H), 7.63 (dd, J$_1$=8.8 Hz, J$_2$=2.5 Hz, 1H), 7.40 (d, J=8.8 Hz, 1H), 4.40-4.45 (m, 1H), 1.53 (d, J=8.5 Hz, 3H). LCMS (Method 1): Rt 1.22 min, m/z 223.1 [M+H]$^+$.

Example 4

Alternate Approach (R)-3-(1-aminoethyl)-6-chloroquinolin-2(1H)-one hydrochloride (III-2)

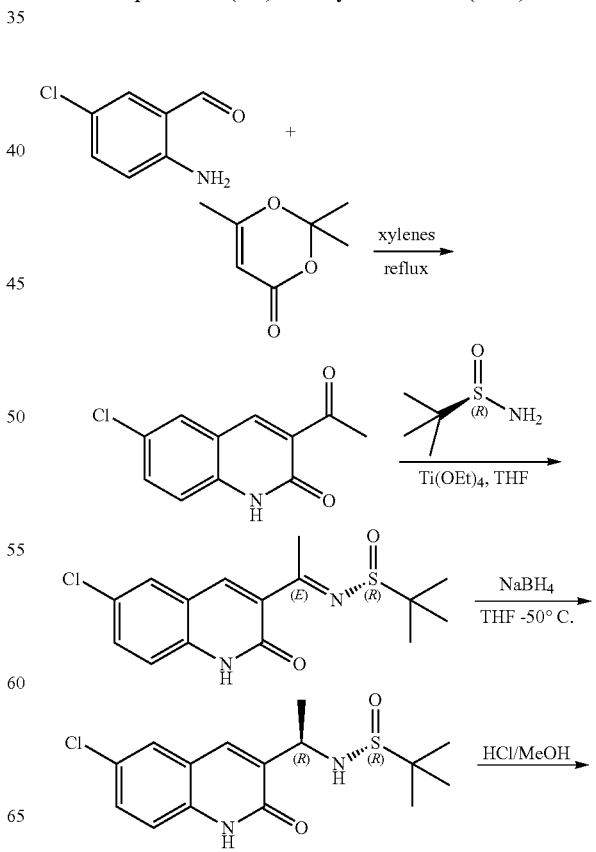

-continued

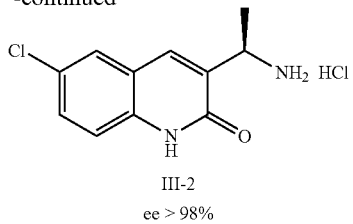

III-2
ee > 98%

Step-1: ((R)—N—((R)-1-(6-chloro-2-oxo-1,2-dihydroquinolin-3-yl)ethyl)-2-methyl propane-2-sulfinamide

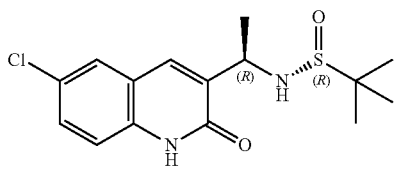

A mixture of tetraethoxytitanium (412 mg, 1.805 mmol) (R)-2-methylpropane-2-sulfinamide (131 mg, 1.083 mmol) and 3-acetyl-6-chloroquinolin-2(1H)-one (160 mg, 0.722 mmol) in THF (20 mL) was heated to 80° C. overnight, then cooled to room temperature. To this mixture was added NaBH$_4$ (137 mg, 3.61 mmol) −50° C. The mixture was then slowly warmed up to room temperature overnight. MeOH (2 mL) was added to quench excess NaBH$_4$ and was followed by the addition of water. The resulting mixture was filtered to remove solids and the aqueous phase was extracted with EtOAc twice, dried over Na$_2$SO$_4$ and concentrated. The residue was purified on a Biotage® chromatography system using a 25 g SiO$_2$ column with gradient elution (20 to 100% EtOAc/Hexanes, then 0-5% MeOH/DCM) to afford ((R)—N—((R)-1-(6-chloro-2-oxo-1,2-dihydroquinolin-3-yl) ethyl)-2-methyl propane-2-sulfinamide (157 mg, 66% yield). $^1$H NMR (300 MHz, CDCl$_3$): δ ppm 11.31 (br, 1H), 7.35 (s, 1H), 7.07-7.22 (m, 2H), 5.86 (d, J=9.3 Hz, 1H), 5.37 (m, 1H), 4.55 (m, 1H), 1.56 (d, J=6.94 Hz, 3H), 1.32 (s, 9H).
LCMS (Method 1): Rt 2.20 min, m/z 327.96 [M+H]$^+$.

Step-2: (R)-3-(1-aminoethyl)-6-chloroquinolin-2 (1H)-one hydrochloride (III-2)

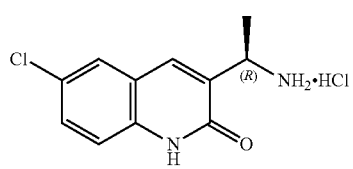

To a solution of (R)—N—((R)-1-(6-chloro-2-oxo-1,2-dihydroquinolin-3-yl)ethyl)-2-methylpropane-2-sulfinamide (150 mg, 0.459 mmol) in MeOH (5 mL) was added HCl (2 mL, 8.00 mmol, 4M in 1,4-dioxane). The mixture was stirred at room temperature overnight. To this mixture was added 6 mL of ethyl ether and the resulting precipitate was collected by filtration, washed with ethyl ether (2×), and then dried to afford (R)-3 (1-aminoethyl)-6-chloroquinolin-2(1H)-one hydrochloride (80 mg, 67% yield). $^1$H NMR (300 MHz, DMSO-d$_6$): δ ppm 12.32 (br s, 1H), 8.34 (br, 2H), 8.06 (s, 1H), 7.81 (s, 1H), 7.58 (d, J=8.82 Hz, 1H), 7.31 (d, J=8.83 Hz, 1H), 4.40-4.45 (m, 1H), 1.53 (d, J=6.81 Hz, 3H).
LCMS (Method 1): Rt 1.20 min, m/z 223.1 [M+H]$^+$.

Example 5

Intermediate III-3: (S)-3-(1-aminoethyl)-6-chloro-7-fluoroquinolin-2(1H)-one

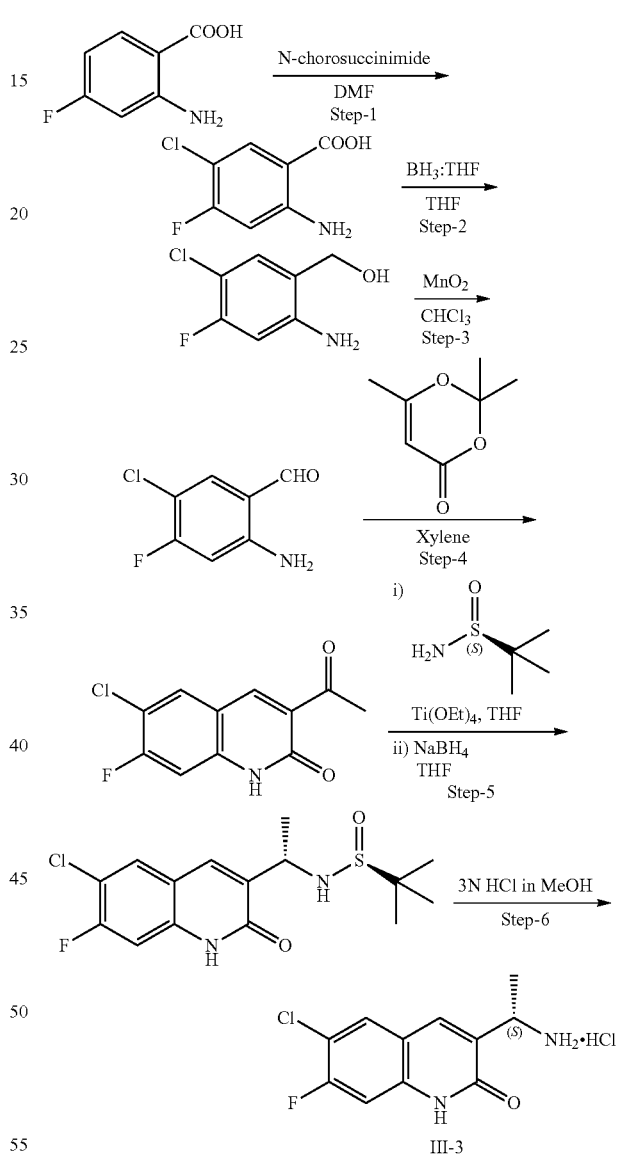

Step-1: 2-Amino-5-chloro-4-fluorobenzoic acid

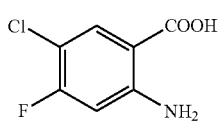

2-Amino-4-fluorobenzoic acid (50 g, 322.6 mmol) was dissolved in 700 mL of DMF and N-chlorosuccinimide (41 g, 305.5 mmol) was added portion wise. The reaction mixture was heated at 50° C. for 5 h. The mixture was cooled to room temperature, poured on to ice cold water to get the solid. The solid was filtered and dissolved in EtOAc, then sat. NaCl (300 mL) was added. The aqueous layer was extracted with EtOAc (3×200 mL). The combined organic phase was dried (Na$_2$SO$_4$) and evaporated to a brown solid (42 g, 69%) as desired product 2-amino-5-chloro-4-fluorobenzoic acid.

Step-2: (2-Amino-5-chloro-4-fluorophenyl)methanol

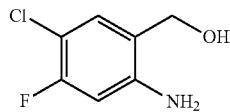

2-Amino-5-chloro-4-fluorobenzoic acid (42 g, 221 mmol) was dissolved in 100 mL of THF and BH$_3$.THF (712 mL of 1 M solution in THF, 712 mmol) was added drop wise over the period of 1 h at room temperature. The reaction mixture was heated at 50° C. overnight (18 h). The mixture was cooled to room temperature, poured onto ice cold water, and sat. NaCl solution was added. The aqueous was extracted with EtOAc (3×200 mL). The combined organic phase was dried (Na$_2$SO$_4$), evaporated and purified by flash chromatography using 0-100% hexanes/ethyl acetate as eluent to afford the desired product as a brown solid (17 g, 45%).

Step-3: 2-Amino-5-chloro-4-fluorobenzaldehyde

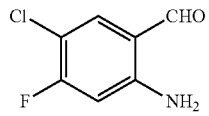

To a solution of (2-amino-5-chloro-4-fluorophenyl)methanol (22 g, 125.7 mmol) in 1000 mL of chloroform was added MnO$_2$ (109 g, 1250 mmol) and the reaction mixture was stirred overnight at ambient temperature. The reaction mixture was filtered, washed with EtOAc and evaporated. The resulting crude product was passed through a pad of silica gel eluting with 0 to 20% hexanes/EtOAc to give the pure product as a brown solid (19 g, 87%).

Step-4:
3-acetyl-6-chloro-7-fluoroquinolin-2(1H)-one

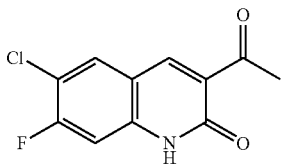 [SMILES: CC(=O)c1cc2cc(Cl)c(F)cc2[nH]c1=O]

A mixture of 2-Amino-5-chloro-4-fluorobenzaldehyde (14 g, 173.6 mmol) and 2,2,6-trimethyl-4H-1,3-dioxin-4-one (16 mL, 121 mmol) in m-xylene (500 mL) was refluxed for 1.5 h. The reaction mixture was cooled to room temperature and filtered. The collected solid was washed with m-xylene and dried to yield the desired product (9.6 g, 50%) as off-white solid.

Step-5: (S)—N—((S)-1-(6-chloro-7-fluoro-2-oxo-1,2-dihydroquinolin-3-yl)ethyl)-2-methyl propane-2-sulfinamide

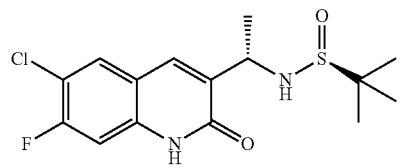 [SMILES: C[C@H](N[S@@](=O)C(C)(C)C)c1cc2cc(Cl)c(F)cc2[nH]c1=O]

To a mixture of 3-acetyl-6-chloro-7-fluoroquinolin-2 (1H)-one (6.4 g, 26.7 mmol) and (S)-2-methylpropane-2-sulfinamide (4.85 g, 40.06 mmol) in THF (450 mL) was added Ti(OEt)$_4$ (14 mL, 66.7 mmol). The resultant mixture was stirred at 80° C. overnight. Upon the completion of the reaction, the reaction mixture was cooled to −60° C. and NaBH$_4$ (5.1 g, 134 mmol) was added portion wise and then allowed to warm to room temperature overnight. The excess NaBH$_4$ was quenched with MeOH (20 mL), then with water (20 mL) and EtOAc (300 mL). The solution was filtered through a pad of celite. The filtrate was taken into a separatory funnel and the organic layer was separated, dried (Na$_2$SO$_4$), concentrated and purified by flash chromatography (SiO$_2$: hexanes/$^i$PrOH 0 to 20%) to give the title compound (4.5 g, 49%) as a yellow solid.

Step-6: (S)-3-(1-aminoethyl)-6-chloro-7-fluoroquinolin-2(1H)-one. HCl, III-3

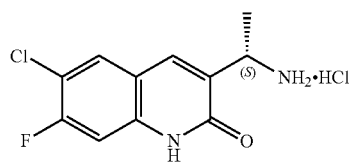

To a mixture of (S)—N—((S)-1-(6-chloro-7-fluoro-2-oxo-1,2-dihydroquinolin-3-yl)ethyl)-2-methyl propane-2-sulfinamide (3.5 g, 10.1 mmol) in MeOH (80 mL) was added 3N methanolic HCl (80 mL, 121 mmol). The resultant mixture was stirred at room temperature overnight. To this mixture was added diethyl ether (60 mL) and the resulting solid was filtered and dried to give the desired product III-3 (2.1 g, 75%) as a yellow solid. $^1$H NMR (300 MHz, DMSO-d$_6$): δ 12.40 (br s, 1H), 8.24 (br s, 2H), 8.07-8.05 (m, 2H), 7.32 (d, J=10.4 Hz, 1H), 4.5-4.15 (m, 1H), 1.53 (d, J=6.8 Hz, 3H). LCMS (method LCMS3, APCI): Rt 3.47 min, m/z 241.1 [M+H]$^+$.

Example 6

Intermediate III-4: 3-(1-aminoethyl)-6-chloro-7-methoxyquinolin-2(1H)-one

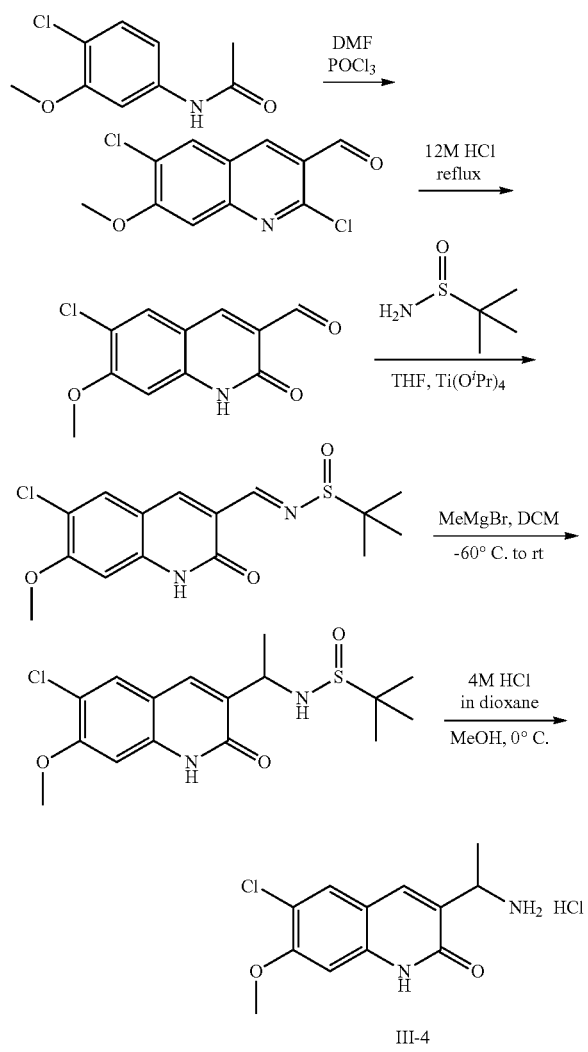

III-4

Step 1: 2,6-dichloro-7-methoxyquinoline-3-carbaldehyde

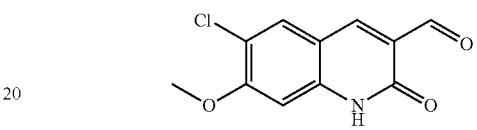

A tube was capped with a septum and placed under an atmosphere of nitrogen. DMF (6.4 mL, 83 mmol) was added by syringe and then cooled on an ice bath. POCl₃ (25 mL, 268 mmol) was added drop wise by syringe (over 20 minutes). The red solution was allowed to warm to room temperature (over 20 minutes), then the septum was removed, and the mixture was treated with N-(4-chloro-3-methoxyphenyl)acetamide (5 g, 25.05 mmol). The tube was sealed and the solution was stirred at 80° C. overnight. The solution was then pipetted onto ice, resulting in formation of a yellow precipitate. The precipitate was collected on a Buchner funnel, washed with water (1200 mL), and dried to provide 5.06 g of the title compound as a pale yellow solid. LCMS and ¹H NMR are consistent with 2,6-dichloro-7-methoxyquinoline-3-carbaldehyde (5.06 g, 19.76 mmol, 79% yield). ¹H NMR (300 MHz, DMSO-d₆): δ ppm 10.33 (s, 1H), 8.87 (s, 1H), 8.47 (s, 1H), 7.64 (s, 1H), 4.08 (s, 3H). LCMS (Method 1): m/z 256 [M+H]⁺.

Step-2: 6-chloro-7-methoxy-2-oxo-1,2-dihydroquinoline-3-carbaldehyde

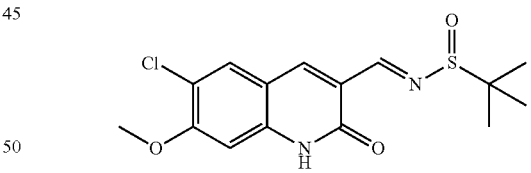

2,6-Dichloro-7-methoxyquinoline-3-carbaldehyde (5.06 g, 19.76 mmol) was heated at reflux in concentrated HCl (12M, 185 mL) overnight. The material went into solution during heating and then a solid precipitated during the course of the reaction. The mixture was allowed to cool and then was poured into water (1500 mL) resulting in further precipitation. The slurry was filtered on a Buchner funnel, washed with water (1500 mL), and dried to provide 4.04 g of the title compound as a yellowish-brown solid. LCMS and ¹H NMR are consistent with 6-chloro-7-methoxy-2-oxo-1,2-dihydroquinoline-3-carbaldehyde (4.04 g, 17.00 mmol, 86% yield). ¹H NMR (300 MHz, DMSO-d₆): δ ppm 12.22 (s, 1H), 10.16-10.18 (m, 1H), 8.43 (s, 1H), 8.08 (s, 1H), 6.95 (s, 1H), 3.94 (s, 3H). LCMS (Method 1): m/z 238 [M+H]⁺.

Step-3: N-((6-chloro-7-methoxy-2-oxo-1,2-dihydroquinolin-3-yl)methylene)-2-methyl propane-2-sulfinamide A mixture of 6-chloro-7-methoxy-2-oxo-1,2-dihydroquinoline-3-carbaldehyde (2.00 g, 8.42 mmol) and 2-methylpropane-2-sulfinamide (1.22 g, 10.07 mmol) was placed under an atmosphere of nitrogen. THF (20 mL) and titanium (IV) isopropoxide (Ti(OⁱPr)₄) (5.0 mL, 17.06 mmol) were added by syringe and the resulting suspension was stirred at room temperature overnight. Once LCMS indicated the reaction had gone to completion, the reaction was quenched by drop wise addition of aqueous saturated NH₄Cl (10 mL). The mixture was triturated with EtOAc (450 mL), then filtered through Celite® 545, and the Celite® was washed further with EtOAc (200 mL). The filter cake was then sonicated in EtOAc (450 mL) for 15 minutes, then filtered on a Buchner funnel. The two filtrates were combined, washed with brine (200 mL), dried (Na₂SO₄), filtered, and evaporated under reduced pressure to provide 1.01 g of the title compound as a yellow solid. LCMS and $^1$H NMR are consistent with (E)-N-((6-chloro-7-methoxy-2-oxo-1,2-dihydroquinolin-3-yl)methylene)-2-methylpropane-2-sulfinamide (1.01 g, 2.96 mmol, 35.2% yield). $^1$H NMR (300 MHz, DMSO-d$_6$): δ ppm 12.21 (s, 1H), 8.74 (s, 1H), 8.59 (s, 1H), 8.08 (s, 1H), 6.97 (s, 1H), 3.94 (s, 3H), 1.19 (s, 9H). LCMS (Method 1): m/z 341 [M+H]$^+$.

Step-4: N-(1-(6-chloro-7-methoxy-2-oxo-1,2-dihydroquinolin-3-yl)ethyl)-2-methylpropane-2-sulfinamide

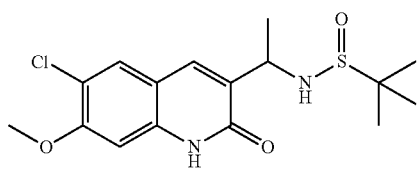 [SMILES: COc1cc2[nH]c(=O)c(C(C)NS(=O)C(C)(C)C)cc2cc1Cl]

N-((6-chloro-7-methoxy-2-oxo-1,2-dihydroquinolin-3-yl)methylene)-2-methylpropane-2-sulfinamide (265 mg, 0.778 mmol) was placed in a 50 mL round-bottom flask under an atmosphere of nitrogen. DCM (7 mL) was added, and the suspension was cooled on a dry ice/chloroform bath (to approx. −60° C.). Methylmagnesium bromide (MeMgBr) (3M in ether, 0.80 mL, 2.40 mmol) was added drop wise. The reaction mixture was stirred at −60° C. for several hours, then allowed to warm to room temperature overnight, resulting in an orange solution. Once LCMS indicated the reaction had gone to completion, the suspension was cooled on an ice bath and treated drop wise with water (3 mL). The resulting mixture was diluted with water (75 mL) and extracted with EtOAc (75 mL+20 mL). Silica gel was added and the EtOAc was evaporated under reduced pressure to provide a wet globular mass. Heptane and MeOH were added and the mixture was evaporated under reduced pressure to provide a powder. The material was purified by column chromatography on a Biotage® MPLC chromatography system (eluted with 0 to 4.2% MeOH in DCM) to yield the title compound as a blue-green brittle foam. LCMS and $^1$H NMR are consistent with N-(1-(6-chloro-7-methoxy-2-oxo-1, 2-dihydroquinolin-3-yl) ethyl)-2-methylpropane-2-sulfinamide (152.7 mg, 0.428 mmol, 55% yield). LCMS (Method 1): m/z 357 [M+H]$^+$.

Step-5: 3-(1-aminoethyl)-6-chloro-7-methoxyquinolin-2(1H)-one hydrochloride (III-4)

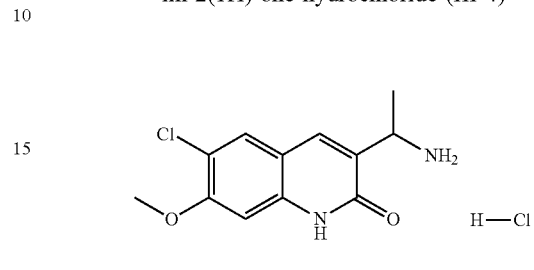

A solution of N-(1-(6-chloro-7-methoxy-2-oxo-1,2-dihydroquinolin-3-yl)ethyl)-2-methyl propane-2-sulfinamide (149.6 mg, 0.419 mmol) in MeOH (3.8 mL) was cooled on an ice bath and treated drop wise with 4M HCl in 1,4-dioxane (2.2 mL). The reaction was stirred for 25 minutes, during which time a small amount of precipitate formed. The solvents were evaporated under reduced pressure at room temperature. The residue was triturated with 10 mL of ethyl ether, then collected on a Hirsch funnel, and washed with more ethyl ether to provide 115.6 mg of the title compound as a pale green solid. LCMS and $^1$H NMR are consistent with 3-(1-aminoethyl)-6-chloro-7-methoxyquinolin-2(1H)-one hydrochloride III-4 (115.6 mg, 0.400 mmol, 95% yield). $^1$H NMR (300 MHz, Methanol-d$_4$): δ ppm 7.95 (s, 1H), 7.77 (s, 1H), 6.97 (s, 1H), 4.51 (q, J=6.84 Hz, 1H), 3.98 (s, 3H), 1.68 (d, J=7.04 Hz, 3H). LCMS (Method 1): m/z 253 [M+H]$^+$.

Example 7

Intermediate III-5: (S)-3-(1-aminoethyl)-6-chloro-7-methoxyquinolin-2(1H)-one

Scheme 3

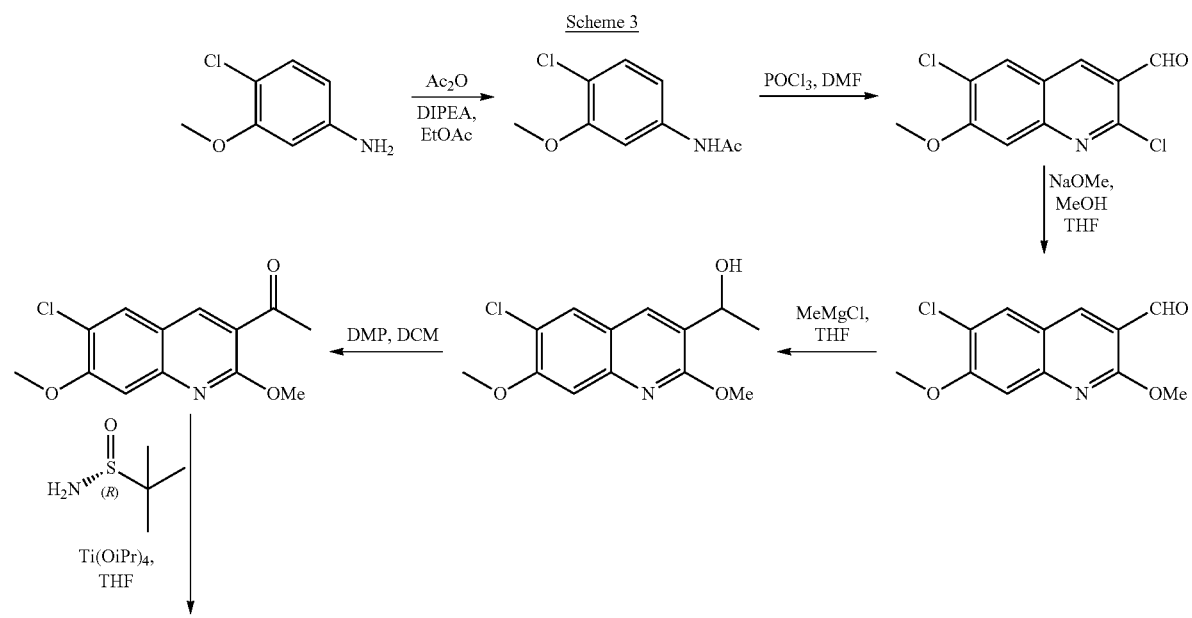

-continued

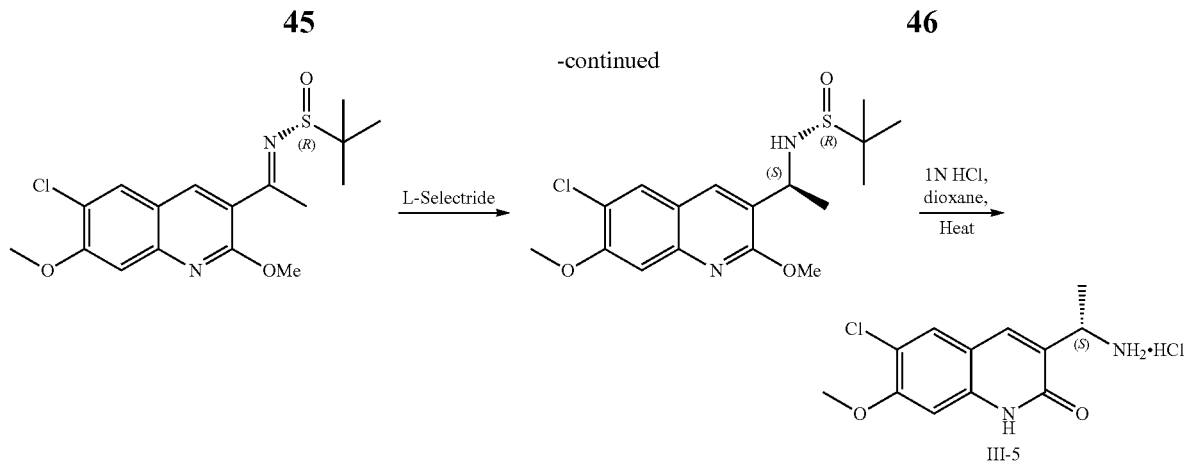

Step-1: N-(4-chloro-3-methoxyphenyl)acetamide

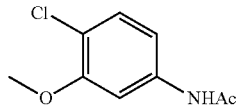

To a solution of 4-chloro-3-methoxyaniline (50 g, 317 mmol) and DIPEA (110 mL, 635 mmol) in CH$_2$Cl$_2$ (700 mL) was added acetic anhydride (36 mL, 381 mmol) drop wise at 0° C. and the reaction mixture was stirred at room temperature for 3 h. The reaction then was quenched with water (250 mL) and the organic layer was separated. The aqueous layer was extracted with CH$_2$Cl$_2$ (100 mL×3). The combined organic layers were dried (Na$_2$SO$_4$), concentrated and purified by flash chromatography with CH$_2$Cl$_2$/MeOH to give N-(4-chloro-3-methoxy phenyl)acetamide (71 g, quantitative yield) as a white solid.

Step-2: 2,6-Dichloro-7-methoxyquinoline-3-carbaldehyde

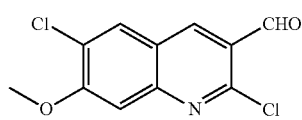 [SMILES: COc1cc2nc(Cl)c(C=O)cc2cc1Cl]

To POCl$_3$ (450 g, 274 mL, 2.95 mol) in a 2 L flask was added anhydrous DMF (83.5 g, 89 mL, 14 mol) drop wise. The reaction mixture was warmed up to room temperature and stirred for 20 min. After that N-(4-chloro-3-methoxyphenyl)acetamide (65 g, 327 mmol) was added portion wise at room temperature and the mixture was heated to 90° C. overnight. The reaction mixture was then cooled to room temperature and carefully quenched into aqueous NaHCO$_3$ solution. The precipitation obtained was filtered, washed with water (100 mL×3) and then dried in vacuum oven to give 60 g of title compound (73%).

Step-3: 6-Chloro-2,7-dimethoxyquinoline-3-carbaldehyde

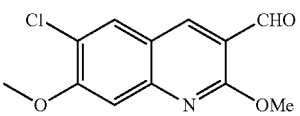 [SMILES: COc1cc2nc(OC)c(C=O)cc2cc1Cl]

To 2,6-dichloro-7-methoxyquinoline-3-carbaldehyde (40 g, 157 mmol) in MeOH (1 L) and THF (200 mL) was added NaOMe (16.9 g, 314 mmol) portion wise at room temperature. The reaction mixture was refluxed for 3 h. After cooling to room temperature, the reaction was quenched by addition of aqueous NH$_4$Cl solution (200 mL). The mixture was extracted with EtOAc (200 mL×3). The combined organic layers were dried (Na$_2$SO$_4$), concentrated and purified by flash chromatography with hexanes/EtOAc (3:1) to give the desired product (37.89 g, 96%) as a yellow solid.

Step-4: 1-(6-chloro-2,7-dimethoxyquinolin-3-yl)ethanol

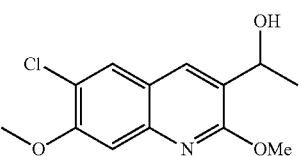 [SMILES: COc1cc2nc(OC)c(C(C)O)cc2cc1Cl]

To a solution of 6-chloro-2,7-dimethoxyquinoline-3-carbaldehyde (36.74 g, 151 mmol) in THF (1 L) at −78° C. was added a solution of MeMgCl in THF (3 M, 75.5 mL, 226 mmol) drop wise. The reaction was stirred at room temperature for 3 h and then quenched with aqueous NH$_4$Cl solution (250 mL). The organic layer was separated and the aqueous layer was extracted with EtOAc (100 mL×3). The combined organic layers were dried (Na$_2$SO$_4$), concentrated, and purified by silica gel chromatography with hexanes/EtOAc (3:1) to afford the title compound (38.06 g, 91%).

Step-5: 1-(6-chloro-2,7-dimethoxyquinolin-3-yl)ethanone

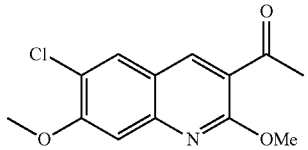 [SMILES: COc1cc2nc(OC)c(C(C)=O)cc2cc1Cl]

To 1-(6-chloro-2,7-dimethoxyquinolin-3-yl)ethanol (36.74 g, 137.6 mmol) in CH$_2$Cl$_2$ (1 L) at 0° C. was added DMP (70.0 g, 165.1 mmol) portion wise. The reaction was stirred at room temperature for 2 h, and then was quenched with an aqueous solution of NaHCO$_3$ and Na$_2$S$_2$O$_3$. After stirring for 15 min, both layers became clear. The organic layer was separated and the aqueous layer was extracted with CH$_2$Cl$_2$ (100 mL×2). The combined organic layers were dried (Na$_2$SO$_4$), concentrated and purified by silica gel chromatography with hexanes/EtOAc (4:1) to afford the title compound (30.02 g, 80%) as a white solid.

Step-6: (R,E)-N-(1-(6-chloro-2,7-dimethoxyquinolin-3-yl)ethylidene)-2-methylpropane-2-sulfinamide

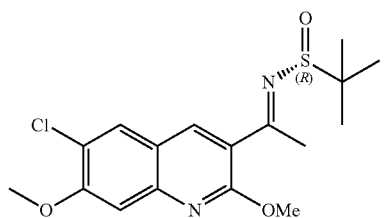

To 1-(6-chloro-2,7-dimethoxyquinolin-3-yl)ethanone (30.07 g, 113.5 mmol) in THF/toluene (100 mL/1 L) at room temperature was added (R)-2-methylpropane-2-sulfinamide (27.5 g, 227 mmol) and Ti(OiPr)$_4$ (97 mL, 340.5 mmol,). The reaction was refluxed with a Dean-Stark apparatus. After the reaction was refluxed for 4 h and 300 mL of solvent was removed, the reaction was cooled to room temperature. The solvent was removed under vacuum, and 200 mL of EtOAc was added to the residue, followed by 100 mL of saturated aqueous NaHCO$_3$ solution. After stirring for 10 min, the reaction mixture was passed through a pad of celite. The filtrate was extracted with EtOAc (200 mL×2), dried (Na$_2$SO$_4$), concentrated and purified by silica gel chromatography with hexanes/EtOAc (1:1) to give the title compound (34.28 g, 82%).

Step-7: (R)—N—((S)-1-(6-chloro-2,7-dimethoxyquinolin-3-yl)ethyl)-2-methylpropane-2-sulfinamide

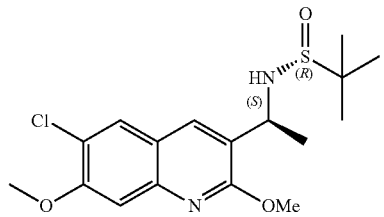

To (R,E)-N-(1-(6-chloro-2,7-dimethoxyquinolin-3-yl)ethylidene)-2-methylpropane-2-sulfinamide (34.28 g, 93.15 mmol) in THF (600 mL) at −78° C., was added 1 M L-selectride (121 mL, 121 mmol) in THF drop wise. The reaction mixture was warmed to room temperature and stirred for 3 h. The reaction was quenched with aqueous saturated NH$_4$Cl (300 mL) solution and then extracted with EtOAc (200 mL×2). The combined organic layers were dried (Na$_2$SO$_4$), concentrated and purified by silica gel chromatography with hexanes/EtOAc (1:1) to afford the title compound (29.27 g, 85%).

Step-8: (S)-3-(1-aminoethyl)-6-chloro-7-methoxyquinolin-2(1)-one hydrochloride salt (III-5)

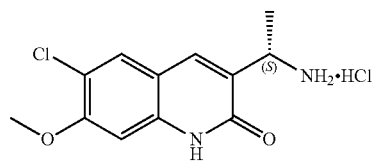

To (R)—N—((S)-1-(6-chloro-2,7-dimethoxyquinolin-3-yl)ethyl)-2-methylpropane-2-sulfinamide (30.35 g, 82 mmol) in dioxane (250 mL) was added 2 N HCl (250 mL) at rt. The reaction mixture was refluxed for 3 h, cooled to room temperature and the solvent was removed under vacuum. The crude residue obtained was dried under vacuum to give a crude product, which was further purified by trituration (CH$_2$Cl$_2$/MeOH/hexane) to obtain pure title compound III-5 (17.65 g, 75%) as a white solid. $^1$H NMR (300 MHz, DMSO-d$_6$): δ 12.18 (s, 1H), 8.24 (br, s, 3H), 7.99 (s, 1H), 7.86 (s, 1H), 7.02 (s, 1H), 4.41 (m, 1H), 3.91 (s, 3H), 1.52 (d, J=6.87 Hz, 3H). LCMS (Method 3): Rt 3.48 min, m/z 253.1 [M+H]$^+$.

Example 8

Intermediate III-6: (R)-3-(1-aminoethyl)-6-chloro-7-methoxyquinolin-2(1H)-one

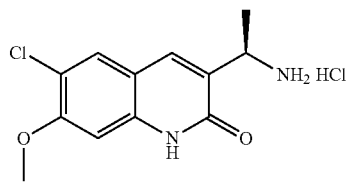

The title compound III-6 was prepared in the same procedure described for III-5, except using (S)-2-methylpropane-2-sulfinamide in Step-6 (Scheme-3). $^1$H NMR (300 MHz, Methanol-d$_4$): δ ppm 7.92 (s, 1H), 7.75 (s, 1H), 6.95 (s, 1H), 4.48 (q, J=6.84 Hz, 1H), 3.96 (s, 3H), 1.65 (d, J=6.74 Hz, 3H). LCMS: m/z 253 [M+H]$^+$.

Example 9

Intermediate III-7: (S)-3-(1-aminoethyl)-6-chloro-7-(pyridin-2-ylmethoxy) quinolin-2(1H)-one

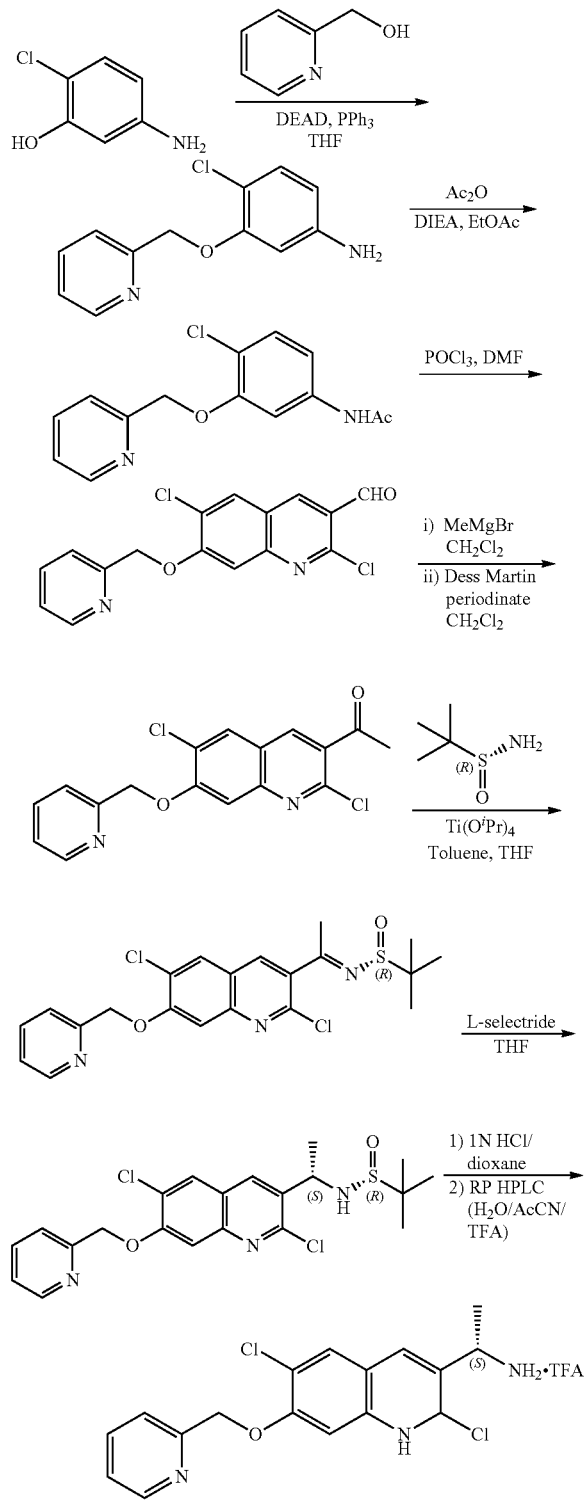

Step-1: 4-Chloro-3-(pyridin-2-ylmethoxy)aniline

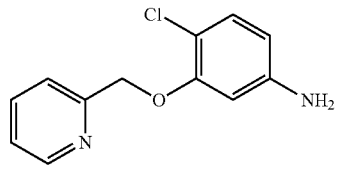 [SMILES: Nc1ccc(Cl)c(OCc2ccccn2)c1]

To a mixture of 5-amino-2-chlorophenol (10 g, 69.63 mmol), pyridin-2-ylmethanol (7.98 g, 73.13 mmol) and triphenylphosphine (21.5 g, 82.07 mmol) in THF (1.1 L) was added slowly diethylazadicarboxylate (DEAD) (13 mL, 82.07 mmol) at room temperature. The resulting mixture was stirred at room temperature for 24 hours. Upon completion of reaction, $SiO_2$ was added and solvents were evaporated to dryness. The crude product was purified by $SiO_2$ column chromatography eluted with 0-100% EtOAc-hexanes and then with 2% MeOH in EtOAc to afford the title compound (11.8 g, 72%) as an off-white solid. Note: The $^1H$ NMR showed a small amount of triphenylphosphine oxide impurity. This material was used in the next step without further purification.

Step-2: N-(4-Chloro-3-(pyridin-2-ylmethoxy)phenyl)acetamide

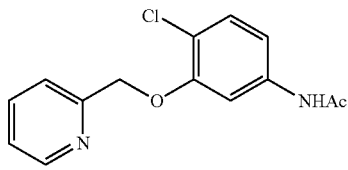 [SMILES: CC(=O)Nc1ccc(Cl)c(OCc2ccccn2)c1]

To a mixture of 4-chloro-3-(pyridin-2-ylmethoxy)aniline (11.8 g, 50.27 mmol) and diisopropylethylamine (DIEA) (9.93 mL, 57.81 mmol) in ethyl acetate (250 mL) was added acetic anhydride ($Ac_2O$) (5.22 mL, 55.3 mmol). The resultant mixture was stirred overnight at ambient temperature. The mixture was diluted with EtOAc (1 L), and washed with water (200 mL). The organic layer was dried over anhydrous $Na_2SO_4$, filtered, and evaporated to dryness. The resulting residue was triturated with hexanes-dichloromethane to afford the title compound as white solid (11.62 g, 84% yield).

Step-3: 2,6-Dichloro-7-(pyridin-2-ylmethoxy)quinoline-3-carbaldehyde

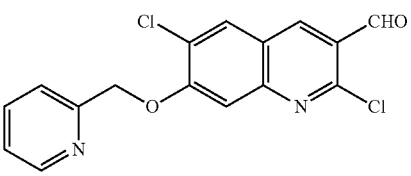 [SMILES: O=Cc1cc2cc(Cl)c(OCc3ccccn3)cc2nc1Cl]

Dimethylformamide (4 mL, 51.6 mmol) was placed in a 150 mL sealed tube and cooled to 0° C. To the DMF was added phosphorous oxychloride ($POCl_3$) (15.6 mL, 168 mmol) drop wise over 30-40 minutes. The resulting mixture was warmed to room temperature and N-(4-chloro-3-(pyridin-2-ylmethoxy)phenyl)acetamide (4.34 g, 15.68 mmol) was added. The reaction mixture was heated at 80° C. overnight. The mixture was then cooled to room temperature and carefully quenched with ice. The solution turned red and a yellow precipitate was formed, filtered, washed with water and dried over $P_2O_5$ overnight to afford the title compound as yellow solid (3.53 g, 68% yield).

Step-4: 1-(2,6-Dichloro-7-(pyridin-2-ylmethoxy)quinolin-3-yl)ethanone

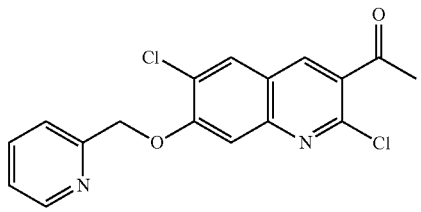 [SMILES: CC(=O)c1cc2cc(Cl)c(OCc3ccccn3)cc2nc1Cl]

To a solution of 2,6-dichloro-7-(pyridin-2-ylmethoxy)quinoline-3-carbaldehyde (1.0 g, 3.0 mmol) in $CH_2Cl_2$ (40 mL) was added drop wise methyl magnesium bromide (MeMgBr) (3 M solution in diethyl ether, 1.5 mL, 4.50 mmol) at 0° C. The resulting mixture was then stirred at ambient temperature for 1.5 hours. Upon completion of reaction, the mixture was slowly quenched with water (3 mL) and extracted with $CH_2Cl_2$ (50 mL). The organic layer was separated and dried over anhydrous $Na_2SO_4$. The solvents were evaporated to dryness. The resulting residue was dissolved in $CH_2Cl_2$ (25 mL) and treated with Dess-Martin Periodinate (2.54 g, 6.00 mmol). The mixture was stirred at ambient temperature overnight. The mixture was then quenched with an aqueous co-solution of 20% $NaHCO_3$ and 20% $Na_2S_2O_3$ (10 mL) and stirred for 5 minutes at room temperature. The solution was extracted with $CH_2Cl_2$ (40 mL), dried over anhydrous $Na_2SO_4$, filtered and evaporated. The resulting residue was purified by column chromatography on an ISCO® chromatography system ($SiO_2$ column: eluted with $CH_2Cl_2$/MeOH 0 to 10%) to afford the title compound (800 mg, 79%).

Step-5: (R,E)-N-(1-(2,6-dichloro-7-(pyridin-2-ylmethoxy)quinolin-3-yl)ethylidene)-2-methylpropane-2-sulfinamide

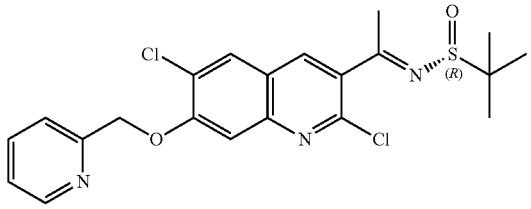

To a mixture of 1-(2,6-dichloro-7-(pyridin-2-ylmethoxy)quinolin-3-yl)ethanone (2.18 g, 6.56 mmol) and (R)-2-methylpropane-2-sulfinamide (1.19 g, 9.84 mmol) in THF: Toluene (40 mL:180 mL), was added titanium (IV) isopropoxide (Ti(O$^i$Pr)$_4$) (3.96 mL, 13.30 mmol). The resulting mixture was refluxed with a Dean-Stark apparatus for 7 hours. The mixture was then cooled to room temperature, quenched with water, and diluted with EtOAc (300 mL). The organic layer was washed with water (100 mL), dried over anhydrous $Na_2SO_4$, filtered and evaporated to dryness. The resulting residue was purified by column chromatography on an ISCO® chromatography system ($SiO_2$ column: eluted with Hex/EtOAc 0 to 100%) to afford the title compound as yellow solid (1.4 g, 50% yield). The starting material ketone was also recovered (250 mg, 11% yield).

Step-6: (R)—N—((S)-1-(2,6-dichloro-7-(pyridin-2-ylethoxy)quinolin-3-yl)ethyl)-2-methyl propane-2-sulfinamide

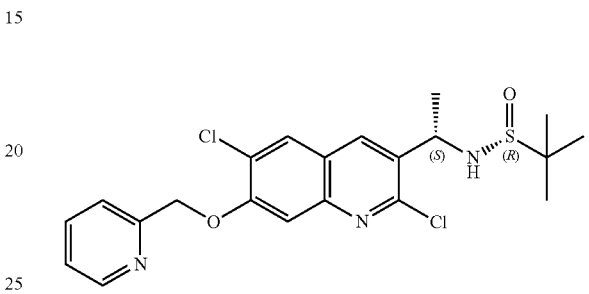

To a solution of (R,E)-N-(1-(2,6-dichloro-7-(pyridin-2-ylmethoxy)quinolin-3-yl) ethylidene)-2-methyl propane-2-sulfinamide (900 mg, 1.99 mmol) in THF (25 mL) at -40 to -50° C. was added L-selectride (1M in THF, 1.98 mL, 2.59 mmol) drop wise. The resulting mixture was stirred at -40 to -50° C. for 2 hours. Upon completion of reaction, the mixture was quenched with ice at -50° C., extracted with EtOAc (100 mL), dried, and evaporated. The resulting residue was purified by column chromatography on an ISCO® chromatography system ($SiO_2$ column: Hex/EtOAc 0 to 100%) followed by trituration with hexanes-methylene chloride to afford the title compound (266 mg, 30% yield).

Step-7: (S)-3-(1-Aminoethyl)-6-chloro-7-(pyridin-2-ylmethoxy)quinolin-2(1H)-one TFA salt (III-7)

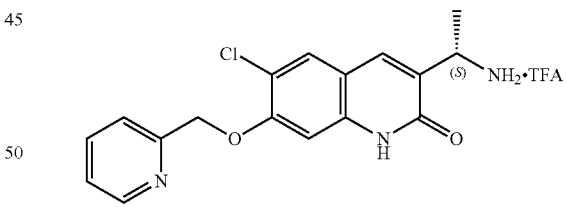

To a mixture of (R)—N—((S)-1-(2,6-dichloro-7-(pyridin-2-ylmethoxy)quinolin-3-yl)ethyl)-2-methylpropane-2-sulfinamide (1.1 g, 2.43 mmol) in 1,4-dioxane (6.6 mL), was added aqueous 1N HCl (6.6 mL) at room temperature. The resulting mixture was heated to 120° C. overnight. After TLC and MS showed completion of reaction, the solvents were removed on a rotary evaporator and lyophilized to provide yellow solid. The crude solid was purified by reverse phase chromatography on an ISCO® chromatography system (C18 column: eluted with $H_2O$/MeCN/0.1% $CF_3CO_2H$ 0 to 100%) and the fractions were monitored by LCMS. The pure fractions were combined and lyophilized to afford the title compound III-7 (920 mg, 86% yield) as the TFA salt. $^1H$ NMR (300 MHz, DMSO-$d_6$): δ 12.17 (br s, 1H), 8.62 (d, J=4.95 Hz, 1H), 8.09 (br s, 2H), 7.96-7.85 (m, 3H), 7.59 (d, J=7.9 Hz, 1H), 7.42-7.37 (m, 1H), 7.08 (d, J=2.5 Hz, 1H), 5.33 (s, 2H), 4.39-4.38 (m, 1H), 1.51 (d, J=6.8 Hz, 3H). LCMS (method 3): Rt 3.3 min, m/z 329.1 [M+H]⁺.

Example 10

Intermediate III-8: (S)-3-(1-aminoethyl)-6-chloro-1,8-naphthyridin-2(1H)-one

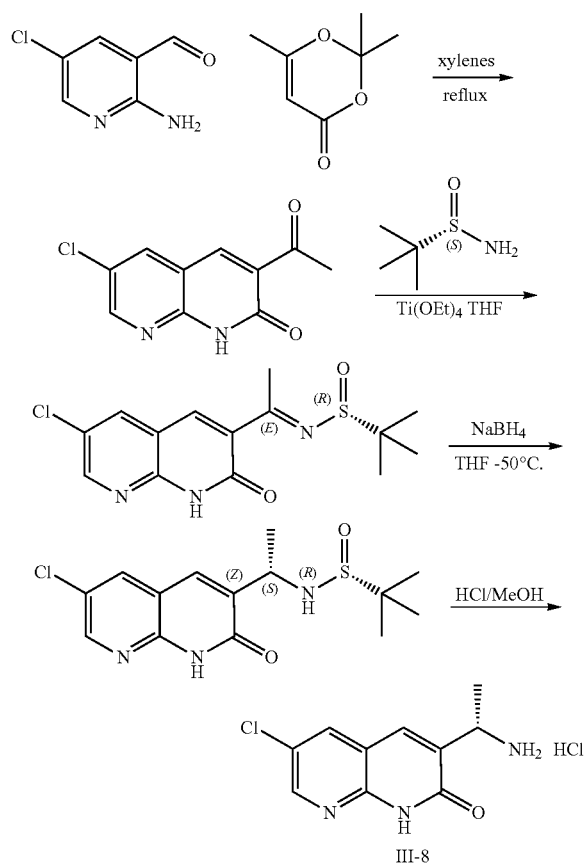

Step-1:
3-acetyl-6-chloro-1,8-naphthyridin-2(1H)-one

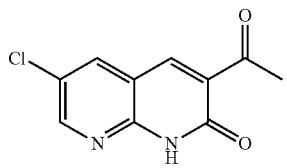

A mixture of 2-amino-5-chloronicotinaldehyde (1 g, 6.39 mmol) and 2,2,6-trimethyl-4H-1,3-dioxin-4-one (1.362 g, 9.58 mmol) in xylenes (10 mL) was heated to reflux for 3 hours, then cooled to room temperature, filtered, and washed with xylenes twice to afford 914 mg of 3-acetyl-6-chloro-1,8-naphthyridin-2(1H)-one (64.3% yield). ¹H NMR (300 MHz, DMSO-d₆): δ 12.68 (br, 1H), 8.63 (s, 1H), 8.49 (s, 1H), 8.39 (s, 1H), 2.48 (s, 3H). LCMS (Method 1): Rt 1.60 min, m/z 223.03[M+H]⁺.

Step-2: (S)—N—((S)-1-(2,6-dichloroquinolin-3-yl)ethyl)-2-methylpropane-2-sulfinamide

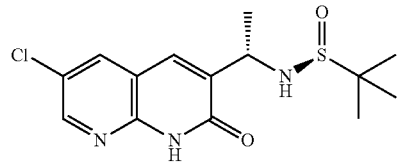 [SMILES: C[C@H](N[S@@](=O)C(C)(C)C)c1cc2cc(Cl)cnc2[nH]c1=O]

A mixture of tetraethoxytitanium (512 mg, 2.25 mmol), (R)-2-methylpropane-2-sulfinamide (163 mg, 1.35 mmol) and 3-acetyl-6-chloro-1,8-naphthyridin-2(1H)-one (200 mg, 0.898 mmol) in THF (15 mL) was heated to 80° C. overnight, then cooled to room temperature. To this mixture was added NaBH₄ (170 mg, 4.49 mmol) and the mixture was slowly warmed up to room temperature overnight. MeOH was then added to quench any excess NaBH₄, followed by the addition of water. The mixture was filtered to remove solids, then extracted with EtOAc twice, dried over Na₂SO₄, and concentrated. The residue was purified on a Biotage® chromatography system using a 25 g SiO₂ column eluted on a gradient (first 20% to 100% EtOAc/Hexanes, then 0-5% MeOH/DCM) to afford (S)—N—((S)-1-(2,6-dichloroquinolin-3-yl)ethyl)-2-methylpropane-2-sulfinamide (123 mg, 42% yield). ¹H NMR (300 MHz, DMSO-d₆): δ 8.40 (s, 1H), 7.74 (s, 1H), 7.75 (s, 1H), 7.24 (s, 1H), 5.24 (d, J=9.45 Hz, 1H), 4.42 (m, 3H), 1.54 (d, J=6.93 Hz, 3H), 1.20 (s, 9H). LCMS (Method 1): Rt 2.07 min, m/z 328.98 [M+H]⁺.

Step-3: (S)-3-(1-aminoethyl)-6-chloro-1,8-naphthyridin-2(1H)-one (III-8)

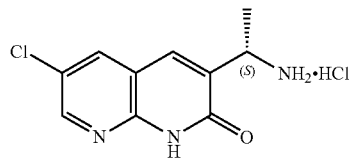

To a solution of ((S)—N—((S)-1-(6-chloro-2-oxo-1,2-dihydro-1,8-naphthyridin-3-yl)ethyl)-2-methylpropane-2-sulfinamide (123 mg, 0.375 mmol) in MeOH (5 mL) was added HCl (2 mL, 8.00 mmol, 4M in 1,4-dioxane). The mixture was then stirred at room temperature overnight. To this mixture was added 6 mL of ethyl ether and the resulting precipitate was filtered, washed with ethyl ether (2×), dried and concentrated to afford (S)-3-(1-aminoethyl)-6-chloro-1,8-naphthyridin-2(1H)-one, HCl (96 mg, 98% yield). ¹H NMR (300 MHz, DMSO-d₆): δ 12.75 (br s, 1H), 8.60-8.35 (s, 1H), 8.26 (br, 1H) 8.07 (s, 1H), 4.40-4.50 (m, 1H), 1.51 (d, J=6.78 Hz, 3H). LCMS (Method 1): Rt 0.87 min, m/z 224.99 [M+H]⁺.

Example 11

Intermediate III-9: (S)-3-(1-Aminoethyl)-6-chloro-8-fluoroquinolin-2(1H)-one

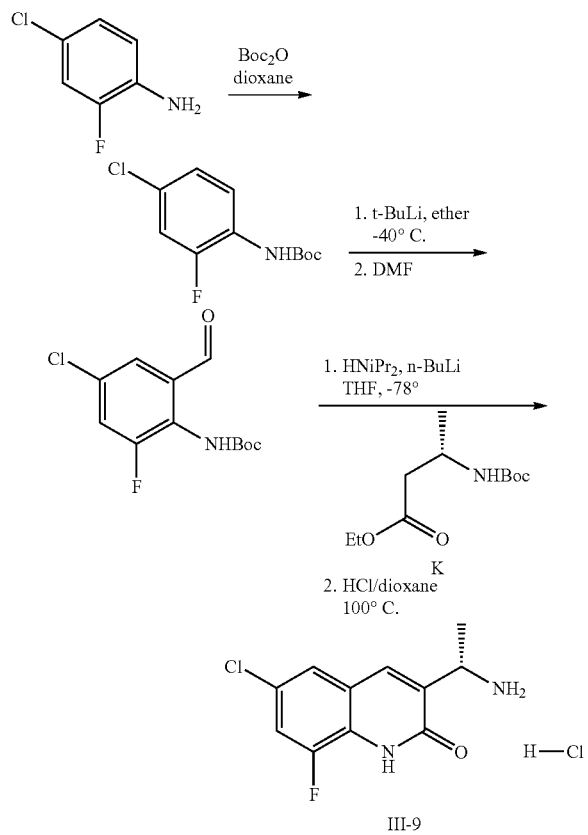

III-9

Step-1: tert-Butyl (4-chloro-2-fluorophenyl)carbamate

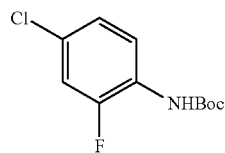 [SMILES: CC(C)(C)OC(=O)Nc1ccc(Cl)cc1F]

A solution of 4-chloro-2-fluoroaniline (2 g, 13.74 mmol) and di-tert-butyl dicarbonate (6.4 mL, 27.6 mmol) in 1,4-dioxane (50 mL) was stirred at reflux for 2 days. The solvent was then evaporated. The resulting oil was diluted with MeOH, water, and aqueous ammonium hydroxide solution (10 mL each) and vigorously stirred for 45 minutes. The organic lower layer was separated. The organic material was diluted with EtOAc (50 mL), and washed with water (50 mL), 3.6% aqueous HCl solution (2×50 mL), saturated aqueous NaHCO₃ solution (50 mL), and then again with water (2×50 mL). The organic layer was dried (MgSO₄), filtered, and evaporated under reduced pressure to provide tert-butyl (4-chloro-2-fluorophenyl)carbamate (3.0011 g, 12.22 mmol, 89% yield) as a reddish liquid that solidified on standing. ¹H NMR (300 MHz, DMSO-d₆): δ ppm 9.12 (s, 1H), 7.63 (t, J=8.65 Hz, 1H), 7.42 (dd, J=10.85, 2.35 Hz, 1H), 7.18-7.24 (m, 1H), 1.45 (s, 9H). LCMS (Method 1): m/z 246 [M+H]⁺.

Step-2: tert-Butyl (4-chloro-2-fluoro-6-formylphenyl)carbamate

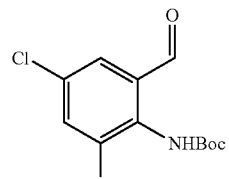

An oven-dried 3-necked 500 mL round bottom flask was fitted with an oven-dried addition funnel and placed under an atmosphere of nitrogen. tert-Butyl (4-chloro-2-fluorophenyl)carbamate (5.44 g, 22.14 mmol) and ethyl ether (91 mL) were added by syringe. The clear solution was cooled on an acetonitrile/dry ice bath (to approximately −40° C.). tert-Butyllithium (1.7M in pentane, 33 mL, 22.14 mmol) was added to the addition funnel by cannula. The t-BuLi solution was added drop wise to the ether solution (over ~10 minutes), during which time the ether solution began to turn orange. The solution was stirred at about −40° C. for 2 hours, during which time it progressively became more orange. DMF (8.7 mL, 112 mmol) was added drop wise (over ~10 minutes), resulting in precipitation of a yellow solid.

The MeCN/dry ice bath was replaced with an ice bath and the mixture was stirred for an additional 2 hours. The reaction was then quenched by drop wise addition of water (20 mL), resulting in a brown mixture and the ice bath was removed. The mixture was diluted with EtOAc (100 mL), washed with water (2×100 mL), dried (Na₂SO₄), filtered, and evaporated under reduced pressure to provide 5.45 g of an oily black solid. The material was triturated with hexanes (50 mL), collected on a Buchner funnel and washed with more hexanes to provide 2.73 g tert-butyl (4-chloro-2-fluoro-6-formylphenyl)carbamate as a yellow powder. The filtrate was evaporated under reduced pressure, the residue was triturated in hexanes (~15 mL), and the resulting yellow solid was collected on a Hirsch funnel to provide a second crop of the title compound (0.66 g). A total of 3.39 g (12.4 mmol, 56% yield) of tert-butyl (4-chloro-2-fluoro-6-formylphenyl)carbamate was recovered. ¹H NMR (300 MHz, DMSO-d₆): δ ppm 9.93 (d, J=0.88 Hz, 1H), 9.47 (s, 1H), 7.81-7.90 (m, 1H), 7.55-7.61 (m, 1H), 1.44 (s, 9H). LCMS (Method 1): m/z 296 [M+Na].

Steps-3 & 4: (S)-3-(1-Aminoethyl)-6-chloro-8-fluoroquinolin-2(1H)-one hydrochloride (III-9)

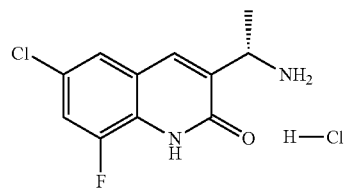

An oven-dried 200 mL round bottom flask and stir bar were placed under an atmosphere of nitrogen. THF (17 mL) and diisopropylamine (1.59 mL, 11.16 mmol) were added by syringe. The resulting solution was cooled on a dry ice/acetone bath (to approximately −78° C.) and then n-butyllithium (1.6M in hexane, 7.1 mL, 11.36 mmol) was added drop wise over a 5 minute period. After stirring for 15 minutes, a solution of (S)-ethyl 3-((tert-butoxycarbonyl)amino)butanoate K (860.7 mg, 3.72 mmol) in THF (3.75 mL) was added drop wise over 5 minutes. The solution was stirred for 80 minutes at −78° C., and a solution of tert-butyl (4-chloro-2-fluoro-6-formylphenyl)carbamate (1016.4 mg, 3.71 mmol) in THF (7.5 mL) was then added drop wise by syringe. The reaction was stirred at −78° C. for another 22 minutes and then quenched by addition of saturated aqueous NH$_4$Cl solution (17 mL). The mixture was partitioned between EtOAc and water (100 mL each). The organic layer was dried (MgSO$_4$), filtered, and evaporated under reduced pressure to provide 1.88 g of the title compound as an orange gum. The material was dissolved in 1,4-dioxane (38 mL), treated with 12M aqueous HCl (0.96 mL), and stirred at 110° C. for 50 minutes. The sample was then allowed to cool. The solvent was evaporated under reduced pressure to provide 1.24 g of a red solid. The material was triturated in IPA (25 mL), collected on a Hirsch funnel and washed sequentially with IPA (5 mL) and ethyl ether (~20 mL) to provide (S)-3-(1-aminoethyl)-6-chloro-8-fluoroquinolin-2(1H)-one hydrochloride (370.4 mg, 1.337 mmol, 36% yield) as a red solid. $^1$H NMR (300 MHz, DMSO-d$_6$): δ ppm 12.41 (s, 1H), 8.33 (br s, 3H), 8.10 (s, 1H), 7.67-7.76 (m, 2H), 4.38-4.53 (m, 1H), 1.52 (d, J=7.04 Hz, 3H). LCMS (Method 1): m/z 241 [M+H]$^+$.

Example 12

Intermediate V-1: 7-chloro-1-methyl-1,4-dihydro-2H-pyrimido[4,5-d][1,3]oxazin-2-one

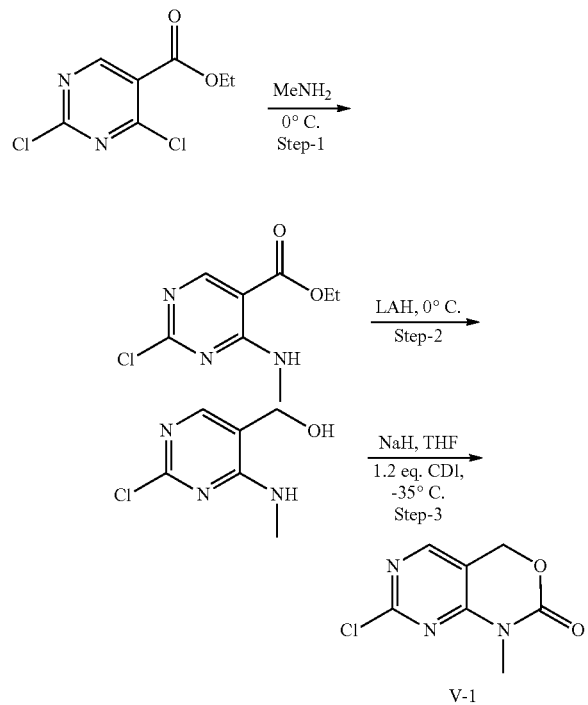

Step-1: Ethyl 2-chloro-4-(methylamino)pyrimidine-5-carboxylate

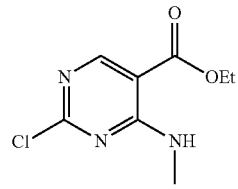

A solution of ethyl 2,4-dichloropyrimidine-5-carboxylate (9.0 g, 40.5 mmol, 1 eq.) in 75 ml MeOH was cooled to −20° C. and treated with methylamine (33 wt % in EtOH, 5.1 ml, 40.5 mmol, 1 eq.) and TEA (7.9 g, 81 mmol, 2 eq.). After stirring for 10 minutes, the reaction was poured into water and the resulting precipitate was collected and rinsed with water.

Chromatography over 80 g silica gel with DCM as eluent followed by trituration with Et$_2$O provided the title compound (5.16 g, 59%) as a white solid.

Step-2: (2-Chloro-4-(methylamino)pyrimidin-5-yl)methanol (3)

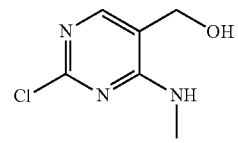

In a dried 3-neck round bottom flask under N$_2$, a solution of ethyl 2-chloro-4-(methylamino)pyrimidine-5-carboxylate (5.16 g, 23.9 mmol, 1 eq.) in 240 ml THF was cooled to 0° C. LAH (1.8 g, 47.4 mmol, 2 eq.) was added portion-wise, followed by stirring at 0° C. After 60 min, 95 mL 5% aqueous NaOH was added drop wise, followed by addition of H$_2$O (50 ml). The mixture was extracted with EtOAc and dried over Na$_2$SO$_4$. The crude material was evaporated to dryness. The resulting solid was triturated with a mixture of DCM/EtOAc to provide the desired product (1.94 g, 46%) as a cream-colored solid. Chromatography of the mother liquor over silica gel with EtOAc as eluent afforded an additional 0.84 g of the product (21%).

Step-3: 7-Chloro-1-methyl-1H-pyrimido[4,5-d][1,3]oxazin-2(4H)-one (V-1)

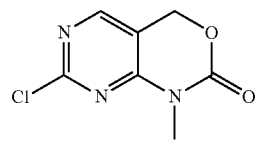

In a dried 3-neck round bottom flask under N$_2$, a solution of (2-chloro-4-(methylamino)pyrimidin-5-yl)methanol (1.94 g, 11.1 mmol, 1 eq.) in DMF (70 mL) was cooled to 0° C. NaH (60 wt % in oil, 445 mg, 11.1 mmol, 1 eq.) was added portion-wise, followed by stirring at room temperature for 30 min. The reaction mixture was then cooled to −40° C. and CDI (1.90 g, 11.7 mmol, 1.05 eq.) was added portion-wise. After 4.5 hours, 15 ml H$_2$O was added followed by extraction into EtOAc (3×). The combined extracts were washed with H$_2$O, then brine, and dried over Na$_2$SO$_4$. The crude extract was evaporated to dryness and the resulting solid triturated with Et$_2$O. The unwanted solid was filtered off, and the filtrate chromatographed over 30 g silica gel using a DCM to DCM:EtOAC (95/5) gradient to provide the title compound V-1 as a white solid (300 mg, 13%). $^1$H-NMR (300 MHz, CDCl$_3$) δ ppm: 8.22 (d, J=0.81, 1H), 5.27 (d, J=0.69, 1H), 3.47 (d, J=0.84, 1H). LC/MS (Method 3): Rt 3.78 min., m/z 200 [M+H]$^+$. Melting point: 143-146° C.

Example 13

Intermediate V-2: 5-chloro-3-methyloxazolo[4,5-d]pyrimidin-2(3H)-one

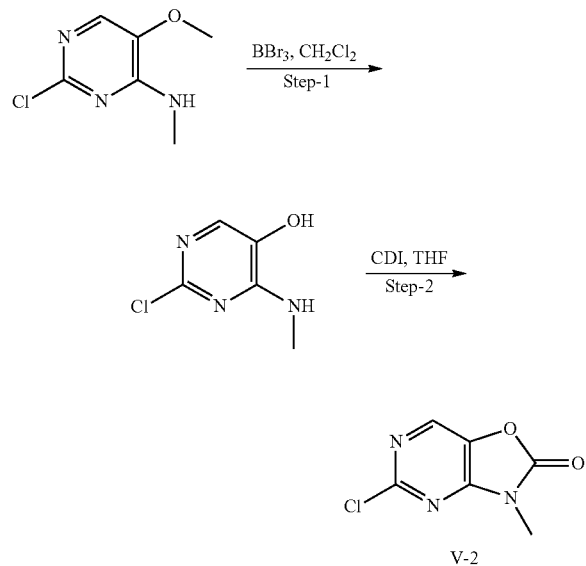

Step-1: 2-chloro-4-(methylamino)pyrimidin-5-ol

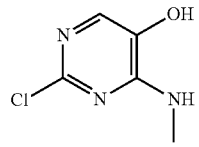

To 2-chloro-5-methoxy-N-methylpyrimidn-4-amine (1.73 g, 10 mmol) in CH$_2$Cl$_2$ (100 mL) at −78° C. was added BBr$_3$ (3.76 g, 15 mmol) drop wise. The reaction mixture was then warmed up to room temperature and stirred overnight. The reaction mixture was then quenched with aqueous NaHCO$_3$ solution (50 mL). The solvents were evaporated and the residue was dried under vacuum. To the residue was added THF (50 mL) and the insoluble solid was filtered. The THF solution was concentrated and dried to give crude compound, 2-chloro-4-(methylamino)pyrimidin-5-ol (1.30 g, 82%) which was used in the next step without further purification.

Step-2: 5-chloro-3-methyloxazolo[4,5-d]pyrimidin-2(3H)-one (V-2)

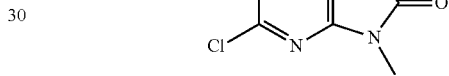

To 2-chloro-4-(methylamino)pyrimidin-5-ol (810 mg, 5.1 mmol) in THF (150 mL) was added CDI (1.24 g, 7.64 mmol) and $^i$Pr$_2$EtN (1 mL) at room temperature. The reaction was refluxed for 6 h. The mixture was then cooled to room temperature and the solvent was removed under vacuum. To the residue was added water (50 mL) and the mixture was extracted with CH$_2$Cl$_2$ (30 mL×3). The combined organic layers were dried (Na$_2$SO$_4$), concentrated and purified by ISCO using CH$_2$Cl$_2$ to CH$_2$Cl$_2$/MeOH (9:1) as eluent to afford the desired compound V-2 (690 mg, 73%). $^1$H NMR (300 MHz, DMSO-d$_6$) δ ppm: 8.22 (s, 1H), 3.49 (s, 3H). LCMS (Method 3): Rt 3.65 min, m/z 186.0 [M+H]$^+$.

TABLE 1

The Intermediates listed in Table 1 were either prepared using the methods described above or obtained from commercial sources.

| Intermediate No. | Chemical names | Structure |
| --- | --- | --- |
| II-1 | 6-chloro-2-oxo-1,2-dihydroquinoline-3-carbaldehyde | 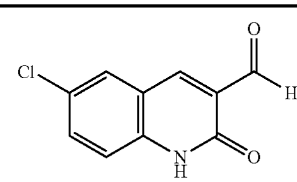 |
| III-1 | (S)-3-(1-aminoethyl)-6-chloroquinolin-2(1H)-one hydrochloride | 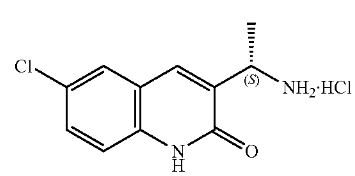 |

TABLE 1-continued

The Intermediates listed in Table 1 were either prepared using the methods described above or obtained from commercial sources.

| Intermediate No. | Chemical names | Structure |
|---|---|---|
| III-2 | (R)-3-(1-aminoethyl)-6-chloroquinolin-2(1H)-one hydrochloride | 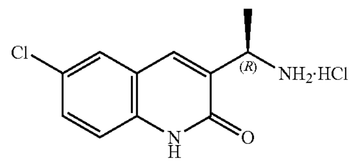 |
| III-3 | (S)-3-(1-aminoethyl)-6-chloro-7-fluoroquinolin-2(1H)-one | 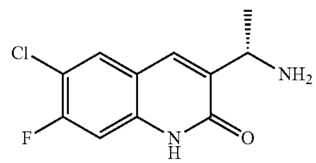 [SMILES: C[C@H](N)c1cc2cc(Cl)c(F)cc2[nH]c1=O] |
| III-4 | 3-(1-aminoethyl)-6-chloro-7-methoxyquinolin-2(1H)-one | 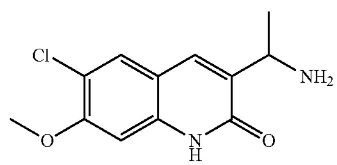 [SMILES: COc1cc2[nH]c(=O)c(C(C)N)cc2cc1Cl] |
| III-5 | (S)-3-(1-aminoethyl)-6-chloro-7-methoxyquinolin-2(1H)-one | 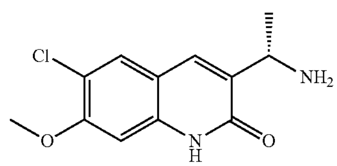 |
| III-6 | (R)-3-(1-aminoethyl)-6-chloro-7-methoxyquinolin-2(1H)-one | 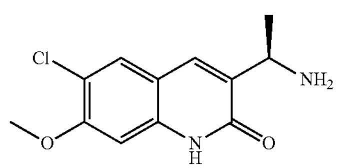 [SMILES: COc1cc2[nH]c(=O)c([C@@H](C)N)cc2cc1Cl] |
| III-7 | (S)-3-(1-aminoethyl)-6-chloro-7-(pyridin-2-ylmethoxy)quinolin-2(1H)-one | 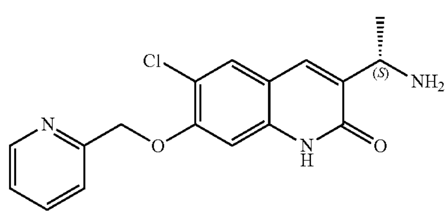 |
| III-8 | (S)-3-(1-aminoethyl)-6-chloro-1,8-naphthyridin-2(1H)-one | 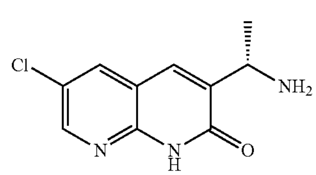 |
| III-9 | (S)-3-(1-aminoethyl)-6-chloro-8-fluoroquinolin-2(1H)-one | 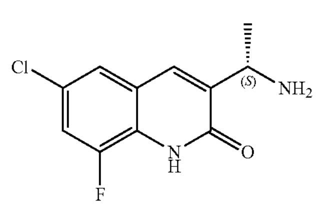 |

TABLE 1-continued

The Intermediates listed in Table 1 were either prepared using the methods described above or obtained from commercial sources.

| Intermediate No. | Chemical names | Structure |
|---|---|---|
| V-1 | 7-chloro-1-methyl-1,4-dihydro-2H-pyrimido[4,5-d][1,3]oxazin-2-one | 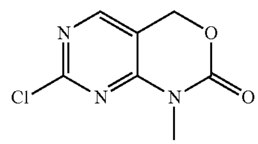 |
| V-2 | 5-chloro-3-methyloxazolo[4,5-d]pyrimidin-2(3H)-one | 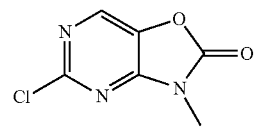 |

Example 14

3-((benzo[d]oxazol-4-ylamino)methyl)-6-chloroquinolin-2(1H)-one (I-1)

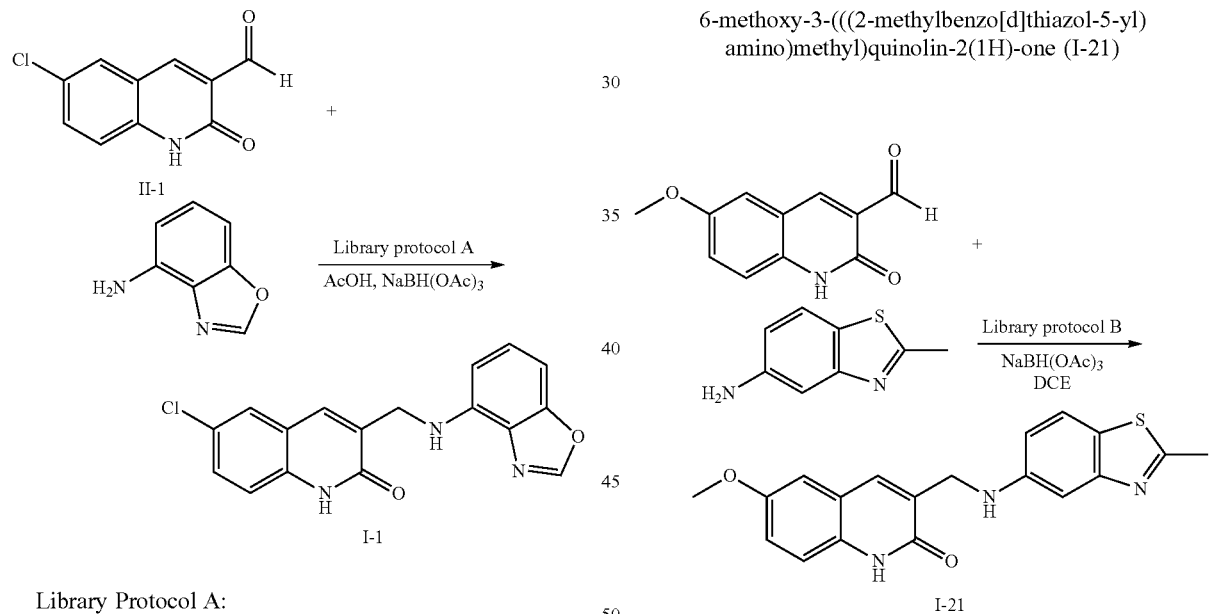

Library Protocol A:

in a 1.5 mL vial was added benzo[d]oxazol-4-amine (158 µL, 0.032 mmol) in methanol, 6-chloro-2-oxo-1,2-dihydroquinoline-3-carbaldehyde (150 µL, 0.030 mmol) in methanol, and acetic acid (30 µL, 0.524 mmol) to give a tan solution. The reaction was heated to 50° C. with shaking for 2 hours. The volatiles were removed by vacuum 200 uL of toluene was added the reaction was shaken at room temperature for 15 minutes. The volatiles were removed by vacuum. 200 uL of DMA were added sodium triacetoxyborohydride (450 µL, 0.090 mmol) in DCE was added. The reaction was shaken at room temperature for 4 hours. The volatiles were removed by vacuum. The residue was partitioned between 0.5 mL of 1N NaOH and 0.5 mL of a 3:1 mixture of EtOAc/ACN. The upper (organic) layer was separated and combined with a second extraction of the aqueous layer with 0.5 mL of a 3:1 mixture of EtOAc/ACN. The volatiles were removed under reduced pressure. The compound was purified using mass-triggered HPLC to yield 1.3 mg (13% yield) of 3-((benzo[d]oxazol-4-ylamino)methyl)-6-chloroquinolin-2(1H)-one. LCMS (method 4): Rt 1.71 min, m/z 326.1 [M+H]$^+$.

Example 15

6-methoxy-3-(((2-methylbenzo[d]thiazol-5-yl)amino)methyl)quinolin-2(1H)-one (I-21)

Library Protocol B:

6-Methoxy-2-oxo-1,2-dihydroquinoline-3-carbaldehyde (4.15 mg, 20 umol) was added as a solid to a 0.2 M solution of 4-aminobenzonitrile in DMA (165 uL, 33 umol). An additional volume of 1,2-dichoroethane (150 mL) was added, and the mixture was agitated at room temperature for 5 minutes. The resultant mixture was charged with a 0.2 M suspension of sodium triacetoxyborohydride in DCE (200 uL, 40 umol) and was agitated overnight at room temperature. After LC-MS analysis confirmed the presence of reductive amination product, the mixture was partitioned between ethyl acetate (500 uL) and saturated aqueous sodium bicarbonate solution (500 uL). The organic layer was transferred, and the aqueous layer was extracted once more with fresh ethyl acetate (500 uL). The organic layers were combined and concentrated under reduced pressure with heat (50° C.).

The crude residue was dissolved in DMSO (500 uL) and purified by mass-triggered preparatory HPLC to yield the title compound I-21 (1.8 mg, 25% yield). LC-MS (Method 4): Rt 1.18 min, m/z 352.14 [M+H]⁺.

TABLE 2

The compounds listed in Table 1 were prepared using methods similar to the one described for the preparation of I-1 & I-21.

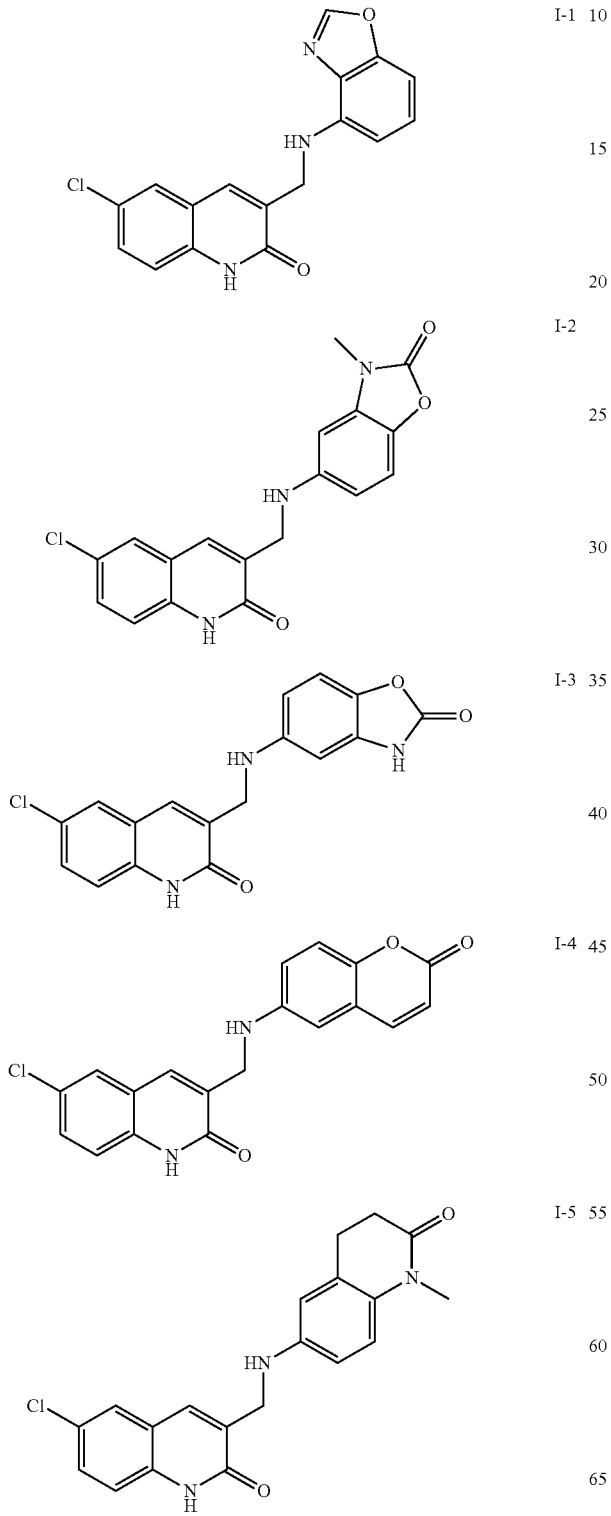

TABLE 2-continued

The compounds listed in Table 1 were prepared using methods similar to the one described for the preparation of I-1 & I-21.

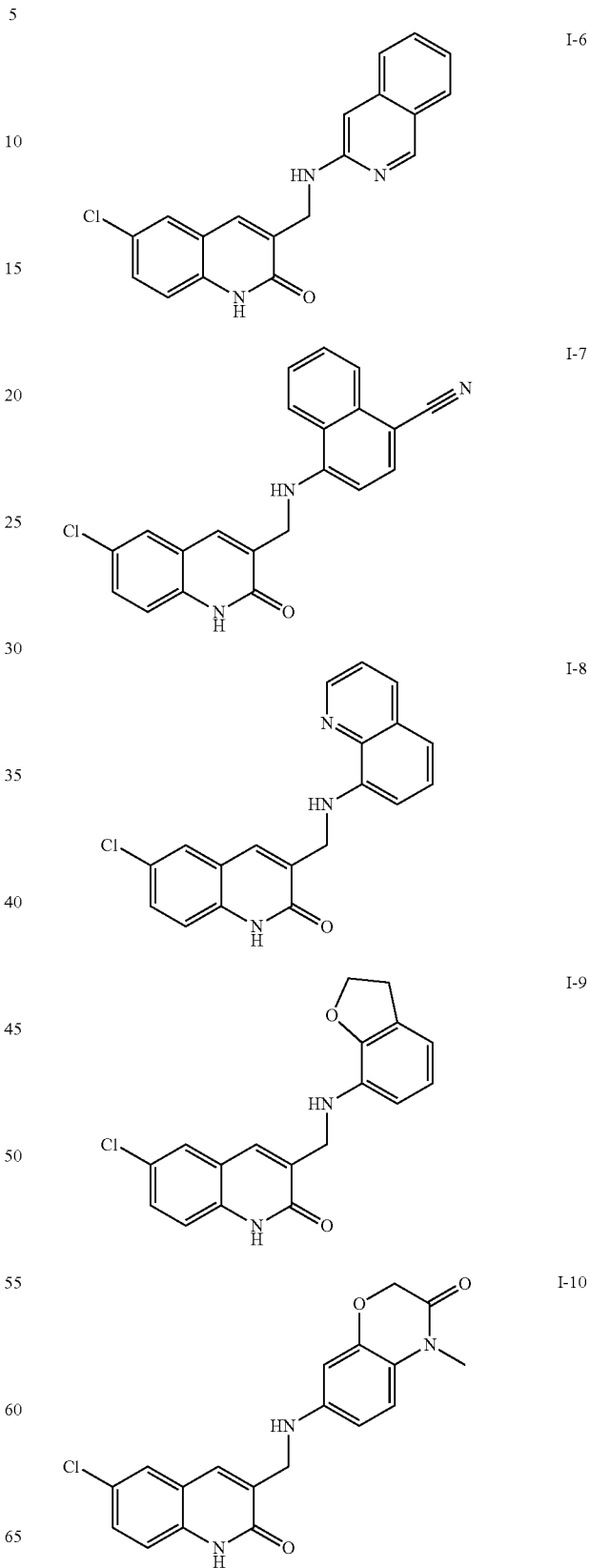

TABLE 2-continued
The compounds listed in Table 1 were prepared using methods similar to the one described for the preparation of I-1 & I-21.
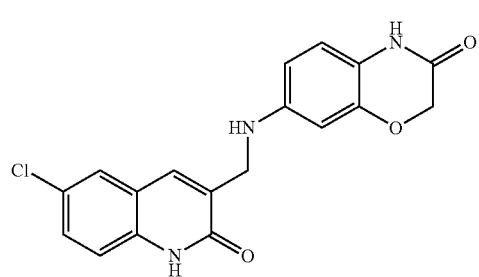 [SMILES: O=C1COc2cc(NCc3cc4cc(Cl)ccc4[nH]c3=O)ccc2N1]
I-11
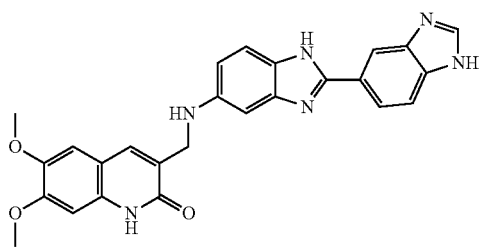 [SMILES: COc1cc2cc(CNc3ccc4[nH]c(-c5ccc6[nH]cnc6c5)nc4c3)c(=O)[nH]c2cc1OC]
I-12
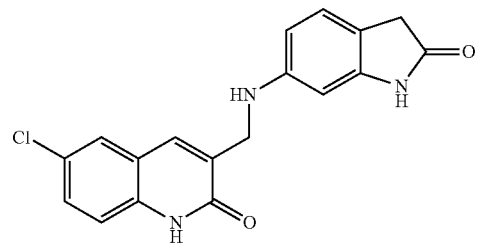 [SMILES: O=C1Cc2ccc(NCc3cc4cc(Cl)ccc4[nH]c3=O)cc2N1]
I-13
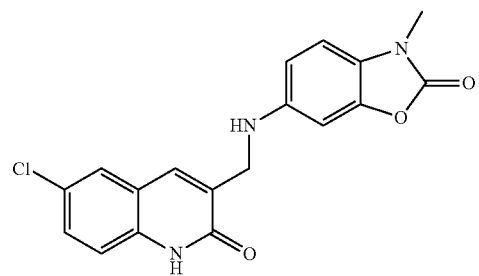 [SMILES: Cn1c(=O)oc2cc(NCc3cc4cc(Cl)ccc4[nH]c3=O)ccc21]
I-14
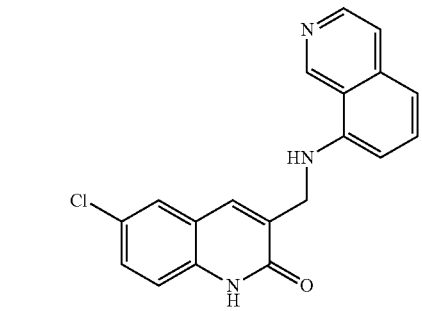 [SMILES: O=c1[nH]c2ccc(Cl)cc2cc1CNc1cccc2ccncc12]
I-15
TABLE 2-continued
The compounds listed in Table 1 were prepared using methods similar to the one described for the preparation of I-1 & I-21.
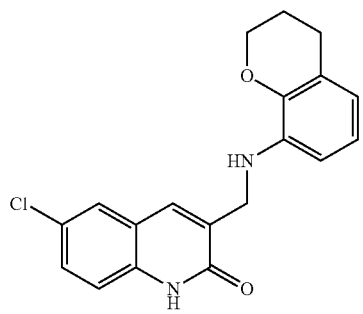 [SMILES: O=c1[nH]c2ccc(Cl)cc2cc1CNc1cccc2c1OCCC2]
I-16
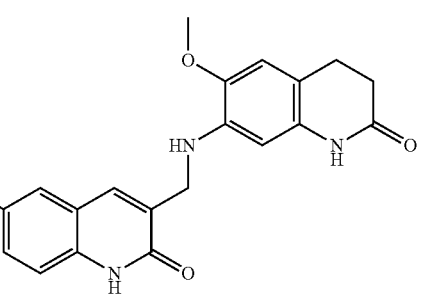
I-17
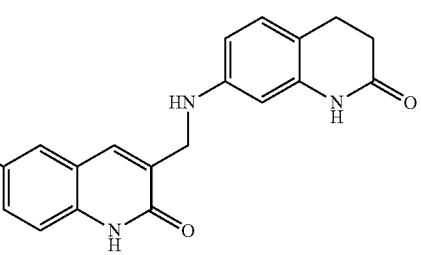
I-18
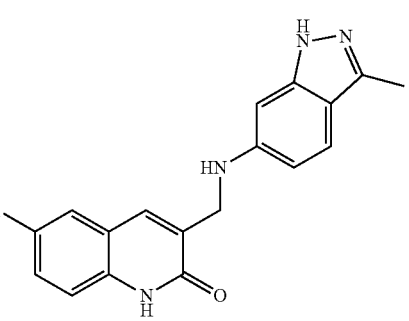
I-19
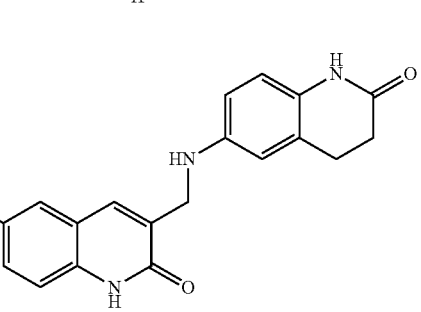
I-20

TABLE 2-continued
The compounds listed in Table 1 were prepared using methods similar to the one described for the preparation of I-1 & I-21.
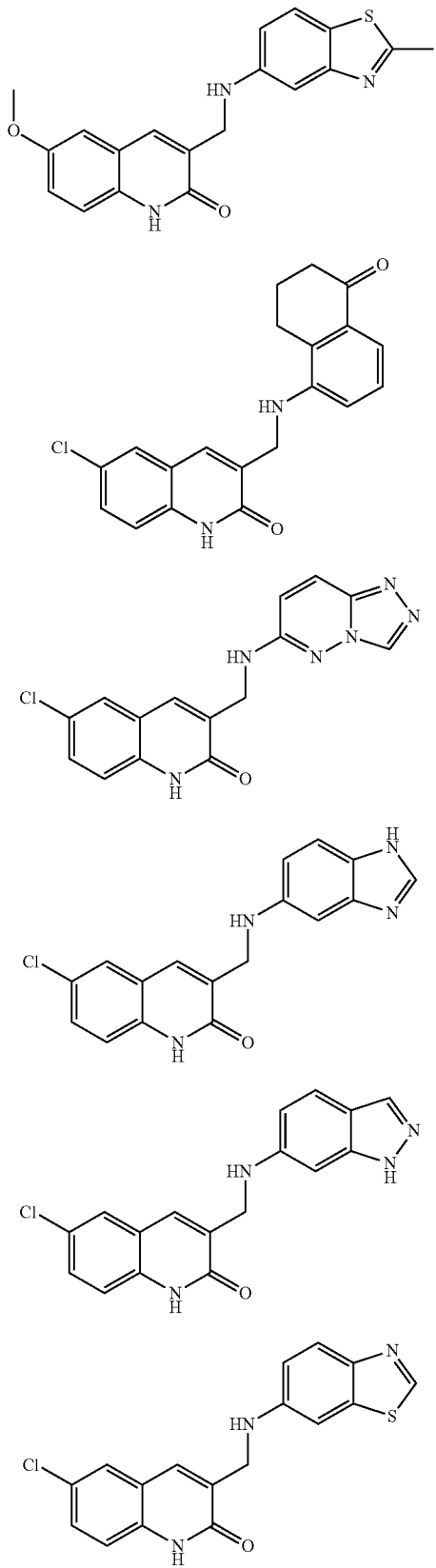
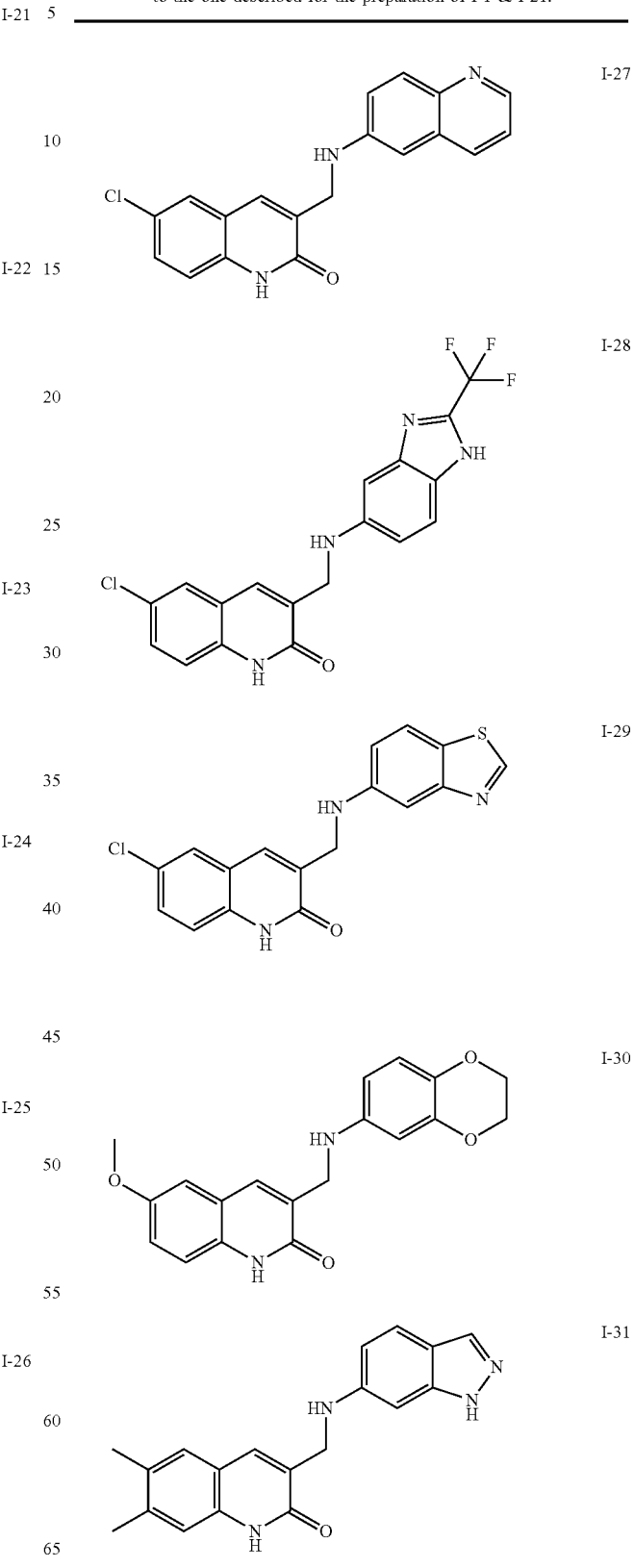

TABLE 2-continued
The compounds listed in Table 1 were prepared using methods similar to the one described for the preparation of I-1 & I-21.
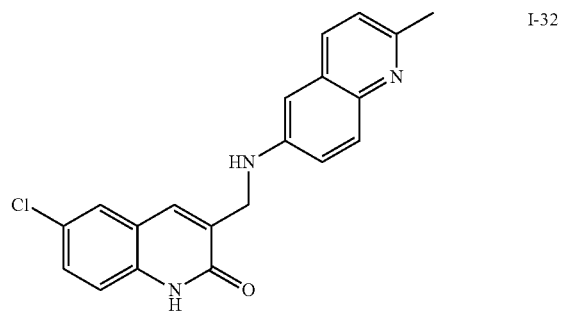
I-32
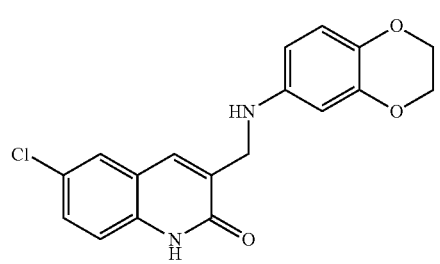 [SMILES: O=c1[nH]c2ccc(Cl)cc2cc1CNc1ccc2c(c1)OCCO2]
I-33
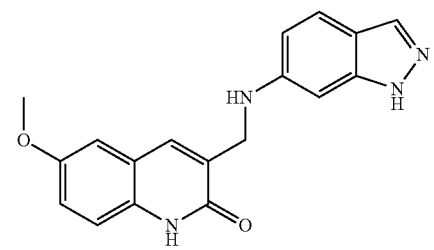 [SMILES: COc1ccc2[nH]c(=O)c(CNc3ccc4cn[nH]c4c3)cc2c1]
I-34
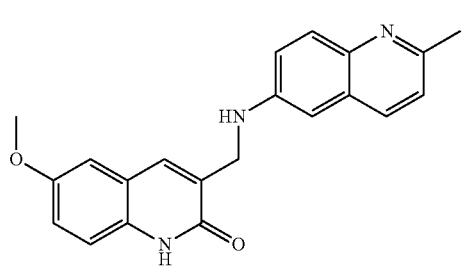 [SMILES: COc1ccc2[nH]c(=O)c(CNc3ccc4nc(C)ccc4c3)cc2c1]
I-35
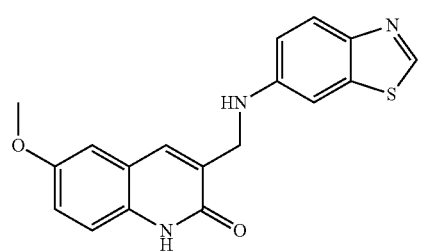 [SMILES: COc1ccc2[nH]c(=O)c(CNc3ccc4ncsc4c3)cc2c1]
I-36
TABLE 2-continued
The compounds listed in Table 1 were prepared using methods similar to the one described for the preparation of I-1 & I-21.
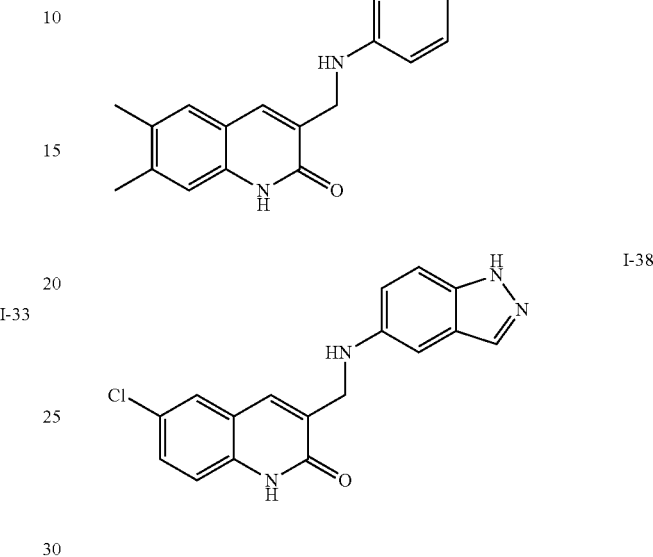
I-37
I-38
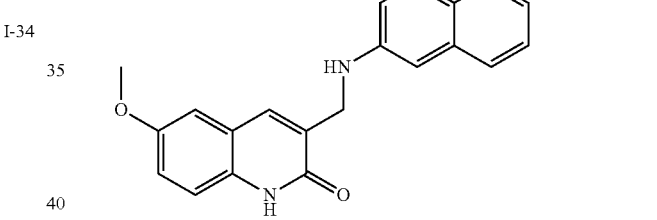
I-39
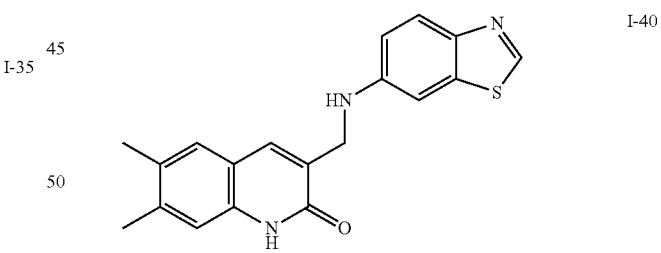
I-40
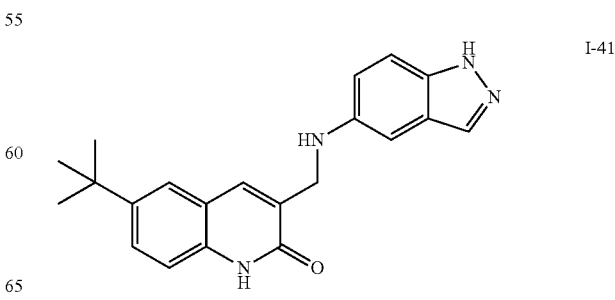
I-41

TABLE 3

LCMS signal and NMR chemical shifts of each compound listed in Table 2.

| Compounds | LCMS[a] | Chemical Name |
|---|---|---|
| I-1 | m/z: 326.03 (M + H)+ Rt (min): 1.35 | 3-{[(1,3-benzoxazol-4-yl)amino]methyl}-6-chloro-1,2-dihydroquinolin-2-one |
| I-2 | m/z: 355.89 (M + H)+ Rt (min): 1.17 | 6-chloro-3-{[(3-methyl-2-oxo-2,3-dihydro-1,3-benzoxazol-5-yl)amino]methyl}-1,2-dihydroquinolin-2-one |
| I-3 | m/z: 341.90 (M + H)+ Rt (min): 1.09 | 6-chloro-3-{[(2-oxo-2,3-dihydro-1,3-benzoxazol-5-yl)amino]methyl}-1,2-dihydroquinolin-2-one |
| I-4 | m/z: 352.90 (M + H)+ Rt (min): 1.19 | 6-chloro-3-{[(2-oxo-2H-chromen-6-yl)amino]methyl}-1,2-dihydroquinolin-2-one |
| I-5 | m/z: 367.95 (M + H)+ Rt (min): 1.12 | 6-chloro-3-{[(1-methyl-2-oxo-1,2,3,4-tetrahydroquinolin-6-yl)amino]methyl}-1,2-dihydroquinolin-2-one |
| I-6 | m/z: 335.94 (M + H)+ Rt (min): 1.29 | 6-chloro-3-{[(isoquinolin-3-yl)amino]methyl}-1,2-dihydroquinolin-2-one |
| I-7 | m/z: 360.06 (M + H)+ Rt (min): 1.48 | 4-{[(6-chloro-2-oxo-1,2-dihydroquinolin-3-yl)methyl]amino}naphthalene-1-carbonitrile |
| I-8 | m/z: 336.04 (M + H)+ Rt (min): 1.53 | 6-chloro-3-{[(quinolin-8-yl)amino]methyl}-1,2-dihydroquinolin-2-one |
| I-9 | m/z: 327.05 (M + H)+ Rt (min): 1.45 | 6-chloro-3-{[(2,3-dihydro-1-benzofuran-7-yl)amino]methyl}-1,2-dihydroquinolin-2-one |
| I-10 | m/z: 369.90 (M + H)+ Rt (min): 1.19 | 7-{[(6-chloro-2-oxo-1,2-dihydroquinolin-3-yl)methyl]amino}-4-methyl-3,4-dihydro-2H-1,4-benzoxazin-3-one |
| I-11 | m/z: 355.92 (M + H)+ Rt (min): 1.02 | 7-{[(6-chloro-2-oxo-1,2-dihydroquinolin-3-yl)methyl]amino}-3,4-dihydro-2H-1,4-benzoxazin-3-one |
| I-12 | | 3-({[2-(1H-1,3-benzodiazol-5-yl)-1H-1,3-benzodiazol-5-yl]amino}methyl)-6,7-dimethoxy-1,2-dihydroquinolin-2-one |
| I-13 | m/z: 339.96 (M + H)+ Rt (min): 1.03 | 6-chloro-3-{[(2-oxo-2,3-dihydro-1H-indol-6-yl)amino]methyl}-1,2-dihydroquinolin-2-one |
| I-14 | m/z: 355.91 (M + H)+ Rt (min): 1.17 | 6-chloro-3-{[(3-methyl-2-oxo-2,3-dihydro-1,3-benzoxazol-6-yl)amino]methyl}-1,2-dihydroquinolin-2-one |
| I-15 | m/z: 336.02 (M + H)+ Rt (min): 0.87 | 6-chloro-3-{[(isoquinolin-8-yl)amino]methyl}-1,2-dihydroquinolin-2-one |
| I-16 | m/z: 341.06 (M + H)+ Rt (min): 1.57 | 6-chloro-3-{[(3,4-dihydro-2H-1-benzopyran-8-yl)amino]methyl}-1,2-dihydroquinolin-2-one |
| I-17 | m/z: 383.91 (M + H)+ Rt (min): 1.16 | 6-chloro-3-{[(6-methoxy-2-oxo-1,2,3,4-tetrahydroquinolin-7-yl)amino]methyl}-1,2-dihydroquinolin-2-one |
| I-18 | m/z: 353.96 (M + H)+ Rt (min): 1.11 | 6-chloro-3-{[(2-oxo-1,2,3,4-tetrahydroquinolin-7-yl)amino]methyl}-1,2-dihydroquinolin-2-one |
| I-19 | m/z: 338.93 (M + H)+ Rt (min): 1.12 | 6-chloro-3-{[(3-methyl-1H-indazol-6-yl)amino]methyl}-1,2-dihydroquinolin-2-one |
| I-20 | m/z: 353.93 (M + H)+ Rt (min): 0.99 | 6-chloro-3-{[(2-oxo-1,2,3,4-tetrahydroquinolin-6-yl)amino]methyl}-1,2-dihydroquinolin-2-one |
| I-21 | m/z: 352.14 (M + H)+ Rt (min): 1.18 | 6-methoxy-3-{[(2-methyl-1,3-benzothiazol-5-yl)amino]methyl}-1,2-dihydroquinolin-2-one |
| I-22 | m/z: 353.00 (M + H)+ Rt (min): 1.25 | 6-chloro-3-{[(5-oxo-5,6,7,8-tetrahydronaphthalen-1-yl)amino]methyl}-1,2-dihydroquinolin-2-one |
| I-23 | m/z: 326.96 (M + H)+ Rt (min): 0.85 | 6-chloro-3-[({[1,2,4]triazolo[4,3-b]pyridazin-6-yl}amino)methyl]-1,2-dihydroquinolin-2-one |
| I-24 | m/z: 324.97 (M + H)+ Rt (min): 0.81 | 3-{[(1H-1,3-benzodiazol-5-yl)amino]methyl}-6-chloro-1,2-dihydroquinolin-2-one |
| I-25 | m/z: 325.10 (M + H)+ Rt (min): 1.12 | 6-chloro-3-{[(1H-indazol-6-yl)amino]methyl}-1,2-dihydroquinolin-2-one |
| I-26 | m/z: 342.10 (M + H)+ Rt (min): 1.23 | 3-{[(1,3-benzothiazol-6-yl)amino]methyl}-6-chloro-1,2-dihydroquinolin-2-one |
| I-27 | m/z: 336.10 (M + H)+ Rt (min): 0.89 | 6-chloro-3-{[(quinolin-6-yl)amino]methyl}-1,2-dihydroquinolin-2-one |
| I-28 | m/z: 392.96 (M + H)+ Rt (min): 1.22 | 6-chloro-3-({[2-(trifluoromethyl)-1H-1,3-benzodiazol-5-yl]amino}methyl)-1,2-dihydroquinolin-2-one |
| I-29 | m/z: 341.92 (M + H)+ Rt (min): 1.27 | 3-{[(1,3-benzothiazol-5-yl)amino]methyl}-6-chloro-1,2-dihydroquinolin-2-one |
| I-30 | m/z: 339.16 (M + H)+ Rt (min): 1.08 | 3-{[(2,3-dihydro-1,4-benzodioxin-6-yl)amino]methyl}-6-methoxy-1,2-dihydroquinolin-2-one |
| I-31 | m/z: 319.19 (M + H)+ Rt (min): 1.14 | 3-{[(1H-indazol-6-yl)amino]methyl}-6,7-dimethyl-1,2-dihydroquinolin-2-one |
| I-32 | m/z: 350.16 (M + H)+ Rt (min): 0.91 | 6-chloro-3-{[(2-methylquinolin-6-yl)amino]methyl}-1,2-dihydroquinolin-2-one |
| I-33 | m/z: 343.11 (M + H)+ Rt (min): 1.28 | 6-chloro-3-{[(2,3-dihydro-1,4-benzodioxin-6-yl)amino]methyl}-1,2-dihydroquinolin-2-one |
| I-34 | m/z: 321.14 (M + H)+ Rt (min): 0.96 | 3-{[(1H-indazol-6-yl)amino]methyl}-6-methoxy-1,2-dihydroquinolin-2-one |
| I-35 | m/z: 346.19 (M + H)+ Rt (min): 0.78 | 6-methoxy-3-{[(2-methylquinolin-6-yl)amino]methyl}-1,2-dihydroquinolin-2-one |
| I-36 | m/z: 338.14 (M + H)+ Rt (min): 1.06 | 3-{[(1,3-benzothiazol-6-yl)amino]methyl}-6-methoxy-1,2-dihydroquinolin-2-one |
| I-37 | m/z: 344.24 (M + H)+ Rt (min): 0.94 | 6,7-dimethyl-3-{[(2-methylquinolin-6-yl)amino]methyl}-1,2-dihydroquinolin-2-one |
| I-38 | m/z: 325.11 (M + H)+ Rt (min): 1.0 | 6-chloro-3-{[(1H-indazol-5-yl)amino]methyl}-1,2-dihydroquinolin-2-one |
| I-39 | m/z: 332.19 (M + H)+ Rt (min): 0.76 | 6-methoxy-3-{[(quinolin-6-yl)amino]methyl}-1,2-dihydroquinolin-2-one |
| I-40 | m/z: 336.15 (M + H)+ Rt (min): 1.25 | 3-{[(1,3-benzothiazol-6-yl)amino]methyl}-6,7-dimethyl-1,2-dihydroquinolin-2-one |
| I-41 | m/z: 347.25 (M + H)+ Rt (min): 1.05 | 6-tert-butyl-3-{[(1H-indazol-5-yl)amino]methyl}-1,2-dihydroquinolin-2-one |

[a]LCMS data are determined by Method 4.

Example 16

(S)-3-(1-(1-acetyl-2,3-dihydro-1H-pyrrolo[3,2-c]pyridin-4-ylamino)ethyl)-6-chloroquinolin-2(1H)-one (I-42)

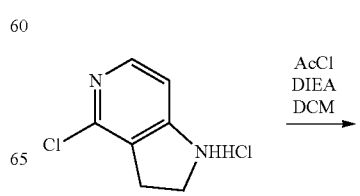

-continued

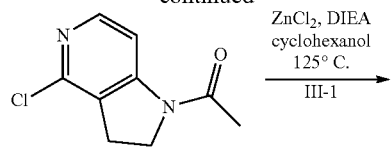

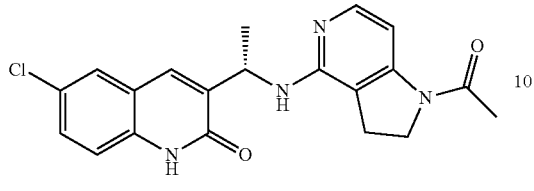

I-42

Step-1: 1-(4-chloro-2,3-dihydro-1H-pyrrolo[3,2-c]pyridin-1-yl)ethanone

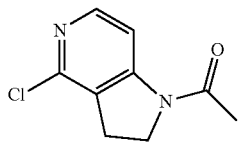

A stirred suspension of 4-chloro-2,3-dihydro-1H-pyrrolo[3,2-c]pyridine hydrochloride (349.7 mg, 1.830 mmol) in DCM (10 ml) was treated with DIEA (0.69 mL, 3.95 mmol), upon which the material went into solution. The solution was treated with acetyl chloride (0.15 mL, 2.11 mmol) and stirred at ambient temperature overnight. LCMS showed the reaction had gone to completion. The solution was diluted with EtOAc (40 mL), washed with brine and water (40 mL each), dried ($Na_2SO_4$), filtered, and evaporated under reduced pressure to provide 1-(4-chloro-2,3-dihydro-1H-pyrrolo[3,2-c]pyridin-1-yl)ethanone (319.7 mg, 1.626 mmol, 89% yield) as an off-white solid. $^1$H NMR (300 MHz, DMSO-$d_6$): δ ppm 8.15 (d, J=5.28 Hz, 1H), 7.85 (br d, J=4.69 Hz, 1H), 4.18 (br t, J=8.35 Hz, 2H), 3.15 (br t, J=8.50 Hz, 2H), 2.19 (s, 3H). LCMS (Method 1): Rt 1.63 min., m/z 197.02 $[M+H]^+$.

Step-2: (S)-3-(1-(1-acetyl-2,3-dihydro-1H-pyrrolo[3,2-c]pyridin-4-ylamino)ethyl)-6-chloro quinolin-2(1H)-one (I-42)

A suspension of (S)-3-(1-aminoethyl)-6-chloroquinolin-2(1H)-one hydrochloride III-1 (59.8 mg, 0.231 mmol), 1-(4-chloro-2,3-dihydro-1H-pyrrolo[3,2-c]pyridin-1-yl)ethanone (29.3 mg, 0.149 mmol), and zinc chloride (20.9 mg, 0.153 mmol) in cyclohexanol (321 μL, 3.04 mmol) was treated with DIEA (0.11 mL, 0.630 mmol) and stirred at 125° C. for six days. The sample was diluted with MeOH and DCM, treated with silica gel, and evaporated under reduced pressure. The sample was chromatographed by Biotage MPLC (10 g silica gel column) with 0 to 10% MeOH in DCM, with isocratic elution at 4.4% MeOH while peaks eluted to provide (S)-3-(1-(1-acetyl-2,3-dihydro-1H-pyrrolo[3,2-c]pyridin-4-ylamino)ethyl)-6-chloroquinolin-2(1H)-one I-42 (3.3 mg, 8.62 μmol, 3.74% yield). LCMS (Method 1): Rt 1.85 min., m/z 382.99 $[M+H]^+$.

Example 17

(S)-6-chloro-3-(1-(1-(methylsulfonyl)-2,3-dihydro-1H-pyrrolo[3,2-c]pyridin-4-ylamino)ethyl)quinolin-2(1H)-one (I-43)

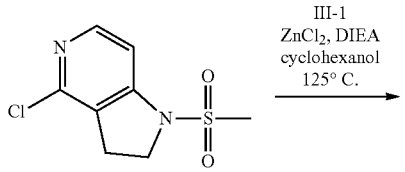

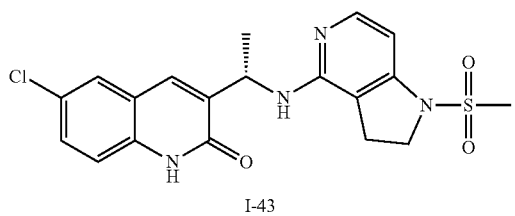

I-43

Step-1: 4-chloro-1-(methylsulfonyl)-2,3-dihydro-1H-pyrrolo[3,2-c]pyridine

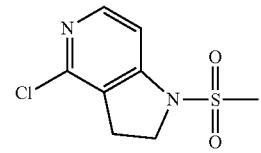

A stirred suspension of 4-chloro-2,3-dihydro-1H-pyrrolo[3,2-c]pyridine hydrochloride (299.8 mg, 1.569 mmol) in DCM (8.5 ml) was treated with DIEA (0.59 mL, 3.38 mmol), upon which the material went into solution. The solution was treated with MsCl (0.14 mL, 1.797 mmol) and stirred at ambient temperature overnight. LCMS showed the reaction had gone to completion. The solution was diluted with EtOAc (40 mL), washed with brine and water (40 mL each), dried ($Na_2SO_4$), filtered, and evaporated under reduced pressure to provide 4-chloro-1-(methylsulfonyl)-2,3-dihydro-1H-pyrrolo[3,2-c]pyridine (307.2 mg, 1.320 mmol, 84% yield) as a white solid. $^1$H NMR (300 MHz, DMSO-$d_6$): δ ppm 8.18 (d, J=5.57 Hz, 1H), 7.19 (d, J=5.28 Hz, 1H), 4.06 (t, J=8.79 Hz, 2H), 3.08-3.22 (m, 5H). LCMS (Method 1): Rt 1.70 min., m/z 232.99 $[M+H]^+$.

Step-2: (S)-6-chloro-3-(1-(1-(methylsulfonyl)-2,3-dihydro-1H-pyrrolo[3,2-c]pyridin-4-ylamino)ethyl)quinolin-2(1H)-one (I-43)

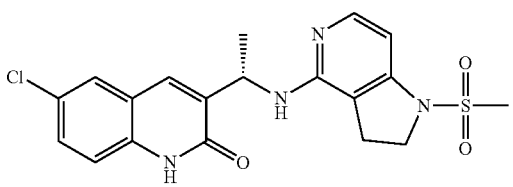 [SMILES: C[C@H](Nc1nccc2c1CCN2S(C)(=O)=O)c1cc2cc(Cl)ccc2[nH]c1=O]

A mixture of (S)-3-(1-aminoethyl)-6-chloroquinolin-2(1H)-one hydrochloride III-1 (60.7 mg, 0.234 mmol), 4-chloro-1-(methylsulfonyl)-2,3-dihydro-1H-pyrrolo[3,2-c]pyridine (34.0 mg, 0.146 mmol), and zinc chloride (25.8 mg, 0.189 mmol) was placed under nitrogen in a 2-dram vial. Cyclohexanol (0.32 mL, 3.03 mmol) and DIEA (0.11 mL, 0.630 mmol) were added by syringe and the mixture was stirred at 125° C. five days. The sample was diluted with MeOH and DCM, treated with silica gel, and evaporated under reduced pressure. The sample was chromatographed by Biotage MPLC (10 g silica gel column) with 0 to 10% MeOH in DCM, with isocratic elution at 4% MeOH to provide impure (S)-6-chloro-3-(1-(1-(methylsulfonyl)-2,3-dihydro-1H-pyrrolo[3,2-c]pyridin-4-ylamino)ethyl)quinolin-2(1H)-one (8.3 mg, 0.020 mmol, 8.46% yield). LCMS (Method 1): Rt 1.94 min., m/z 418.90 [M+H]$^+$.

Example 18

(S)-3-(1-(1-acetyl-2,3-dihydro-1H-pyrido[3,4-b][1,4]oxazin-5-ylamino)ethyl)-6-chloroquinolin-2(1H)-one (I-44)

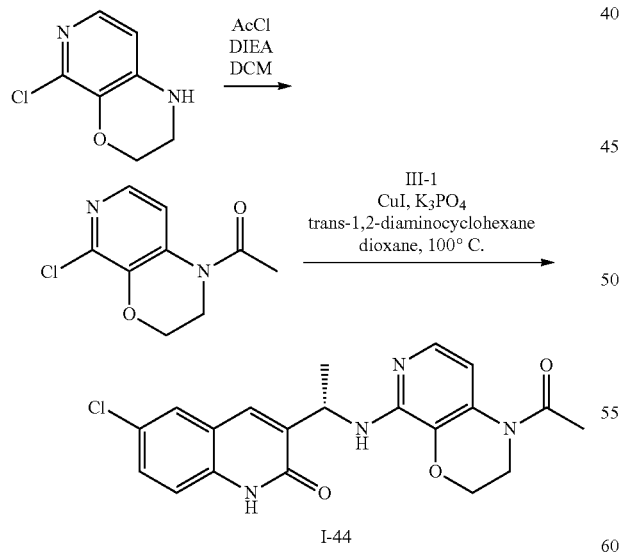

Step-1: 1-(5-chloro-2,3-dihydro-1H-pyrido[3,4-b][1,4]oxazin-1-yl)ethanone

A solution of 5-chloro-2,3-dihydro-1H-pyrido[3,4-b][1,4]oxazine (0.50 g, 2.93 mmol) in DCM (15 ml) was treated with DIEA (1.05 ml, 6.01 mmol) and acetyl chloride (0.42 ml, 5.91 mmol) and stirred at ambient temperature overnight. LCMS indicated the reaction had gone cleanly to completion. The solution was diluted with EtOAc (50 mL), washed with brine and water (50 mL each), dried (Na$_2$SO$_4$), filtered, and evaporated under reduced pressure to provide 1-(5-chloro-2,3-dihydro-1H-pyrido[3,4-b][1,4]oxazin-1-yl)ethanone (529.4 mg, 2.490 mmol, 85% yield) as a light yellow solid, pure enough for use as is. 1H NMR (300 MHz, DMSO-d$_6$): δ ppm 8.04 (br s, 1H), 7.85 (d, J=5.57 Hz, 1H), 4.35-4.47 (m, 2H), 3.88-3.98 (m, 2H), 2.31 (s, 3H). LCMS (Method 1): Rt 1.52 min., m/z+212.99 [M+H]$^+$.

Step-2: (S)-3-(1-(1-acetyl-2,3-dihydro-1H-pyrido[3,4-b][1,4]oxazin-5-ylamino)ethyl)-6-chloroquinolin-2(1H)-one (I-44)

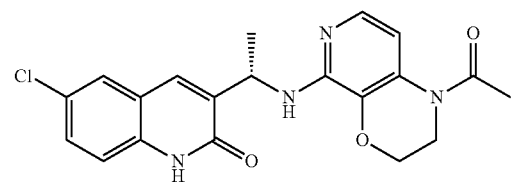 [SMILES: CC(=O)N1CCOc2c1ccnc2N[C@@H](C)c1cc2cc(Cl)ccc2[nH]c1=O]

A 40 mL vial was charged with (S)-3-(1-aminoethyl)-6-chloroquinolin-2(1H)-one hydrochloride III-1 (50.0 mg, 0.193 mmol), copper(I) iodide (68.6 mg, 0.360 mmol), 1-(5-chloro-2,3-dihydro-1H-pyrido[3,4-b][1,4]oxazin-1-yl)ethanone (69.9 mg, 0.329 mmol), and tripotassium phosphate (342.5 mg, 1.614 mmol) and placed under nitrogen. Dioxane (5.5 ml) and trans-1,2-diaminocyclohexane (0.04 mL, 0.333 mmol) were added by syringe and the mixture was stirred at 100° C. for 24 h. The sample was diluted with MeOH, treated with silica gel, and evaporated under reduced pressure. The material was chromatographed by Biotage MPLC (10 g silica gel cartridge) with 0 to 100% EtOAc in hexanes followed by with 10% MeOH in EtOAc to provide very impure (S)-3-(1-(1-acetyl-2,3-dihydro-1H-pyrido[3,4-b][1,4]oxazin-5-ylamino)ethyl)-6-chloroquinolin-2(1H)-one (15.9 mg, 0.040 mmol, 20.66% yield). LCMS (Method 1): Rt 1.83 min., m/z 398.92 [M+H]$^+$. The material was registered in CORE and sent to Branford for further purification; was not returned to WTN, no NMR.

Example 19

(S)-3-(1-(1-acetyl-2,3-dihydro-1H-pyrrolo[3,2-c]pyridin-4-ylamino)ethyl)-6-chloroquinolin-2(1H)-one (I-46)

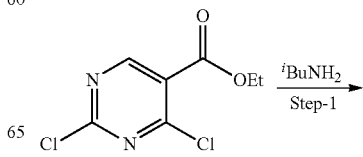

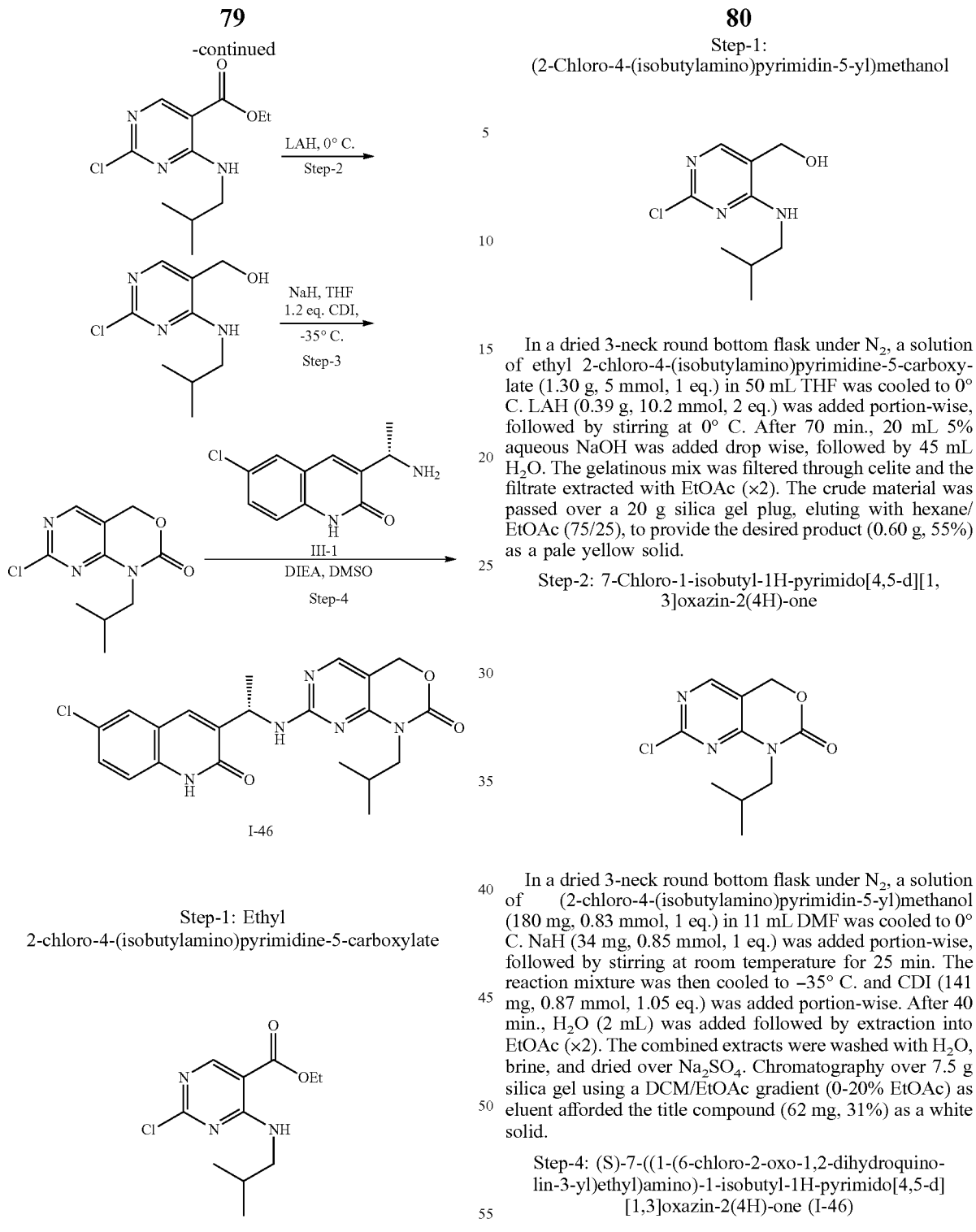

Step-1: (2-Chloro-4-(isobutylamino)pyrimidin-5-yl)methanol

In a dried 3-neck round bottom flask under N$_2$, a solution of ethyl 2-chloro-4-(isobutylamino)pyrimidine-5-carboxylate (1.30 g, 5 mmol, 1 eq.) in 50 mL THF was cooled to 0° C. LAH (0.39 g, 10.2 mmol, 2 eq.) was added portion-wise, followed by stirring at 0° C. After 70 min., 20 mL 5% aqueous NaOH was added drop wise, followed by 45 mL H$_2$O. The gelatinous mix was filtered through celite and the filtrate extracted with EtOAc (×2). The crude material was passed over a 20 g silica gel plug, eluting with hexane/EtOAc (75/25), to provide the desired product (0.60 g, 55%) as a pale yellow solid.

Step-2: 7-Chloro-1-isobutyl-1H-pyrimido[4,5-d][1,3]oxazin-2(4H)-one

In a dried 3-neck round bottom flask under N$_2$, a solution of (2-chloro-4-(isobutylamino)pyrimidin-5-yl)methanol (180 mg, 0.83 mmol, 1 eq.) in 11 mL DMF was cooled to 0° C. NaH (34 mg, 0.85 mmol, 1 eq.) was added portion-wise, followed by stirring at room temperature for 25 min. The reaction mixture was then cooled to −35° C. and CDI (141 mg, 0.87 mmol, 1.05 eq.) was added portion-wise. After 40 min., H$_2$O (2 mL) was added followed by extraction into EtOAc (×2). The combined extracts were washed with H$_2$O, brine, and dried over Na$_2$SO$_4$. Chromatography over 7.5 g silica gel using a DCM/EtOAc gradient (0-20% EtOAc) as eluent afforded the title compound (62 mg, 31%) as a white solid.

Step-4: (S)-7-((1-(6-chloro-2-oxo-1,2-dihydroquinolin-3-yl)ethyl)amino)-1-isobutyl-1H-pyrimido[4,5-d][1,3]oxazin-2(4H)-one (I-46)

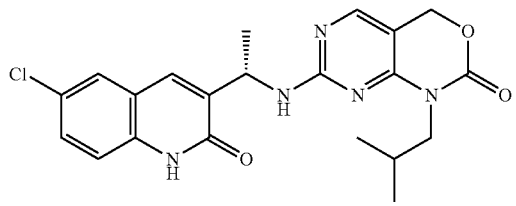 [SMILES: CC(C)CN1C(=O)OCc2cnc(N[C@@H](C)c3cc4cc(Cl)ccc4[nH]c3=O)nc21]

Step-1: Ethyl 2-chloro-4-(isobutylamino)pyrimidine-5-carboxylate

A solution of ethyl 2,4-dichloropyrimidine-5-carboxylate (1.65 g, 7.5 mmol, 1 eq.) in 45 mL DCM/THF (70/30) was cooled to −78° C. and treated with i-butylamine (552 mg, 7.5 mmol, 1 eq.) and TEA (1.5 g, 15 mmol, 2 eq.). After 80 minutes, the reaction was poured into water and extracted with DCM (×2). The combined extracts were washed with saturated aqueous NaHCO$_3$, dried over Na$_2$SO$_4$ and evaporated to provide 1.79 g of crude product. Chromatography over 60 g silica gel with DCM/EtOAc (99/1) as eluent afforded 1.05 g title compound (53%) as white waxy solid.

A mixture of 7-chloro-1-isobutyl-1H-pyrimido[4,5-d][1,3]oxazin-2(4H)-one (60 mg, 0.25 mmol, 1 eq.), (S)-3-(1-aminoethyl)-6-chloroquinolin-2(1H)-one III-1 free base (55 mg, 0.25 mmol, 1 eq.) and DIPEA (37 mg, 0.29 mmol, 1.1 eq.) in 2 mL DMSO was heated in a sealed tube at 110° C. for 50 minutes. The reaction was then poured into water and extracted with EtOAc (×2). The combined extracts were washed with brine and dried over Na$_2$SO$_4$. The crude extract was chromatographed over 3.5 g silica gel eluting with an EtOAc to EtOAc/EtOH (98/2) gradient to afford I-46 (19 mg, 18%) as a white solid. $^1$H-NMR (300 MHz, CDCl$_3$, 50° C.) δ ppm: 10.5 (broad s, 0.8H), 7.90 (s, 1H), 7.62 (s, 1H), 7.49 (s, 1H), 7.40 (d, J=7.98, 1H), 7.16 (d, J=8.52, 1H), 6.00 (d, J=6.84, 1H), 5.27 (m, 1H), 5.06 (s, 2H), 3.82 (m, 2H), 2.05 (m, 1H), 1.61 (d, J=6.87, 3H) 0.82 (m, 6H). LC/MS (Method 3): Rt 4.6 min., m/z 428 [M+H]$^+$.

Example 20

(S)-7-((1-(6-chloro-2-oxo-1,2-dihydroquinolin-3-yl)ethyl)amino)-1-methyl-1H-pyrimido[4,5-d][1,3]oxazin-2(4H)-one (I-47)

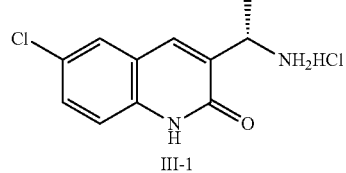

III-1

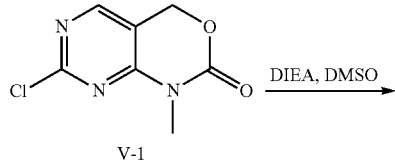

V-1

DIEA, DMSO →

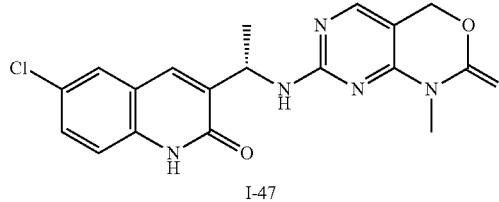

I-47

A mixture of ((S)-3-(1-aminoethyl)-6-chloroquinolin-2(1H)-one hydrochloride III-1 (243 mg, 0.94 mmol, 1.3 eq.), 7-chloro-1-methyl-1H-pyrimido[4,5-d][1,3]oxazin-2(4H)-one V-1 (144 mg, 0.72 mmol, 1 eq.) and DIEA (260 mg, 2.0 mmol, 2.8 eq.) in 4 mL DMSO in a sealed tube was heated at 110° C. for 1 hour. The reaction was then poured into water followed by extraction (2×) with EtOAc. Chromatography over 10 g silica gel using an EtOAc to EtOAc:EtOH (98/2) gradient followed by trituration with Et$_2$O provided 60 mg of I-47 as a gold solid (21%). $^1$H-NMR (300 MHz, CDCl$_3$): δ ppm 11.40 (broad s, 0.8H), 7.90 (s, 1H), 7.67 (s, 1H), 7.50 (broad s, 1H), 7.40 (dd, J=2.19, 8.79, 1H), 7.27 (m, 1H), 6.17 (d, J=8.49, 1H), 5.30 (m, 1H), 5.07 (s, 2H), 3.31 (s, 3H), 1.62 (d, J=6.87, 3H). LC/MS (Method 3): Rt 4.0 min., m/z 386 [M+H]$^+$.

Example 21

(S)-7-((1-(6-chloro-2-oxo-1,2-dihydroquinolin-3-yl)ethyl)amino)-1-methyl-1H-pyrimido[4,5-d][1,3]oxazin-2(4H)-one (I-48)

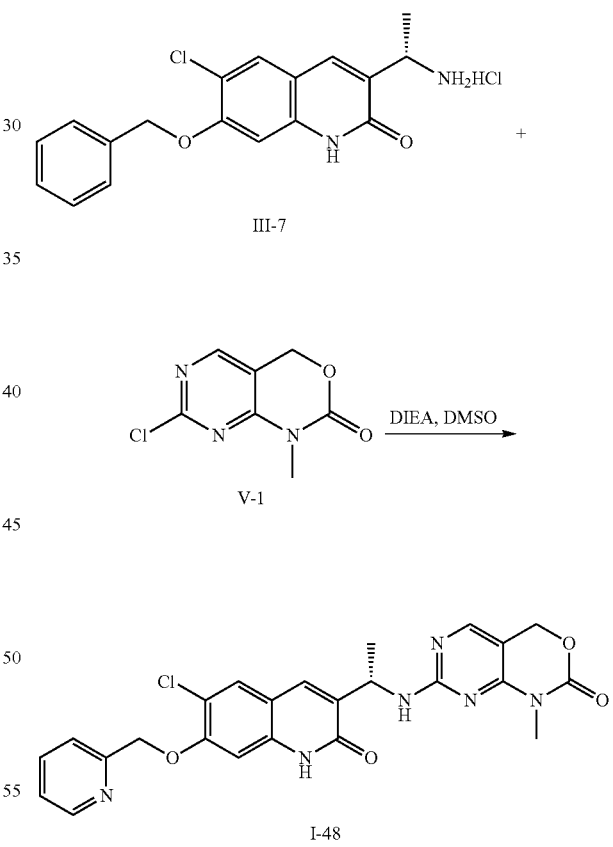

The title compound I 48 was prepared in the same procedure described for example 19 by using amine III-7. $^1$H NMR (300 MHz, DMSO-d$_6$): δ ppm 11.78 (br s, 1H), 8.61 (d, J=4.9 Hz, 1H), 7.98 (br s, 1H), 7.91-7.85 (m, 1H), 7.79 (s, 1H), 7.75-7.62 (m, 2H), 7.56 (d, J=7.7 Hz, 1H), 7.39-7.35 (m, 1H), 7.01 (s, 1H), 5.28 (s, 2H), 5.16-5.09 (m, 3H), 3.24-3.20 (m, 3H), 1.38 (d, J=6.9 Hz, 3H). LCMS (Method-3): Rt 3.75 min, m/z 493.1[M+H]$^+$.

Example 22

(S)-7-((1-(6-chloro-2-oxo-1,2-dihydroquinolin-3-yl)ethyl)amino)-1H-pyrimido[4,5-d][1,3]oxazin-2(4H)-one (I-49)

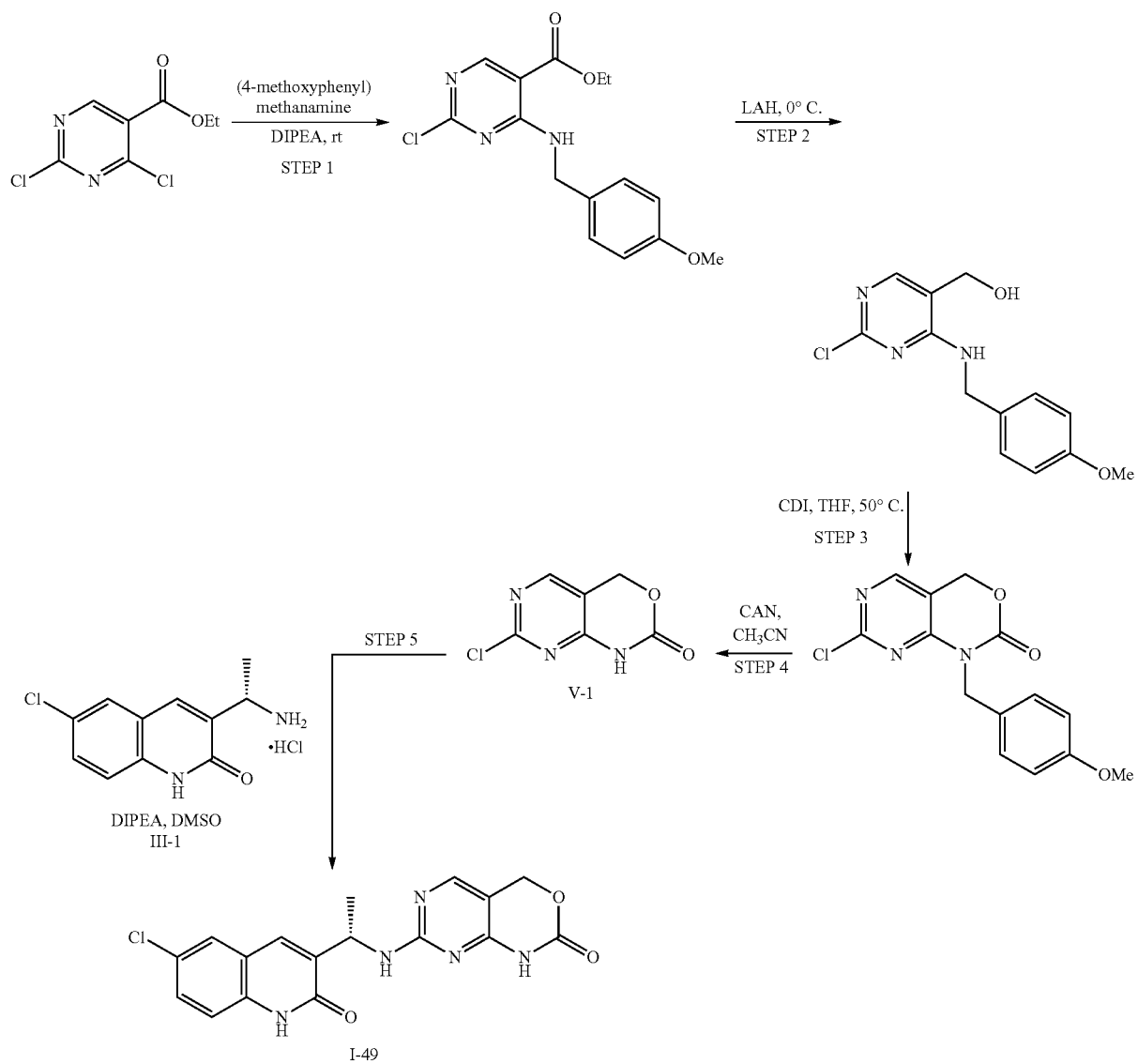

Step-1: Ethyl 2-chloro-4-((4-methoxybenzyl)amino)pyrimidine-5-carboxylate

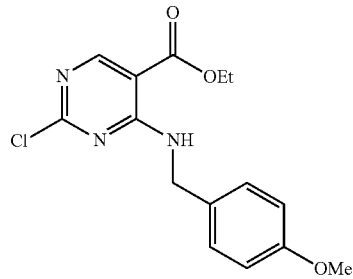 [SMILES: CCOC(=O)c1cnc(Cl)nc1NCc1ccc(OC)cc1]

To an ice-cold solution of ethyl 2,4-dichloropyrimidine-5-carboxylate (10 g, 45.2 mmol) in anhydrous EtOH (100 mL) was added neat (4-methoxyphenyl)methanamine (7.68 mL, 58.8 mmol) and DIEA (16 mL, 91.0 mmol). The reaction mixture was stirred at 0° C. for 2 h 30 min, then diluted with EtOH and filtered. The filtrate cake was washed with EtOH and $CH_2Cl_2$. The filtrates were combined and concentrated. The crude was triturated with $Et_2O$/MeOH to provide 2 g of the title compound. The rest of material was purified by ISCO, using a gradient elution of EtOAc in $CH_2Cl_2$, to afford 6.5 g of the title compound. Total yield obtained was 8.5 g, 59%.

Step-2: (2-chloro-4-((4-methoxybenzyl)amino)pyrimidin-5-yl)methanol

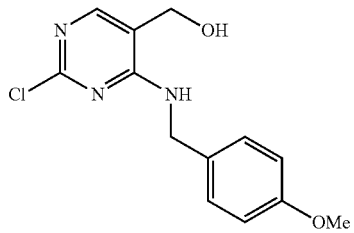 [SMILES: COc1ccc(CNc2nc(Cl)ncc2CO)cc1]

To an ice-cold solution of ethyl 2-chloro-4-((4-methoxybenzyl)amino)pyrimidine-5-carboxylate (6.5 g, 20.2 mmol) in 160 mL of THF was added LAH (20.2 mL, 40.4 mmol; 2M in THF) drop wise. After stirring at 0° C. for 2 h the reaction was quenched by slow addition of 25 mL of 0.5 M NaOH. The reaction mixture was diluted with $CH_2Cl_2$, stirred for 10 min and filtered through celite. The organic phase was dried over $Na_2SO_4$, filtered and concentrated to dryness under reduced pressure. The crude was purified by ISCO, using 120 g $SiO_2$-column with a gradient elution of EtOAc in $CH_2Cl_2$, providing 3.17 g (57% yield) of the title compound.

Step-3: 7-chloro-1-(4-methoxybenzyl)-1H-pyrimido[4,5-d][1,3]oxazin-2(4H)-one

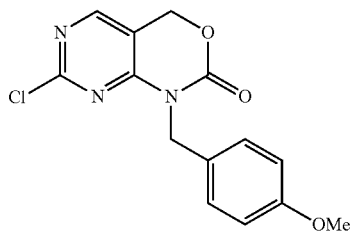 [SMILES: COc1ccc(CN2C(=O)OCc3cnc(Cl)nc32)cc1]

A mixture of (2-chloro-4-((4-methoxybenzyl)amino)pyrimidin-5-yl)methanol (3.17 g, 11.3 mmol) and CDI (2.39 g, 14.7 mmol) in THF (78 mL) was stirred in a sealed tube at 45° C. over 3 days then concentrated and purified by ISCO, using a gradient elution of EtOAc in $CH_2Cl_2$, providing the title compound (2.07 g, 60% yield).

Step-4: 7-chloro-1H-pyrimido[4,5-d][1,3]oxazin-2(4H)-one

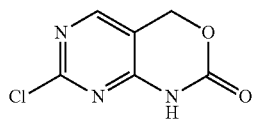 [SMILES: O=C1Nc2nc(Cl)ncc2CO1]

To a solution of 7-chloro-1-(4-methoxybenzyl)-1H-pyrimido[4,5-d][1,3]oxazin-2(4H)-one (2.07 g, 6.8 mmol) in $CH_3CN$ (90 mL) and $H_2O$ (45 mL) was added solid $(NH_4)_2[Ce(NO_3)_6]$ and the reaction mixture was stirred at room temperature for 2 h 30 min. The reaction was quenched by addition of 11 mL of 1N HCl at 0° C., and then diluted with $CH_2Cl_2$, stirred for 20 min and filtered through celite. The layers were separated. The pH of aq. layer was brought to 7-8 followed by second extraction with $CH_2Cl_2$/MeOH solvent mixture (9:1). The organic layers were combined, filtered through $SiO_2$ pad, dried over $Na_2SO_4$, and concentrated to dryness under reduced pressure. Sequential trituration with $CH_3Cl$/MeOH and $CH_2Cl_2$/MeOH provided 1.07 g (85% yield) of the pure title compound.

Step-5: (S)-7-((1-(6-chloro-2-oxo-1,2-dihydroquinolin-3-yl)ethyl)amino)-1H-pyrimido[4,5-d][1,3]oxazin-2(4H)-one (I-49)

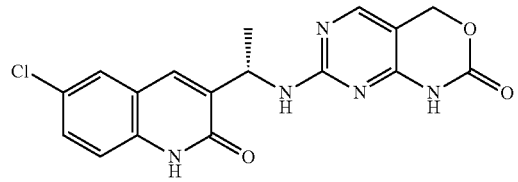 [SMILES: C[C@H](Nc1ncc2c(n1)NC(=O)OC2)c1cc2cc(Cl)ccc2[nH]c1=O]

A mixture containing 7-chloro-1H-pyrimido[4,5-d][1,3]oxazin-2(4H)-one (200 mg, 1.1 mmol), (S)-3-(1-aminoethyl)-6-chloroquinolin-2(1H)-one HCl III-1 (360 mg, 1.4 mmol) and DIEA (0.48 mL, 2.8 mmol) in 3 mL of anhydrous DMSO was stirred at 110° C. for 75 min in a sealed tube. The reaction mixture was diluted with water and extracted several times with $CH_2Cl_2$ and $CH_2Cl_2$/MeOH solvent mixture. The combined organic layers were dried over $Na_2SO_4$ and concentrated to dryness under reduced pressure. The crude was twice purified by ISCO and then triturated with $CH_2Cl_2$/MeOH to afford the title compound I-49 (16 mg, 4% yield). $^1$H NMR (300 MHz, DMSO-d6, 80° C.) δ ppm: 11.70 (br s 1H), 10.38 (br s, 1H), 7.98 (s, 1H), 7.78 (s, 1H), 7.67 (d, J=2.4 Hz, 1H), 7.45 (dd, $J_1$=8.5 Hz, $J_2$=2.4 Hz, 1H), 7.32 (d, J=8.5 Hz, 1H), 7.15 (br d, 1H), 5.15-5.25 (m, 1H), 5.13 (s, 2H), 1.45 (d, J=6.6 Hz, 3H). LCMS (Method 3), Rt 3.78 min. m/z 372.1 [M+H]$^+$.

Example 23

7-((1-(6-chloro-7-methoxy-2-oxo-1,2-dihydroquinolin-3-yl)ethyl)amino)-1-methyl-1H-pyrimido[4,5-d][1,3]oxazin-2(4H)-one. (I-50, I-51, and I-52)

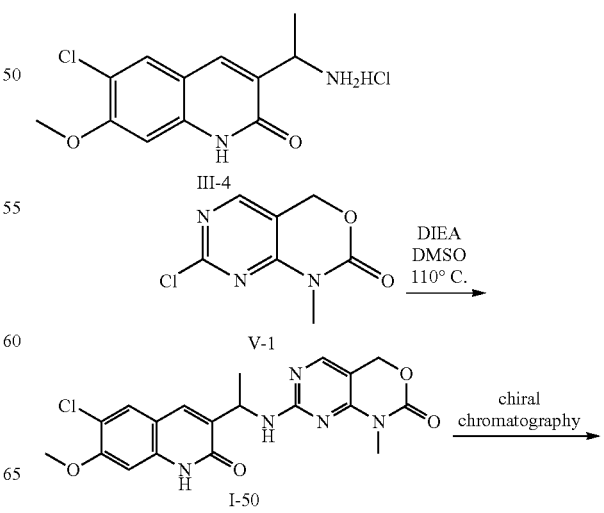

87

-continued

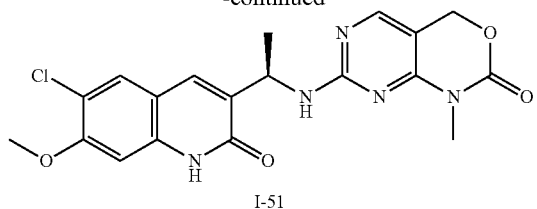

I-51

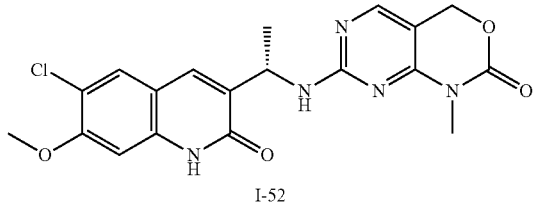

I-52

A mixture of 7-chloro-1-methyl-1H-pyrimido[4,5-d][1,3]oxazin-2(4H)-one V-1 (53.0 mg, 0.266 mmol) and 3-(1-aminoethyl)-6-chloro-7-methoxyquinolin-2(1H)-one hydrochloride III-4 (69.9 mg, 0.242 mmol) was treated with DMSO (1.5 ml) and DIEA (126 µL, 0.721 mmol). The solution was stirred at 110° C. four hours. The sample was mixed with water (20 mL) and extracted with DCM (2×15 mL) and EtOAc (15 mL). Silica gel was added and the solvent was evaporated under reduced pressure. The material was chromatographed by Biotage MPLC (10 g silica gel column) with 0 to 8% MeOH in DCM, with isocratic elution when peaks came off to provide 7-((1-(6-chloro-7-methoxy-2-oxo-1,2-dihydroquinolin-3-yl)ethyl)amino)-1-methyl-1H-pyrimido[4,5-d][1,3]oxazin-2(4H)-one (I-50) (45.1 mg, 0.093 mmol, 38.7% yield, HPLC purity 86.2% at 220 nm) as a solid racemic mixture. 1H NMR (300 MHz, DMSO-d$_6$): δ ppm 11.81 (s, 1H), 7.99 (br s, 1H), 7.62-7.80 (m, 3H), 6.94 (s, 1H), 5.07-5.21 (m, 3H), 3.87 (s, 3H), 3.23 (br s, 3H), 1.38 (d, J=7.04 Hz, 3H). LCMS (Method 1): Rt 2.22 min., m/z+415.91 [M+H]$^+$. Chiral separation of the racemic mixture was performed to provide two pure enantiomers.

Chiral HPLC Condition:

Injection Volume: 5 uL

Column: Repaired ODH

Size: 0.46*10 cm; 5 um

Mobile phase: Hex:EtOH=70:30

Flow: 1.0 ml/min

Detector: 254 nm

Instrument: LC-09

Temperature: 25° C.

(R)-7-((1-(6-chloro-7-methoxy-2-oxo-1,2-dihydroquinolin-3-yl)ethyl)amino)-1-methyl-1H-pyrimido[4,5-d][1,3]oxazin-2(4H)-one (I-51): 12 mg obtained, Chiral HPLC: Rt: 8.051 min, ee: >99.9%. LCMS (Method 4): Rt 1.16 min., m/z 416.12 [M+H]$^+$.

(S)-7-((1-(6-chloro-7-methoxy-2-oxo-1,2-dihydroquinolin-3-yl)ethyl)amino)-1-methyl-1H-pyrimido[4,5-d][1,3]oxazin-2(4H)-one (I-52) Chiral HPLC: Rt: 8.05 min, ee: >99%. LCMS (Method 1): 18 mg obtained, Chiral HPLC Rt: 10.10 min, ee: >98.7%. LCMS (Method 4): Rt 1.16 min., m/z 416.12 [M+H]$^+$.

88

Example 24

(R)-7-((1-(6-chloro-7-fluoro-2-oxo-1,2-dihydroquinolin-3-yl)ethyl)amino)-1-methyl-1H-pyrimido[4,5-d][1,3]oxazin-2(4H)-one (I-53)

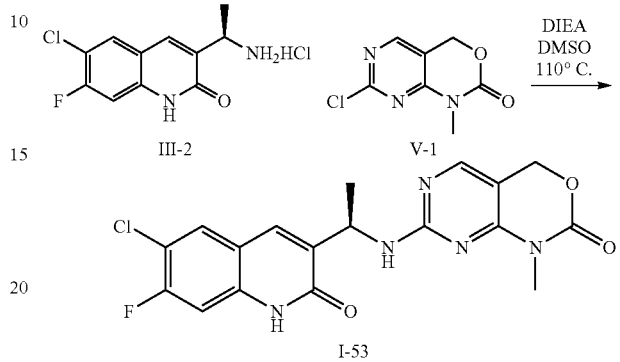

A mixture of 7-chloro-1-methyl-1H-pyrimido[4,5-d][1,3]oxazin-2(4H)-one V-1 (51.4 mg, 0.258 mmol) and (R)-3-(1-aminoethyl)-6-chloro-7-fluoroquinolin-2(1H)-one hydrochloride III-2 (70.2 mg, 0.253 mmol) was treated with DMSO (1.6 ml) and DIEA (132 µL, 0.756 mmol). The solution was stirred at 110° C. for ninety minutes. The sample was mixed with water (20 mL) and extracted with DCM (2×15 mL). The extracts were dried (Na$_2$SO$_4$) and filtered, silica gel was added, and the solvent was evaporated under reduced pressure. The material was chromatographed by Biotage MPLC (10 g silica gel column) with 0 to 100% EtOAc in hexanes, with isocratic elution when peaks came off. The product fractions were washed with water (2×40 mL), then dried (Na$_2$SO$_4$), filtered, and evaporated. The material was dissolved with AcCN (0.8 mL) and water (0.4 mL), frozen on a dry ice/acetone bath, then lyophilized to provide (R)-7-((1-(6-chloro-7-fluoro-2-oxo-1,2-dihydroquinolin-3-yl)ethyl)amino)-1-methyl-1H-pyrimido[4,5-d][1,3]oxazin-2(4H)-one (28.7 mg, 0.071 mmol, 28.1% yield, HPLC purity 86% at 220 nm) as a white solid. 1H NMR (300 MHz, DMSO-d$_6$): δ ppm 7.91-8.02 (m, 2H), 7.74 (br s, 2H), 7.13-7.26 (m, 2H), 5.06-5.21 (m, 3H), 3.23 (br s, 3H), 1.39 (d, J=6.74 Hz, 3H). LCMS (Method 1): Rt 2.21 min., m/z 403.81 [M+H]$^+$.

Example 25

(S)-7-((1-(6-chloro-2-oxo-1,2-dihydro-1,8-naphthyridin-3-yl)ethyl)amino)-1-methyl-1H-pyrimido[4,5-d][1,3]oxazin-2(4H)-one (I-54)

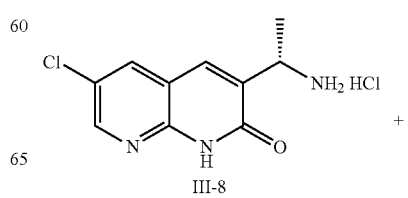

+

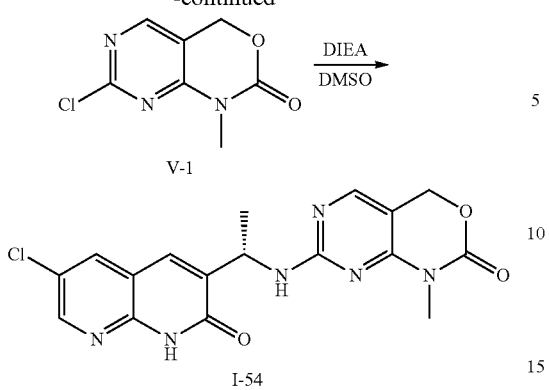

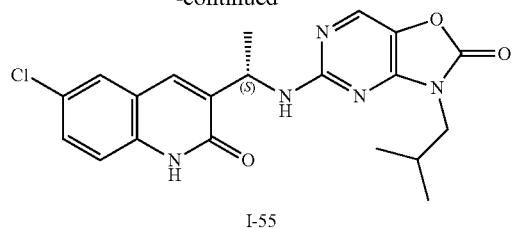

Step-1: 2-Chloro-N-isobutyl-5-methoxypyrimidin-4-amine

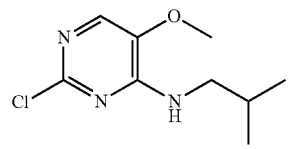

The mixture of DIEA (0.142 ml, 0.812 mmol), (S)-3-(1-aminoethyl)-6-chloro-1,8-naphthyridin-2(1H)-one III-8 (60.5 mg, 0.271 mmol), and 7-chloro-1-methyl-1H-pyrimido[4,5-d][1,3]oxazin-2(4H)-one V-1 (54 mg, 0.271 mmol) in DMSO (1 ml) was heated to 110° C. for 4 hours. EtOAc was added. The organic extract was washed with water (2×50 mL) and brine (50 mL), dried (Na$_2$SO$_4$), filtered, and evaporated under reduced pressure. The biotage purification with 0-10% MeOH/DCM on a 25 g column to afford 24.8 mg of (S)-7-((1-(6-chloro-2-oxo-1,2-dihydro-1,8-naphthyridin-3-yl)ethyl)amino)-1-methyl-1H-pyrimido[4,5-d][1,3]oxazin-2(4H)-one (23.7%). $^1$H NMR (300 MHz, DMSO-d$_6$) δ ppm 12.39 (s, 1H), 8.46 (s, 1H), 8.26 (s, 1H), 7.95 (s, 1H), 7.73 (s, 1H), 6.78 (s, 1H), 5.03-5.18 (m, 3H), 3.40 (s, 3H),), 1.38 (d, J=7.04 Hz, 3H). LCMS (Method 1): Rt 1.88 min, m/z 387.00 [M+H]$^+$.

Example 26

(S)-5-((1-(6-Chloro-2-oxo-1,2-dihydroquinolin-3-yl)ethyl)amino)-3-isobutyloxazolo[4,5-d]pyrimidin-2(3H)-one (I-55)

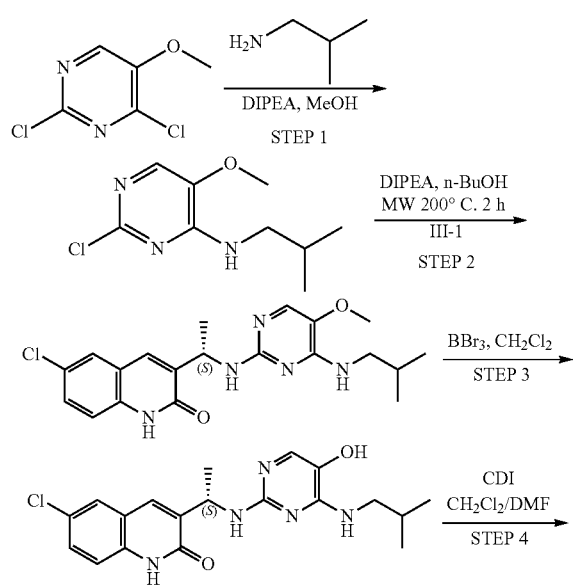

A mixture of 2,4-dichloro-5-methoxypyrimidine (2.0 g, 11.2 mmol), 2-methylpropan-1-amine (1.4 mL, 14.0 mmol) and N, N-diisopropylethylamine (5.8 mL, 33.5 mmol) in MeOH (25 mL) was stirred at room temperature for 3 days. TLC showed clean conversion. The reaction mixture was concentrated to dryness, and the residue was partitioned between EtOAc and water. The organic layer was dried over Na$_2$SO$_4$, filtered and concentrated, and the residue was purified by ISCO (SiO$_2$: hexanes/EtOAc 0 to 30%) to afford the title compound as pale yellow oil (2.47 g, quant.), $^1$H NMR (300 MHz, CDCl$_3$): δ 7.48 (s, 1H), 5.45 (bs, 1H), 3.86 (s, 3H), 3.30 (t, J=6.0 Hz, 2H), 1.89 (m, 1H), 0.96 (d, J=6.6 Hz, 6H). m/z 216.1 [M+H]$^+$.

Step-2: (S)-6-Chloro-3-(1-((4-(isobutylamino)-5-methoxypyrimidin-2-yl)amino)ethyl) quinolin-2(1H)-one

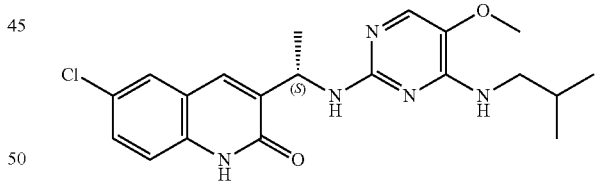

A mixture of 2-chloro-N-isobutyl-5-methoxypyrimidin-4-amine (500 mg, 2.32 mmol), (S)-3-(1-aminoethyl)-6-chloroquinolin-2(1H)-one hydrochloride III-1 (300 mg, 1.16 mmol) and diisopropylethylamine (0.60 mL, 3.47 mmol) in 1-butanol (10 mL) was heated in microwave at 200° C. for 2 h. MS showed the product. The reaction mixture was diluted with EtOAc and water, separated and washed with water and brine. After drying over sodium sulfate, the solution was concentrated and the residue was purified by ISCO (SiO$_2$: dichloromethane/MeOH 0 to 10%) to give the title compound as brown foam (293 mg, 63%). $^1$H NMR (300 MHz, CD$_3$OD): δ 7.79 (s, 1H), 7.64 (d, J=2.2 Hz, 1H), 7.48 (dd, J=8.8 Hz, 2.2 Hz, 1H), 7.32 (d, J=8.5 Hz, 1H), 7.24 (s, 1H), 5.17 (q, J=6.9 Hz, 1H), 3.79 (s, 3H), 3.02 (dd, J=10.3 Hz, 7.7 Hz, 1H), 1.74-1.62 (m, 1H), 1.54 (d, J=6.9 Hz, 3H), 1.03-0.88 (m, 1H), 0.77 (d, J=6.6 Hz, 3H), 0.72 (d, J=6.6 Hz, 3H). m/z=402.2, 404.2 [M+H]+.

Step-3: (S)-6-Chloro-3-(1-((5-hydroxy-4-(isobutylamino)pyrimidin-2-yl)amino)ethyl) quinolin-2(1H)-one

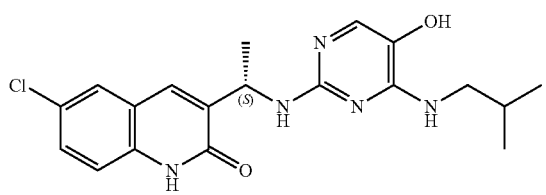

To a solution of (S)-6-chloro-3-(1-((4-(isobutylamino)-5-methoxypyrimidin-2-yl)amino)ethyl)quinolin-2(1H)-one (73 mg, 0.182 mmol) in dichloromethane (5 mL), BBr₃ (1.0 M in dichloromethane, 2.7 mL, 2.7 mmol) was added slowly and the mixture was stirred at room temperature for 3 days. MS analysis showed product. The reaction mixture was cooled to 0° C. and MeOH was slowly added. The resulting solution was stirred at room temperature for 30 min. After evaporation to dryness for 3 times, the title compound was obtained as brown foam (150 mg). ¹H NMR (300 MHz, CD₃OD): δ 7.82 (s, 1H), 7.67 (d, J=2.2 Hz, 1H), 7.49 (dd, J=8.8 Hz, 2.2 Hz, 1H), 7.33 (d, J=9.0 Hz, 1H), 7.03 (s, 1H), 5.19 (q, J=7.4 Hz, 1H), 3.11-3.01 (m, 1H), 1.76-1.64 (m, 1H), 1.55 (d, J=6.9 Hz, 3H), 1.02 (d, J=0.8 Hz, 1H), 0.98-0.92 (m, 1H), 0.78 (d, J=6.6 Hz, 3H), 0.72 (d, J=6.6 Hz, 3H). m/z 388.2, 390.2 [M+H]+.

Step-3: (S)-5-((1-(6-Chloro-2-oxo-1,2-dihydroquinolin-3-yl)ethyl)amino)-3-isobutyloxazolo[4,5-d]pyrimidin-2(3H)-one

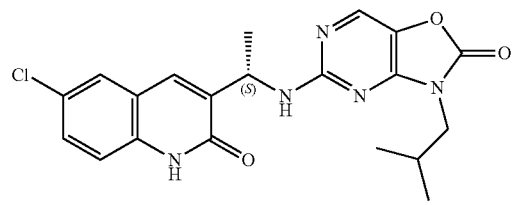

To a solution of (S)-6-chloro-3-(1-((5-hydroxy-4-(isobutylamino)pyrimidin-2-yl)amino)ethyl)quinolin-2(1H)-one (150 mg, 0.182 mmol) in dichloromethane (10 mL), CDI (59 mg, 0.364 mmol) was added and stirred at room temperature overnight. MS showed the product. The reaction mixture was concentrated to dryness, and the residue was partitioned by water and EtOAc. The organic layer was washed with water and brine, and then dried over sodium sulfate. After filtration and concentration, the crude was purified by ISCO (SiO₂: Hexanes/EtOAc 0 to 100%) to give the title compound as glassy film (32 mg, 42%). After lyophilization, the title compound I-55 was obtained as white solid (30 mg). ¹H NMR (300 MHz, CD₃OD): δ 7.92 (s, 1H), 7.77 (s, 1H), 7.58 (d, J=2.2 Hz, 1H), 7.44 (dd, J=8.6 Hz, 2.2 Hz, 1H), 7.33 (d, J=8.8 Hz, 1H), 5.26 (q, J=6.9 Hz, 1H), 3.59-3.48 (m, 2H), 2.06 (bs, 1H), 1.51 (d, J=6.9 Hz, 3H), 0.79 (bs, 6H). LCMS (Method 3): Rt 4.86 min, m/z 414.1, 416.1 [M+H]+.

Example 27

(S)-5-((1-(6-Chloro-2-oxo-1,2-dihydroquinolin-3-yl)ethyl)amino)oxazolo[4,5-d]pyrimidin-2(3H)-one (I-56)

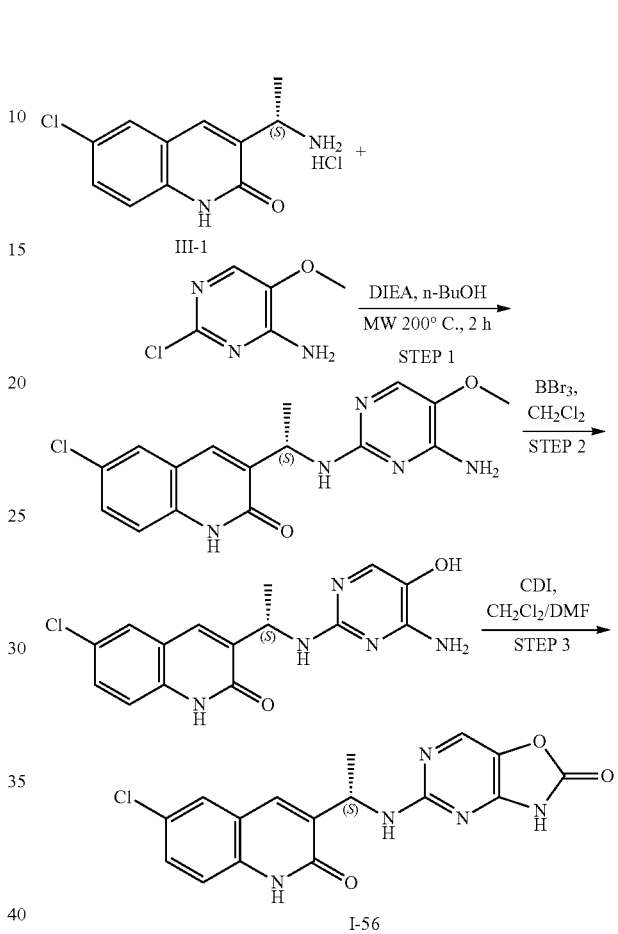

Step-1: (S)-3-(1-((4-Amino-5-methoxypyrimidin-2-yl)amino)ethyl)-6-chloroquinolin-2(1H)-one

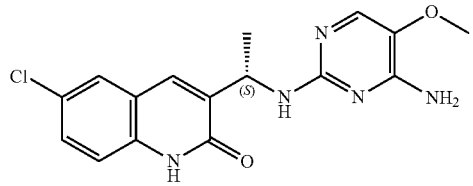

A mixture of 2-chloro-5-methoxypyrimidin-4-amine (370 mg, 2.32 mmol), (S)-3-(1-aminoethyl)-6-chloroquinolin-2(1H)-one hydrochloride III-1 (300 mg, 1.16 mmol) and diisopropylethylamine (0.60 mL, 3.47 mmol) in 1-butanol (8 mL) was heated in microwave at 200° C. for 2 h. MS showed the product. The reaction mixture was diluted with EtOAc and water, separated and washed with water and brine. After drying over sodium sulfate, the solution was concentrated and the residue was purified by ISCO (SiO₂: hexanes/EtOAc 0 to 100% then dichloromethane/MeOH 0 to 20%) to give the title compound as brown solid (174 mg, 43%). ¹H NMR (300 MHz, CD$_3$OD): δ 7.79 (s, 1H), 7.61 (d, J=2.2 Hz, 1H), 7.44 (dd, J=8.8 Hz, 2.2 Hz, 1H), 7.35 (s, 1H), 7.29 (d, J=8.8 Hz, 1H), 5.11 (q, J=6.9 Hz, 1H), 3.73 (s, 3H), 1.48 (d, J=6.9 Hz, 3H). m/z=346.1, 348.1 [M+H]$^+$.

Step-2: (S)-3-(1-((4-Amino-5-hydroxypyrimidin-2-yl)amino)ethyl)-6-chloroquinolin-2(1H)-one

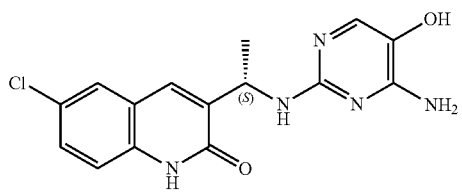

To a solution of (S)-3-(1-((4-amino-5-methoxypyrimidin-2-yl)amino)ethyl)-6-chloroquinolin-2(1H)-one (90 mg, 0.26 mmol) in dichloromethane (5 mL), BBr$_3$ (1.0 M in dichloromethane, 3.9 mL, 3.9 mmol) was added slowly and the mixture was stirred at room temperature for 2 days. MS showed >90% conversion. The reaction mixture was cooled to 0° C. and MeOH was slowly added. The resulting solution was stirred at room temperature for 30 min. After evaporation to dryness for 3 times, the title compound 3 was obtained as brown foam (100 mg). This was used in the next step without further purification. $^1$H NMR (300 MHz, CD$_3$OD): δ 7.88 (s, 1H), 7.71 (d, J=2.2 Hz, 1H), 7.49 (dd, J=8.8 Hz, 2.0 Hz, 1H), 7.33 (d, J=8.7 Hz, 1H), 7.09 (s, 1H), 5.22 (q, J=6.9 Hz, 1H), 1.56 (d, J=6.9 Hz, 3H). m/z 332.1, 334.1 [M+H]$^+$.

Step-3: (S)-5-((1-(6-Chloro-2-oxo-1,2-dihydroquinolin-3-yl)ethyl)amino)oxazolo[4,5-d]pyrimidin-2(3H)-one (I-56)

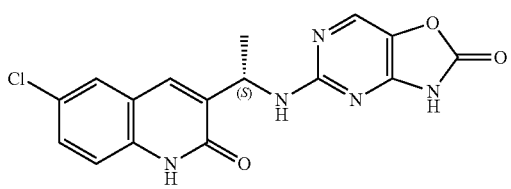

To a solution of (S)-3-(1-((4-amino-5-hydroxypyrimidin-2-yl)amino)ethyl)-6-chloroquinolin-2(1H)-one (100 mg, 0.26 mmol) in dichloromethane (5 mL) and DMF (2 mL), CDI (84 mg, 0.52 mmol) was added and stirred at room temperature overnight. MS showed the product. The reaction mixture was concentrated to dryness, and the residue was partitioned with water and EtOAc. The organic layer was washed with water and brine, and then dried over sodium sulfate. After filtration and concentration, the crude was purified by ISCO (SiO$_2$:Hexanes/EtOAc 0 to 100%) to give the title compound as glass film (32 mg, 42%). After lyophilization, the desired product I-56 was obtained as white solid (44 mg, 47%). $^1$H NMR (300 MHz, CD$_3$OD): δ 7.81 (s, 1H), 7.66 (s, 1H), 7.31 (d, J=2.2 Hz, 1H), 7.45 (dd, J=8.8 Hz, 2.2 Hz, 1H), 7.30 (d, J=8.8 Hz, 1H), 5.21 (q, J=6.9 Hz, 1H), 1.52 (d, J=6.8 Hz, 3H). LCMS (Method 3): Rt 8.01 min, m/z 358.1, 360.1 [M+H]$^+$.

Example 28

(S)-5-((1-(6-Chloro-2-oxo-1,2-dihydroquinolin-3-yl)ethyl)amino)-3-methyloxazolo[4,5-d]pyrimidin-2(3H)-one (I-57)

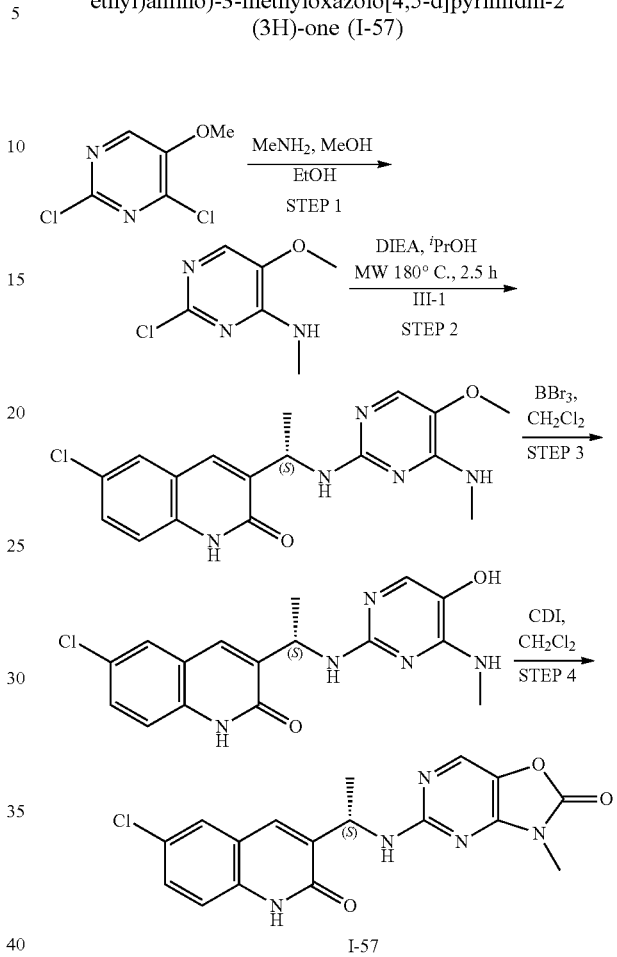

Step-1: 2-Chloro-5-methoxy-N-methylpyrimidin-4-amine

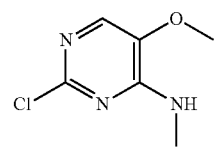

At 0° C., to a solution of 2,4-dichloro-5-methoxypyrimidine (5.2 g, 29.0 mmol) in MeOH (50 mL), a solution of methylamine in EtOH (8 M, 8.3 mL, 66.8 mmol) was added slowly, and then allowed the mixture to warm to room temperature for 30 min. TLC showed completed reaction. The reaction mixture was concentrated to dryness, and the solid was dissolved in dichloromethane and washed with saturated sodium bicarbonate. The organic layer was dried over magnesium sulfate and concentrated to give the desired product as white solid (4.80 g, 95%). $^1$H NMR (300 MHz, CDCl$_3$): δ 7.48 (s, 1H), 5.46 (bs, 1H), 3.85 (s, 3H), 3.04 (d, J=4.9 Hz, 3H).

Step-2: (S)-6-Chloro-3-(1-((5-methoxy-4-(methylamino)pyrimidin-2-yl)amino)ethyl) quinolin-2(1H)-one

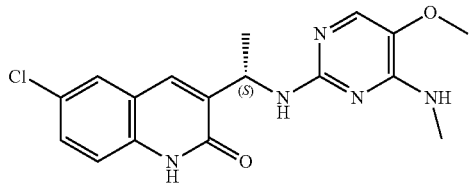

A mixture of 2-chloro-5-methoxy-N-methylpyrimidin-4-amine (603 mg, 3.47 mmol), (S)-3-(1-aminoethyl)-6-chloroquinolin-2(1H)-one hydrochloride III-1 (300 mg, 1.16 mmol) and diisopropylethylamine (0.60 mL, 3.47 mmol) in isopropanol (10 mL) was heated in microwave at 180° C. for 2.5 h. MS analysis showed the product. The reaction mixture was diluted with EtOAc and water, separated and washed with water and brine. After drying over sodium sulfate, the solution was concentrated and the residue was purified by ISCO (SiO$_2$: Hexanes/EtOAc 0 to 100%) to give the title compound as brown foam (110 mg, 26%). $^1$H NMR (300 MHz, CDCl$_3$): δ 10.86 (bs, 1H), 9.59 (bs, 1H), 7.82 (s, 1H), 7.56 (d, J=2.2 Hz, 1H), 7.42 (dd, J=8.8 Hz, 2.2 Hz, 1H), 7.22 (d, J=8.8 Hz, 1H), 7.01 (m, 1H), 6.07 (m, 1H), 5.46 (m, 1H), 3.73 (s, 3H), 2.99 (d, J=5.2 Hz, 3H), 1.60 (d, J=6.9 Hz, 3H). m/z 360.1, 362.1 [M+H]$^+$.

Step-3: (S)-6-Chloro-3-(1-((5-hydroxy-4-(methylamino)pyrimidin-2-yl)amino)ethyl) quinolin-2(1H)-one

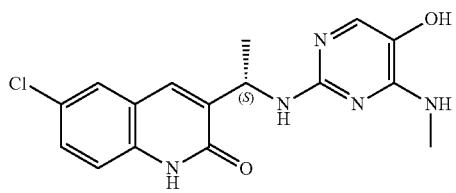

To a solution of (S)-6-chloro-3-(1-((5-methoxy-4-(methylamino)pyrimidin-2-yl)amino)ethyl)quinolin-2(1H)-one (110 mg, 0.306 mmol) in dichloromethane (40 mL), BBr$_3$ (0.44 mL, 4.59 mmol) was added and stirred at room temperature overnight. MS showed the presence of product. The reaction mixture was cooled to 0° C. and MeOH was slowly added. The resulting solution was stirred at room temperature for 30 min. After evaporation to dryness, the residue was diluted with water and EtOAc, and the organic layer was separated and washed with brine. After drying over sodium sulfate, the solution was concentrated to give the title compound 5 as yellow solid (87 mg, 82%), which was used for the next step without further purification. $^1$H NMR (300 MHz, CD$_3$OD): δ 7.88 (s, 1H), 7.69 (s, 1H), 7.50 (dd, J=8.8 Hz, 2.2 Hz, 1H), 7.32 (d, J=8.6 Hz, 1H), 6.99 (s, 1H), 5.24 (m, 1H), 2.97 (s, 3H), 1.58 (d, J=6.9 Hz, 3H). m/z 346.1, 348.1 [M+H]$^+$.

Step-4: (S)-5-((1-(6-Chloro-2-oxo-1,2-dihydroquinolin-3-yl)ethyl)amino)-3-methyloxazolo[4,5-d]pyrimidin-2(3H)-one (I-57)

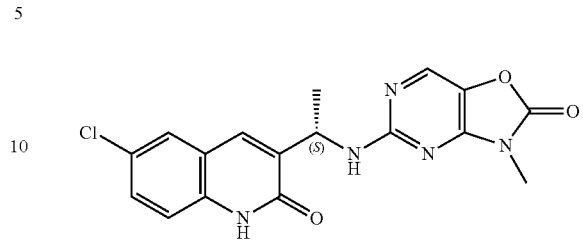

To a solution of (S)-6-chloro-3-(1-((5-hydroxy-4-(methylamino)pyrimidin-2-yl) amino) ethyl)quinolin-2(1H)-one (87 mg, 0.25 mmol) in dichloromethane (30 mL), CDI (45 mg, 0.28 mmol) was added and stirred at room temperature overnight. MS showed the product. The reaction mixture was concentrated to dryness, and the residue was purified by ISCO (SiO$_2$: Hexanes/EtOAc 0 to 100%) to give the desired product I-57 as brown foam (55 mg, 59%). $^1$H NMR (300 MHz, CDCl$_3$): δ 10.94 (s, 1H), 7.89 (s, 1H), 7.67 (s, 1H), 7.51 (d, J=2.2 Hz, 1H), 7.50 (dd, J=8.8 Hz, 2.2 Hz, 1H), 6.05 (d, J=8.2 Hz, 1H), 5.28 (m, 1H), 3.32 (s, 3H), 1.63 (d, J=6.9 Hz, 3H). LCMS (method 3): Rt 4.19 min, m/z 372.1, 374.1 [M+H]$^+$.

Example 29

(S)-6-chloro-3-(1-((9-methyl-8-oxo-8,9-dihydro-7H-purin-2-yl)amino)ethyl)quinolin-2(1H)-one (I-58)

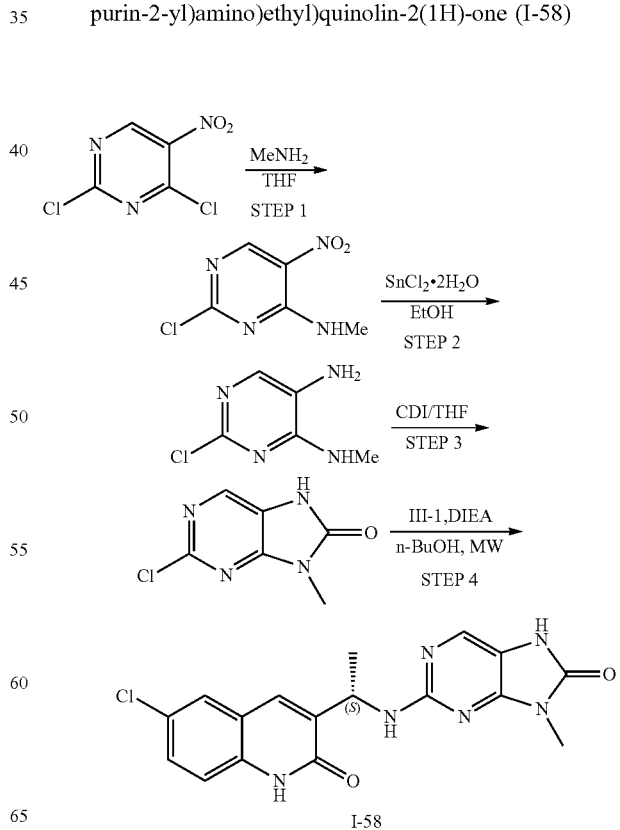

Step-1: 2-chloro-N-methyl-5-nitropyrimidin-4-amine

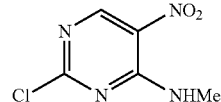

To a solution of 2,4-dichloro-5-nitropyrimidine (1.0 g, 5.2 mmol) in THF (15 mL) at −78° C., was added MeNH$_2$ (5.1 mL, 2M in THF, 10.2 mmol) drop wise over a period of 20 minutes. The reaction mixture was stirred for another 2.5 hours. It was then allowed to warm up to room temperature slowly. The mixture was concentrated under reduced pressure and the residue was partitioned between EtOAc and water. The organic layer was separated and the aqueous layer was extracted with EtOAc. The combined organic layers were washed with brine, dried (Na$_2$SO$_4$) and concentrated in vacuum. The residue was purified on ISCO (40 g silica gel column, EtOAc/hexanes 0-20%) to give the title compound (0.78 g, 80%).

Step-2: 2-chloro-N$^4$-methylpyrimidine-4,5-diamine

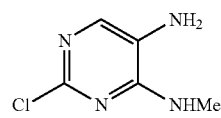

A mixture of 2-chloro-N-methyl-5-nitropyrimidin-4-amine (0.77 g, 4.1 mmol) and SnCl$_2$.2H$_2$O (3.6 g, 16.3 mmol) in EtOH (45 mL) was heated to 80° C. under N$_2$ and stirred for two hours. It was then concentrated under reduced pressure. EtOAc and Celite were added to the residue and the mixture was basified with saturated Na$_2$CO$_3$ (aq.) to pH 9-10. The mixture was filtered through a pad of Celite and washed with EtOAc. The organic layer was separated and washed with brine, dried (Na$_2$SO$_4$) and concentrated in vacuum. The residue was purified on ISCO (12 g silica gel column, EtOAc/hexanes 0-100%) to give the title compound (0.43 g, 66%).

Step-3: 2-chloro-9-methyl-7H-purin-8(9H)-one

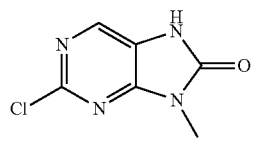

To a solution of 2-chloro-N$^4$-methylpyrimidine-4,5-diamine (150 mg, 0.95 mmol) in anhydrous THF (20 mL) was added CDI (310 mg, 1.9 mmol) under N$_2$. The reaction mixture was stirred at room temperature overnight. It was concentrated in vacuum and the residue was purified on ISCO (20 g silica gel column, MeOH/dichloromethane 0-10%) to afford the title compound (0.11 g, 63%).

Step-4 (S)-6-chloro-3-(1-((9-methyl-8-oxo-8,9-dihydro-7H-purin-2-yl)amino)ethyl)-quinolin-2(1H)-one (I-58)

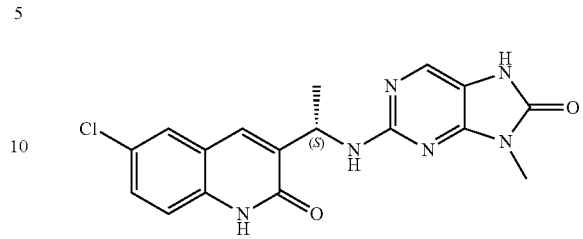

A mixture of (S)-3-(1-aminoethyl)-6-chloroquinolin-2(1H)-one hydrochloride III-1 (52 mg, 0.20 mmol), 2-chloro-9-methyl-7H-purin-8(9H)-one (110 mg, 0.60 mmol) and N,N-diisopropylethylamine (150 L, 0.86 mmol) in n-BuOH (1.5 mL) was heated in the microwave at 200° C. for 3.5 hours. It was combined with another batch and purified on ISCO (20 g silica gel column, EtOAc/hexanes 0~100%) to afford the desired product I-58 as an off-white solid (33 mg, 22%). m.p. 104-106° C. $^1$H NMR (300 MHz, DMSO-d$_6$) δ ppm: 11.93 (s, 1H), 10.67 (s, 1H), 7.74 (s, 1H), 7.71 (d, J=2.5 Hz, 1H), 7.70 (s, 1H), 7.46 (dd, J=8.8, 2.5 Hz, 1H), 7.28 (d, J=8.8 Hz, 1H), 7.18 (d, J=7.7 Hz, 1H), 5.12 (m, 1H), 3.16 (s, 3H), 1.37 (d, J=6.9 Hz, 3H). LCMS (LCMS method 1, APCI): 98% pure @254 nm, Rt 3.87 min, m/z 371, 373 [M+H]$^+$.

Example 30

(S)-6-Chloro-3-(1-((8-oxo-8,9-dihydro-7H-purin-2-yl)amino)ethyl)quinolin-2(1H)-one (I-59)

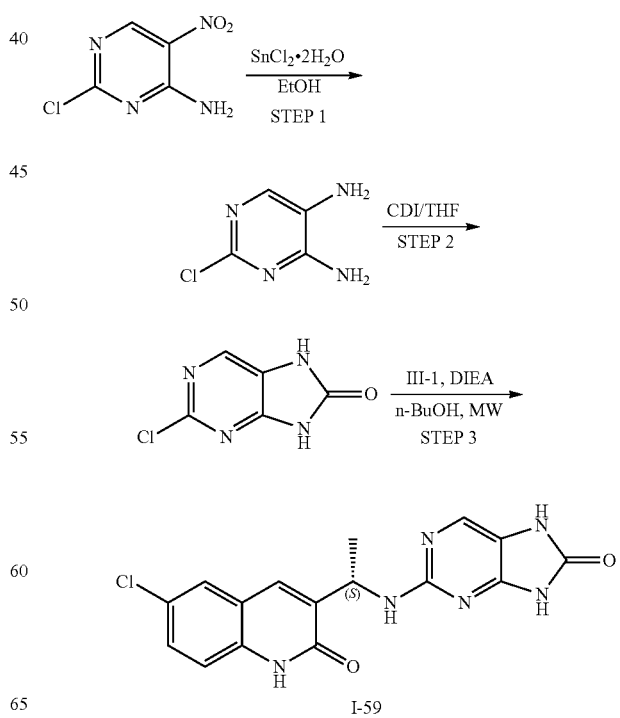

Step-1: 2-chloropyrimidine-4,5-diamine

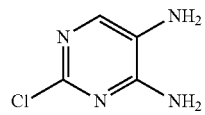

A mixture of 2-chloro-5-nitropyrimidin-4-amine (1.0 g, 5.7 mmol) and SnCl$_2$.2H$_2$O (5.2 g, 22.9 mmol) in EtOH (55 mL) under N$_2$ was heated to 80° C. and stirred for two hours. The mixture was then concentrated under reduced pressure. EtOAc and Celite were added to the residue and the mixture was basified with saturated Na$_2$CO$_3$ (aq.) to pH 9-10. The mixture was filtered through a pad of Celite and washed with EtOAc. The organic layer was separated and washed with brine, dried (Na$_2$SO$_4$) and concentrated in vacuum. The residue was purified on ISCO (20 g silica gel column, EtOAc/hexanes 0-100%) to give the title compound (0.41 g, 49%).

Step-2: 2-chloro-7H-purin-8(9H)-one

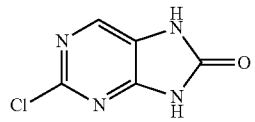 [SMILES: O=c1[nH]c2cnc(Cl)nc2[nH]1]

To a solution of 2-chloropyrimidine-4,5-diamine (200 mg, 1.38 mmol) in anhydrous THF (25 mL) was added CDI (225 mg, 1.38 mmol) under N$_2$. The reaction mixture was stirred at room temperature overnight. It was concentrated in vacuum and the residue was purified on ISCO (12 g silica gel column, EtOAc/hexanes 0-100%). The solid obtained was a mixture of the desired product and imidazole. It was dissolved in DCM, washed with 1N HCl (aq.) and water, dried (Na$_2$SO$_4$) and concentrated in vacuum to afford the title compound as a white solid (170 mg, 72%).

Step-3: (S)-6-chloro-3-(1-((8-oxo-8,9-dihydro-7H-purin-2-yl)amino)ethyl)quinolin-2(1H)one (I-59)

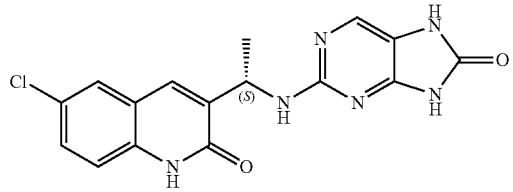

A mixture of (S)-3-(1-aminoethyl)-6-chloroquinolin-2 (1H)-one hydrochloride III-1 (52 mg, 0.20 mmol), 2-chloro-7H-purin-8(9H)-one (100 mg, 0.60 mmol) and N,N-diisopropylethylamine (200 L, 1.15 mmol) in n-BuOH (1.5 mL) was heated in the microwave at 200° C. for three hours. It was purified on ISCO (12 g silica gel column, EtOAc/hexanes 0~100%, then MeOH/DCM 0~10%) to afford the desired product I-59 as a pale yellow solid (20 mg, 19%). m.p. 138-140° C. $^1$H NMR (300 MHz, DMSO-d$_6$) δ: 11.92 (s, 1H), 11.27 (br.s, 1H), 10.40 (s, 1H), 7.71 (s, 1H), 7.70 (d, J=2.2 Hz, 1H), 7.67 (s, 1H), 7.46 (dd, J=8.8, 2.2 Hz, 1H), 7.28 (d, J=8.8 Hz, 1H), 7.02 (d, J=8.0 Hz, 1H), 5.07 (m, 1H), 1.36 (d, J=6.9 Hz, 3H). LCMS (method 3): 95% pure @254 nm, Rt 7.58 min, m/z 357, 359 [M+H]$^+$.

Example 31

(S)-6-Chloro-3-(1-((6-oxo-6,7-dihydro-5H-pyrrolo [2,3-d]pyrimidin-2-yl)amino)ethyl) quinolin-2(1H)-one (I-60)

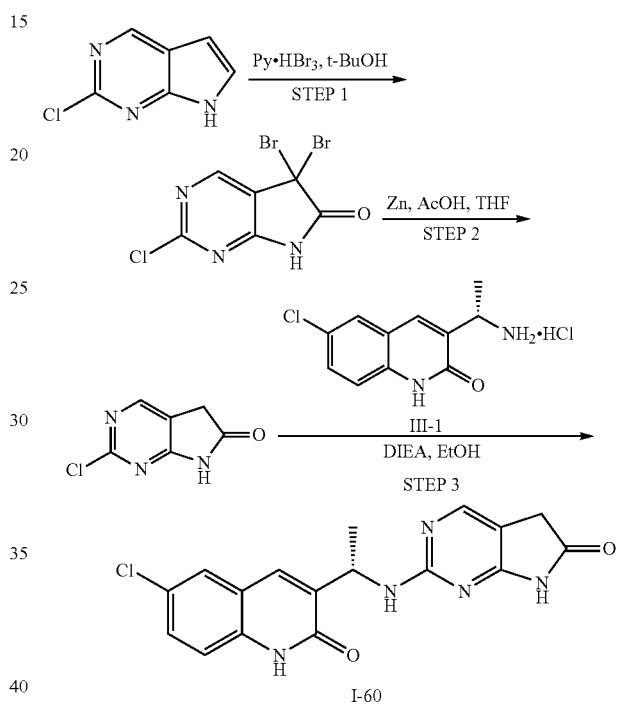

Step-1: 5,5-Dibromo-2-chloro-5H-pyrrolo[2,3-d] pyrimidin-6(7H)-one

To a solution of 2-chloro-7H-pyrrolo[2,3-d]pyrimidine (400 mg, 2.6 mmol) in t-BuOH (25 mL) was added 90% Py.HBr$_3$ (2.77 g, 7.8 mmol) over the period of 30 min. and stirred for 3 h at room temperature. The reaction mixture was concentrated and dissolved in EtOAc (50 mL) and water (30 mL). The EtOAc layer was separated and aqueous layer was extracted with EtOAc (30 mL). The combined extracts were washed with H$_2$O, brine, dried (Na$_2$SO$_4$) and concentrated to give crude 5,5-dibromo-2-chloro-5H-pyrrolo[2,3-d]pyrimidin-6(7H)-one (855 mg) which was used for the next step.

Step-2:
2-Chloro-5H-pyrrolo[2,3-d]pyrimidin-6(7H)-one

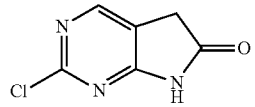

To a solution of 5,5-dibromo-2-chloro-5H-pyrrolo[2,3-d]pyrimidin-6(7H)-one (855 mg, 2.6 mmol) in THF (20 mL), was added acetic acid (10 mL) at 0° C. and followed by Zn dust (683 mg, 10.45 mmol). The resultant mixture was stirred at 0° C. for 5 min., then warmed to rt and stirred for 1 h. The reaction mixture was filtered through a pad of celite and washed with EtOAc (50 mL). The filtrate was concentrated and purified by ISCO (SiO$_2$: DCM/MeOH 0 to 10%) to give the pure 2-chloro-5H-pyrrolo[2,3-d]pyrimidin-6(7H)-one (330 mg, 75%).

Step-2: (S)-6-Chloro-3-(1-((6-oxo-6,7-dihydro-5H-pyrrolo[2,3-d]pyrimidin-2-yl)amino)ethyl)-quinolin-2(1H)-one (I-60)

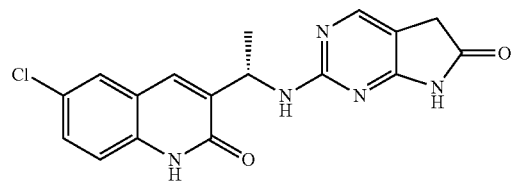 [SMILES: C[C@H](Nc1ncc2c(n1)NC(=O)C2)c1cc2cc(Cl)ccc2[nH]c1=O]

To a mixture of 2-chloro-5H-pyrrolo[2,3-d]pyrimidin-6(7H)-one (300 mg, 1.15 mmol) and (S)-3-(1-aminoethyl)-6-chloroquinolin-2(1H)-one hydrochloride III-1 (300 mg, 1.77 mmol) in EtOH (2 mL) was added DIEA (0.4 mL, 2.3 mmol). The resultant mixture was heated at 145° C. for 4.5 h in a microwave. After TLC and MS showed completion of the reaction, the mixture was cooled to room temperature and diluted with EtOAc (20 mL). The organic layer was washed with water (20 mL), brine, dried over anhydrous Na$_2$SO$_4$, filtered and evaporated to dryness. The resulting residue was purified by reverse phase to give the title compound as a white solid I-60 (50 mg, 12%). mp. 154-156° C. $^1$H NMR (300 MHz, DMSO-d$_6$) δ 12.07 (brs, NH), 11.92 (brs, NH), 7.96 (brs, NH), 7.81 (m, 1H), 7.77 (d, J=2.2 Hz, 1H), 7.53 (dd, J=2.2 Hz, 6.6 Hz, 1H), 7.33 (d, J=8.8 Hz, 1H), 5.18 (m, 1H), 3.47 (s, 2H), 1.45 (d, J=6.6 Hz, 1H). LCMS: Rt 3.85 min, m/z 356.1 [M+H]$^+$.

Example 32

(S)-6-Chloro-3-(1-((7-methyl-6-oxo-6,7-dihydro-5H-pyrrolo[2,3-d]pyrimidin-2-yl)amino)ethyl)-quinolin-2(1H)-one (I-61)

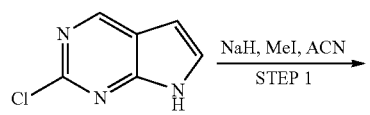

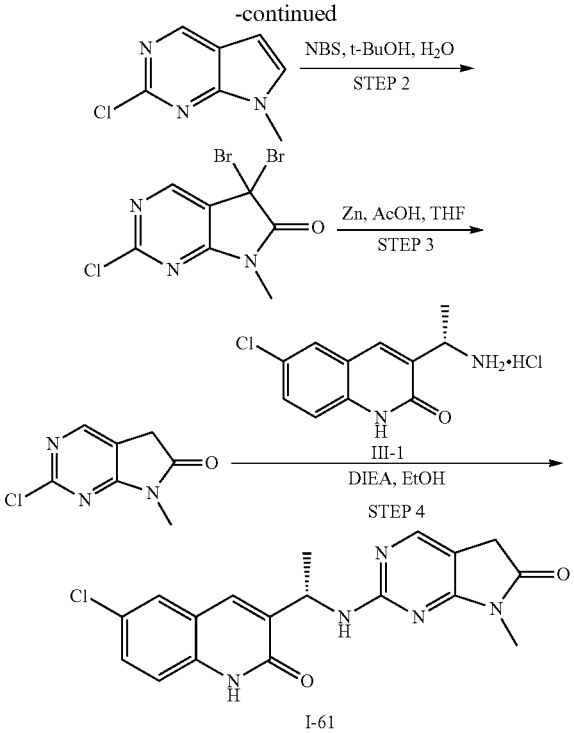

Step-1:
2-Chloro-7-methyl-7H-pyrrolo[2,3-d]pyrimidine

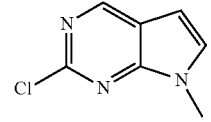

To a stirred solution of 2-chloro-7H-pyrrolo[2,3-d]pyrimidine (1 g, 6.5 mmol) in MeCN (25 mL) at 5° C. was added NaH (313 mg, 7.8 mmol). The resultant mixture was brought to room temperature and stirred for 30 min. Then MeI was added at 0° C. and continued stirring at room temperature for overnight. The reaction mixture was filtered through a pad of celite and washed with MeCN (10 mL). The filtrate was concentrated and recrystallized from Et$_2$O. The mother liquor was concentrated and purified by ISCO (SiO$_2$: DCM/EtOAc 0 to 30%). Altogether, the recrystallized and purified provided the pure compound (835 mg, 77%).

Step-2: 5,5-Dibromo-2-chloro-7-methyl-5H-pyrrolo[2,3-d]pyrimidin-6(7H)-one

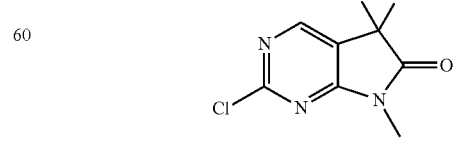

To a solution of 2-chloro-7-methyl-7H-pyrrolo[2,3-d]pyrimidine (835 mg, 5 mmol) in t-BuOH/H$_2$O ((10 mL/3 mL)

was added NBS (2.67 g, 15 mmol) and stirred for 3 h at room temperature. The reaction mixture was concentrated and dissolved in EtOAc (30 mL). The EtOAc layer was washed with NaHCO$_3$, brine, dried (Na$_2$SO$_4$) and concentrated to give crude 5,5-Dibromo-2-chloro-7-methyl-5H-pyrrolo[2,3-d]pyrimidin-6(7H)-one (1.72 g) which was used for the next step.

Step-3: 2-Chloro-7-methyl-5H-pyrrolo[2,3-d]pyrimidin-6(7H)-one

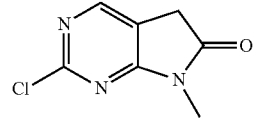

To a solution of 5,5-Dibromo-2-chloro-7-methyl-5H-pyrrolo[2,3-d]pyrimidin-6(7H)-one (1.7 g, 5 mmol) in THF (10 mL), was added acetic acid (20 mL) at 0° C. and followed by Zn dust (1.3 g, 20 mmol). The resultant mixture was stirred at 0° C. for 5 min., then warmed to room temperature and stirred for 1 h. The reaction mixture was filtered through a pad of celite and washed with EtOAc (50 mL). The filtrate was concentrated and recrystallized from EtOH (414 mg). The mother liquor was concentrated and purified by ISCO (SiO$_2$: DCM/MeOH 0 to 10%). Altogether, the recrystallized and purified provided the pure title compound (573 mg, 62%).

Step-4: (S)-6-Chloro-3-(1-((7-methyl-6-oxo-6,7-dihydro-H-pyrrolo[2,3-d]pyrimidin-2-yl)-amino) ethyl)-quinolin-2(1H)-one (I-61)

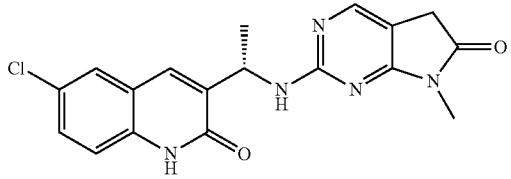 [SMILES: C[C@H](Nc1ncc2c(n1)N(C)C(=O)C2)c1cc2cc(Cl)ccc2[nH]c1=O]

To a mixture of 2-chloro-7-methyl-5H-pyrrolo[2,3-d]pyrimidin-6(7H)-one (212 mg, 1.16 mmol) and (S)-3-(1-aminoethyl)-6-chloroquinolin-2(1H)-one hydrochloride III-1 (200 mg, 0.77 mmol) in EtOH (2 mL) was added DIEA (0.2 mL, 1.16 mmol). The resultant mixture was heated at 145° C. for 4.5 h in microwave. After TLC and MS showed completion of the reaction, the mixture was cooled to room temperature and diluted with EtOAc (20 mL). The organic layer was washed with water (20 mL), brine, dried over anhydrous Na$_2$SO$_4$, filtered and evaporated to dryness. The resulting residue was purified by ISCO (SiO$_2$: CH$_2$Cl$_2$/MeOH 0 to 10% and SiO$_2$:EtOAc/MeOH 0 to 8%) to give the title compound as off-white solid 1-61 (184 mg, 65%), which was recrystallized from Teac/Hexane (157 mg). mp. 150° C. (decomposed). $^1$H NMR (300 MHz, DMSO-d$_6$) δ 11.92 (brs, NH), 7.82 (brs, NH), 7.74-7.72 (m, 2H), 7.60 (d, J=6.2 Hz, 1H), 7.44 (dd. J=2.2 Hz, 6.2 Hz, 1H), 7.27 (d, J=8.8 Hz, 1H), 5.19 (m, 1H), 3.46 (s, 2H) 3.03 (s, 3H), 1.37 (d, J=6.6 Hz, 1H). LCMS: Rt 4.08 min, m/z 370.1 [M+H]$^+$.

Example 33

(S)-2-((1-(6-chloro-2-oxo-1,2-dihydroquinolin-3-yl) ethyl)amino)-5,6-dihydropyrido[2,3-d]pyrimidin-7 (8H)-one (I-62)

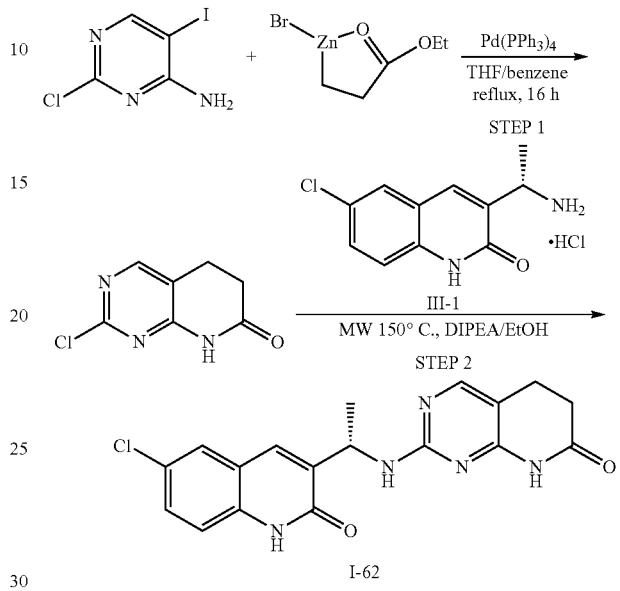

Step-1: 2-chloro-5,6-dihydropyrido[2,3-d]pyrimidin-7(8H)-one

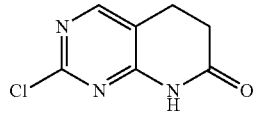 [SMILES: O=C1CCc2cnc(Cl)nc2N1]

A mixture of 2-chloro-5-iodopyrimidin-4-amine (256 mg, 1 mmol), 3-ethoxy-3-oxopropylzinc bromide 2 (6 mL, 0.5 M in THF, 3 mmol) and Pd(PPh$_3$)$_4$(116 mg, 0.1 mmol) in anhydrous benzene (5 mL) was refluxed under N$_2$ overnight. After removal of solvents under reduced pressure, the residue was purified on ISCO (40 g silica gel column, EtOAc/hexanes 0-100%; then 20 g silica gel column, MeOH/dichloromethane 010%) to give the title compound as an off-white solid (29 mg, 16%).

Step-2: (S)-2-((1-(6-chloro-2-oxo-1,2-dihydroquinolin-3-yl)ethyl)amino)-5,6-dihydropyrido[2,3-d]pyrimidin-7(8H)-one (I-62)

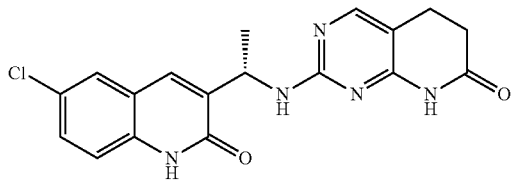 [SMILES: C[C@H](Nc1ncc2c(n1)NC(=O)CC2)c1cc2cc(Cl)ccc2[nH]c1=O]

A mixture of (S)-3-(1-aminoethyl)-6-chloroquinolin-2 (1H)-one hydrochloride III-1 (102 mg, 0.39 mmol), 2-chloro-5,6-dihydropyrido[2,3-d]pyrimidin-7(8H)-one (36 mg, 0.20 mmol) and N,N-diisopropylethylamine (100 μL, 0.59 mmol) in EtOH (1.5 mL) was heated in the microwave at 150° C. for two hours. After removal of solvent under reduced pressure, the residue was purified on ISCO (20 g silica gel column, MeOH/dichloromethane 0-10%) to give the desired product as an off-white solid. It was dissolved in acetonitrile, mixed with water and lyophilized to afford the title compound I-62 as white foam (25 mg, 35%). $^1$H NMR (300 MHz, MeOD-d$_3$) δ ppm: 7.92 (s, 1H), 7.82 (s, 1H), 7.61 (d, J=2.2 Hz, 1H), 7.45 (dd, J=8.8, 2.2 Hz, 1H), 7.30 (d, J=8.8 Hz, 1H), 5.24 (m, 1H), 2.75 (m, 2H), 2.56 (m, 2H), 1.50 (d, J=6.9 Hz, 3H). LCMS (Method 3): 97% pure @254 nm, Rt 5.30 min, m/z 370, 372 [M+H]$^+$.

TABLE 4

The compounds listed in Table 1 were prepared using methods similar to the one described for the preparation of I-42 to I-62.

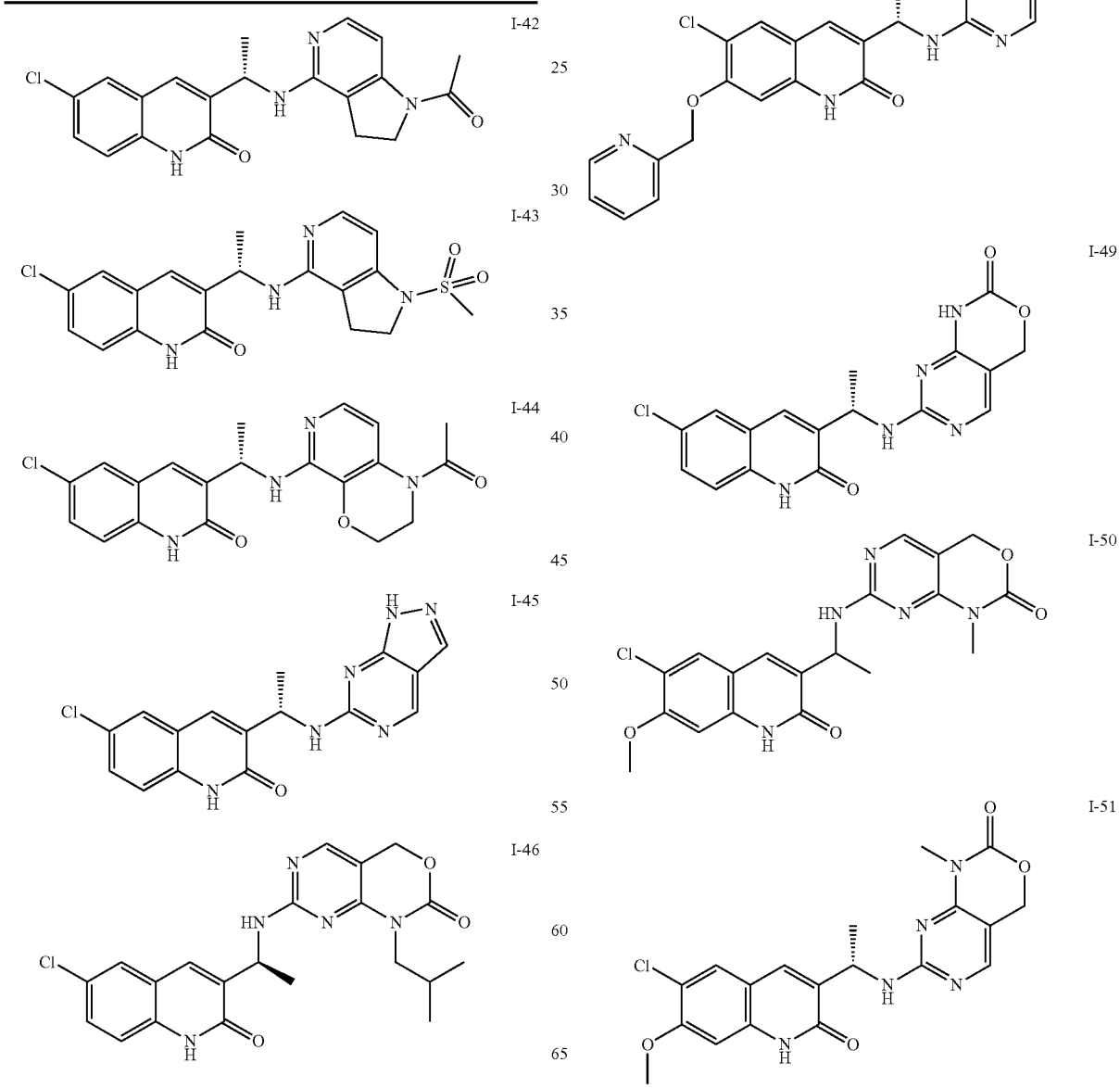

TABLE 4-continued
The compounds listed in Table 1 were prepared using methods similar to the one described for the preparation of I-42 to I-62.
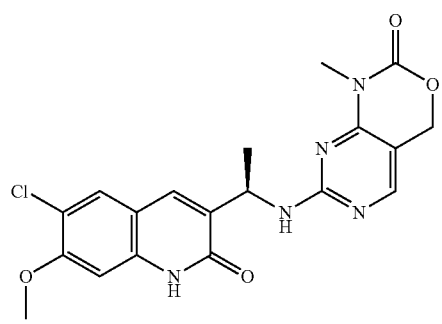 [SMILES: COc1cc2[nH]c(=O)c([C@@H](C)Nc3ncc4c(n3)N(C)C(=O)OC4)cc2cc1Cl]
I-52
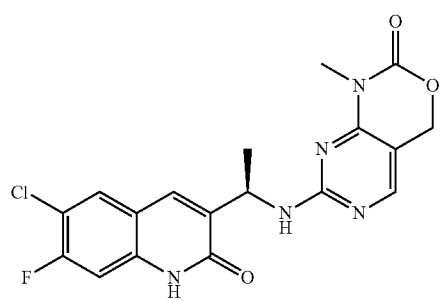 [SMILES: C[C@@H](Nc1ncc2c(n1)N(C)C(=O)OC2)c1cc2cc(Cl)c(F)cc2[nH]c1=O]
I-53
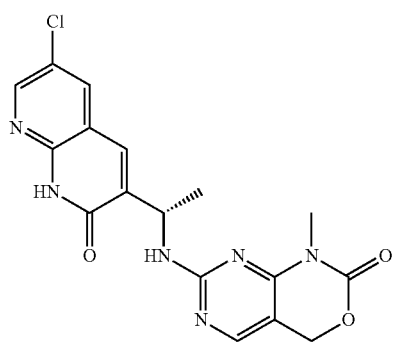 [SMILES: C[C@H](Nc1ncc2c(n1)N(C)C(=O)OC2)c1cc2cc(Cl)cnc2[nH]c1=O]
I-54
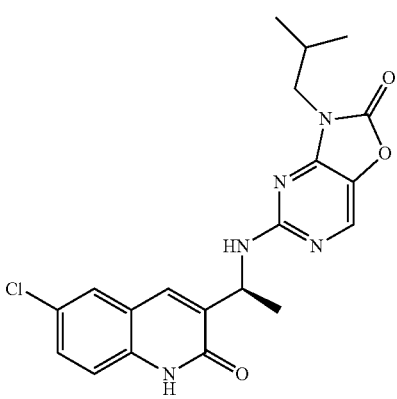 [SMILES: CC(C)Cn1c(=O)oc2cnc(N[C@@H](C)c3cc4cc(Cl)ccc4[nH]c3=O)nc21]
I-55
TABLE 4-continued
The compounds listed in Table 1 were prepared using methods similar to the one described for the preparation of I-42 to I-62.
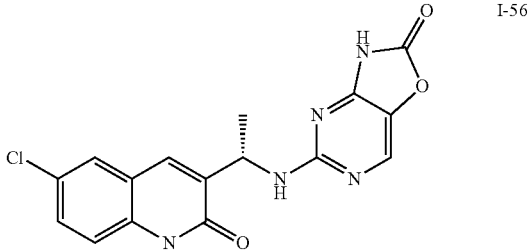
I-56
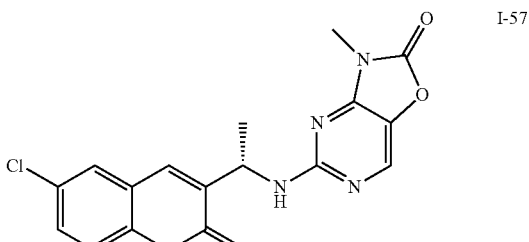
I-57
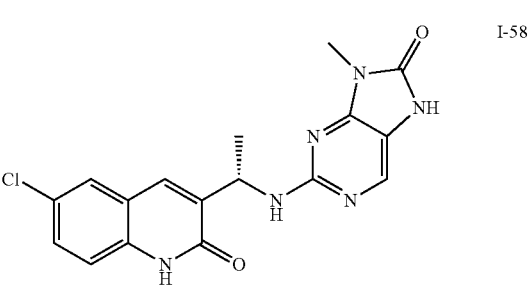
I-58
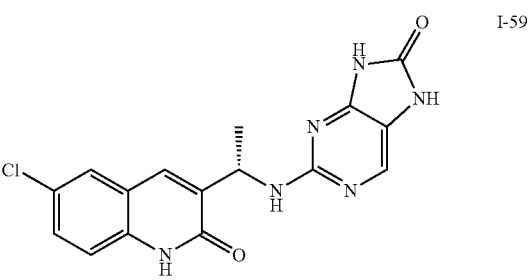
I-59
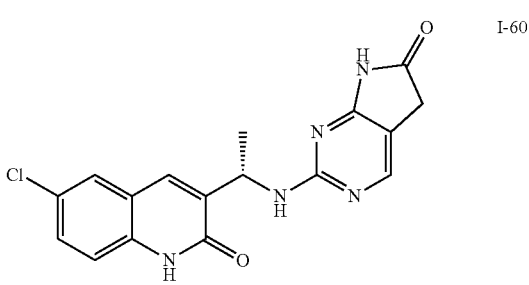
I-60

TABLE 4-continued

The compounds listed in Table 1 were prepared using methods similar to the one described for the preparation of I-42 to I-62.

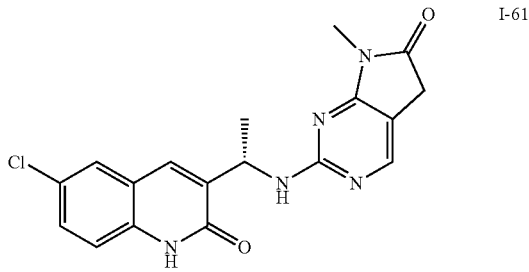

I-61

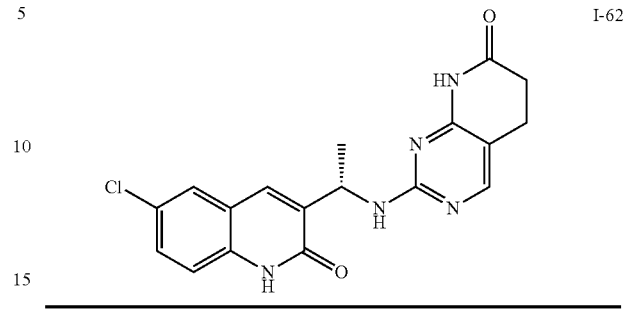

I-62

TABLE 5

LCMS signal and NMR chemical shifts of each compound listed in Table 4.

| Compounds | LCMS<sup>a</sup> | <sup>1</sup>H NMR (300 MHz) δ ppm | Chemical Name |
|---|---|---|---|
| I-42 | m/z: 383.16 (M + H)<sup>+</sup> Rt (min): 0.88 | | 3-[(1S)-1-({1-acetyl-1H,2H,3H-pyrrolo[3,2-c]pyridin-4-yl}amino)ethyl]-6-chloro-1,2-dihydroquinolin-2-one |
| I-43 | m/z: 419.10 (M + H)<sup>+</sup> Rt (min): 0.93 | | 6-chloro-3-[(1S)-1-({1-methanesulfonyl-1H,2H,3H-pyrrolo[3,2-c]pyridin-4-yl}amino)ethyl]-1,2-dihydroquinolin-2-one |
| I-44 | m/z: 399.13 (M + H)<sup>+</sup> Rt (min): 0.89 | | 3-[(1S)-1-({1-acetyl-1H,2H,3H-pyrido[3,4-b][1,4]oxazin-5-yl}amino)ethyl]-6-chloro-1,2-dihydroquinolin-2-one |
| I-45 | m/z: 341.05 (M + H)<sup>+</sup> Rt (min): 0.98 | | 6-chloro-3-[(1S)-1-({1H-pyrazolo[3,4-d]pyrimidin-6-yl}amino)ethyl]-1,2-dihydroquinolin-2-one |
| I-46 | m/z: 428.13 (M + H)<sup>+</sup> Rt (min): 1.2884 | <sup>1</sup>H-NMR (300 MHz, CDCl3, 50° C.) δ: 10.5 (broad s, 0.8H), 7.90 (s, 1H), 7.62 (s, 1H), 7.49 (s, 1H), 7.40 (d, J = 7.98, 1H), 7.16 (d, J = 8.52, 1H), 6.00 (d, J = 6.84, 1H), 5.27 (m, 1H), 5.06 (s, 2H), 3.82 (m, 2H), 2.05 (m, 1H), 1.61 (d, J = 6.87, 3H) 0.82 (m, 6H) | 6-chloro-3-[(1S)-1-{[1-(2-methylpropyl)-2-oxo-1H,2H,4H-pyrimido[4,5-d][1,3]oxazin-7-yl]amino}ethyl]-1,2-dihydroquinolin-2-one |
| I-47 | m/z: 385.98 (M + H)<sup>+</sup> Rt (min): 1.07 | <sup>1</sup>H-NMR (300 MHz, CDCl3) δ: 11.40 (broad s, 0.8H), 7.90 (s, 1H), 7.67 (s, 1H), 7.50 (broad s, 1H), 7.40 (dd, J = 2.19, 8.79, 1H), 7.27 (m, 1H), 6.17 (d, J = 8.49, 1H), 5.30 (m, 1H), 5.07 (s, 2H), 3.31 (s, 3H), 1.62 (d, J = 6.87, 3H). | 6-chloro-3-[(1S)-1-({1-methyl-2-oxo-1H,2H,4H-pyrimido[4,5-d][1,3]oxazin-7-yl}amino)ethyl]-1,2-dihydroquinolin-2-one |
| I-48 | m/z: 493.20 (M + H)<sup>+</sup> Rt (min): 1.24 | <sup>1</sup>H NMR (300 MHz, DMSO-d6): δ 11.78 (br s, 1H), 8.61 (d, J = 4.9 Hz, 1H), 7.98 (br s, 1H), 7.91-7.85 (m, 1H), 7.79 (s, 1H), 7.75-7.62 (m, 2H), 7.56 (d, J = 7.7 Hz, 1H), 7.39-7.35 (m, 1H), 7.01 (s, 1H), 5.28 (s, 2H), 5.16-5.09 (m, 3H), 3.24-3.20 (m, 3H), 1.38 (d, J = 6.9 Hz, 3H). | 6-chloro-3-[(1S)-1-({1-methyl-2-oxo-1H,2H,4H-pyrimido[4,5-d][1,3]oxazin-7-yl}amino)ethyl]-7-(pyridin-2-ylmethoxy)-1,2-dihydroquinolin-2-one |
| I-49 | m/z: 372.1 (M + H)<sup>+</sup> Rt (min): 3.78* | <sup>1</sup>H NMR (300 MHz, DMSO-d6, 80° C.): δ ppm: 11.70 (br s 1H), 10.38 (br s, 1H), 7.98 (s, 1H), 7.78 (s, 1H), 7.67 (d, J = 2.4 Hz, 1H), 7.45 (dd, J1 = 8.5 Hz, J2 = 2.4 Hz, 1H), 7.32 (d, J = 8.5 Hz, 1H), 7.15 (br d, 1H), 5.15-5.25 (m, 1H), 5.13 (s, 2H), 1.45 (d, J = 6.6 Hz, 3H). | 6-chloro-3-[(1S)-1-({2-oxo-1H,2H,4H-pyrimido[4,5-d][1,3]oxazin-7-yl}amino)ethyl]-1,2-dihydroquinolin-2-one |
| I-50 | m/z: 416.05 (M + H)<sup>+</sup> Rt (min): 1.09 | 1H NMR (300 MHz, DMSO-d6): δ ppm 11.81 (s, 1 H), 7.99 (br s, 1 H), 7.62-7.80 (m, 3 H), 6.94 (s, 1 H), 5.07-5.21 (m, 3 H), 3.87 (s, 3 H), 3.23 (br s, 3 H), 1.38 (d, J = 7.04 Hz, 3 H). | 6-chloro-7-methoxy-3-[1-({1-methyl-2-oxo-1H,2H,4H-pyrimido[4,5-d][1,3]oxazin-7-yl}amino)ethyl]-1,2-dihydroquinolin-2-one |

TABLE 5-continued

LCMS signal and NMR chemical shifts of each compound listed in Table 4.

| Compounds | LCMS[a] | ¹H NMR (300 MHz) δ ppm | Chemical Name |
|---|---|---|---|
| I-51 | m/z: 416.12 (M + H)⁺ Rt (min): 1.16 | | 6-chloro-7-methoxy-3-[(1S)-1-({1-methyl-2-oxo-1H,2H,4H-pyrimido[4,5-d][1,3]oxazin-7-yl}amino)ethyl]-1,2-dihydroquinolin-2-one |
| I-52 | m/z: 416.12 (M + H)⁺ Rt (min): 1.16 | | 6-chloro-7-methoxy-3-[(1R)-1-({1-methyl-2-oxo-1H,2H,4H-pyrimido[4,5-d][1,3]oxazin-7-yl}amino)ethyl]-1,2-dihydroquinolin-2-one |
| I-53 | m/z: 404.09 (M + H)⁺ Rt (min): 1.22 | ¹H NMR (300 MHz, DMSO-d6): δ ppm 7.91-8.02 (m, 2 H), 7.74 (br s, 2 H), 7.13-7.26 (m, 2 H), 5.06-5.21 (m, 3 H), 3.23 (br s, 3 H), 1.39 (d, J = 6.74 Hz, 3 H). | 6-chloro-7-fluoro-3-[(1R)-1-({1-methyl-2-oxo-1H,2H,4H-pyrimido[4,5-d][1,3]oxazin-7-yl}amino)ethyl]-1,2-dihydroquinolin-2-one |
| I-54 | m/z: 387.00 (M + H)⁺ Rt (min): 1.88 | ¹H NMR (300 MHz, DMSO-d₆) δ ppm 12.39 (s, 1 H), 8.46 (s, 1 H), 8.26 (s, 1 H), 7.95 (s, 1 H), 7.73 (s, 1 H), 6.78 (s, 1 H), 5.03-5.18 (m, 3 H), 3.40 (s, 3 H),), 1.38 (d, J = 7.04 Hz, 3H) | 6-chloro-3-[(1S)-1-({1-methyl-2-oxo-1H,2H,4H-pyrimido[4,5-d][1,3]oxazin-7-yl}amino)ethyl]-1,2-dihydro-1,8-naphthyridin-2-one |
| I-55 | m/z: 414.08 (M + H)⁺ Rt (min): 1.43 | ¹H NMR (300 MHz, CD₃OD): δ 7.92 (s, 1H), 7.77 (s, 1H), 7.58 (d, J = 2.2 Hz, 1H), 7.44 (dd, J = 8.6 Hz, 2.2 Hz, 1H), 7.33 (d, J = 8.8 Hz, 1H), 5.26 (q, J = 6.9 Hz, 1H), 3.59-3.48 (m, 2H), 2.06 (bs, 1H), 1.51 (d, J = 6.9 Hz, 3H), 0.79 (bs, 6H). | 6-chloro-3-[(1S)-1-{[3-(2-methylpropyl)-2-oxo-2H,3H-[1,3]oxazolo[4,5-d]pyrimidin-5-yl]amino}ethyl]-1,2-dihydroquinolin-2-one |
| I-56 | m/z: 358.04 (M + H)⁺ Rt (min): 0.96 | ¹H NMR (300 MHz, CD₃OD): δ 7.81 (s, 1H), 7.66 (s, 1H), 7.31 (d, J = 2.2 Hz, 1H), 7.45 (dd, J = 8.8 Hz, 2.2 Hz, 1H), 7.30 (d, J = 8.8 Hz, 1H), 5.21 (q, J = 6.9 Hz, 1H), 1.52 (d, J = 6.8 Hz, 3H). | 6-chloro-3-[(1S)-1-({2-oxo-2H,3H-[1,3]oxazolo[4,5-d]pyrimidin-5-yl}amino)ethyl]-1,2-dihydroquinolin-2-one |
| I-57 | m/z: 372.05 (M + H)⁺ Rt (min): 1.1649 | ¹H NMR (300 MHz, CDCl3): δ 10.94 (s, 1H), 7.89 (s, 1H), 7.67 (s, 1H), 7.51 (d, J = 2.2 Hz, 1H), 7.50 (dd, J = 8.8 Hz, 2.2 Hz, 1H), 6.05 (d, J = 8.2 Hz, 1H), 5.28 (m, 1H), 3.32 (s, 3H), 1.63 (d, J = 6.9 Hz, 3H) | 6-chloro-3-[(1S)-1-({3-methyl-2-oxo-2H,3H-[1,3]oxazolo[4,5-d]pyrimidin-5-yl}amino)ethyl]-1,2-dihydroquinolin-2-one |
| I-58 | m/z: 371.08 (M + H)⁺ Rt (min): 0.88 | ¹H NMR (300 MHz, DMSO-d6) δ: 11.93 (s, 1H), 10.67 (s, 1H), 7.74 (s, 1H), 7.71 (d, J = 2.5 Hz, 1H), 7.70 (s, 1H), 7.46 (dd, J = 8.8, 2.5 Hz, 1H), 7.28 (d, J = 8.8 Hz, 1H), 7.18 (d, J = 7.7 Hz, 1H), 5.12 (m, 1H), 3.16 (s, 3H), 1.37 (d, J = 6.9 Hz, 3H). LCMS (LCMS method 1, APCI): 98% pure @ 254 nm, RT = 3.87 min, m/z = 371, 373 [M + H]+. | 6-chloro-3-[(1S)-1-[(9-methyl-8-oxo-8,9-dihydro-7H-purin-2-yl)amino]ethyl]-1,2-dihydroquinolin-2-one |
| I-59 | m/z: 357.04 (M + H)⁺ Rt (min): 0.79 | ¹H NMR (300 MHz, DMSO-d6) δ: 11.92 (s, 1H), 11.27 (br.s, 1H), 10.40 (s, 1H), 7.71 (s, 1H), 7.70 (d, J = 2.2 Hz, 1H), 7.67 (s, 1H), 7.46 (dd, J = 8.8, 2.2 Hz, 1H), 7.28 (d, J = 8.8 Hz, 1H), 7.02 (d, J = 8.0 Hz, 1H), 5.07 (m, 1H), 1.36 (d, J = 6.9 Hz, 3H) | 6-chloro-3-[(1S)-1-[(8-oxo-8,9-dihydro-7H-purin-2-yl)amino]ethyl]-1,2-dihydroquinolin-2-one |
| I-60 | m/z: 356.10 (M + H)⁺ Rt (min): 0.79 | ¹H NMR (300 MHz, DMSO-d6) δ 12.07 (brs, NH), 11.92 (brs, NH), 7.96 (brs, NH), 7.81 (m, 1H), 7.77 (d, J = 2.2 Hz, 1H), 7.53 (dd, J = 2.2 Hz, 6.6 Hz, 1H), 7.33 (d, J = 8.8 Hz, 1H), 5.18 (m, 1H), 3.47 (s, 2H), 1.45 (d, J = 6.6 Hz, 1H) | 6-chloro-3-[(1S)-1-({6-oxo-5H,6H,7H-pyrrolo[2,3-d]pyrimidin-2-yl}amino)ethyl]-1,2-dihydroquinolin-2-one |
| I-61 | m/z: 370.04 (M + H)⁺ Rt (min): 0.9 | ¹H NMR (300 MHz, DMSO-d6) δ 11.92 (brs, NH), 7.82 (brs, NH), 7.74-7.72 (m, 2H), 7.60 (d, J = 6.2 Hz, 1H), 7.44 (dd, J = 2.2 Hz, 6.2 Hz, 1H), 7.27 (d, J = 8.8 Hz, 1H), 5.19 (m, 1H), 3.46 (s, 2H), 3.03 (s, 3H), 1.37 (d, J = 6.6 Hz, 1H). | 6-chloro-3-[(1S)-1-({7-methyl-6-oxo-5H,6H,7H-pyrrolo[2,3-d]pyrimidin-2-yl}amino)ethyl]-1,2-dihydroquinolin-2-one |

TABLE 5-continued

LCMS signal and NMR chemical shifts of each compound listed in Table 4.

| Compounds | LCMS[a] | $^1$H NMR (300 MHz) δ ppm | Chemical Name |
|---|---|---|---|
| I-62 | m/z: 370.04 (M + H)$^+$ Rt (min): 0.88 | $^1$H NMR (300 MHz, MeOD-d3) δ: 7.92 (s, 1H), 7.82 (s, 1H), 7.61 (d, J = 2.2 Hz, 1H), 7.45 (dd, J = 8.8, 2.2 Hz, 1H), 7.30 (d, J = 8.8 Hz, 1H), 5.24 (m, 1H), 2.75 (m, 2H), 2.56 (m, 2H), 1.50 (d, J = 6.9 Hz, 3H) | 6-chloro-3-[(1S)-1-({7-oxo-5H,6H,7H,8H-pyrido[2,3-d]pyrimidin-2-yl}amino)ethyl]-1,2-dihydroquinolin-2-one |

[a]LCMS data are determined by Method 4.

Example 34

IDH1-R132H and IDH1-R132C Enzymatic Assay

Assays were performed in a 384-well black plate. An aliquot of 250 nL of compound was incubated with 10 μL of 30 nM IDH1-R132H or 10 nM IDH1-R132C recombinant protein in assay buffer (50 mM Tris pH=7.5, 150 mM NaCl, 5 mM MgCl$_2$, 0.1% (w/v) Bovine Serum Albumin, and 0.01% Triton X-100) in each well at 25° C. for 15 minutes. After the plate was centrifuged briefly, an aliquot of 10 μL of 2 mM α-ketoglutarate and 20 μM NADPH solution prepared in assay buffer was then added to each well and the reaction was maintained at 25° C. for 45 minutes. An aliquot of 10 μL of diaphorase solution (0.15 U/mL diaphorase and 30 μM Resazurin in assay buffer) was added to each well. The plate was maintained at 25° C. for 15 minutes and then read on a plate reader with excitation and emission wavelengths at 535 nm and 590 nm, respectively. The IC$_{50}$ of a given compound was calculated by fitting the dose response curve of inhibition of NADPH consumption at a given concentration with the four parameter logistic equation.

Example 35

Cellular 2-HG Assay Using HCT116 Mutant IDH1 Cells

HCT116 isogenic IDH1-R132H and IDH1-R132C mutant cells were cultured in growth media (McCoy's 5A, 10% fetal bovine serum, 1× antibiotic-antimycotic solution and 0.3 mg/mL G418) in 5% CO$_2$ in an incubator at 37° C. To prepare the assay, cells were trypsinized and resuspended in assay media (McCoy's 5A with no L-glutamine, 10% fetal bovine serum, 1× antibiotic-antimycotic solution and 0.3 mg/mL G418). An aliquot of 10,000 cells/100 L was transferred to each well of a clear 96-well tissue culture plate. The cells were incubated in 5% CO$_2$ at 37° C. in an incubator overnight to allow for proper cell attachment. An aliquot of 50 μL of compound containing assay media were then added to each well and the assay plate was kept in 5% CO$_2$ at 37° C. in an incubator for 24 hours. The media was then removed from each well and 150 μL of a methanol/water mixture (80/20 v/v) was added to each well. The plates were kept at −80° C. freezer overnight to allow for complete cell lysis. An aliquot of 125 μL of extracted supernatant was analyzed by RapidFire high-throughout-mass spectrometry (Agilent) to determine the cellular 2-HG level. The IC$_{50}$ of a given compound was calculated by fitting the dose response curve of cellular 2-HG inhibition at a given concentration with the four parameter logistic equation.

Table 6 below provides activity of each compound according to the legend that "++++" indicates an inhibition at a concentration <0.1 μM; "+++" indicates inhibition at a concentration between 0.1 μM and 1 μM of the disclosed compound; "++" indicates inhibition at a concentration from 1 μM to 10 μM of the disclosed compound; and "+" indicates inhibition at a concentration >10 μM.

TABLE 6

Results of the illustrative compounds of Formula I in IDH1-R132H, IDH1-R132C, IDH1-MS-HTC116-R132H, and IDH1-MS-HTC116-R132C assays.

| No | Enzyme IDH1 R132H IC50 (uM) | Enzyme IDH1 R132C IC50 (uM) | HCT116 IDH1 R132H IC50 (uM) | HCT116 IDH1 R132C IC50 (uM) |
|---|---|---|---|---|
| I-1 | +++ | +++ | | |
| I-2 | +++ | | | |
| I-3 | +++ | | | |
| I-4 | +++ | + | | |
| I-5 | +++ | | | |
| I-6 | ++ | | | |
| I-7 | ++ | | | |
| I-8 | ++ | | | |
| I-9 | ++ | | | |
| I-10 | ++ | | | |
| I-11 | ++ | | | |
| I-12 | + | | | |
| I-13 | + | | | |
| I-14 | + | | | |
| I-15 | + | | | |
| I-16 | + | | | |
| I-17 | + | | | |
| I-18 | + | | | |
| I-19 | + | | | |
| I-20 | ++ | | | |
| I-21 | + | | | |
| I-22 | + | | | |
| I-23 | + | | | |
| I-24 | + | | | |
| I-25 | + | | | |
| I-26 | + | | | |
| I-27 | + | | | |
| I-28 | + | | | |
| I-29 | + | | | |
| I-30 | + | | | |
| I-31 | + | | | |
| I-32 | + | | | |
| I-33 | + | | | |
| I-34 | + | | | |
| I-35 | + | | | |
| I-36 | + | | | |
| I-37 | + | | | |
| I-38 | + | | | |
| I-39 | + | | | |
| I-40 | + | | | |
| I-41 | ++ | | | |
| I-42 | +++ | ++ | | |
| I-43 | ++ | | | |
| I-44 | ++ | + | | |
| I-45 | +++ | ++ | +++ | +++ |

TABLE 6-continued

Results of the illustrative compounds of Formula I in IDH1-R132H, IDH1-R132C, IDH1-MS-HTC116-R132H, and IDH1-MS-HTC116-R132C assays.

| No | Enzyme IDH1 R132H IC50 (uM) | Enzyme IDH1 R132C IC50 (uM) | HCT116 IDH1 R132H IC50 (uM) | HCT116 IDH1 R132C IC50 (uM) |
|---|---|---|---|---|
| I-46 | ++++ | ++++ | | |
| I-47 | ++++ | ++++ | ++++ | ++++ |
| I-48 | ++++ | ++++ | ++++ | ++++ |
| I-49 | ++++ | +++ | ++++ | +++ |
| I-50 | ++++ | ++++ | ++++ | ++++ |
| I-51 | ++++ | ++++ | ++++ | ++++ |
| I-52 | +++ | ++ | | |
| I-53 | ++ | + | | |
| I-54 | | | | |
| I-55 | ++++ | ++++ | +++ | ++ |
| I-56 | ++++ | +++ | ++ | + |
| I-57 | ++++ | +++ | +++ | +++ |
| I-58 | +++ | ++ | +++ | ++ |
| I-59 | ++ | ++ | | |
| I-60 | +++ | ++ | +++ | ++ |
| I-61 | +++ | +++ | +++ | +++ |
| I-62 | ++ | ++ | | |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of formula I:

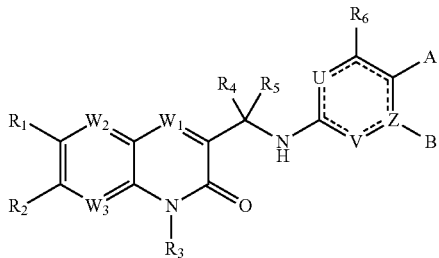

(I)

or a pharmaceutically acceptable salt, enantiomer, hydrate, solvate, prodrug, isomer, or tautomer thereof, wherein:

each $W_1$ and $W_2$ is independently CH, CF, or N;
$W_3$ is CF, $CR_2$, or N;
U is N or $CR_6$;
V is N or $CR_9$;
Z is N or C;
═══ indicates a single or double bond but never two double bonds adjacent to one another in the ring in which the ----- occurs;
A and B, A and $R_6$, or B and $R_9$ are taken together with the atoms to which they are attached and form an aryl or a 5 to 7-membered heterocyclyl or heteroaryl ring system which can be further substituted with one or more $R_{10}$ substituents;

A and B, when not part of the fused aryl, heteroaryl, or 5 to 7-membered heterocyclyl, are each independently H, $R_6$, CN, $C_1$-$C_6$ alkyl, or $C_1$-$C_6$ alkoxy;

$R_1$ is independently H, OH, CN, halogen, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, 3 to 8-membered heterocyclyl, aryl, or heteroaryl, wherein each $C_1$-$C_6$ alkyl, $C_2$-$C_6$ alkenyl, $C_2$-$C_6$ alkynyl, $C_3$-$C_8$ cycloalkyl, $C_3$-$C_8$ heterocyclyl, aryl, or heteroaryl is optionally substituted one or more times with substituents selected from the group consisting of halogen, OH, $NH_2$, CN, $C_1$-$C_6$ alkyl, and $C_1$-$C_6$ alkoxy;

$R_2$ is independently H, OH, CN, halogen, $CF_3$, $CHF_2$, $C_1$-$C_6$ alkyl, $C_1$-$C_6$ alkoxy, $NH_2$, —O(CH$_2$)$_n$R$_7$, —O(CH$_2$)$_n$C(O)NHR$_7$, —O(CH$_2$)$_n$C(O)R$_7$, NHR$_7$, —N(R$_7$)(R$_8$), NHC(O)R$_7$, NHS(O)R$_7$, NHS(O)$_2$R$_7$, NHC(O)OR$_7$, NHC(O)NHR$_7$, —S(O)$_2$NHR$_7$, NHC(O)N(R$_8$)R$_7$, OCH(R$_7$)(R$_8$), or —CH(R$_7$)(R$_8$), wherein $C_1$-$C_6$ alkyl, $C_1$-$C_6$ alkoxy is optionally substituted with one or more substituents selected from the group consisting of $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, 3 to 8-membered heterocyclyl substituted with one or more halogen, 3 to 8-membered heterocyclyl, aryl, -heteroaryl-C(O)NH$_2$, and heteroaryl;

$R_3$ is H or $C_1$-$C_6$ alkyl;

$R_4$ and $R_5$ are independently H, halogen, $CH_2OH$, $C_1$-$C_3$ alkyl, or $C_1$-$C_3$ haloalkyl, or $R_4$ and $R_5$ when combined can form a $C_3$-$C_6$ cycloalkyl or 3 to 8-membered heterocyclyl;

$R_6$ is H, halogen, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, $C_2$-$C_6$ alkynyl, $C_3$-$C_8$ cycloalkyl, 3 to 8-membered heterocyclyl, aryl, or heteroaryl;

$R_7$ and $R_8$ are independently H, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, 3 to 8-membered heterocyclyl, aryl, and heteroaryl; or when combined $R_7$ and $R_8$ can form a 3 to 8-membered heterocyclyl or heteroaryl ring; and $R_9$ is independently selected from the group consisting of H, ═O, halogen, OH, CN, —CH$_2$CN, $C_1$-$C_6$ alkyl, $R_7S(O)_2$—, $C_1$-$C_6$ alkoxy, $C_2$-$C_6$ alkenyl, $C_2$-$C_6$ alkenyl, $C_3$-$C_8$ cycloalkyl, $C_3$-$C_8$ cycloalkylalkyl, 3 to 8-membered heterocyclyl, aryl, and heteroaryl, wherein alkyl, alkoxy, alkenyl, cycloalkyl, cycloalkylalkyl, 3 to 8-membered heterocyclyl, aryl, and heteroaryl are optionally further substituted with one or more substituents selected from the group consisting of OH, halogen, $C_1$-$C_6$ alkoxy, $NH_2$, $R_7S(O)_2$—, CN, $C_3$-$C_8$ cycloalkyl, 3 to 8-membered heterocyclyl, aryl, heteroaryl, and $R_7S(O)$—;

each $R_{10}$ is independently H, OH, CN, ═O, —COOR$_{11}$, —C(O)R$_{11}$, —CH$_2$CN, $C_1$-$C_6$ alkyl, $C_1$-$C_6$ haloalkyl $R_{11}S(O)_2$—, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, $C_3$-$C_8$ heterocyclyl, aryl, or heteroaryl; and each $R_{11}$ is independently H, $C_1$-$C_6$ alkyl, $C_1$-$C_6$ haloalkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, 3 to 8-membered heterocyclyl, aryl, or heteroaryl;

provided that:
(1) when A and B or A and $R_6$ form a 1,4-dioxane ring, $R_1$ and $R_2$ are not both methyl;
(2) when A and B or A and $R_6$ form a 1,3-dioxolane ring, $R_1$ is not H or methyl;
(3) when A and B or A and $R_6$ form a pyridine ring, $R_1$ is not H or $R_2$ is not methyl;

(4) when A and B or A and $R_6$ form a pyrazole ring, $R_1$ is not H, ethyl, or ethoxy;
(5) when A and B or A and $R_6$ form a pyrazole ring and $R_1$ is methyl, $R_2$ is not H; or
(6) when A and B or A and $R_6$ form a phenyl ring, $R_1$ is not H.

2. The compound of claim 1 having a Formula Ia:

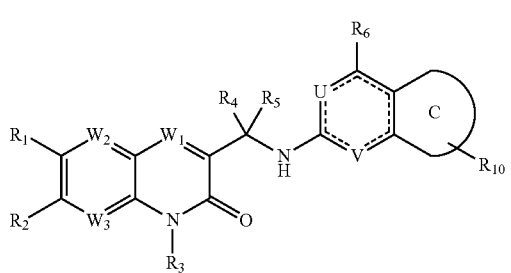

(Ia)

wherein:
the C ring is pyrrolidinyl, piperidinyl, phenyl, thienyl, oxazolyl, dioxanyl, dioxolanyl, thiazolyl, isoxazolyl, isothiazolyl, pyrrolyl, pyrazolyl, oxadiazolyl, thiadiazolyl, furyl, imidazolyl, pyridyl, pyrimidinyl, pyrrolyl, furyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, pyrimidinyl, morpholinyl, thiomorpholinyl, oxazolonyl, oxazinonyl, dihydrooxazinonyl, imidazolonyl, pyrrolonyl, thiazolonyl, dihydropyridinonyl, dihydrothiazinedioxide, dihydrodioxinyl, dihydropyranonyl, dihydrothiophenedioxide, piperidinonyl, or dihydrooxazinony; and $R_{10}$ is independently H, OH, CN, =O, —COOR$_{11}$, —C(O)R$_{11}$, —CH$_2$CN, $C_1$-$C_6$ alkyl, $C_1$-$C_6$ haloalkyl $R_{11}$S(O)$_2$—, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, $C_3$-$C_8$ heterocyclyl, aryl, or heteroaryl; and each $R_{11}$ is independently H, $C_1$-$C_6$ alkyl, $C_1$-$C_6$ haloalkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, $C_3$-$C_8$ heterocyclyl, aryl, or heteroaryl.

3. The compound of claim 2, wherein $R_{10}$ is methyl, ethyl, isopropyl, or isobutyl.

4. The compound of claim 1 having a Formula Ib:

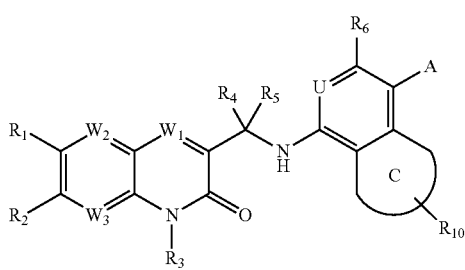

(Ib)

wherein:
the C ring is pyrrolidinyl, piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl, pyrrolyl, furyl, oxazolyl, thiazolyl, isoxazolyl, isothiazolyl, dazolyl, pyrazolyl, oxadiazolyl, thiadiazolyl, triazolyl, tetrazolyl, pyrazinyl, pyridazinyl, triazinyl, pyridinyl, pyrimidinyl, morpholinyl, thiomorpholinyl, oxazolonyl, oxazinonyl, dihydrooxazinonyl, imidazolonyl, pyrrolonyl, thiazolonyl, dihydropyridinonyl, dihydrothiazinedioxide, dihydrodioxinyl, dihydropyranonyl, dihydrothiophenedioxide, piperidinonyl, or dihydrooxazinonyl;

$R_{10}$ is independently H, OH, CN, =O, —COOR$_{11}$, —C(O)R$_{11}$, —CH$_2$CN, $C_1$-$C_6$ alkyl, $C_1$-$C_6$ haloalkyl $R_{11}$S(O)$_2$—, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, $C_3$-$C_8$ heterocyclyl, aryl, or heteroaryl; and each $R_1$1 is independently H, $C_1$-$C_6$ alkyl, $C_1$-$C_6$ haloalkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, $C_3$-$C_8$ heterocyclyl, aryl, or heteroaryl.

5. The compound of claim 4, wherein $R_{10}$ is methyl, ethyl, isopropyl, or isobutyl.

6. The compound of claim 1, wherein $R_4$ and $R_5$ are H.

7. The compound of claim 1, wherein $R_4$ is H and $R_5$ is methyl.

8. The compound of claim 1, wherein $R_4$ is H and $R_5$ is (S)-methyl.

9. The compound of claim 1, wherein $R_4$ and $R_5$ are halogen.

10. The compound of claim 1, wherein $R_4$ is F and $R_5$ is methyl.

11. The compound of claim 1, wherein $R_4$ and $R_5$ can combine to form a $C_3$-$C_5$ cycloalkyl.

12. The compound of claim 1, wherein $W_1$, $W_2$ and $W_3$ are CH or CF.

13. The compound of claim 1, wherein $W_1$, $W_2$, or $W_3$ is N.

14. The compound of claim 1, wherein $R_1$ is halogen.

15. The compound of claim 14, wherein $R_1$ is chloro.

16. The compound of claim 1, wherein $R_2$ is H or $C_1$-$C_6$ alkoxy.

17. The compound of claim 1, wherein $R_2$ is $C_1$-$C_6$ alkoxy substituted with heteroaryl or $C_3$-$C_8$ heterocyclyl.

18. The compound of claim 1 selected from:
3-{[(1,3-benzoxazol-4-yl)amino]methyl}-6-chloro-1,2-dihydroquinolin-2-one;
6-chloro-3-{[(3-methyl-2-oxo-2,3-dihydro-1,3-benzoxazol-5-yl)amino]methyl}-1,2-dihydroquinolin-2-one;
6-chloro-3-{[(2-oxo-2,3-dihydro-1,3-benzoxazol-5-yl)amino]methyl}-1,2-dihydroquinolin-2-one;
6-chloro-3-{[(2-oxo-2H-chromen-6-yl)amino]methyl}-1,2-dihydroquinolin-2-one;
6-chloro-3-{[(1-methyl-2-oxo-1,2,3,4-tetrahydroquinolin-6-yl)amino]methyl}-1,2-dihydroquinolin-2-one;
6-chloro-3-{[(isoquinolin-3-yl)amino]methyl}-1,2-dihydroquinolin-2-one;
4-{[(6-chloro-2-oxo-1,2-dihydroquinolin-3-yl)methyl]amino}naphthalene-1-carbonitrile;
6-chloro-3-{[(quinolin-8-yl)amino]methyl}-1,2-dihydroquinolin-2-one;
6-chloro-3-{[(2,3-dihydro-1-benzofuran-7-yl)amino]methyl}-1,2-dihydroquinolin-2-one;
7-{[(6-chloro-2-oxo-1,2-dihydroquinolin-3-yl)methyl]amino}-4-methyl-3,4-dihydro-2H-1,4-benzoxazin-3-one;
7-{[(6-chloro-2-oxo-1,2-dihydroquinolin-3-yl)methyl]amino}-3,4-dihydro-2H-1,4-benzoxazin-3-one;
3-({[2-(1H-1,3-benzodiazol-5-yl)-1H-1,3-benzodiazol-5-yl]amino}methyl)-6,7-dimethoxy-1,2-dihydroquinolin-2-one;

6-chloro-3-{[(2-oxo-2,3-dihydro-1H-indol-6-yl)amino]
methyl}-1,2-dihydroquinolin-2-one;
6-chloro-3-{[(3-methyl-2-oxo-2,3-dihydro-1,3-benzoxazol-6-yl)amino]methyl}-1,2-dihydroquinolin-2-one;
6-chloro-3-{[(isoquinolin-8-yl)amino]methyl}-1,2-dihydroquinolin-2-one;
6-chloro-3-{[(3,4-dihydro-2H-1-benzopyran-8-yl)amino]
methyl}-1,2-dihydroquinolin-2-one;
6-chloro-3-{[(6-methoxy-2-oxo-1,2,3,4-tetrahydroquinolin-7-yl)amino]methyl}-1,2-dihydroquinolin-2-one;
6-chloro-3-{[(2-oxo-1,2,3,4-tetrahydroquinolin-7-yl)
amino]methyl}-1,2-dihydroquinolin-2-one;
6-chloro-3-{[(3-methyl-1H-indazol-6-yl)amino]methyl}-
1,2-dihydroquinolin-2-one;
6-chloro-3-{[(2-oxo-1,2,3,4-tetrahydroquinolin-6-yl)
amino]methyl}-1,2-dihydroquinolin-2-one;
6-methoxy-3-{[(2-methyl-1,3-benzothiazol-5-yl)amino]
methyl}-1,2-dihydroquinolin-2-one;
6-chloro-3-{[(5-oxo-5,6,7,8-tetrahydronaphthalen-1-yl)
amino]methyl}-1,2-dihydroquinolin-2-one;
6-chloro-3-[({[1,2,4]triazolo[4,3-b]pyridazin-6-
yl}amino)methyl]-1,2-dihydroquinolin-2-one;
3-{[(1H-1,3-benzodiazol-5-yl)amino]methyl}-6-chloro-
1,2-dihydroquinolin-2-one;
6-chloro-3-{[(1H-indazol-6-yl)amino]methyl}-1,2-dihydroquinolin-2-one;
3-{[(1,3-benzothiazol-6-yl)amino]methyl}-6-chloro-1,2-
dihydroquinolin-2-one;
6-chloro-3-{[(quinolin-6-yl)amino]methyl}-1,2-dihydroquinolin-2-one;
6-chloro-3-({[2-(trifluoromethyl)-1H-1,3-benzodiazol-5-
yl]amino}methyl)-1,2-dihydroquinolin-2-one;
3-{[(1,3-benzothiazol-5-yl)amino]methyl}-6-chloro-1,2-
dihydroquinolin-2-one;
3-{[(2,3-dihydro-1,4-benzodioxin-6-yl)amino]methyl}-
6-methoxyl-1,2-dihydroquinolin-2-one;
3-{[(1H-indazol-6-yl)amino]methyl}-6,7-dimethyl-1,2-
dihydroquinolin-2-one;
6-chloro-3-{[(2-methylquinolin-6-yl)amino]methyl}-1,2-
dihydroquinolin-2-one;
6-chloro-3-{[(2,3-dihydro-1,4-benzodioxin-6-yl)amino]
methyl}-1,2-dihydroquinolin-2-one;
3-{[(1H-indazol-6-yl)amino]methyl}-6-methoxy-1,2-dihydroquinolin-2-one;
6-methoxy-3-{[(2-methylquinolin-6-yl)amino]methyl}-
1,2-dihydroquinolin-2-one;
3-{[(1,3-benzothiazol-6-yl)amino]methyl}-6-methoxy-1,
2-dihydroquinolin-2-one;
6,7-dimethyl-3-{[(2-methylquinolin-6-yl)amino]
methyl}-1,2-dihydroquinolin-2-one;
6-chloro-3-{[(1H-indazol-5-yl)amino]methyl}-1,2-dihydroquinolin-2-one;
6-methoxy-3-{[(quinolin-6-yl)amino]methyl}-1,2-dihydroquinolin-2-one;
3-{[(1,3-benzothiazol-6-yl)amino]methyl}-6,7-dimethyl-
1,2-dihydroquinolin-2-one;
6-tert-butyl-3-{[(1H-indazol-5-yl)amino]methyl}-1,2-dihydroquinolin-2-one;
3-[(1S)-1-({1-acetyl-1H,2H,3H-pyrrolo[3,2-c]pyridin-4-
yl}amino)ethyl]-6-chloro-1,2-dihydroquinolin-2-one;
6-chloro-3-[(1S)-1-({1-methanesulfonyl-1H,2H,3H-pyrrolo[3,2-c]pyridin-4-yl}amino)ethyl]-1,2-dihydroquinolin-2-one;
3-[(1S)-1-({1-acetyl-1H,2H,3H-pyrido[3,4-b][1,4]oxazin-5-yl}amino)ethyl]-6-chloro-1,2-dihydroquinolin-
2-one;
6-chloro-3-[(1S)-1-({1H-pyrazolo[3,4-d]pyrimidin-6-
yl}amino)ethyl]-1,2-dihydroquinolin-2-one;
6-chloro-3-[(1S)-1-{[1-(2-methylpropyl)-2-oxo-1H,2H,
4H-pyrimido[4,5-d][1,3]oxazin-7-yl]amino}ethyl]-1,
2-dihydroquinolin-2-one;
6-chloro-3-[(1S)-1-({1-methyl-2-oxo-1H,2H,4H-pyrimido[4,5-d][1,3]oxazin-7-yl}amino)ethyl]-1,2-dihydroquinolin-2-one;
6-chloro-3-[(1S)-1-({1-methyl-2-oxo-1H,2H,4H-pyrimido[4,5-d][1,3]oxazin-7-yl}amino)ethyl]-7-(pyridin-2-ylmethoxy)-1,2-dihydroquinolin-2-one;
6-chloro-3-[(1S)-1-({2-oxo-1H,2H,4H-pyrimido[4,5-d]
[1,3]oxazin-7-yl}amino)ethyl]-1,2-dihydroquinolin-2-
one;
6-chloro-7-methoxy-3-[1-({1-methyl-2-oxo-1H,2H,4H-
pyrimido[4,5-d][1,3]oxazin-7-yl}amino)ethyl]-1,2-dihydroquinolin-2-one;
6-chloro-7-methoxy-3-[(1S)-1-({1-methyl-2-oxo-1H,2H,
4H-pyrimido[4,5-d][1,3]oxazin-7-yl}amino)ethyl]-1,
2-dihydroquinolin-2-one;
6-chloro-7-methoxy-3-[(1R)-1-({1-methyl-2-oxo-1H,2H,
4H-pyrimido[4,5-d][1,3]oxazin-7-yl}amino)ethyl]-1,
2-dihydroquinolin-2-one;
6-chloro-7-fluoro-3-[(1R)-1-({1-methyl-2-oxo-1H,2H,
4H-pyrimido[4,5-d][1,3]oxazin-7-yl}amino)ethyl]-1,
2-dihydroquinolin-2-one;
6-chloro-3-[(1S)-1-({1-methyl-2-oxo-1H,2H,4H-pyrimido[4,5-d][1,3]oxazin-7-yl}amino)ethyl]-1,2-dihydro-1,8-naphthyridin-2-one;
6-chloro-3-[(1S)-1-{[3-(2-methylpropyl)-2-oxo-2H,3H-
[1,3]oxazolo[4,5-d]pyrimidin-5-yl]amino}ethyl]-1,2-
dihydroquinolin-2-one;
6-chloro-3-[(1S)-1-({2-oxo-2H,3H-[1,3]oxazolo[4,5-d]
pyrimidin-5-yl}amino)ethyl]-1,2-dihydroquinolin-2-
one;
6-chloro-3-[(1S)-1-({3-methyl-2-oxo-2H,3H-[1,3]oxazolo[4,5-d]pyrimidin-5-yl}amino)ethyl]-1,2-dihydroquinolin-2-one;
6-chloro-3-[(1S)-1-[(9-methyl-8-oxo-8,9-dihydro-7H-purin-2-yl)amino]ethyl]-1,2-dihydroquinolin-2-one;
6-chloro-3-[(1S)-1-[(8-oxo-8,9-dihydro-7H-purin-2-yl)
amino]ethyl]-1,2-dihydroquinolin-2-one;
6-chloro-3-[(1S)-1-({6-oxo-5H,6H,7H-pyrrolo[2,3-d]pyrimidin-2-yl}amino)ethyl]-1,2-dihydroquinolin-2-one;
6-chloro-3-[(1S)-1-({7-methyl-6-oxo-5H,6H,7H-pyrrolo
[2,3-d]pyrimidin-2-yl}amino)ethyl]-1,2-dihydroquinolin-2-one; or
6-chloro-3-[(1S)-1-({7-oxo-5H,6H,7H,8H-pyrido[2,3-d]
pyrimidin-2-yl}amino)ethyl]-1,2-dihydroquinolin-2-
one.
19. The compound of claim 1 selected from:
6-chloro-3-[(1S)-1-({1-cyclopropyl-2-oxo-1H,2H,4H-
pyrimido[4,5-d][1,3]oxazin-7-yl}amino)ethyl]-1,2-dihydroquinolin-2-one;
6-chloro-3-[(1S)-1-{[2-oxo-1-(propan-2-yl)-1H,2H,4H-
pyrimido[4,5-d][1,3]oxazin-7-yl]amino}ethyl]-1,2-dihydroquinolin-2-one;
6-chloro-3-[(1S)-1-({1-methyl-2-oxo-1H,2H,4H-pyrido
[4,3-d][1,3]oxazin-7-yl}amino)ethyl]-1,2-dihydroquinolin-2-one;
6-{[(1S)-1-(6-chloro-2-oxo-1,2-dihydroquinolin-3-yl)
ethyl]amino}-1-methyl-1H,3H-2$\lambda^6$,1,5,7-[1$\lambda^6$,2]thiazolo[3,4-d]pyrimidine-2,2-dione;
6-{[(1S)-1-(6-chloro-2-oxo-1,2-dihydroquinolin-3-yl)
ethyl]amino}-1-methyl-1H,3H-2$\lambda^6$,1,5-[1$\lambda^6$,2]thiazolo
[4,3-c]pyridine-2,2-dione;

6-chloro-3-[(1S)-1-({3-methyl-2-oxo-2H,3H-[1,3]thi-azolo[4,5-d]pyrimidin-5-yl}amino)ethyl]-1,2-dihydroquinolin-2-one;

6-chloro-3-[(1S)-1-({1-methyl-2-oxo-1H,2H-[1,3]thi-azolo[5,4-c]pyridin-6-yl}amino)ethyl]-1,2-dihydroquinolin-2-one;

6-chloro-3-[(1S)-1-({1-oxo-1H,2H,3H-pyrrolo[3,4-c]pyridin-4-yl}amino)ethyl]-1,2-dihydroquinolin-2-one;

4-{[(1S)-1-(6-chloro-2-oxo-1,2-dihydroquinolin-3-yl)ethyl]amino}-2H,3H-1λ⁶,2,5-[1λ⁶,2]thiazolo[4,5-c]pyridine-1,1-dione;

5-{[(1S)-1-(6-chloro-2-oxo-1,2-dihydroquinolin-3-yl)ethyl]amino}-1,2,3,4-tetrahydro-2,6-naphthyridin-1-one;

6-chloro-3-[(1S)-1-({3-oxo-1H,2H,3H,4H-pyrimido[4,5-c]pyridazin-7-yl}amino)ethyl]-1,2-dihydroquinolin-2-one;

6-chloro-3-[(1S)-1-({6-oxo-6H-pyrano[3,2-d]pyrimidin-2-yl}amino)ethyl]-1,2-dihydroquinolin-2-one;

6-chloro-3-[(1S)-1-({1-methyl-2-oxo-1H,2H-pyrido[3,4-b]pyrazin-7-yl}amino)ethyl]-1,2-dihydroquinolin-2-one;

6-chloro-3-[(1S)-1-({3-oxo-1H,2H,3H,4H-pyrido[4,3-c]pyridazin-7-yl}amino)ethyl]-1,2-dihydroquinolin-2-one 2-{[(1S)-1-(6-chloro-2-oxo-1,2-dihydroquinolin-3-yl)ethyl]amino}-8-methyl-7,8-dihydropteridin-7-one;

6-chloro-3-[(1S)-1-({2-methyl-1-oxo-1H,2H,3H-pyrrolo[3,4-c]pyridin-4-yl}amino)ethyl]-1,2-dihydroquinolin-2-one;

6-chloro-3-[(1S)-1-{[6-(2-oxo-1,3-oxazolidin-3-yl)-[1,3]oxazolo[4,5-c]pyridin-4-yl]amino}ethyl]-1,2-dihydroquinolin-2-one;

4-{[(1S)-1-(6-chloro-2-oxo-1,2-dihydroquinolin-3-yl)ethyl]amino}-[1,3]oxazolo[4,5-c]pyridine-7-carbonitrile;

N-(4-{[(1S)-1-(6-chloro-2-oxo-1,2-dihydroquinolin-3-yl)ethyl]amino}-[1,3]oxazolo[4,5-c]pyridin-6-yl)acetamide;

3-[(1S)-1-[(1H-1,3-benzodiazol-4-yl)amino]ethyl]-6-chloro-1,2-dihydroquinolin-2-one;

6-chloro-3-[(1S)-1-({1H-imidazo[4,5-c]pyridin-4-yl}amino)ethyl]-1,2-dihydroquinolin-2-one;

4-{[(1S)-1-(6-chloro-2-oxo-1,2-dihydroquinolin-3-yl)ethyl]amino}-1H-imidazo[4,5-c]pyridine-7-carbonitrile;

6-chloro-3-[(1S)-1-({1-ethyl-1H-imidazo[4,5-c]pyridin-4-yl}amino)ethyl]-1,2-dihydroquinolin-2-one;

6-chloro-3-{[(2-oxo-1,2,3,4-tetrahydroquinolin-7-yl)amino]methyl}-1,2-dihydroquinolin-2-one;

6-chloro-3-[({[1,2,4]triazolo[4,3-b]pyridazin-6-yl}amino)methyl]-1,2-dihydroquinolin-2-one;

6-chloro-3-{[(3-methyl-1H-indazol-6-yl)amino]methyl}-1,2-dihydroquinolin-2-one;

6-chloro-3-{[(3-methyl-2-oxo-2,3-dihydro-1,3-benzoxazol-6-yl)amino]methyl}-1,2-dihydroquinolin-2-one;

6-chloro-3-{[(6-methoxy-2-oxo-1,2,3,4-tetrahydroquinolin-7-yl)amino]methyl}-1,2-dihydroquinolin-2-one;

6-chloro-3-{[(2-oxo-1,2,3,4-tetrahydroquinolin-6-yl)amino]methyl}-1,2-dihydroquinolin-2-one;

6-chloro-3-{[(1-methyl-2-oxo-1,2,3,4-tetrahydroquinolin-6-yl)amino]methyl}-1,2-dihydroquinolin-2-one;

6-chloro-3-{[(3-methyl-2-oxo-2,3-dihydro-1,3-benzoxazol-5-yl)amino]methyl}-1,2-dihydroquinolin-2-one;

6-chloro-3-{[(2-oxo-2H-chromen-6-yl)amino]methyl}-1,2-dihydroquinolin-2-one;

6-chloro-3-{[(2-oxo-2,3-dihydro-1,3-benzoxazol-5-yl)amino]methyl}-1,2-dihydroquinolin-2-one;

6-chloro-3-{[(2-oxo-2,3-dihydro-1H-indol-6-yl)amino]methyl}-1,2-dihydroquinolin-2-one;

7-{[(6-chloro-2-oxo-1,2-dihydroquinolin-3-yl)methyl]amino}-3,4-dihydro-2H-1,4-benzoxazin-3-one;

7-{[(6-chloro-2-oxo-1,2-dihydroquinolin-3-yl)methyl]amino}-4-methyl-3,4-dihydro-2H-1,4-benzoxazin-3-one;

6-chloro-3-[(1S)-1-{[1-(2-methylpropyl)-2-oxo-1H,2H,4H-pyrimido[4,5-d][1,3]oxazin-7-yl]amino}ethyl]-1,2-dihydroquinolin-2-one;

6-chloro-3-[(1S)-1-({3-methyl-2-oxo-2H,3H-[1,3]ox-azolo[4,5-d]pyrimidin-5-yl}amino)ethyl]-1,2-dihydroquinolin-2-one;

6-chloro-3-[(1S)-1-{[7-oxo-8-(propan-2-yl)-5H,6H,7H,8H-[1,3]diazino[4,5-d]pyrimidin-2-yl]amino}ethyl]-1,2-dihydroquinolin-2-one;

6-chloro-3-[(1S)-1-({8-ethyl-7-oxo-5H,6H,7H,8H-[1,3]diazino[4,5-d]pyrimidin-2-yl}amino)ethyl]-1,2-dihydroquinolin-2-one;

6-chloro-3-[(1S)-1-{[2-oxo-1-(propan-2-yl)-1H,2H,4H-pyrido[4,3-d][1,3]oxazin-7-yl]amino}ethyl]-1,2-dihydroquinolin-2-one;

7-{[(1S)-1-(6-chloro-2-oxo-1,2-dihydroquinolin-3-yl)ethyl]amino}-1-methyl-2,4-dihydro-1H-3,1-benzoxazin-2-one;

6-chloro-3-[(1S)-1-({1-ethyl-2-oxo-1H,2H,4H-pyrido[4,3-d][1,3]oxazin-7-yl}amino)ethyl]-1,2-dihydroquinolin-2-one;

7-{[(1S)-1-(6-chloro-2-oxo-1,2-dihydroquinolin-3-yl)ethyl]amino}-2,4-dihydro-1H-3,1-benzoxazin-2-one;

3-[(1S)-1-({1-acetyl-1H,2H,3H-pyrrolo[3,2-b]pyridin-5-yl}amino)ethyl]-6-chloro-1,2-dihydroquinolin-2-one;

6-chloro-3-[(1S)-1-{[1-(2-methylpropyl)-2-oxo-1,2,3,4-tetrahydroquinolin-6-yl]amino}ethyl]-1,2-dihydroquinolin-2-one;

6-chloro-3-[(1S)-1-{[8-(2-methylpropyl)-7-oxo-5H,6H,7H,8H-[1,3]diazino[4,5-d]pyrimidin-2-yl]amino}ethyl]-1,2-dihydroquinolin-2-one;

7-{[(1S)-1-(6-chloro-2-oxo-1,2-dihydroquinolin-3-yl)ethyl]amino}-1-(2-methylpropyl)-2,4-dihydro-1H-3,1-benzoxazin-2-one;

6-chloro-3-[(1S)-1-{[1-(2-methylpropyl)-2-oxo-1H,2H,4H-pyrido[4,3-d][1,3]oxazin-7-yl]amino}ethyl]-1,2-dihydroquinolin-2-one;

6-{[(1S)-1-(6-chloro-2-oxo-1,2-dihydroquinolin-3-yl)ethyl]amino}-1-methyl-4-(2-methylpropyl)-1,2,3,4-tetrahydroquinoxalin-2-one;

6-chloro-3-[(1S)-1-{[4-methyl-1-(2-methylpropyl)-3-oxo-1H,2H,3H,4H-pyrido[3,4-b]pyrazin-7-yl]amino}ethyl]-1,2-dihydroquinolin-2-one;

6-chloro-3-[(1S)-1-{[(4R)-1-methyl-4-(2-methylpropyl)-2-oxo-1,2,3,4-tetrahydroquinolin-6-yl]amino}ethyl]-1,2-dihydroquinolin-2-one;

6-chloro-3-[(1S)-1-{[9-(2-methylpropyl)-9H-purin-2-yl]amino}ethyl]-1,2-dihydroquinolin-2-one;

6-chloro-3-[(1S)-1-{[3-(2-methylpropyl)-2-oxo-2,3-dihydro-1,3-benzoxazol-6-yl]amino}ethyl]-1,2-dihydroquinolin-2-one;

6-chloro-3-[(1S)-1-{[3-(2-methylpropyl)-2-oxo-2,3-dihydro-1,3-benzoxazol-5-yl]amino}ethyl]-1,2-dihydroquinolin-2-one;

6-chloro-3-[(1S)-1-{[1-(2-methylpropyl)-2-oxo-1H,2H-[1,3]oxazolo[5,4-c]pyridin-6-yl]amino}ethyl]-1,2-dihydroquinolin-2-one;

6-chloro-3-[(1S)-1-{[2-oxo-3-(propan-2-yl)-2H,3H-[1,3]
oxazolo[4,5-d]pyrimidin-5-yl]amino}ethyl]-1,2-dihydroquinolin-2-one;
6-chloro-3-[(1S)-1-{[9-(propan-2-yl)-9H-purin-2-yl]
amino}ethyl]-1,2-dihydroquinolin-2-one;
6-chloro-3-[(1S)-1-{[1-(propan-2-yl)-1H-pyrazolo[3,4-d]
pyrimidin-6-yl]amino}ethyl]-1,2-dihydroquinolin-2-one;
6-chloro-3-[(1S)-1-{[2-oxo-1-(propan-2-yl)-1H,2H-[1,3]
oxazolo[5,4-c]pyridin-6-yl]amino}ethyl]-1,2-dihydroquinolin-2-one;
6-chloro-3-[(1S)-1-{[6-methyl-7-oxo-8-(propan-2-yl)-5H,6H,7H,8H-[1,3]diazino[4,5-d]pyrimidin-2-yl]
amino}ethyl]-1,2-dihydroquinolin-2-one;
6-{[(1S)-1-(6-chloro-2-oxo-1,2-dihydroquinolin-3-yl)
ethyl]amino}-4-methyl-1-(2-methylpropyl)-1,2,3,4-tetrahydroquinoxalin-2-one;
6-chloro-3-[(1S)-1-[(2-oxo-2,3-dihydro-1,3-benzoxazol-6-yl)amino]ethyl]-1,2-dihydroquinolin-2-one;
6-chloro-3-[(1S)-1-({2-oxo-2H,3H-[1,3]oxazolo[4,5-c]
pyridin-6-yl}amino)ethyl]-1,2-dihydroquinolin-2-one;
6-chloro-3-[(1S)-1-[(2-oxo-2,3-dihydro-1,3-benzoxazol-5-yl)amino]ethyl]-1,2-dihydroquinolin-2-one;
6-chloro-3-[(1S)-1-({2-oxo-1H,2H-[1,3]oxazolo[5,4-c]
pyridin-6-yl}amino)ethyl]-1,2-dihydroquinolin-2-one;
6-chloro-3-[(1S)-1-({2-oxo-1H,2H-[1,3]oxazolo[5,4-d]
pyrimidin-5-yl}amino)ethyl]-1,2-dihydroquinolin-2-one;
6-chloro-3-[(1S)-1-[(1-methyl-2-oxo-1,2,3,4-tetrahydroquinolin-6-yl)amino]ethyl]-1,2-dihydroquinolin-2-one;
6-{[(1S)-1-(6-chloro-2-oxo-1,2-dihydroquinolin-3-yl)
ethyl]amino}-1,4-dimethyl-1,2,3,4-tetrahydroquinoxalin-2-one
6-{[(1S)-1-(6-chloro-2-oxo-1,2-dihydroquinolin-3-yl)
ethyl]amino}-1,2,3,4-tetrahydroquinoxalin-2-one;
6-chloro-3-[(1S)-1-[(3-methyl-2-oxo-2,3-dihydro-1,3-benzoxazol-5-yl)amino]ethyl]-1,2-dihydroquinolin-2-one;
6-{[(1S)-1-(6-chloro-2-oxo-1,2-dihydroquinolin-3-yl)
ethyl]amino}-1-methyl-1,2,3,4-tetrahydro-1,7-naphthyridin-2-one;
6-chloro-3-[(1S)-1-({1-methyl-2-oxo-1H,2H-[1,3]oxazolo[5,4-c]pyridin-6-yl}amino)ethyl]-1,2-dihydroquinolin-2-one;
6-chloro-3-[(1S)-1-({1-cyclopropyl-2-oxo-1H,2H-[1,3]
oxazolo[5,4-c]pyridin-6-yl}amino)ethyl]-1,2-dihydroquinolin-2-one;
6-chloro-3-[(1S)-1-({1-cyclobutyl-2-oxo-1H,2H-[1,3]oxazolo[5,4-c]pyridin-6-yl}amino)ethyl]-1,2-dihydroquinolin-2-one;
6-chloro-3-[(1S)-1-({1-ethyl-2-oxo-1H,2H-[1,3]oxazolo
[5,4-c]pyridin-6-yl}amino)ethyl]-1,2-dihydroquinolin-2-one;
6-chloro-3-[(1S)-1-({1-cyclobutyl-2-oxo-1H,2H,4H-pyrido[4,3-d][1,3]oxazin-7-yl}amino)ethyl]-1,2-dihydroquinolin-2-one;
6-chloro-3-[(1S)-1-({1-cyclopropyl-2-oxo-1H,2H,4H-pyrido[4,3-d][1,3]oxazin-7-yl}amino)ethyl]-1,2-dihydroquinolin-2-one;
6-chloro-3-[(1S)-1-({5-methyl-6-oxo-5H,6H,7H,8H-pyrido[3,2-d]pyrimidin-2-yl}amino)ethyl]-1,2-dihydroquinolin-2-one;
6-{[(6-chloro-2-oxo-1,2-dihydroquinolin-3-yl)methyl]
amino}-2-(prop-2-yn-1-yl)-1H-1,3-benzodiazol-3-ium;

6-chloro-3-{[(2-ethynyl-1,3-benzoxazol-6-yl)amino]
methyl}-1,2-dihydroquinolin-2-one;
6-chloro-3-{[(2-ethynyl-1,3-benzoxazol-5-yl)amino]
methyl}-1,2-dihydroquinolin-2-one;
6-chloro-3-{[(1-methyl-2-oxo-2,3-dihydro-1H-indol-6-yl)amino]methyl}-1,2-dihydroquinolin-2-one;
6-chloro-3-[({1-methyl-2-oxo-1H,2H,3H-pyrrolo[3,2-c]
pyridin-6-yl}amino)methyl]-1,2-dihydroquinolin-2-one;
6-chloro-3-{[(5-fluoro-2-oxo-2,3-dihydro-1H-indol-6-yl)
amino]methyl}-1,2-dihydroquinolin-2-one;
6-chloro-3-{[(4-methyl-2-oxo-2,3-dihydro-1H-indol-6-yl)amino]methyl}-1,2-dihydroquinolin-2-one;
6-chloro-3-[({2-oxo-1H,2H,3H-pyrrolo[3,2-c]pyridin-6-yl}amino)methyl]-1,2-dihydroquinolin-2-one;
6-chloro-3-({[(1R)-1-oxo-2,3-dihydro-1λ⁴-benzothiophen-6-yl]amino}methyl)-1,2-dihydroquinolin-2-one;
6-chloro-3-[({5H,7H,8H-pyrano[4,3-d]pyrimidin-2-yl}amino)methyl]-1,2-dihydroquinolin-2-one;
6-chloro-3-{[(1-methyl-1,3-dihydro-2,1-benzoxazol-6-yl)amino]methyl}-1,2-dihydroquinolin-2-one;
3-[({3-tert-butyl-[1,2,4]triazolo[4,3-a]pyridin-6-yl}amino)methyl]-6-chloro-1,2-dihydroquinolin-2-one;
6-chloro-3-[(1R)-1-{[1-(2-methylpropyl)-2-oxo-1H,2H,4H-pyrimido[4,5-d][1,3]oxazin-7-yl]amino}ethyl]-1,2-dihydroquinolin-2-one;
(4R)-6-{[(1S)-1-(6-chloro-2-oxo-1,2-dihydroquinolin-3-yl)ethyl]amino}-1-methyl-4-(2-methylpropyl)-1,2,3,4-tetrahydro-1,5-naphthyridin-2-one
6-{[(6-chloro-2-oxo-1,2-dihydroquinolin-3-yl)methyl]
amino}-2-(propan-2-yl)imidazo[1,2-a]pyridin-1-ium;
6-chloro-3-({[3-(propan-2-yl)-[1,2,4]triazolo[4,3-a]pyridin-6-yl]amino}methyl)-1,2-dihydroquinolin-2-one;
6-chloro-3-({[3-(propan-2-yl)-2H-indazol-5-yl]
amino}methyl)-1,2-dihydroquinolin-2-one;
6-chloro-3-({[3-(propan-2-yl)-1,2-benzoxazol-6-yl]
amino}methyl)-1,2-dihydroquinolin-2-one
6-chloro-3-[({3-propyl-[1,2,4]triazolo[4,3-a]pyridin-6-yl}amino)methyl]-1,2-dihydroquinolin-2-one;
6-chloro-3-{[(1-ethyl-2-oxo-2,3-dihydro-1H-indol-6-yl)
amino]methyl}-1,2-dihydroquinolin-2-one;
6-chloro-3-({[(3 S)-3-ethyl-2-oxo-2,3-dihydro-1H-indol-6-yl]amino}methyl)-1,2-dihydroquinolin-2-one;
6-chloro-3-({[(3 S)-3-ethyl-2-oxo-2,3-dihydro-1H-indol-5-yl]amino}methyl)-1,2-dihydroquinolin-2-one;
6-chloro-3-[({3-ethyl-7-methyl-[1,2,4]triazolo[4,3-a]
pyridin-6-yl}amino)methyl]-1,2-dihydroquinolin-2-one;
6-chloro-3-[({3-ethyl-[1,2,4]triazolo[4,3-a]pyridin-6-yl}amino)methyl]-1,2-dihydroquinolin-2-one;
6-chloro-3-[({3-ethyl-8-methyl-[1,2,4]triazolo[4,3-a]
pyridin-6-yl}amino)methyl]-1,2-dihydroquinolin-2-one;
6-chloro-3-{[(3-ethyl-6-methyl-2H-indazol-5-yl)amino]
methyl}-1,2-dihydroquinolin-2-one;
6-chloro-3-{[(3-ethyl-7-methyl-1,2-benzoxazol-5-yl)
amino]methyl}-1,2-dihydroquinolin-2-one;
6-chloro-3-{[(2-methyl-2,3-dihydro-1,2-benzoxazol-6-yl)amino]methyl}-1,2-dihydroquinolin-2-one;
6-{[(6-chloro-2-oxo-1,2-dihydroquinolin-3-yl)methyl]
amino}-1-methyl-2-oxo-1,2,3,4-tetrahydroquinoline-8-carboxamide;
6-{[(6-chloro-2-oxo-1,2-dihydroquinolin-3-yl)methyl]
amino}-4-fluoro-2-methyl-1H-1,3-benzodiazol-3-ium;
6-{[(6-chloro-2-oxo-1,2-dihydroquinolin-3-yl)methyl]
amino}-2,3-dimethylimidazo[1,2-a]pyridin-1-ium;

6-{[(6-chloro-2-oxo-1,2-dihydroquinolin-3-yl)methyl]
  amino}-2,5-dimethylimidazo[1,2-a]pyridin-1-ium;
6-chloro-3-({[6-(dimethylamino)-8,9-dimethyl-9H-purin-2-yl]amino}methyl)-1,2-dihydroquinolin-2-one;
6-chloro-3-{[(5-fluoro-2-methyl-1,3-benzoxazol-6-yl)
  amino]methyl}-1,2-dihydroquinolin-2-one;
6-chloro-3-{[(2,7-dimethyl-1,3-benzoxazol-5-yl)amino]
  methyl}-1,2-dihydroquinolin-2-one;
6-chloro-3-{[(7-fluoro-2-methyl-1,3-benzoxazol-5-yl)
  amino]methyl}-1,2-dihydroquinolin-2-one;
6-{[(6-chloro-2-oxo-1,2-dihydroquinolin-3-yl)methyl]
  amino}-3-methyl-1-benzofuran-5-carbonitrile;
6-chloro-3-({[2-oxo-4-(trifluoromethyl)-2H-chromen-7-yl]amino}methyl)-1,2-dihydroquinolin-2-one;
5-{[(6-chloro-2-oxo-1,2-dihydroquinolin-3-yl)methyl]
  amino}-2-cyano-1H-1,3-benzodiazol-1-ide;
6-{[(6-chloro-2-oxo-1,2-dihydroquinolin-3-yl)methyl]
  amino}-1H-indole-2-carbonitrile;
6-{[(6-chloro-2-oxo-1,2-dihydroquinolin-3-yl)methyl]
  amino}imidazo[1,2-a]pyridine-2-carbonitrile;
6-{[(6-chloro-2-oxo-1,2-dihydroquinolin-3-yl)methyl]
  amino)}-1,3-benzothiazole-2-carbonitrile;
6-{[(6-chloro-2-oxo-1,2-dihydroquinolin-3-yl)methyl]
  amino}-2H-indazole-3-carbonitrile;
5-{[(6-chloro-2-oxo-1,2-dihydroquinolin-3-yl)methyl]
  amino}-2H-indazole-3-carbonitrile;
6-{[(6-chloro-2-oxo-1,2-dihydroquinolin-3-yl)methyl]
  amino}-2-methyl-1H-indole-3-carbonitrile;
6-{[(6-chloro-2-oxo-1,2-dihydroquinolin-3-yl)methyl]
  amino}-7-methyl-1H-indole-3-carbonitrile;
5-{[(6-chloro-2-oxo-1,2-dihydroquinolin-3-yl)methyl]
  amino}-7-methyl-1H-indole-3-carbonitrile;
6-{[(6-chloro-2-oxo-1,2-dihydroquinolin-3-yl)methyl]
  amino}-5-methyl-1H-indole-3-carbonitrile;
3-{[(6-chloro-2-oxo-1,2-dihydroquinolin-3-yl)methyl]
  amino}isoquinoline-8-carbonitrile;
6-chloro-3-{[(2-methyl-1-oxo-2,3-dihydro-1H-isoindol-5-yl)amino]methyl}-1,2-dihydroquinolin-2-one;
5-{[(6-chloro-2-oxo-1,2-dihydroquinolin-3-yl)methyl]
  amino}-2-oxo-2,3-dihydro-1,3-benzoxazole-7-carboxamide;
6-chloro-3-{[(7-methyl-2-oxo-2,3-dihydro-1,3-benzoxazol-5-yl)amino]methyl}-1,2-dihydroquinolin-2-one;
6-chloro-3-{[(7-fluoro-2-oxo-2,3-dihydro-1,3-benzoxazol-5-yl)amino]methyl}-1,2-dihydroquinolin-2-one;
6-chloro-3-{[(7-methoxy-2-oxo-2,3-dihydro-1,3-benzoxazol-5-yl)amino]methyl}-1,2-dihydroquinolin-2-one;
6-chloro-3-[({4-methyl-2-oxo-1H,2H-[1,3]oxazolo[5,4-c]pyridin-6-yl}amino)methyl]-1,2-dihydroquinolin-2-one;
6-chloro-3-{[(7-methyl-2-oxo-2,3-dihydro-1,3-benzoxazol-6-yl)amino]methyl}-1,2-dihydroquinolin-2-one;
6-chloro-3-[({2-oxo-2H,3H-[1,3]oxazolo[4,5-b]pyridin-5-yl}amino)methyl]-1,2-dihydroquinolin-2-one;
6-{[(6-chloro-2-oxo-1,2-dihydroquinolin-3-yl)methyl]
  amino}-2-oxo-2H-chromene-8-carboxamide;
6-chloro-3-{[(8-methyl-2-oxo-2H-chromen-6-yl)amino]
  methyl}-1,2-dihydroquinolin-2-one;
6-chloro-3-{[(8-methoxy-2-oxo-2H-chromen-6-yl)
  amino]methyl}-1,2-dihydroquinolin-2-one
6-chloro-3-[({8-methyl-2-oxo-2H-pyrano[2,3-c]pyridin-6-yl}amino)methyl]-1,2-dihydroquinolin-2-one
5-{[(6-chloro-2-oxo-1,2-dihydroquinolin-3-yl)methyl]
  amino}-3-methyl-2-oxo-2,3-dihydro-1,3-benzoxazole-7-carboxamide;

6-chloro-3-{[(7-methoxy-3-methyl-2-oxo-2,3-dihydro-1,3-benzoxazol-5-yl)amino]methyl}-1,2-dihydroquinolin-2-one;
6-chloro-3-[({1,4-dimethyl-2-oxo-1H,2H-[1,3]oxazolo[5,4-c]pyridin-6-yl}amino)methyl]-1,2-dihydroquinolin-2-one;
6-chloro-3-[({3-methyl-2-oxo-2H,3H-[1,3]oxazolo[4,5-b]pyridin-5-yl}amino)methyl]-1,2-dihydroquinolin-2-one;
6-chloro-3-({[2-(hydroxymethyl)-1,3-benzoxazol-6-yl]
  amino}methyl)-1,2-dihydroquinolin-2-one;
6-chloro-3-({[2-(hydroxymethyl)-1,3-benzoxazol-5-yl]
  amino}methyl)-1,2-dihydroquinolin-2-one;
6-chloro-3-({[3-(hydroxymethyl)-1,2-benzoxazol-5-yl]
  amino}methyl)-1,2-dihydroquinolin-2-one;
6-chloro-3-{[(3-hydroxy-1-benzothiophen-6-yl)amino]
  methyl}-1,2-dihydroquinolin-2-one;
3-{[(6-chloro-2-oxo-1,2-dihydroquinolin-3-yl)methyl]
  amino}isoquinoline-5-carboxylate;
4-chloro-5-{[(6-chloro-2-oxo-1,2-dihydroquinolin-3-yl)
  methyl]amino}-1H-1,3-benzodiazol-3-ium;
3-chloro-6-{[(6-chloro-2-oxo-1,2-dihydroquinolin-3-yl)
  methyl]amino}imidazo[1,2-a]pyridin-1-ium;
6-{[(6-chloro-2-oxo-1,2-dihydroquinolin-3-yl)methyl]
  amino}-7-formylimidazo[1,2-a]pyridin-1-ium;
6-chloro-3-[({2-oxo-1H,2H,3H-imidazo[4,5-b]pyridin-5-yl}amino)methyl]-1,2-dihydroquinolin-2-one;
6-chloro-3-{[(6-methyl-2-oxo-2,3-dihydro-1,3-benzoxazol-5-yl)amino]methyl}-1,2-dihydroquinolin-2-one;
6-chloro-3-{[(5-methyl-2-oxo-2,3-dihydro-1,3-benzoxazol-6-yl)amino]methyl}-1,2-dihydroquinolin-2-one;
6-chloro-3-{[(5-fluoro-2-oxo-2,3-dihydro-1,3-benzoxazol-6-yl)amino]methyl}-1,2-dihydroquinolin-2-one;
6-chloro-3-{[(2-oxo-2,3-dihydro-1,3-benzoxazol-6-yl)
  amino]methyl}-1,2-dihydroquinolin-2-one;
6-chloro-3-{[(4-methyl-2-oxo-2,3-dihydro-1,3-benzoxazol-6-yl)amino]methyl}-1,2-dihydroquinolin-2-one;
6-chloro-3-[({2-oxo-1H,2H-[1,3]oxazolo[5,4-c]pyridin-6-yl}amino)methyl]-1,2-dihydroquinolin-2-one;
6-chloro-3-{[(2-oxo-2,3-dihydro-1,3-benzothiazol-6-yl)
  amino]methyl}-1,2-dihydroquinolin-2-one;
6-chloro-3-{[(2-oxo-2,3-dihydro-1,3-benzothiazol-5-yl)
  amino]methyl}-1,2-dihydroquinolin-2-one;
5-{[(6-chloro-2-oxo-1,2-dihydroquinolin-3-yl)methyl]
  amino}-6-cyano-1H-1,3-benzodiazol-3-ium;
6-chloro-5-{[(6-chloro-2-oxo-1,2-dihydroquinolin-3-yl)
  methyl]amino}-1H-1,3-benzodiazol-3-ium;
7-chloro-5-{[(6-chloro-2-oxo-1,2-dihydroquinolin-3-yl)
  methyl]amino}-1H-1,3-benzodiazol-3-ium;
6-chloro-3-{[(7-methyl-1H-1,2,3-benzotriazol-5-yl)
  amino]methyl}-1,2-dihydroquinolin-2-one;
6-chloro-3-{[(7-methoxy-1H-1,2,3-benzotriazol-5-yl)
  amino]methyl}-1,2-dihydroquinolin-2-one;
6-chloro-3-{[(7-ethyl-2H-indazol-6-yl)amino]methyl}-1,2-dihydroquinolin-2-one;
6-chloro-3-{[(7-ethyl-2H-indazol-5-yl)amino]methyl}-1,2-dihydroquinolin-2-one;
6-chloro-3-{[(6-methyl-1H-indol-5-yl)amino]methyl}-1,2-dihydroquinolin-2-one;
6-chloro-3-{[(6-methyl-1H-indazol-5-yl)amino]methyl}-1,2-dihydroquinolin-2-one;
6-chloro-3-{[(6-methyl-1-benzofuran-5-yl)amino]
  methyl}-1,2-dihydroquinolin-2-one;
6-chloro-3-{[(6-fluoro-2-methyl-1,3-benzoxazol-5-yl)
  amino]methyl}-1,2-dihydroquinolin-2-one;
6-chloro-3-({[6-(dimethylamino)-1H-indol-5-yl]
  amino}methyl)-1,2-dihydroquinolin-2-one;

6-chloro-3-{[(6-hydroxy-3-methyl-1,2-benzoxazol-5-yl)amino]methyl}-1,2-dihydroquinolin-2-one;
6-chloro-3-{[(7-methyl-3-oxo-2,3-dihydro-1H-isoindol-5-yl)amino]methyl}-1,2-dihydroquinolin-2-one;
6-chloro-3-{[(7-methyl-1H-indol-5-yl)amino]methyl}-1,2-dihydroquinolin-2-one;
6-chloro-3-{[(7-methyl-1H-indazol-5-yl)amino]methyl}-1,2-dihydroquinolin-2-one;
6-chloro-3-{[(7-methyl-1,2-benzoxazol-5-yl)amino]methyl}-1,2-dihydroquinolin-2-one;
6-chloro-3-{[(3,7-dimethyl-1,2-benzoxazol-5-yl)amino]methyl}-1,2-dihydroquinolin-2-one;
6-chloro-3-{[(7-cyclopropyl-1,2-benzoxazol-5-yl)amino]methyl}-1,2-dihydroquinolin-2-one;
6-chloro-3-{[(7-fluoro-2-oxo-2,3-dihydro-1H-indol-5-yl)amino]methyl}-1,2-dihydroquinolin-2-one;
6-chloro-3-{[(7-methoxy-3-methyl-1H-indol-5-yl)amino]methyl}-1,2-dihydroquinolin-2-one;
6-chloro-3-{[(7-methoxy-1,2-benzoxazol-5-yl)amino]methyl}-1,2-dihydroquinolin-2-one;
6-chloro-3-{[(2-methyl-3-oxo-2,3-dihydro-1H-isoindol-5-yl)amino]methyl}-1,2-dihydroquinolin-2-one;
6-chloro-3-{[(3-oxo-1,3-dihydro-2-benzofuran-5-yl)amino]methyl}-1,2-dihydroquinolin-2-one;
6-chloro-3-{[(1-methyl-2-oxo-2,3-dihydro-1H-indol-5-yl)amino]methyl}-1,2-dihydroquinolin-2-one;
6-chloro-3-{[(2-oxo-2,3-dihydro-1H-indol-5-yl)amino]methyl}-1,2-dihydroquinolin-2-one;
6-chloro-3-({[(3R)-3-methyl-2-oxo-2,3-dihydro-1H-indol-5-yl]amino}methyl)-1,2-dihydroquinolin-2-one;
6-chloro-3-{[(2-oxo-2,3-dihydro-1-benzofuran-5-yl)amino]methyl}-1,2-dihydroquinolin-2-one;
6-{[(6-chloro-2-oxo-1,2-dihydroquinolin-3-yl)methyl]amino}-3,4-dihydro-2H-1,4-benzoxazin-3-one;
6-chloro-3-({[(1R)-1-methyl-3-oxo-2,3-dihydro-1H-isoindol-5-yl]amino}methyl)-1,2-dihydroquinolin-2-one;
6-chloro-3-({[(1R)-1-methyl-3-oxo-1,3-dihydro-2-benzofuran-5-yl]amino}methyl)-1,2-dihydroquinolin-2-one;
6-chloro-3-({[(1S)-1-methyl-3-oxo-2,3-dihydro-1H-isoindol-5-yl]amino}methyl)-1,2-dihydroquinolin-2-one;
6-chloro-3-{[(3-methyl-2-oxo-2,3-dihydro-1H-1,3-benzodiazol-5-yl)amino]methyl}-1,2-dihydroquinolin-2-one;
6-chloro-3-{[(3-methyl-1H-indol-5-yl)amino]methyl}-1,2-dihydroquinolin-2-one;
6-chloro-3-{[(3-cyclopropyl-1H-indol-5-yl)amino]methyl}-1,2-dihydroquinolin-2-one;
6-chloro-3-{[(3-methyl-1H-indazol-5-yl)amino]methyl}-1,2-dihydroquinolin-2-one;
6-chloro-3-{[(3-cyclopropyl-1H-indazol-5-yl)amino]methyl}-1,2-dihydroquinolin-2-one;
6-chloro-3-{[(1-methyl-1H-1,2,3-benzotriazol-6-yl)amino]methyl}-1,2-dihydroquinolin-2-one;
6-chloro-3-{[(1-hydroxy-1H-1,2,3-benzotriazol-6-yl)amino]methyl}-1,2-dihydroquinolin-2-one;
6-chloro-3-{[(3-oxo-2,3-dihydro-1,2-benzoxazol-5-yl)amino]methyl}-1,2-dihydroquinolin-2-one;
6-chloro-3-{[(3-methyl-1-benzofuran-5-yl)amino]methyl}-1,2-dihydroquinolin-2-one;
3-{[(1,2-benzoxazol-5-yl)amino]methyl}-6-chloro-1,2-dihydroquinolin-2-one;
6-chloro-3-{[(3-methoxy-1,2-benzoxazol-5-yl)amino]methyl}-1,2-dihydroquinolin-2-one;
6-chloro-3-{[(3-hydroxy-1-benzothiophen-5-yl)amino]methyl}-1,2-dihydroquinolin-2-one;
6-chloro-3-{[(3-methyl-1,2-benzothiazol-5-yl)amino]methyl}-1,2-dihydroquinolin-2-one;
6-chloro-3-[({3-oxo-2H,3H,4H-pyrido[3,2-b][1,4]oxazin-7-yl}amino)methyl]-1,2-dihydroquinolin-2-one;
6-{[(6-chloro-2-oxo-1,2-dihydroquinolin-3-yl)methyl]amino}-1H,2H,3H,4H-pyrido[2,3-d]pyrimidine-2,4-dione;
6-chloro-3-[({1-methyl-1H-pyrazolo[3,4-b]pyridin-5-yl}amino)methyl]-1,2-dihydroquinolin-2-one;
6-chloro-3-({[5-(pyrrolidin-1-yl)-[1,2,4]triazolo[1,5-c]pyrimidin-7-yl]amino}methyl)-1,2-dihydroquinolin-2-one;
6-chloro-3-[({1-methyl-2-oxo-1H,2H,3H-pyrrolo[2,3-c]pyridin-5-yl}amino)methyl]-1,2-dihydroquinolin-2-one;
6-chloro-3-[({2-oxo-1H,2H,3H-pyrrolo[2,3-c]pyridin-5-yl}amino)methyl]-1,2-dihydroquinolin-2-one;
6-chloro-3-[({2-oxo-2H-pyrano[2,3-c]pyridin-6-yl}amino)methyl]-1,2-dihydroquinolin-2-one;
6-chloro-3-[({1-methyl-2-oxo-1H,2H-[1,3]oxazolo[5,4-c]pyridin-6-yl}amino)methyl]-1,2-dihydroquinolin-2-one;
6-chloro-3-{[(1,5-dimethyl-2-oxo-1,2,3,4-tetrahydroquinolin-6-yl)amino]methyl}-1,2-dihydroquinolin-2-one;
6-chloro-3-{[(4-methyl-2-oxo-2,3-dihydro-1H-indol-5-yl)amino]methyl}-1,2-dihydroquinolin-2-one;
6-chloro-3-{[(4-methyl-1H-indol-5-yl)amino]methyl}-1,2-dihydroquinolin-2-one;
6-chloro-3-{[(4-methyl-1H-indazol-5-yl)amino]methyl}-1,2-dihydroquinolin-2-one;
6-chloro-3-{[(5-methyl-2-oxo-2H-chromen-6-yl)amino]methyl}-1,2-dihydroquinolin-2-one;
6-chloro-3-{[(4-methyl-1-benzofuran-5-yl)amino]methyl}-1,2-dihydroquinolin-2-one;
6-chloro-3-[({4-chloro-1-methyl-1H-pyrazolo[3,4-b]pyridin-5-yl}amino)methyl]-1,2-dihydroquinolin-2-one;
6-chloro-3-{[(4-fluoro-3-oxo-2,3-dihydro-1H-isoindol-5-yl)amino]methyl}-1,2-dihydroquinolin-2-one;
6-chloro-3-{[(4-methoxy-7-methyl-1H-indol-5-yl)amino]methyl}-1,2-dihydroquinolin-2-one;
6-chloro-3-{[(4-methoxy-1-benzofuran-5-yl)amino]methyl}-1,2-dihydroquinolin-2-one;
6-chloro-3-{[(2-methyl-1-oxo-1,2,3,4-tetrahydroisoquinolin-6-yl)amino]methyl}-1,2-dihydroquinolin-2-one;
6-chloro-3-{[(1-oxo-1,2,3,4-tetrahydroisoquinolin-6-yl)amino]methyl}-1,2-dihydroquinolin-2-one;
6-chloro-3-({[(3R)-3-methyl-2-oxo-2,3-dihydro-1H-indol-6-yl]amino}methyl)-1,2-dihydroquinolin-2-one;
6-chloro-3-{[(3-methyl-1H-indol-6-yl)amino]methyl}-1,2-dihydroquinolin-2-one;
6-chloro-3-{[(3-cyclopropyl-1H-indol-6-yl)amino]methyl}-1,2-dihydroquinolin-2-one;
6-chloro-3-{[(3-methoxy-1H-indazol-6-yl)amino]methyl}-1,2-dihydroquinolin-2-one;
6-chloro-3-{[(3-methyl-2H-indazol-6-yl)amino]methyl}-1,2-dihydroquinolin-2-one;
6-chloro-3-[({3-cyclobutyl-[1,2,4]triazolo[4,3-a]pyridin-6-yl}amino)methyl]-1,2-dihydroquinolin-2-one;
7-{[(6-chloro-2-oxo-1,2-dihydroquinolin-3-yl)methyl]amino}-4-methyl-1,2-dihydro-1,8-naphthyridin-2-one;
6-chloro-3-{[(1,8-dimethyl-2-oxo-1,2,3,4-tetrahydroquinolin-6-yl)amino]methyl}-1,2-dihydroquinolin-2-one;
6-chloro-3-{[(3,4-dimethyl-1,2-benzoxazol-6-yl)amino]methyl}-1,2-dihydroquinolin-2-one;

6-chloro-3-{[(8-methoxy-1-methyl-2-oxo-1,2,3,4-tetrahydroquinolin-6-yl)amino]methyl}-1,2-dihydroquinolin-2-one;
6-chloro-3-{[(1,5-naphthyridin-2-yl)amino]methyl}-1,2-dihydroquinolin-2-one;
6-chloro-3-{[(quinoxalin-2-yl)amino]methyl}-1,2-dihydroquinolin-2-one;
6-chloro-3-({[6-(thiophen-2-yl)-9H-purin-2-yl]amino}methyl)-1,2-dihydroquinolin-2-one;
6-chloro-3-({[6-(furan-3-yl)-9H-purin-2-yl]amino}methyl)-1,2-dihydroquinolin-2-one;
6-chloro-3-({[6-(morpholin-4-yl)-9H-purin-2-yl]amino}methyl)-1,2-dihydroquinolin-2-one;
6-chloro-3-[({4,7-dimethyl-5-oxo-5H,6H-pyrimido[4,5-d][1,3]diazin-2-yl}amino)methyl]-1,2-dihydroquinolin-2-one;
6-chloro-3-{[(7-hydroxy-1,2,4-benzotriazin-3-yl)amino]methyl}-1,2-dihydroquinolin-2-one;
6-chloro-3-{[(7-methyl-1H-indol-6-yl)amino]methyl}-1,2-dihydroquinolin-2-one;
6-chloro-3-{[(5-methyl-1H-indol-6-yl)amino]methyl}-1,2-dihydroquinolin-2-one;
6-chloro-3-{[(5-ethyl-1H-indol-6-yl)amino]methyl}-1,2-dihydroquinolin-2-one;
6-chloro-3-{[(4-methyl-1H-indol-6-yl)amino]methyl}-1,2-dihydroquinolin-2-one;
6-chloro-3-{[(4-ethyl-1H-indol-5-yl)amino]methyl}-1,2-dihydroquinolin-2-one;
6-chloro-3-[({5-fluoro-1H-pyrrolo[2,3-b]pyridin-6-yl}amino)methyl]-1,2-dihydroquinolin-2-one;
3-[({4-bromo-1H-pyrrolo[2,3-b]pyridin-6-yl}amino)methyl]-6-chloro-1,2-dihydroquinolin-2-one;
6-chloro-3-[({4-chloro-7H-pyrrolo[2,3-d]pyrimidin-2-yl}amino)methyl]-1,2-dihydroquinolin-2-one;
3-{[(6-chloro-2-oxo-1,2-dihydroquinolin-3-yl)methyl]amino}quinoxaline-2-carbonitrile;
6-chloro-3-{[(5-methyl-1-benzofuran-6-yl)amino]methyl}-1,2-dihydroquinolin-2-one;
6-chloro-3-{[(4-methoxy-1-benzofuran-6-yl)amino]methyl}-1,2-dihydroquinolin-2-one;
6-chloro-3-{[(1,6-naphthyridin-2-yl)amino]methyl}-1,2-dihydroquinolin-2-one;
6-chloro-3-{[(1-methyl-1H-indazol-6-yl)amino]methyl}-1,2-dihydroquinolin-2-one;
6-chloro-3-[({1-methyl-1H-pyrazolo[3,4-d]pyrimidin-6-yl}amino)methyl]-1,2-dihydroquinolin-2-one;
6-chloro-3-[({4-chloro-1-methyl-1H-pyrazolo[3,4-d]pyrimidin-6-yl}amino)methyl]-1,2-dihydroquinolin-2-one;
5-{[(6-chloro-2-oxo-1,2-dihydroquinolin-3-yl)methyl]amino}-1,2-benzoxazole-7-carbonitrile;
6-chloro-3-{[(7-methyl-1,2-benzoxazol-6-yl)amino]methyl}-1,2-dihydroquinolin-2-one;
3-{[(1,2-benzoxazol-6-yl)amino]methyl}-6-chloro-1,2-dihydroquinolin-2-one;
6-chloro-3-{[(4-methyl-1,2-benzoxazol-6-yl)amino]methyl}-1,2-dihydroquinolin-2-one;
6-chloro-3-[({3H-imidazo[4,5-b]pyridin-5-yl}amino)methyl]-1,2-dihydroquinolin-2-one;
6-chloro-3-{[(6-chloro-9H-purin-2-yl)amino]methyl}-1,2-dihydroquinolin-2-one;
6-chloro-3-({[6-(dimethylamino)-9H-purin-2-yl]amino}methyl)-1,2-dihydroquinolin-2-one;
6-chloro-3-[({imidazo[1,2-a]pyrazin-6-yl}amino)methyl]-1,2-dihydroquinolin-2-one;
6-chloro-3-[({imidazo[1,2-b]pyridazin-6-yl}amino)methyl]-1,2-dihydroquinolin-2-one;
6-chloro-3-[({3-methyl-3H-imidazo[4,5-b]pyridin-6-yl}amino)methyl]-1,2-dihydroquinolin-2-one;
6-chloro-3-({[5-(methylsulfanyl)-[1,2,4]triazolo[1,5-c]pyrimidin-7-yl]amino}methyl)-1,2-dihydroquinolin-2-one;
3-{[(6-chloro-2-oxo-1,2-dihydroquinolin-3-yl)methyl]amino}-[1,2,4]triazolo[3,2-c][1,2,4]triazin-4-olate;
6-chloro-3-[({[1,2,4]triazolo[1,5-a]pyridin-6-yl}amino)methyl]-1,2-dihydroquinolin-2-one;
6-chloro-3-{[(4,7-dimethyl-1,3-benzoxazol-5-yl)amino]methyl}-1,2-dihydroquinolin-2-one;
6-chloro-3-{[(5-hydroxy-1,3-benzoxazol-6-yl)amino]methyl}-1,2-dihydroquinolin-2-one;
3-{[(1,3-benzoxazol-6-yl)amino]methyl}-6-chloro-1,2-dihydroquinolin-2-one;
3-{[(1,3-benzoxazol-5-yl)amino]methyl}-6-chloro-1,2-dihydroquinolin-2-one;
6-chloro-3-{[(4-methyl-1,3-benzoxazol-5-yl)amino]methyl}-1,2-dihydroquinolin-2-one;
6-chloro-3-{[(6-methyl-1,3-benzothiazol-5-yl)amino]methyl}-1,2-dihydroquinolin-2-one;
6-chloro-3-{[(4-hydroxy-1,3-benzothiazol-6-yl)amino]methyl}-1,2-dihydroquinolin-2-one;
6-chloro-3-{[(4-methyl-1,3-benzothiazol-5-yl)amino]methyl}-1,2-dihydroquinolin-2-one;
6-chloro-3-({[3-(trifluoromethyl)-[1,2,4]triazolo[4,3-b]pyridazin-6-yl]amino}methyl)-1,2-dihydroquinolin-2-one;
6-chloro-3-[({3,5-dimethyl-[1,2,4]triazolo[4,3-a]pyridin-6-yl}amino)methyl]-1,2-dihydroquinolin-2-one;
6-chloro-3-[({3-methyl-[1,2,4]triazolo[4,3-a]pyridin-6-yl}amino)methyl]-1,2-dihydroquinolin-2-one;
3-[({8-bromo-3-methyl-[1,2,4]triazolo[4,3-a]pyridin-6-yl}amino)methyl]-6-chloro-1,2-dihydroquinolin-2-one;
6-chloro-3-[({3-methyl-[1,2,4]triazolo[4,3-a]pyridin-7-yl}amino)methyl]-1,2-dihydroquinolin-2-one;
6-chloro-3-({[3-(hydroxymethyl)-[1,2,4]triazolo[4,3-a]pyridin-6-yl]amino}methyl)-1,2-dihydroquinolin-2-one;
6-chloro-3-[({5-methyl-[1,2,4]triazolo[4,3-a]pyridin-6-yl}amino)methyl]-1,2-dihydroquinolin-2-one;
6-chloro-3-[({7-methyl-[1,2,4]triazolo[4,3-a]pyridin-6-yl}amino)methyl]-1,2-dihydroquinolin-2-one;
6-chloro-3-[({8-methyl-[1,2,4]triazolo[4,3-a]pyridin-6-yl}amino)methyl]-1,2-dihydroquinolin-2-one;
6-chloro-3-[({7-methyl-[1,2,3,4]tetrazolo[1,5-a]pyridin-6-yl}amino)methyl]-1,2-dihydroquinolin-2-one;
6-chloro-3-[({[1,2,3,4]tetrazolo[1,5-a]pyridin-6-yl}amino)methyl]-1,2-dihydroquinolin-2-one;
3-{[(1,2,3-benzoxadiazol-6-yl)amino]methyl}-6-chloro-1,2-dihydroquinolin-2-one;
6-chloro-3-{[(5-fluoro-1,2,3-benzothiadiazol-6-yl)amino]methyl}-1,2-dihydroquinolin-2-one;
3-{[(2,1,3-benzoxadiazol-5-yl)amino]methyl}-6-chloro-1,2-dihydroquinolin-2-one;
6-chloro-3-{[(6-methyl-2,1,3-benzothiadiazol-5-yl)amino]methyl}-1,2-dihydroquinolin-2-one;
6-chloro-3-{[(7-methyl-2,1,3-benzothiadiazol-5-yl)amino]methyl}-1,2-dihydroquinolin-2-one;
6-chloro-3-{[(4-methyl-2,1,3-benzothiadiazol-5-yl)amino]methyl}-1,2-dihydroquinolin-2-one;
6-chloro-3-{[(4-hydroxy-2,1,3-benzothiadiazol-5-yl)amino]methyl}-1,2-dihydroquinolin-2-one;
6-chloro-3-({[7-(propan-2-yl)-1,3-benzoxazol-5-yl]amino}methyl)-1,2-dihydroquinolin-2-one;

6-chloro-3-{[(7-methyl-1,3-benzothiazol-5-yl)amino]
methyl}-1,2-dihydroquinolin-2-one;
6-chloro-3-{[(7-methyl-1,3-benzothiazol-6-yl)amino]
methyl}-1,2-dihydroquinolin-2-one;
6-chloro-3-[(1S)-1-({2-oxo-1H,2H,3H-pyrrolo[3,2-c]
pyridin-6-yl}amino)ethyl]-1,2-dihydroquinolin-2-one;
6-chloro-3-[(1S)-1-({2-oxo-1H,2H,3H-pyrrolo[2,3-c]
pyridin-5-yl}amino)ethyl]-1,2-dihydroquinolin-2-one;
6-chloro-3-[(1S)-1-({2-oxo-1H,2H,3H-pyrrolo[2,3-b]
pyridin-6-yl}amino)ethyl]-1,2-dihydroquinolin-2-one;
6-chloro-3-[(1S)-1-({2-oxo-1H,2H,3H-pyrrolo[3,2-b]
pyridin-5-yl}amino)ethyl]-1,2-dihydroquinolin-2-one;
6-chloro-3-[(1S)-1-({2-oxo-2H,3H-[1,3]oxazolo[4,5-b]
pyridin-5-yl}amino)ethyl]-1,2-dihydroquinolin-2-one;
6-chloro-3-[(1S)-1-({2-oxo-1H,2H-[1,3]oxazolo[5,4-b]
pyridin-5-yl}amino)ethyl]-1,2-dihydroquinolin-2-one;
2-{[(1S)-1-(6-chloro-2-oxo-1,2-dihydroquinolin-3-yl)
ethyl]amino}-5H,7H-6$\lambda^6$,1,3-[1$\lambda^6$]thieno[3,4-d]pyridine-6,6-dione;
6-{[(1S)-1-(6-chloro-2-oxo-1,2-dihydroquinolin-3-yl)
ethyl]amino}-1H,3H-2$\lambda^6$,1,5,7-[1$\lambda^6$,2]thiazolo[3,4-d]
pyrimidine-2,2-dione;
2-{[(1S)-1-(6-chloro-2-oxo-1,2-dihydroquinolin-3-yl)
ethyl]amino}-5H,6H,8H-7$\lambda^6$,1,3-[1$\lambda^6$]thiopyrano[3,4-d]pyrimidine-7,7-dione;
2-{[(1S)-1-(6-chloro-2-oxo-1,2-dihydroquinolin-3-yl)
ethyl]amino}-5H,7H,8H-6$\lambda^6$,1,3-[1$\lambda^6$]thiopyrano[4,3-d]pyrimidine-6,6-dione;
6-chloro-3-[(1S)-1-({6-methyl-7-oxo-5H,6H,7H,8H,9H-pyrimido[4,5-e][1,4]diazepin-2-yl}amino)ethyl]-1,2-dihydroquinolin-2-one;
6-chloro-3-[(1S)-1-({5H,6H,7H,8H,9H-pyrimido[4,5-b]
azepin-2-yl}amino)ethyl]-1,2-dihydroquinolin-2-one;
6-chloro-3-[(1S)-1-({2-oxo-1H,2H,4H-pyrimido[4,5-d]
[1,3]oxazin-7-yl}amino)ethyl]-1,2-dihydroquinolin-2-one;
6-chloro-3-[(1S)-1-({1-methyl-2-oxo-1H,2H,4H-pyrimido[4,5-d][1,3]oxazin-7-yl}amino)ethyl]-1,2-dihydroquinolin-2-one;
6-chloro-3-[({3-methyl-2-oxo-2H,3H-[1,3]oxazolo[4,5-d]pyrimidin-5-yl}amino)methyl]-1,2-dihydroquinolin-2-one;
6-chloro-3-[({1-methyl-2-oxo-1H,2H,4H-pyrimido[4,5-d][1,3]oxazin-7-yl}amino)methyl]-1,2-dihydroquinolin-2-one;
(S)-7-((1-(6-chloro-2-oxo-1,2-dihydroquinolin-3-yl)
ethyl)amino)-6H-pyrido[1,2-a]pyrazin-6-one;
(S)-6-((1-(6-chloro-2-oxo-1,2-dihydroquinolin-3-yl)
ethyl)amino)-5H-[1,2,4]oxadiazolo[4,5-a]pyridin-5-one;
(S)-6-((1-(6-chloro-2-oxo-1,2-dihydroquinolin-3-yl)
ethyl)amino)-2,3-dihydro-5H-oxazolo[3,2-a]pyridin-5-one;
(S)-6-chloro-3-(1-((5-oxo-1,5-dihydro-[1,2,4]triazolo[4,3-a]pyridin-6-yl)amino)ethyl)quinolin-2(1H)-one; or
(S)-6-chloro-3-(1-((5-oxo-1,5-dihydro-[1,2,4]triazolo[1,5-a]pyridin-6-yl)amino)ethyl)quinolin-2(1H)-one.

20. A pharmaceutical composition comprising the compound according to claim 1 and pharmaceutically acceptable carrier.

21. A method of treating a cell proliferative disease or cancer associated with mutant isocitrate dehydrogenase comprising administering to a patient in need thereof a compound of claim 1, wherein the disease or cancer is selected from the group consisting of glioma, glioblastoma multiforme, paraganglioma, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), and myeloproliferative disease (MPD).

22. The method of claim 21, wherein the disease or cancer is glioma, glioblastoma multiforme (GBM), acute myeloid leukemia (AML), chondrosarcoma, intrahepatic cholangiocarcinoma (IHCC), myelodysplastic syndrome (MDS), or myeloproliferative disease (MPD).

23. The method of claim 21, wherein administering is performed orally, parentally, subcutaneously, by injection, or by infusion.

24. A method of inhibiting mutant isocitrate dehydrogenase comprising administering to a patient in need thereof a compound of claim 1.

25. A method of reducing 2-hydroxyglutarate comprising administering to a patient in need thereof a compound of claim 1.

26. A method of treating a cell proliferative disease or cancer associated with mutant isocitrate dehydrogenase comprising administering to a patient in need thereof a compound of claim 2, wherein the disease or cancer is selected from the group consisting of glioma, glioblastoma multiforme, paraganglioma, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), and myeloproliferative disease (MPD).

27. A method of treating a cell proliferative disease or cancer associated with mutant isocitrate dehydrogenase comprising administering to a patient in need thereof a compound of claim 4, wherein the disease or cancer is selected from the group consisting of glioma, glioblastoma multiforme, paraganglioma, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), and myeloproliferative disease (MPD).

28. A method of treating a cell proliferative disease or cancer associated with mutant isocitrate dehydrogenase comprising administering to a patient in need thereof a compound of claim 18, wherein the disease or cancer is selected from the group consisting of glioma, glioblastoma multiforme, paraganglioma, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), and myeloproliferative disease (MPD).

29. A compound of claim 1 selected from the group consisting of:
6-chloro-3-[(1S)-1-({1H-pyrazolo[3,4-d]pyrimidin-6-yl}amino)ethyl]-1,2-dihydroquinolin-2-one;
6-chloro-3-[(1S)-1-{[1-(2-methylpropyl)-2-oxo-1H,2H,4H-pyrimido[4,5-d][1,3]oxazin-7-yl]amino}ethyl]-1,2-dihydroquinolin-2-one;
6-chloro-3-[(1S)-1-({1-methyl-2-oxo-1H,2H,4H-pyrimido[4,5-d][1,3]oxazin-7-yl}amino)ethyl]-1,2-dihydroquinolin-2-one;
6-chloro-3-[(1S)-1-({1-methyl-2-oxo-1H,2H,4H-pyrimido[4,5-d][1,3]oxazin-7-yl}amino)ethyl]-7-(pyridin-2-ylmethoxy)-1,2-dihydroquinolin-2-one; and
6-chloro-3-[(1S)-1-({2-oxo-1H,2H,4H-pyrimido[4,5-d][1,3]oxazin-7-yl}amino)ethyl]-1,2-dihydroquinolin-2-one.

30. A compound of claim 29, wherein the compound is 6-chloro-3-[(1S)-1-({1H-pyrazolo[3,4-d]pyrimidin-6-yl}amino)ethyl]-1,2-dihydroquinolin-2-one.

31. A compound of claim 29, wherein the compound is 6-chloro-3-[(1S)-1-{[1-(2-methylpropyl)-2-oxo-1H,2H,4H-pyrimido[4,5-d][1,3]oxazin-7-yl]amino}ethyl]-1,2-dihydroquinolin-2-one.

32. A compound of claim 29, wherein the compound is 6-chloro-3-[(1S)-1-({1-methyl-2-oxo-1H,2H,4H-pyrimido[4,5-d][1,3]oxazin-7-yl}amino)ethyl]-1,2-dihydroquinolin-2-one.

33. A compound of claim 29, wherein the compound is 6-chloro-3-[(1S)-1-({1-methyl-2-oxo-1H,2H,4H-pyrimido[4,5-d][1,3]oxazin-7-yl}amino)ethyl]-7-(pyridin-2-ylmethoxy)-1,2-dihydroquinolin-2-one.

34. A compound of claim 29, wherein the compound is 6-chloro-3-[(1S)-1-({2-oxo-1H,2H,4H-pyrimido[4,5-d][1,3]oxazin-7-yl}amino)ethyl]-1,2-dihydroquinolin-2-one.

35. A method of treating a cell proliferative disease or cancer associated with mutant isocitrate dehydrogenase comprising administering to a patient in need thereof a compound of claim 30, wherein the disease or cancer is selected from the group consisting of glioma, glioblastoma multiforme, paraganglioma, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), and myeloproliferative disease (MPD).

36. A method of treating a cell proliferative disease or cancer associated with mutant isocitrate dehydrogenase comprising administering to a patient in need thereof a compound of claim 31, wherein the disease or cancer is selected from the group consisting of glioma, glioblastoma multiforme, paraganglioma, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), and myeloproliferative disease (MPD).

37. A method of treating a cell proliferative disease or cancer associated with mutant isocitrate dehydrogenase comprising administering to a patient in need thereof a compound of claim 32, wherein the disease or cancer is selected from the group consisting of glioma, glioblastoma multiforme, paraganglioma, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), and myeloproliferative disease (MPD).

38. A method of treating a cell proliferative disease or cancer associated with mutant isocitrate dehydrogenase comprising administering to a patient in need thereof a compound of claim 33, wherein the disease or cancer is selected from the group consisting of glioma, glioblastoma multiforme, paraganglioma, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), and myeloproliferative disease (MPD).

39. A method of treating a cell proliferative disease or cancer associated with mutant isocitrate dehydrogenase comprising administering to a patient in need thereof a compound of claim 34, wherein the disease or cancer is selected from the group consisting of glioma, glioblastoma multiforme, paraganglioma, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), and myeloproliferative disease (MPD).

\* \* \* \* \*